US012121584B2

(12) United States Patent
Hershberger et al.

(10) Patent No.: US 12,121,584 B2
(45) Date of Patent: *Oct. 22, 2024

(54) CONJUGATE MOLECULES

(71) Applicant: Diverse Biotech, Inc., Miami, FL (US)

(72) Inventors: Paul Hershberger, Miami, FL (US); Philip Arlen, Miami Beach, FL (US)

(73) Assignee: Diverse Biotech, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/509,504

(22) Filed: Nov. 15, 2023

(65) Prior Publication Data

US 2024/0075149 A1 Mar. 7, 2024

Related U.S. Application Data

(63) Continuation of application No. 17/768,921, filed as application No. PCT/US2020/039267 on Jun. 24, 2020, now Pat. No. 11,877,988.

(60) Provisional application No. 62/960,070, filed on Jan. 12, 2020, provisional application No. 62/915,352, filed on Oct. 15, 2019.

(51) Int. Cl.
*A61K 47/55* (2017.01)
*A61K 47/52* (2017.01)
*A61K 47/54* (2017.01)
*A61K 47/68* (2017.01)

(52) U.S. Cl.
CPC .............. *A61K 47/55* (2017.08); *A61K 47/52* (2017.08); *A61K 47/542* (2017.08); *A61K 47/545* (2017.08); *A61K 47/552* (2017.08); *A61K 47/6803* (2017.08)

(58) Field of Classification Search
None
See application file for complete search history.

(56) References Cited

U.S. PATENT DOCUMENTS

| | | |
|---|---|---|
| 7,053,150 B2 | 5/2006 | Kozlowski et al. |
| 2008/0176885 A1 | 7/2008 | Holtman et al. |
| 2009/0214534 A1* | 8/2009 | Holmes .............. A61K 47/6843 435/328 |

(Continued)

FOREIGN PATENT DOCUMENTS

| | | |
|---|---|---|
| EP | 0402846 A2 | 12/1990 |
| EP | 3813863 A1 | 5/2021 |

(Continued)

OTHER PUBLICATIONS

Tsui et al., Canadian Journal of Biochemistry, vwol. 52, No. 3, 1974, pp. 252-258 (Year: 1974).*

(Continued)

*Primary Examiner* — Karl J Puttlitz
(74) *Attorney, Agent, or Firm* — Banner & Witcoff, Ltd.

(57) ABSTRACT

This disclosure provides multifunctional conjugate molecules comprising a target binding component covalently linked to one or more cannabinoids and/or one or more cannabinoid conjugate components. In some embodiments, the target binding component also is covalently linked to one or more active agent components. The disclosed conjugate molecules are designed to deliver therapeutic benefits of each component of the conjugate molecules and can be used to treat cancer and other disorders.

16 Claims, 10 Drawing Sheets

(56) References Cited

U.S. PATENT DOCUMENTS

| | | | | |
|---|---|---|---|---|
| 2020/0332006 A1* | 10/2020 | Finlay | ..................... | A61P 35/00 |
| 2021/0137987 A1 | 5/2021 | Novina et al. | | |
| 2021/0228699 A1 | 7/2021 | Novina et al. | | |

FOREIGN PATENT DOCUMENTS

| | | | | |
|---|---|---|---|---|
| WO | WO-2009099670 A2 | 8/2009 | | |
| WO | WO-2009099670 A3 | 1/2010 | | |
| WO | WO-2014/197854 A1 | 12/2014 | | |
| WO | 2017072196 | * | 5/2017 | |
| WO | WO-2017072196 A1 | * | 5/2017 | ............. A61K 31/40 |
| WO | WO-2019018536 A1 | 1/2019 | | |
| WO | WO-2020214220 A2 | 10/2020 | | |
| WO | WO-2020263888 A1 | 12/2020 | | |

OTHER PUBLICATIONS

Van Dolah et al., "Clinicians' Guide to Cannabidiol and Hemp Oils". Mayo Clinic Proceedings. Sep. 2019, 94 (9): 1840-1851 (Year: 2019).*

Berding et al., "Feasibility of central cannabinoid CB1 receptor imaging with [^124I]AM281 PET demonstrated in a schizophrenic patient," Psychiatry Research: Neuroimaging 147, 249-56, 2006.

Donohue et al., "Synthesis and in vitro autoradiographic evaluation of a novel high-affinity radioiodinated ligand for imaging brain cannabinoid subtype-1 receptors," Bioorganic & Medicinal Chemistry Letters 19, 6209-12, 2009.

Frau et al., "Pyrazole-type cannabinoid ligands conjugated with fluoro-deoxy-carbohydrates as potential PET-imaging agents: Synthesis and CB1/CB2 receptor affinity evaluation," J. Fluorine Chemistry 152, 166-72, 2013.

Hershberger & Arlen, U.S. Appl. No. 17/768,921, Notice of Allowance, Examiner's Amendment, and Interview Summary, dated Jul. 10, 2023, 10 pages.

International Search Report and Written Opinion for PCT/US2020/039267 dated Nov. 5, 2020, 12 pages.

Nikas et al., "The role of halogen substitution in classical cannabinoids: A CB1 pharmacophore model," The APPS Journal 6, 23-35, 2004.

Noble et al., "Application of an activity-based receptor bioassay to investigate the in vitro activity of selected indole- and indazole-3-carboxamide-based synthetic cannabinoids at CB1 and CB2 receptors," Drug Testing and Analysis 11, 501-11, 2019.

Pubchem-CID 101614426, Dec. 18, 2015, 8 pages.

Supplementary Partial European Search Report for EP 20876123.9 dated May 5, 2023, 19 pages.

Tsui et al., "Delta.9-Tetrahydrocannabinol-Protein Conjugates," Canadian Journal of Biochemistry 52, 252-58, 1974.

* cited by examiner

CONJUGATE MOLECULES

Each reference cited in this disclosure is incorporated herein in its entirety.

TECHNICAL FIELD

This disclosure relates generally to therapeutic treatments.

BRIEF DESCRIPTION OF THE DRAWINGS

FIG. 3A, examples 3a and 3a'. FIG. 3B, examples 5b and 5b'.

■ and ▌ each represents a cannabinoid leaving ligand, which can be the same or different, and * is the point of attachment to linker L$_{pc}$.

FIGS. 5A-E. Non-limiting examples of comprising a cannabinoid axial ligand, in which, for simplicity each cannabinoid axial ligand is a cannabidiol axial ligand.

Figure 5A:
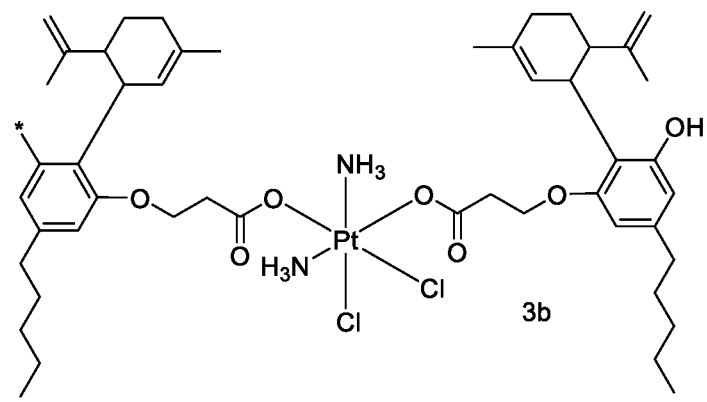
Figure 5A:
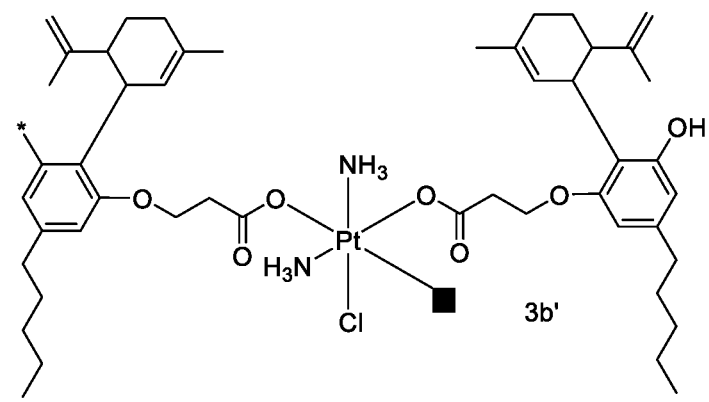
Figure 5A:
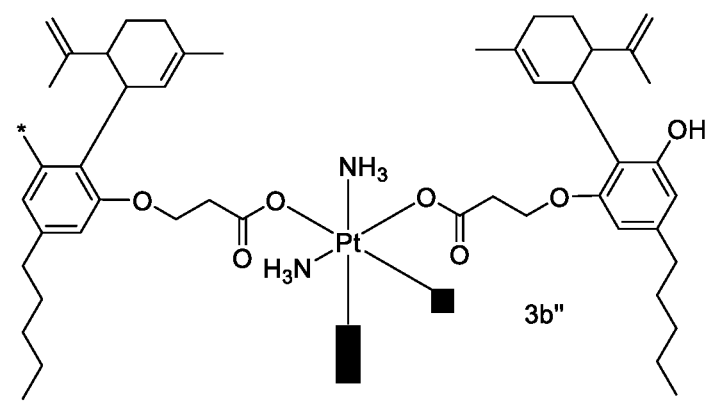
Figure 5B:
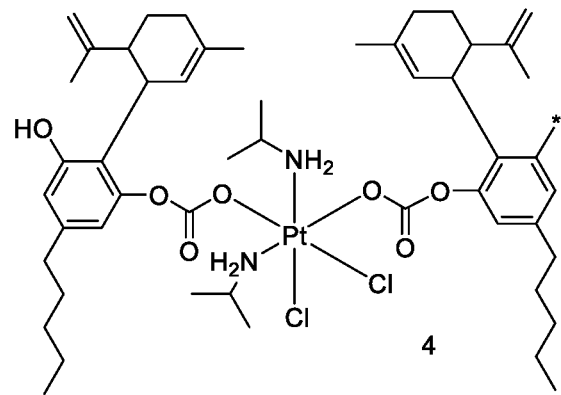
Figure 5B:
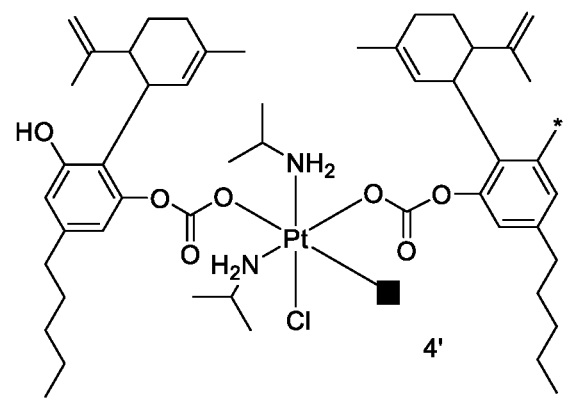
Figure 5B:
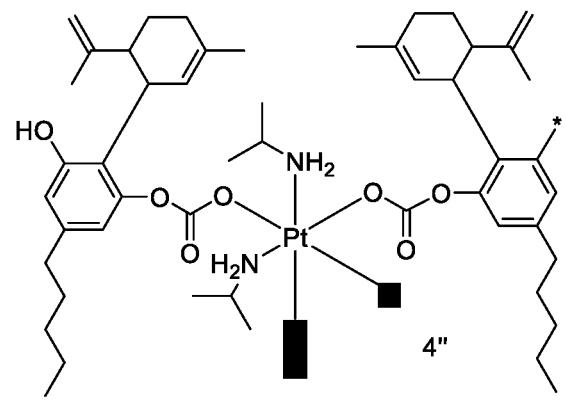
Figure 5C:
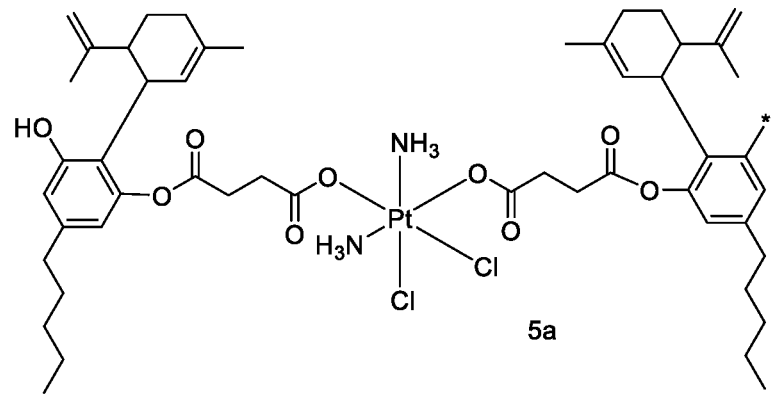
Figure 5C:
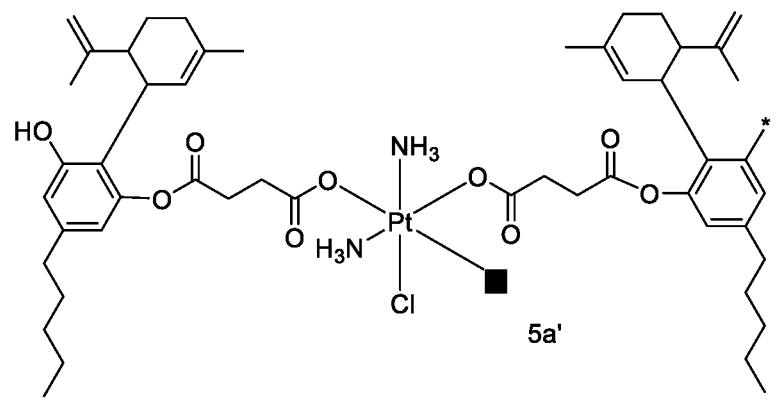
Figure 5C:
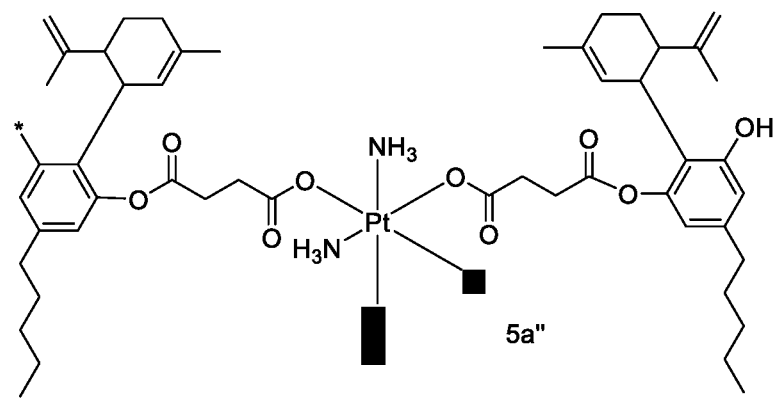
Figure 5D:
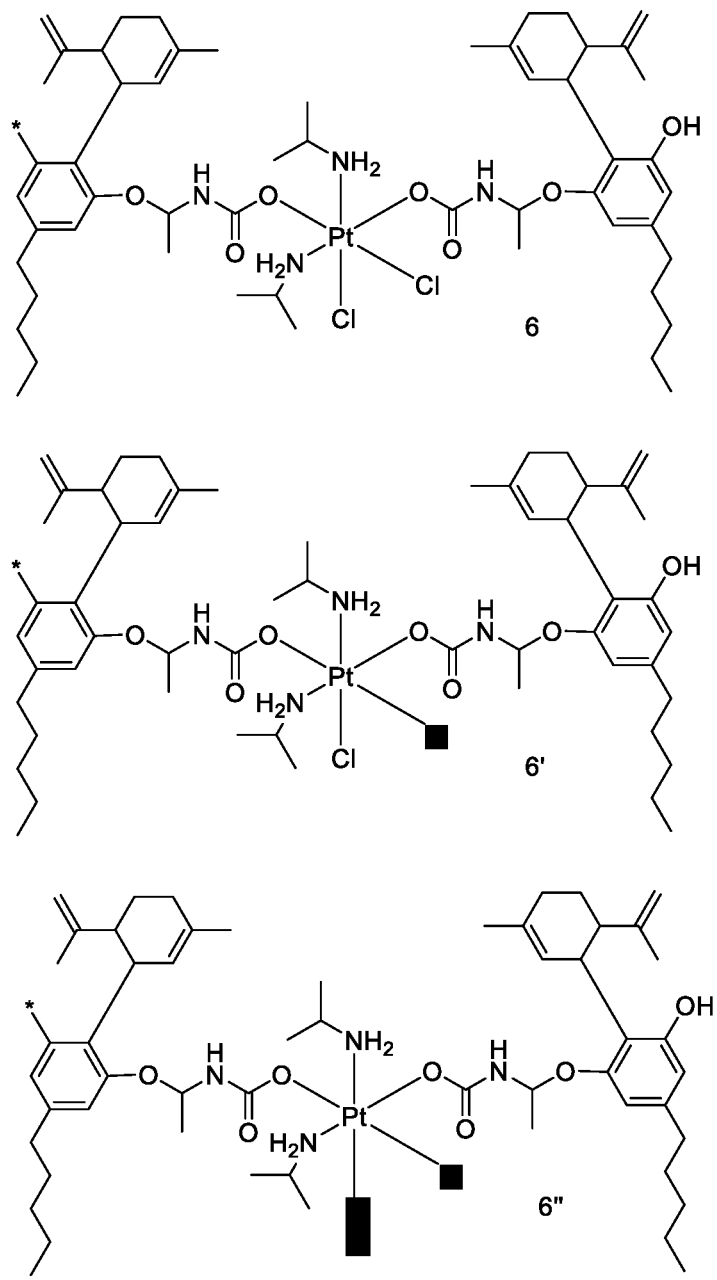

■ and ▌ each represents a cannabinoid leaving ligand, which can be the same or different, in which * marks the point of attachment to linker L$_{pc}$. FIG. 5A, examples 3b, 3b', and 3b". FIG. 5B, examples 4, 4', and 4". FIG. 5C, 5a, 5a', and 5a". FIG. 5D, examples 6, 6', and 6".

Figure 5E:
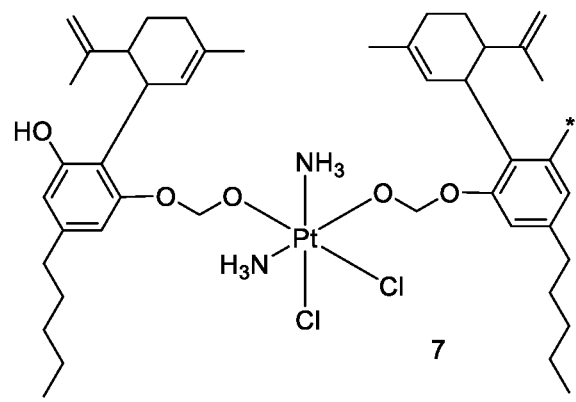
Figure 5E:
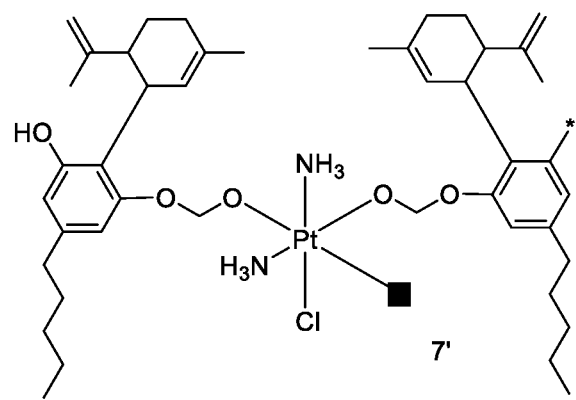
Figure 5E:
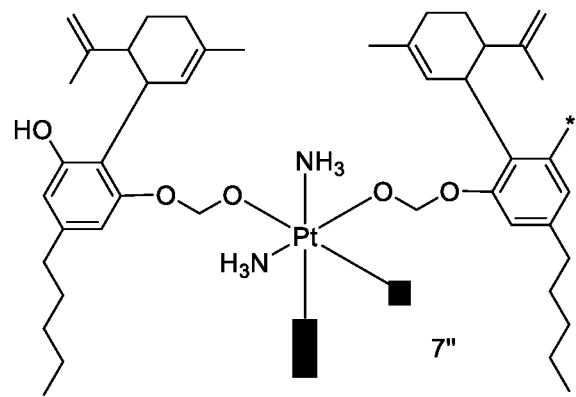

FIG. 5E, examples 7, 7', and 7".

DETAILED DESCRIPTION

Definitions

"C1-C3 linear or branched alkyl" means "methyl, ethyl, propyl, and isopropyl."

"C1-C8 linear or branched alkyl" means "methyl, ethyl, C3, C4, C5, C6, C7, and C8 linear alkyl and C3, C4, C5, C6, C7, and C8 branched alkyl."

"C1-C3 linear or branched heteroalkyl" means "a linear or branched heteroalkyl containing 1, 2, or 3 carbon atoms."

"C1-C8 linear or branched heteroalkyl" means "each of a C1, C2, C3, C4, C5, C6, C7, and C8 linear heteroalkyl and C1, C2, C3, C4, C5, C6, C7, and C8 branched heteroalkyl."

"C1-C12 linear or branched heteroalkyl" means each of a C1, C2, C3, C4, C5, C6, C7, C8, C9, C10, C11, and C12 linear heteroalkyl and C1, C2, C3, C4, C5, C6, C7, C8, C9, C10, C11, and C12 branched heteroalkyl."

"C1-C24 linear or branched heteroalkyl" means each of a C1, C2, C3, C4, C5, C6, C7, C8, C9, C10, C11, C12, C13, C14, C15, C16, C17, C18, C19, C20, C21, C22, C23, and C24 linear heteroalkyl and C1, C2, C3, C4, C5, C6, C7, C8, C9, C10, C11, C12, C13, C14, C15, C16, C17, C18, C19, C20, C21, C22, C23, and C24 branched heteroalkyl."

"C1-C6 linear or branched alkoxyl" means "a linear or branched alkoxyl containing 1, 2, 3, 4, 5, or 6 carbon atoms."

"C1-C6 linear or branched alkylamino" means "a linear or branched alkylamino containing 1, 2, 3, 4, 5, or 6 carbon atoms."

"C1-C6 linear or branched dialkylamino" means "each linear or branched dialkylamino in which each alkyl independently contains 1, 2, 3, 4, 5, or 6 carbon atoms."

"6-10-membered aromatic" means "each of a 6-, 7-, 8-, 9-, and 10-membered aromatic."

"5- to 10-membered heteroaromatic" means "each of a 6-, 7-, 8-, 9-, and 10-membered heteroaromatic."

"3- to 9-membered cycloheteroalkyl" means "each of a 3-, 4-, 5-, 6-, 7-, 8-, and 9-membered cycloheteroalkyl."

"C3-C6 cycloalkyl" means "C3, C4, C5, and C6 cycloalkyl."

"Halide" means "Cl, Br, and I."

"Group One Substituents" is a group of substituents consisting of:
(a) —OH;
(b) —NH$_2$;
(c) =O;
(d) =S;
(e) =NR$_7$, where R$_7$ is H or is C1-C3 linear or branched alkyl or C1-C3 linear or branched heteroalkyl comprising an O, N, or S atom;
(f) —C(O)OR$_4$, wherein R$_4$ is H or C1-C3 linear or branched alkyl;
(g) —C(O)NR$_5$R$_6$, wherein R$_5$ and R$_6$ independently are H or C1-C6 linear or branched alkyl;
(h) halide;
(i) C1-C6 linear or branched alkoxyl;
(j) C1-C6 linear or branched alkylamino;
(k) C1-C6 linear or branched dialkylamino;
(l) 6- to 10-membered aromatic, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents;
(m) 5- to 10-membered heteroaromatic, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and (v) C1-C6 linear or branched heteroalkyl containing 1, 2, or 3 atoms independently selected from O, N, and S and optionally substituted with
  (1) 1, 2, 3, 4, 5, 6, 7, 8, or 9 fluorine atoms; and/or
  (2) 1, 2, or 3 substituents independently selected from the Group Two Substituents;
(n) 3- to 9-membered cycloheteroalkyl having 1, 2, or 3 heteroatoms independently selected from O, N, and S, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents; and
(o) C3-C6 cycloalkyl, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents.

"Group Two Substituents" is a group of substituents consisting of:
(a) —OH;
(b) —NH$_2$;
(c) =O;
(d) =S;
(e) =NR$_7$, where R$_7$ is H or is C1-C3 linear or branched alkyl or C1-C3 linear or branched heteroalkyl comprising an O, N, or S atom;
(f) —C(O)OR$_4$, wherein R$_4$ is H or C1-C3 linear or branched alkyl;
(g) —C(O)NR$_5$R$_6$, wherein R$_5$ and R$_6$ independently are H or C1-C6 linear or branched alkyl;
(h) halide;
(i) cyano;
(j) trifluoromethyl;
(k) C1-C6 linear or branched alkoxyl;
(l) C1-C6 linear or branched alkylamino;
(m) C1-C6 linear or branched dialkylamino;
(n) 6- to 10-membered aromatic; and
(o) 5- to 10-membered heteroaromatic comprising 1, 2, 3, 4, 5, or 6 heteroatoms independently selected from O, N, and S.

The definitions above apply to the descriptions that follow. For example, the phrase "R$_4$ is H or C1-C3 linear or branched alkyl" should be read as describing each of five sets of embodiments in which R$_4$ is H, R$_4$ is methyl, R$_4$ is ethyl, R$_4$ is propyl, and R$_4$ is isopropyl, respectively.

Conjugate Molecules

Conjugate molecules comprise a target binding component covalently linked to one or more cannabinoids and/or one or more cannabinoid conjugate components. In some embodiments, the target binding component also is covalently linked to one or more active agent components. The disclosed conjugate molecules are designed to deliver therapeutic benefits of each component of the conjugate molecules and can be used to treat cancer and other disorders.

For the purpose of this disclosure, conjugate molecules described below are divided into Types I, II, and III, described briefly below, followed by detailed descriptions of the various components of conjugate molecules.

In the Type I, Type II, and Type III embodiments described in this disclosure, the values of m and n apply to embodiments in which the binding component is an antibody. However, other target binding components can be used; in these embodiments, the values for m and n will vary according to the type of binding component. For example:
1. In some embodiments in which B is an oligonucleotide (e.g., an aptamer), m is 1-20, n is 0-20, and the sum of m+n is 1-20. See, e.g., Xuan et al., Biomaterials 182, 216-226, 2018; Zhu et al. PNAS, 110, 7998-8003, 2013.
2. In some embodiments in which B is a DARPin, m is 1 and n is 0; see, e.g., Simon et al. Bioconjug Chem. 24, 1955-1966, 2013; Laviolette et al. Cancer Research Proceedings: AACR Annual Meeting 2019, Abstract 215, 2019.
3. In some embodiments in which B is a peptide, m is 1-3 and n is 0. See, e.g., Fureder et al. Neuro-Oncology 18, iv16-iv17, 2016; Vrettos et al. Beilstein J Org Chem. 14, 930-954, 2018.

Type I conjugate molecules have the formula:

$$(CBNC\text{-}L_{cc})_m\text{-}B\text{-}(L_a\text{-}A)_n \qquad (I)$$

in which, as described below, CBNC is a cannabinoid conjugate component comprising a therapeutic agent component covalently linked, directly or via a linker, to a cannabinoid component; L$_{cc}$ is a CBNC linker, which may be absent; B is a target binding component; L$_a$ is an active component linker; and A is an active component. In embodiments in which B is an antibody, m is 1-30, n is 0-29, and the sum of m+n is 1-30. Type II conjugate molecules have the formula:

$$(PCAN\text{-}L_{pc})_m B\text{-}(L_a\text{-}A)_n \qquad (II)$$

in which, as described below, PCAN is a platinum complex anti-neoplastic agent component; L$_{pc}$ is a PCAN linker, which may be absent; B is a target binding component; L$_a$ is an active component linker; and A is an active component. In embodiments in which B is an antibody, m is 1-30; n is 0-29; and the sum of m+n is 1-30.

Type III conjugate molecules have the formula:

$$(CBN\text{-}L_c)_m\text{-}B\text{-}(L_a\text{-}A)_n \qquad (III)$$

in which, as described below, CBN is a cannabinoid component; L$_c$ is a cannabinoid component linker, which may be absent; B is a target binding component; and A is an active component. In embodiments in which B is an antibody, m is 1-30; n is 0-29; and the sum of m+n is 1-30.

Target Binding Components (B)

A "target binding component" as used in this disclosure is a moiety that binds to a target molecule (e.g., a cell surface or circulating target molecule). The target binding component may itself have a therapeutic effect, or it may function simply to target the component molecule.

In some embodiments, the target binding component is a peptide. See, e.g., Reverdatto et al. (Curr. Top. Med. Chem. 15, 1082-1101, 2015); Yakimchuk (Mater. Methods 5, 1417, 2015); Squillacioti et al. (Acta Vet Scand. 61, 46, 2019); Ojeda et al. (Drug Discov. Today 2019).

In some embodiments, the target binding component is an oligonucleotide. See, e.g., Yakimchuk (Mater. Methods 5, 1417, 2015); Santosh and Yadava (BioMed Res. Intl. 2014, 540451, 2014).

In some embodiments, the target binding component is a receptor binding domain. See, e.g., Xia et al. (Curr. Top. Microbiol. Immunol. 199, 39-46, 1995); Zhou et al. (J. Formos. Med. Assoc. 113, 143-147, 2014); Zhang et al. (Virus. Res. 202, 151-159, 2015); Liu et al. (Biomed. Res Int. 2015, 594109, 2015); Zhou et al. (Viruses 11, E60, 2019).

In some embodiments, the target binding component is a designed ankyrin repeat protein (DARPin). See, e.g., Pluckthun (Ann. Rev. Pharmacol. Toxicol. 55, 489-511, 2015); Binz et al. (J. Mol. Biol. 332, 489-503, 2003); Mosavi et al. (Proc. Nat'l. Acad. Sci (USA) 99, 16029-34, 2002); Binz et al. (Nature Biotechnology 22, 575-82, 2004); Steiner et al. (Mol. Biol. 382, 1211-27, 2008); Steiner et al. (Nature Biotechnology 24, 823-31, 2006); Kohl et al. (Proc. Natl. Acad. Sci. USA. 100, 1700-75, 2003); Wetzel et al. (J. Mol. Biol. 376, 241-57, 2008); Simon et al. (Bioconjugate Chem. 24, 1955-66, 2013); Martin-Killias et al. (Clin. Cancer Res. 17, 100-10, 2011); Zahnd et al. (Cancer Res. 70, 1595-1605, 2010).

In some embodiments, the target binding component is an interferon, e.g., interferon α-2a (ROFERON-A®), interferon α-2b (INTRON-A®), interferon α-n3 (ALFERON-N®), peginterferon α-2b (PEGINTRON®, SYLATRON®), interferon β-1a (AVONEX®), interferon β-1a (REBIF®), interferon β-1b (BETASERON®), interferon β-1b (EXTAVIA®).

In some embodiments, the target binding component is an antibody. An "antibody" can be, for example, an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof. In some embodiments, an antibody is an IgG, an IgE, an IgM, an IgD, an IgA, or an IgY. IgG antibodies include IgG1, IgG2 (e.g., IgG2a, IgG2b), IgG3, and IgG4 antibodies. IgA antibodies include IgA1 and IgA2 antibodies.

In some embodiments, the antibody is radiolabeled.

Types of antigens to which an antibody can bind include, but are not limited to, antigens from the following categories (which, in some cases, are listed in belong in more than one category):

i. cluster of differentiation (CD) antigens, such as CD2, CD3, CD4, CD11a, CD19, CD20, CD25 (ILR2), CD30, CD33, CD38, CD52, CD139, CD152 (cytotoxic T lymphocyte-associated protein 4, CTLA-4), CD274 (PD-L1), CD319 (signaling lymphocyte activation molecule family 7, SLAMF7);

ii. checkpoint inhibitors, such as programmed cell death protein 1 (PD-1), programmed death ligand 1 (PD-L1, CD274);

iii. vascular target antigens, such as prostate-specific membrane antigen (PSMA);

iv. stromal antigens, such as Bone Marrow Stromal Antigen 2;

v. extracellular matrix antigen, such as type I, III, IV, and V collagens (CI, CIII, CIV, CV), laminin (LM), fibronectin (FN);

vi. circulating antigens, such as Factor IXa, Factor X;

vii. interleukins, such as IL-13, IL-2, IL-5, IL-6, IL-12, IL-17A, IL-23;

viii. interleukin receptors, e.g., ILR2 (CD25), IL-4RA, IL-5RA, IL-6R, IL-17RA;

ix. growth factors, such as vascular endothelial growth factor A (VEGFA);

x. growth factor receptors, such as epidermal growth factor receptor (EGFR, ErbB1), fibroblast growth factor receptor 1, 2, 3, 4, 23 (FGFR, FGFR2, FGFR3, FGFR4, FGFR23), human epidermal growth factor 2 (HER2/neu), ErbB2 receptor tyrosine kinase 3 (HER3, ErbB3), ErbB2 receptor tyrosine kinase 4 (HER4), platelet-derive growth factor receptor alpha (PDG-FRA), vascular endothelial growth factor receptor 1, 2, 3 (VEGFR1, VEGFR2, VEGFR3), ephrin type-A receptor 1, 2, 3, 4, 5, 6, 7, 8 (EphA1, EphA2, EphA3, EphA4, EphA5, EphA6, EphA7, EphA8), ephrin type-B receptor 1, 2, 3, 4, 5, 6, 7 (EphB1, EphB2, EphB3, EphB4, EphB5, EphB6, EphB7), hepatocyte growth factor receptor (HGFR, c-Met), insulin-like growth factor 2 receptor (IGF2R);

xi. drugs, such as digoxin, dabigatran;

xii. adhesion molecules, such as epithelial cell adhesion molecule (EpCAM);

xiii. tumor necrosis factors, such as TNF-α, TNF-β;

xiv. tumor necrosis factor-related apoptosis-inducing ligand receptors, such as TRAIL-R1, TRAIL-R2;

xv. insulin receptors (IR);

xvi. receptor tyrosine kinases (RTK), such as FMS-like receptor tyrosine kinase-3 (FLT3), macrophage colony-stimulating factor 1 receptor (CSF-1R), mast/stem cell growth factor receptor (KIT/SCFR), macrophage stimulating 1 receptor (RON, SEA), Axl receptor tyrosine kinase (AXL, UFO), Mer receptor tyrosine kinase (MER), TYRO3, MUSK, RET, TIE1, discoidin domain receptor family member 1, 2 (DDR1, DDR2), receptor tyrosine kinase-like orphan receptor 1, 2 (ROR1, ROR2), ROS, LTL, ALK, KLG, "related to tyrosine kinase receptor" (RYK);

xvii. cytokine receptors, such as type I, type II, immunoglobulin superfamily, tumor necrosis factor family, chemokine, C-C motif chemokine receptor 4 (CCR4), TGF-β receptors (including activin receptors);

xviii. tropomyosin receptor kinases (TRK), such as TRKA, TRKB, TRKC;

xix. integrins, such as integrin α4, integrin α4β1, integrin α4β7;

xx. immunoglobulins, such as IgE;

xxi. antigens of infectious organisms, such as respiratory syncytial virus (e.g., Protein F), *Bacillus anthracis* (e.g., *B. anthracis* protective antigen), *Clostridium difficile* (e.g., *C. difficile* toxin B); and xxii. other antigens, such as proprotein convertase subtilisin/kexin type 9 (PSCK9), calcitonin-gene related peptide receptor (CGRPR)/calcitonin receptor-like receptor (CRLR), receptor activator of nuclear factor kappa-B ligand (RANKL), glycoprotein (GP) IIb/IIIa receptor, ganglioside G2 (GD2), B lymphocyte stimulator (BLyS), complement component 5 (C5), insulin receptor-related receptor (IRR), tumor-associated glycoprotein 72 (TAG72).

Examples of therapeutic antibodies include, but are not limited to, abciximab (e.g., REOPRO®), adalimumab (e.g., HUMIRA®, TRUDEXA®), adalimumab-adbm (e.g., CYLTEZO®, XARXIO®), adalimumab-atto (e.g., AMJEVITA®), alefacept (e.g., AMEVIVE®), alemtuzumab (e.g., CAMPATH®, MABCAMPATH®), alirocumab (e.g., PRALUENT®), atezolizumab (e.g., TECENTRIQ®), avelumab (e.g., BAVENCIO®), basiliximab (e.g., SIMULECT®), belimumab (e.g., BENLYSTA®), benralizumab (e.g., FASENRA®), bevacizumab (e.g., AVASTIN®), bevacizumab-awwb (e.g., MVASI®), bezlotoxumab (e.g., ZINPLAVA®), blinatumomab (e.g., BLINCYTO®), brodalumab (e.g., SILIQ®), burosumab-twza (e.g., CRYSVITA®), canakinumab (e.g., ILARIS®), catumaxomab (e.g., REMOVAB®), cemiplimab (e.g., LIBTAYO®), certolizumab pegol (e.g., CIMZIA®), cetuximab (e.g., ERBITUX®), daclizumab (e.g., ZENAPAX®, ZINBRYTA®), daratumumab (e.g., PROLIA®, XGEVA®, DARZALEX®), denileukin diftitox (e.g., ONTAK®), denosumab (e.g., PROLIA®, XGEVA®), digoxin immune Fab (e.g., DIGIBIND®, DIGIFAB®), dinutuximab (e.g., UNITUXIN®), dupilumab (e.g., DUPIXENT®), durvalumab (e.g., IMFINZI®), eculizumab (e.g., SOLIRIS®), efalizumab (e.g., RAPTIVA®), elotuzumab (e.g., EMPLICITI®), emicizumab-kxwh (e.g., HEMLIBRA®), erenumab-aooe (e.g., AIMOVIG®), etanercept (e.g., ENBREL®), evolocumab (e.g., REPATHA®), golimumab (e.g., SIMPONI®), guselkumab (e.g., TREMFYA®), ibalizumab-uiyk (e.g., TROGARZO®), ibritumomab tiuxetan (e.g., ZEVALIN®), idarucizumab (e.g., PRAXBIND®), infliximab (e.g., REMICADE®), infliximab-abda (e.g., ENFLEXIS®), infliximab-dyyb (e.g., INFLECTRA®), infliximab-qbtx (e.g., IXIFI®), ipilimumab (e.g., YERVOY®), ixekizumab (e.g., TALTZ®), mepolizumab (e.g., NUCALA®), mogamulizumab (e.g., POTELIGEO®), muromomab (e.g., ORTHOCLONE®), natalizumab (e.g., TYSABRI®), necitumumab (e.g., PORTRAZZA®), nivolumab (e.g., OPDIVO®), nofetumomab (e.g., VERLUMA®), obiltoxaximab (e.g., ANTHEM®), obinutuzumab (e.g., GAZYVA®), ocrelizumab (e.g., OCREVUS®), ofatumumab (e.g., ARZERRA®), olaratumab (e.g., LARTRUVO®), omalizumab (e.g., XOLAIR®), palivizumab (e.g., SYNAGIS®), panitumumab (e.g., VECTIBIX®), pembrolizumab (e.g., KEYTRUDA®), pertuzumab (e.g., PERJETA®), ramucirumab (e.g., CYRAMZA®), ranibizumab (e.g., LUCENTIS®), raxibacumab (e.g., ABTHRAX®), reslizumab (e.g., CINQAIR®), rituximab (e.g., RITUXAN, MABTHERA®), rituximab (e.g., RITUXAN®) and hyaluronidase (e.g., HYCELA®), sarilumab (e.g., KEVZARA®), satumomab (e.g., ONTOSCINT®), secukinumab (e.g., COSENTYX®), siltuximab (e.g., SYLVANT®), tildrakizumab-asmn (e.g., ILUMYA®), tocilizumab (e.g., ACTEMRA, ROACTEMRA®), tositumomab iodine 131 (e.g., BEXXAR®), trastuzumab (e.g., HERCEPTIN®), trastuzumab-dkst (e.g., OGIVRI®), ustekinumab (e.g., STELARA®), and vedolizumab (e.g., ENTYVIO®).

In some embodiments, the antibody is part of an antibody drug conjugate (ADC); in these embodiments, the active agent component is the "warhead" portion of the ADC. Examples of ADCs include, but are not limited to, ado-trastuzumab emtansine (e.g., KADCYLA®), brentuximab vedotin (e.g., ADCETRIS®), inotuzumab ozogamicin (BESPONSA®), and gemtuzumab ozogamicin (e.g., MYLOTARG®).

Active Agent Components (A)

An "active agent component" as used in this disclosure is a component having a therapeutic activity. As mentioned above, in some embodiments the active agent component is the "warhead" portion of an ADC, either when B is an antibody or when B is another type of target binding component.

Active Component Linkers ($L_a$) and Cannabinoid Component Linkers ($L_{cc}$)

An "active component linker" as used in this disclosure, when present, links a target binding component to an active agent component. A "cannabinoid component linker" as used in this disclosure links a target binding component to a cannabinoid conjugate component (described below). In each case, these linkers include self-cleaving linkers such as acid-labile linkers and protease-labile linkers, non-cleavable linkers, linkers comprising negatively charged groups, linkers comprising sugar moieties, and other linkers used in the ADC field.

Examples of acid-labile linkers include acetals, hydrazones (including acylhydrazones, hydrazines), imines, esters, linkers containing disulfide bonds, and linkers containing pH-sensitive chelators. See, e.g., Vlahov & Leamon, Bioconjug. Chem. 23, 1357-69, 2012); Xiao et al., Nanoscale 4, 7185-93, 2012; Abu et al., Eur. J. Cancer 48, 2054-65, 2011; DiJoseph et al., Clin Cancer Res. 12, 242-49, 2006; Kale & Torchilin, Bioconjugate Chemistry 18, 363-70, 2007; Sawant et al., Bioconjugate Chemistry 17, 943-49, 2006; Reddy et al., Sci. Rep. 8, 8943, 2018.

Examples of protease-labile linkers include linkers comprising a valine-citrulline bond, (3-glucuronic acid-based linkers, and imides. See, e.g., Weinstain et al., Chem. Commun. (Camb.) 46, 553-55, 2010; Shao et al., Cancer 118, 2986-96, 2010; Liang et al., J. Controlled Release 160, 618-29, 2012; Barthel et al., J. Med. Chem. 55, 6595-607, 2012; Nolting, Methods Mol. Biol. 1045, 71-100, 2013; Erickson, Cancer Res. 66, 4426-33, 2006; Jeffrey et al., Bioconjugate Chem. 17, 831-40, 2006; Dubowchik et al., Bioconjugate Chem. 13, 855-69, 2002; Mhidia et al., Org. Lett. 12, 3982-85, 2010.

Examples of non-cleavable linkers include thioether-based linkers and N-succinimidyl-4-(N-maleimidylmethyl)cyclohexane-1-carboxylate (SMCC) linker (see, e.g., Juárez-Hernández et al., ACS Med. Chem. Lett. 3, 799-803, 2012).

Examples of linkers comprising negatively charged groups are disclosed, for example, in Leamon et al., J. Pharm. Exp. Ther. 336, 336-43, 2011.

Examples of linkers containing sugar moieties are disclosed, for example in Mikuni et al., Biol. Pharm. Bull. 31, 1155-58, 2008.

Other types of linkers include:
i. linkers comprising an acetamide moiety and linkers comprising sulfur-containing amides or esters (Davaran et al., J. Pharm. Pharmacol. 55, 513-17, 2003);
ii. linkers comprising an enzyme-hydrolyzable unit, such as:
  1. a carboxylic ester or an amide bond (e.g., succinyl, glutaryl); or
  2. peptides recognized by cathepsin B (e.g., Val-Cit (valine-citrulline), GFLG (SEQ ID NO:1) or peptides recognized by MMP-2 and MMP-9, such as GPLGIAGQ (SEQ ID NO:2), PLGLAG (SEQ ID NO:3), and GPVGLIGK (SEQ ID NO:4);

iii. stimuli-responsive or degradable linkers (e.g., linkers comprising an imine, oxime, hydrazone, orthoester, acetal, vinyl ether, or polyketal bond); and
iv. linkers comprising para-amino benzyl alcohol (PABC).

Cannabinoid Conjugate Components

A "cannabinoid conjugate component" as used in this disclosure comprises at least one therapeutic agent component covalently linked, directly or via a linker, to at least one cannabinoid component. A "cannabinoid component" is that portion of a cannabinoid molecule that is present either in a Type III conjugate molecule or in a cannabinoid conjugate component of a Type I or II conjugate molecule, as described below. A "therapeutic agent component" as used in this disclosure is a therapeutic agent or portion of a therapeutic agent that is present in a cannabinoid conjugate component (described below).

In some embodiments, a therapeutic agent component is covalently attached directly to a hydroxy or carboxylic acid group of a cannabinoid component. In some embodiments, cannabinoid conjugate components comprise a therapeutic agent component and a cannabinoid component attached by means of a linker which is covalently attached at one end to the therapeutic agent component and at the other end to a hydroxy or carboxylic acid group of the cannabinoid component. In some embodiments, the hydroxy group is an "aromatic hydroxy group;" i.e., a hydroxy group bonded directly to an aromatic hydrocarbon. In some embodiments, the hydroxy group is an "aliphatic hydroxy group;" i.e., a hydroxy group bound to a carbon that is not part of an aromatic ring.

In some embodiments, conjugate molecules contain only one therapeutic agent component. In other embodiments, for example, when a cannabinoid component has at least two hydroxy groups, or at least one hydroxy group and at least one carboxylic acid group, or at least two carboxylic acid groups, conjugate molecules can contain two or more therapeutic agent components, which can be the same or different.

In some embodiments, in which therapeutic agent components are attached via a linker, the two or more linkers can be the same or different and, independently, the two or more therapeutic agent components can be the same or different. Also independently, when a cannabinoid component contains two or more hydroxy groups, the two or more hydroxy groups can be aliphatic or the two or more hydroxy groups can be aromatic, or, for example, a first hydroxy group can be aliphatic and a second hydroxy group can be aromatic.

In some embodiments using particular types of linkers described below, conjugate molecules can contain two therapeutic agent components which are both attached to a single linker. The two therapeutic agent components can be the same or different.

In some embodiments, a conjugate molecule can contain an additional cannabinoid component.

Cannabinoid Components

The cannabinoid component can be provided by a naturally occurring molecule, either isolated or synthesized, or a modified version of a naturally occurring molecule. See, for example, Morales et al., Frontiers in Pharmacology June 2017 review, 1-18.

Examples of cannabinoids include, but are not limited to, cannabigerols, cannabichromenes, cannabidiols, tetrahydrocannabinols, cannabicyclols, cannabielsoins, cannabinols, cannabinodiols, cannabitriols, dehydrocannabifurans, cannabifurans, cannabichromanons, and cannabiripsols.

Examples of cannabigerols include cannabigerolic acid (CBGA), cannabigerolic acid monomethylether (CBGAM), cannabigerol (CBG), cannabigerol monomethyleither (CBGM), cannabigerovarinic acid (CBGVA), and cannabigerovarin (CBGV).

Examples of cannabichromenes include cannabichromenic acid (CBC), cannabichromene (CBC), cannabichromevarinic acid (CBCVA), and cannabichromevarin (CBCV).

Examples of cannabidiols include cannabidiolic acid (CBDA), cannabidiol (CBD), cannabidiol monomethylether (CBDM), cannabidiol-$C_4$ (CBD-$C_4$), cannabidivarinic acid (CBDVA), cannabidivarin (CBDV), and cannabidiorcol (CBD-$C_1$).

Examples of tetrahydrocannabinols include Δ-9-tetrahydrocannabinolic acid A (THCA-A), Δ-9-tetrahydrocannabinolic acid B (THCA-B), Δ-9-tetrahydrocannabinol (THC), Δ-9-tetrahydrocannabinolic acid-$C_4$ (THCA-$C_4$), Δ-9-tetrahydrocannabinol-$C_4$ (THC-$C_4$), Δ-9-tetrahydrocannabivarinic acid (THCVA), Δ-9-tetrahydrocannabivarin (THCV), Δ-9-tetrahydrocannabiorcolic acid (THCA-$C_1$), Δ-9-tetrahydrocannabiorcol (THC-$C_1$), Δ-7-cis-tetrahydrocannabivarin, Δ-8-tetrahydrocannabinolic acid ($Δ^8$-THCA), and Δ-8-tetrahydrocannabinol ($Δ^8$-THC).

Examples of cannabicyclols include cannabicyclolic acid (CBLA), cannabicyclol (CBL), and cannabicyclovarin (CBLV).

Examples of cannabielsoins include cannabielsoic acid A (CBEA-A), cannabielsoic acid B (CBEA-B), and cannabielsoin (CBE).

Examples of cannabinols and cannabinodiols include cannabinolic acid (CBNA), cannabinol (CBN), cannabinol-$C_4$ (CBN-$C_4$), cannabivarin (CBV), cannabinol-$C_2$ (CBN-$C_2$), cannabiorcol (CBN-$C_1$), cannabinodiol (CBND), and cannabinodivarin (CBVD).

Examples of cannabitriols include cannabitriol (CBT), 10-ethoxy-9-hydroxy-Δ-6a-tetrahydrocannabinol, cannabitriolvarin (CBTV), and ethoxy-cannabitriolvarin (CBTVE).

Cannabifurans include dehydrocannabifuran (DCBF) and cannabifuran (CBF).

Examples of other cannabinoids include cannabichromanon (CBCN), 10-oxo-Δ-6a-tetrahydrocannabinol (OTHC), cannabiripsol (CBR), and trihydroxy-Δ-9-tetrahydrocannabinol (triOH-THC).

Cannabinoid conjugate components can have one or more centers of asymmetry and can therefore be prepared either as a mixture of isomers (e.g., a racemic or diasteromeric mixture) or in an enantiomerically or diasteromerically pure form. Such forms include, but are not limited to, diastereomers, enantiomers, and atropisomers. Conjugate molecules can also include alkenes and can therefore be prepared either as a mixture of double bond isomers or independently as either an E or Z isomer. Isotopic variants of cannabinoid conjugate components can also be prepared.

Type I Conjugate Molecules

As disclosed above, Type I conjugate molecules have the formula:

$$(CBNC\text{-}L_{cc})_m\text{-}B\text{-}(L_a\text{-}A)_n \qquad (I)$$

in which CBNC is a cannabinoid conjugate component comprising a therapeutic agent component covalently linked, directly or via a linker, to a cannabinoid component; $L_{cc}$ is a CBNC linker; B is a target binding component; $L_a$ is an active component linker; and A is an active component. In embodiments in which B is an antibody, m is 1-30; n is 0-29; and the sum of m+n is 1-30.

In Type I conjugate molecules, B, $L_a$, $L_{cc}$, and A are as defined above.

In some embodiments, a cannabinoid component is provided by a cannabigerol, a cannabichromene, a cannabidiol, a tetrahydrocannabinol, a cannabicyclol, a cannabielsoin, a cannabinol, a cannabinodiol, a cannabitriol, a dehydrocannabifuran, a cannabifuran, a cannabichromanon, or a cannabiripsol. In some embodiments, a cannabinoid component is provided by cannabidiol. In some embodiments, a cannabinoid component is provided by cannabigerol.

In embodiments in which m is at least two, each of the cannabinoid components can be the same or different; and, independently, each of linkers $L_c$ can be the same or different.

In embodiments in which n is at least 2, each of the active agent components can be the same or different; and, independently, each of linkers $L_a$ can be the same or different.

In some embodiments, n is 0; and m is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, n is 1; and m is 1, 2, 3, 4, 5, 6, 7, 8, 9, 10, 11, 12, 13, 14, 15, 16, 17, 18, 19, 20, 21, 22, 23, 24, 25, 26, 27, 28, or 29.

In some embodiments, n is 2; and m is 1, 2, 3, 4, 5, 6, 7, 8, 9, 10, 11, 12, 13, 14, 15, 16, 17, 18, 19, 20, 21, 22, 23, 24, 25, 26, 27, or 28.

In some embodiments, n is 3; and m is 1, 2, 3, 4, 5, 6, 7, 8, 9, 10, 11, 12, 13, 14, 15, 16, 17, 18, 19, 20, 21, 22, 23, 24, 25, 26, or 27.

In some embodiments, n is 4; and m is 1, 2, 3, 4, 5, 6, 7, 8, 9, 10, 11, 12, 13, 14, 15, 16, 17, 18, 19, 20, 21, 22, 23, 24, 25, or 26.

In some embodiments, n is 5; and m is 1, 2, 3, 4, 5, 6, 7, 8, 9, 10, 11, 12, 13, 14, 15, 16, 17, 18, 19, 20, 21, 22, 23, 24, or 25.

In some embodiments, n is 6; and m is 1, 2, 3, 4, 5, 6, 7, 8, 9, 10, 11, 12, 13, 14, 15, 16, 17, 18, 19, 20, 21, 22, 23, or 24.

In some embodiments, n is 7; and m is 1, 2, 3, 4, 5, 6, 7, 8, 9, 10, 11, 12, 13, 14, 15, 16, 17, 18, 19, 20, 21, 22, or 23.

In some embodiments, n is 8; and m is 1, 2, 3, 4, 5, 6, 7, 8, 9, 10, 11, 12, 13, 14, 15, 16, 17, 18, 19, 20, 21, or 22.

In some embodiments, n is 9; and m is 1, 2, 3, 4, 5, 6, 7, 8, 9, 10, 11, 12, 13, 14, 15, 16, 17, 18, 19, 20, or 21.

In some embodiments, n is 10; and m is 1, 2, 3, 4, 5, 6, 7, 8, 9, 10, 11, 12, 13, 14, 15, 16, 17, 18, 19, or 20.

In some embodiments, n is 11; and m is 1, 2, 3, 4, 5, 6, 7, 8, 9, 10, 11, 12, 13, 14, 15, 16, 17, 18, or 19.

In some embodiments, n is 12; and m is 1, 2, 3, 4, 5, 6, 7, 8, 9, 10, 11, 12, 13, 14, 15, 16, 17, or 18.

In some embodiments, n is 13; and m is 1, 2, 3, 4, 5, 6, 7, 8, 9, 10, 11, 12, 13, 14, 15, 16, or 17.

In some embodiments, n is 14; and m is 1, 2, 3, 4, 5, 6, 7, 8, 9, 10, 11, 12, 13, 14, 15, or 16.

In some embodiments, n is 15; and m is 1, 2, 3, 4, 5, 6, 7, 8, 9, 10, 11, 12, 13, 14, or 15.

In some embodiments, n is 16; and m is 1, 2, 3, 4, 5, 6, 7, 8, 9, 10, 11, 12, 13, or 14.

In some embodiments, n is 17; and m is 1, 2, 3, 4, 5, 6, 7, 8, 9, 10, 11, 12, or 13.

In some embodiments, n is 18; and m is 1, 2, 3, 4, 5, 6, 7, 8, 9, 10, 11, or 12.

In some embodiments, n is 19; and m is 1, 2, 3, 4, 5, 6, 7, 8, 9, 10, or 11.

In some embodiments, n is 20; and m is 1, 2, 3, 4, 5, 6, 7, 8, 9, or 10.

In some embodiments, n is 21; and m is 1, 2, 3, 4, 5, 6, 7, 8, or 9.

In some embodiments, n is 22; and m is 1, 2, 3, 4, 5, 6, 7, or 8.

In some embodiments, n is 23; and m is 1, 2, 3, 4, 5, 6, or 7.

In some embodiments, n is 24; and m is 1, 2, 3, 4, 5, or 6.

In some embodiments, n is 25; and m is 1, 2, 3, 4, or 5.

In some embodiments, n is 26; and m is 1, 2, 3, or 4.

In some embodiments, n is 27; and m is 1, 2, or 3.

In some embodiments, n is 28; and m is 1 or 2.

In some embodiments, n is 29. In these embodiments, m is 1.

In embodiments in which B is an antibody, the antibody is an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof.

In some embodiments in which B is an antibody, the antibody is an IgG, an IgE, an IgM, an IgD, an IgA, or an IgY.

In some embodiments in which B is an antibody, the antibody is an IgG1, IgG2 (e.g., IgG2a, IgG2), IgG3, IgG4, IgA1, or IgA2.

In some embodiments in which B is an antibody, the antibody binds to
   i. a cluster of differentiation (CD) antigen;
   ii. a checkpoint inhibitor;
   iii. a vascular target antigen;
   iv. a stromal antigen;
   v. an extracellular matrix antigen;
   vi. a circulating antigen;
   vii. an interleukin;
   viii. an interleukin receptor;
   ix. a growth factor;
   x. a growth factor receptor;
   xi. a drug;
   xii. an adhesion molecule;
   xiii. a tumor necrosis factor;
   xiv. a tumor necrosis factor-related apoptosis-inducing ligand receptor;
   xv. an insulin receptor;
   xvi. a receptor tyrosine kinase;
   xvii. a cytokine receptor;
   xviii. a tropomyosin receptor kinase;
   xix. an integrin;
   xx. an immunoglobulin; or
   xxi. an antigen of an infectious organism.

In some embodiments in which B is an antibody, "B-($L_a$-A)" is an ADC.

In some embodiments in which B is an antibody, the antibody binds to binds to:
   i. an antigen selected from the group consisting of CD2, CD3, CD4, CD11a, CD19, CD20, CD25 (ILR2), CD30, CD33, CD38, CD52, CD139, CD152 (CTLA-4), CD274 (PD-L1), or CD319 (SLAMF);
   ii. an antigen selected from the group consisting of PD-1 and PD-L1 (CD274);
   iii. PSMA;
   iv. Bone Marrow Stromal Antigen 2;
   v. an antigen selected from the group consisting of CI, CIII, CIV, CV, LM, and FN;
   vi. Factor IXa or Factor X;

vii. an antigen selected from the group consisting of IL-1β, IL-2, IL-5, IL-6, IL-12, IL-17A, and IL-23;
viii. an antigen selected from the group consisting of ILR2 (CD25), IL-4RA, IL-5RA, IL-6R, and IL-17RA;
ix. VEGFA;
x. an antigen selected from the group consisting of EGFR (ErbB1), FGFR, FGFR2, FGFR3, FGFR4, FGFR23, HER2/neu, HER3, (ErbB3), HER4, PDGFRA, VEGFR1, VEGFR2, VEGFR3, EphA1, EphA2, EphA3, EphA4, EphA5, EphA6, EphA7, EphA8, EphB1, EphB2, EphB3, EphB4, EphB5, EphB6, EphB7, HGFR (c-Met), and IGF2R;
xi. digoxin or dabigatran;
xii. EpCAM;
xiii. TNF-α or TNF-β;
xiv. TRAIL-R1 or TRAIL-R2;
xv. IR;
xvi. an antigen selected from the group consisting of FLT3, CSF-1R, KIT/SCFR, RON (SEA), AXL (UFO), MER, TYRO3, MUSK, RET, TIE1, DDR1, DDR2, ROR1, ROR2, ROS, LTL, ALK, KLG, and RYK;
xvii. an antigen selected from the group consisting of type I cytokine receptor, type II cytokine receptor, TNF receptors, CCR4, TGF-β receptors, and activin receptors;
xviii. an antigen selected from the group consisting of TRKA, TRKB, and TRKC;
xix. an antigen selected from the group consisting of integrin α4, integrin α4β1, and integrin α4β7;
xx. an IgE;
xxi. an antigen selected from the group of infectious organisms consisting of respiratory syncytial virus, *Bacillus anthracis*, and *Clostridium difficile*; or
xxii. an antigen selected from the group consisting of PSCK9, CGRPR, CRLR, RANKL, GP IIb/IIIa receptor, GD2, BLyS, C5, IRR, and TAG72.

This disclosure describes three types of Type I conjugate molecules:
i. Type I-A conjugate molecules comprise a cannabinoid conjugate component in which one or more therapeutic agent components are directly linked to one or more cannabinoid components.
ii. Type I-B conjugate molecules comprise a cannabinoid conjugate component in which one or more therapeutic agent components are covalently linked via a linker to one or more cannabinoid components.
iii. Type I-C conjugate molecules comprise a cannabinoid conjugate component in which one or more β-lactam antibiotic components are covalently linked via a linker to one or more cannabinoid components.

Type I-A Cannabinoid Conjugate Molecules

Type I-A conjugate molecules comprise a cannabinoid conjugate component in which one or more therapeutic agent components is directly linked to a one or more cannabinoid components.

In some embodiments, the therapeutic agent component is a Michael Acceptor component having a structure selected from

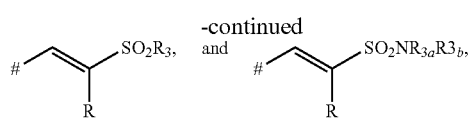

in which # indicates a site of covalent attachment to the cannabinoid component and in which
R is selected from the group consisting of:
(a) H;
(b) C1-C8 linear or branched alkyl, optionally substituted with
(1) 1, 2, 3, 4, 5, 6, 7, 8, or 9 fluorine atoms; and/or
(2) 1, 2, or 3 substituents independently selected from the Group One Substituents;
(c) C1-C8 linear or branched heteroalkyl containing 1, 2, or 3 heteroatoms independently selected from O, N, and S and optionally substituted with
(1) 1, 2, 3, 4, 5, 6, 7, 8, or 9 fluorine atoms; and/or
(2) 1, 2, or 3 substituents independently selected from the Group One Substituents;
(d) phenyl, optionally substituted with 1, 2, or 3 substituents independently selected from the group consisting of:
(1) C1-C6 linear or branched alkyl, optionally substituted with
(i) 1, 2, 3, 4, 5, or 6 fluorine atoms; and/or
(ii) 1 or 2 substituents independently selected from the Group Two Substituents; and
(2) C1-C6 linear or branched heteroalkyl containing 1 or 2 heteroatoms independently selected from O, N, and S and optionally substituted with
(i) 1, 2, 3, 4, 5, or 6 fluorine atoms; and/or
(ii) 1 or 2 substituents independently selected from the Group One Substituents;
(e) a 6- to 10-membered aromatic, optionally substituted with 1, 2, 3, or 4 substituents independently selected from the group consisting of:
(1) phenyl;
(2) halide;
(3) cyano;
(4) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents, and
(5) C1-C6 linear or branched heteroalkyl containing 1, 2, or 3 atoms independently selected from O, N, and S and optionally substituted with
(i) 1, 2, 3, 4, 5, 6, 7, 8, or 9 fluorine atoms; and/or
(ii) 1, 2, or 3 substituents independently selected from the Group Two Substituents;
(f) 5- to 10-membered heteroaromatic comprising 1, 2, 3, 4, 5, or 6 heteroatoms independently selected from O, N, and S and optionally substituted with 1, 2, 3, or 4 substituents independently selected from
(1) phenyl;
(2) halide;
(3) cyano;
(4) trifluoromethyl;
(5) C1-C6 linear or branched alkyl optionally substituted with
(i) 1, 2, 3, 4, 5, 6, 7, 8, or 9 fluorine atoms; and/or
(ii) 1, 2, or 3 substituents independently selected from the Group Two Substituents; and (6) C1-C6 linear or branched heteroalkyl containing 1, 2, or 3 atoms independently selected from O, N, and S and optionally substituted with
(i) 1, 2, 3, 4, 5, 6, 7, 8, or 9 fluorine atoms; and/or
(ii) 1, 2, or 3 substituents independently selected from the Group Two Substituents;
(g)

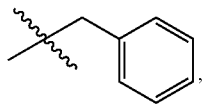

optionally substituted with 1, 2, or 3 substituents independently selected from the group consisting of:
(1) C1-C6 linear or branched alkyl, optionally substituted with
(i) 1, 2, 3, 4, 5, or 6 fluorine atoms; and/or
(ii) 1, 2, or 3 substituents independently selected from the Group Two Substituents;
(h) 3- to 9-membered cycloheteroalkyl having 1, 2, or 3 heteroatoms independently selected from O, N, and S and optionally substituted with 1, 2, or 3 substituents independently selected from the group consisting of:
(1) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents,
(2) C1-C6 linear or branched heteroalkyl, optionally substituted with
(i) 1, 2, 3, 4, 5, 6, 7, 8, or 9 fluorine atoms and/or
(ii) 1, 2, or 3 substituents independently selected from the Group Two Substituents,
(3) phenyl, optionally substituted with 1, 2, or 3 substituents independently selected from the Group Two Substituents, and
(4) 5- to 10-membered heteroaromatic, optionally substituted with 1, 2, or 3 substituents independently selected from the Group Two Substituents; and
(i) C3-C6 cycloalkyl, optionally substituted with 1, 2, or 3 substituents independently selected from:
(1) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents,
(2) C1-C6 linear or branched heteroalkyl, optionally substituted with
(i) 1, 2, 3, 4, 5, 6, 7, 8, or 9 fluorine atoms; and/or
(ii) 1, 2, or 3 substituents independently selected from the Group Two Substituents,
(3) phenyl, optionally substituted with 1, 2, or 3 substituents independently selected from Group Two Substituents; and
(4) 5- to 10-membered heteroaromatic, optionally substituted with 1, 2, or 3 substituents independently selected from the Group Two Substituents;
$R_1$ and $R_2$ independently are selected from the group consisting of:
(a) C1-C12 linear or branched alkyl, optionally substituted with
(1) 1, 2, 3, 4, 5, 6, 7, 8, or 9 fluorine atoms; and/or
(2) 1, 2, or 3 substituents selected from the Group One Substituents;
(b) C2-C12 linear or branched alkenyl, optionally substituted with
(1) 1, 2, 3, 4, 5, 6, 7, 8, or 9 fluorine atoms; and/or
(2) 1, 2, or 3 substituents selected from the Group One Substituents;
(c) C1-C12 linear or branched heteroalkyl containing 1, 2, 3, or 4 heteroatoms independently selected from O, N, and S, optionally substituted with
(1) 1, 2, 3, 4, 5, 6, 7, 8, or 9 fluorine atoms; and/or
(2) 1, 2, or 3 substituents selected from the Group One Substituents; and
(d) R;
OR
$R_1$ and $R_2$, together with the atom to which they are attached, form a 3- to 9-membered cycloheteroalkyl having 1, 2, 3, or 4 heteroatoms independently selected from O, S, and N, wherein the cycloheteroalkyl optionally is substituted with 1, 2, or 3 substituents independently selected from the group consisting of:
(a) C1-C6 linear or branched alkyl optionally substituted with
(1) 1, 2, 3, 4, 5, 6, 7, 8, or 9 fluorine atoms and/or
(2) 1, 2, or 3 substituents independently selected from the Group Two Substituents;
(b) C1-C6 linear or branched heteroalkyl, optionally substituted with
(1) 1, 2, 3, 4, 5, 6, 7, 8, or 9 fluorine atoms; and/or
(2) 1, 2, or 3 substituents independently selected from the Group Two Substituents;
(c) phenyl optionally substituted with 1, 2, or 3 substituents independently selected from the Group Two Substituents; and
(d) 5- to 10-membered heteroaromatic optionally substituted with 1, 2, or 3 independently selected from the Group Two Substituents; and
$R_3$, $R_{3a}$, and $R_{3b}$ independently are selected from
(a) C1-C8 linear or branched alkyl, optionally substituted with
(1) 1, 2, 3, 4, 5, 6, 7, 8, or 9 fluorine atoms; and/or
(2) 1, 2, or 3 substituents independently selected from the Group One Substituents; or
(b) phenyl, optionally substituted with 1, 2, or 3 substituents independently selected from the group consisting of C1-C6 linear or branched alkyl, optionally substituted with
(1) 1, 2, 3, 4, 5, or 6 fluorine atoms; and/or
(2) 1 or 2 substituents independently selected from the Group Two Substituents.

In some embodiments, the therapeutic agent component has the structure

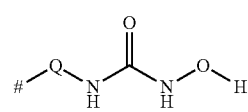

in which Q is CO, CS, or $CR_{6a}R_{6b}$, and $R_{6a}$ and $R_{6b}$ independently are R.

In some embodiments, the therapeutic agent component has the structure

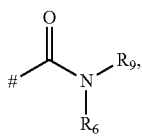

in which $R_8$ and $R_9$ independently are selected from H, $CH_3$, and $CH_2CH_3$.

Examples of therapeutic agents that can be used to provide a Michael acceptor component include, but are not limited to:

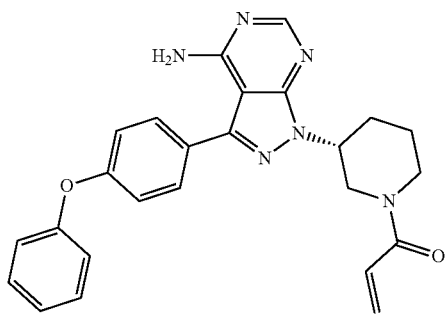

Ibrutinib (e.g., IMBRUVICA ®)

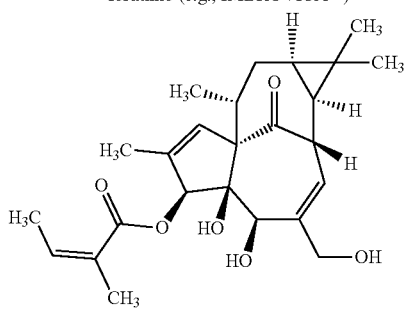

Ingenol mebutate (e.g., PICATO ®)

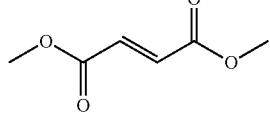

dimethyl fumarate (e.g., SKILARENCE ®)

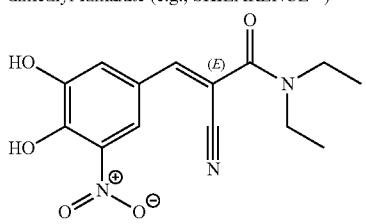

Entacapone (e.g., ADCAPONE ®)

Type I-B Conjugate Molecules

Type I-B conjugate molecules comprise a cannabinoid conjugate component in which one or more therapeutic agent components are covalently linked via a linker to one or more cannabinoid components.

In some embodiments, the therapeutic agent component is attached to the cannabinoid component via "Type I-B linker," as shown below.

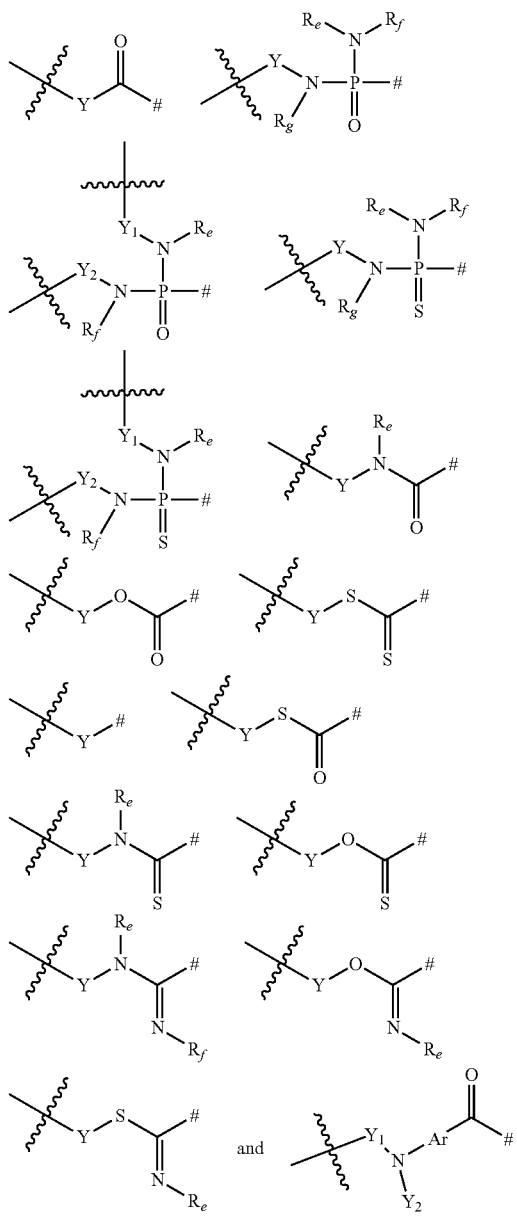

in which ⌇ marks a bond attaching the Type (Ib) linker to the therapeutic agent component, # indicates a site of covalent attachment to the cannabinoid component, and in which:

Y, $Y_1$, and $Y_2$ independently are absent or Y, $Y_1$, and $Y_2$ independently are selected from the group consisting of:

(a) C1-C12 linear or branched alkyl, optionally substituted with
  (1) 1, 2, 3, 4, 5, 6, 7, 8, or 9 fluorine atoms; and/or
  (2) 1, 2, or 3 substituents selected from the Group One Substituents;

(b) C2-C12 linear or branched alkenyl, optionally substituted with
  (1) 1, 2, 3, 4, 5, 6, 7, 8, or 9 fluorine atoms; and/or
  (2) 1, 2, or 3 substituents selected from the Group One Substituents;

(c) C1-C12 linear or branched heteroalkyl containing 1, 2, 3, or 4 heteroatoms independently selected from O, N, and S, optionally substituted with (1) 1, 2, 3, 4, 5, 6, 7, 8, or 9 fluorine atoms; and/or
(2) 1, 2, or 3 substituents selected from the Group One Substituents;
(d) a 6- to 10-membered aromatic, optionally substituted with 1, 2, 3, or 4 substituents independently selected from the group consisting of:
(1) phenyl,
(2) halide,
(3) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents, and
(4) C1-C6 linear or branched heteroalkyl containing 1, 2, or 3 atoms independently selected from O, N, and S and optionally substituted with
(i) 1, 2, 3, 4, 5, 6, 7, 8, or 9 fluorine atoms; and/or
(ii) 1, 2, or 3 substituents independently selected from the Group Two Substituents;
(e) a 6- to 10-membered heteroaromatic comprising 1, 2, 3, 4, 5, or 6 heteroatoms independently selected from O, N, and S and optionally substituted with 1, 2, 3, or 4 substituents independently selected from
(1) phenyl,
(2) halide,
(3) trifluoromethyl,
(4) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents, and
(5) C1-C6 linear or branched heteroalkyl containing 1, 2, or 3 atoms independently selected from O, N, and S and optionally substituted with
(i) 1, 2, 3, 4, 5, 6, 7, 8, or 9 fluorine atoms; and/or
(ii) 1, 2, or 3 substituents independently selected from the Group Two Substituents; and
(f) a C1-C24 linear or branched heteroalkyl containing 1, 2, 3, 4, 5, 6, 7, or 8 heteroatoms independently selected from O, N, and S, optionally substituted with
(i) 1, 2, 3, 4, 5, 6, 7, 8, or 9 fluorine atoms; and/or
(ii) 1, 2, 3, 4, 5, or 6 substituents selected from the Group One Substituents;
Ar is either:
(a) a 6- to 10-membered aromatic, optionally substituted with 1, 2, 3, or 4 substituents independently selected from the group consisting of:
(1) phenyl,
(2) halide,
(3) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents; or
(b) a 6- to 10-membered heteroaromatic comprising 1, 2, 3, 4, 5, or 6 heteroatoms independently selected from O, N, and S and optionally substituted with 1, 2, 3, or 4 substituents independently selected from
(1) phenyl,
(2) halide,
(3) trifluoromethyl,
(4) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents, and
(5) C1-C6 linear or branched heteroalkyl containing 1, 2, or 3 atoms independently selected from O, N, and S and optionally substituted with
(i) 1, 2, 3, 4, 5, 6, 7, 8, or 9 fluorine atoms; and/or
(ii) 1, 2, or 3 substituents independently selected from the Group Two Substituents; and $R_e$, $R_f$, and $R_g$ independently are R as defined above.

In some embodiments, the therapeutic agent component is

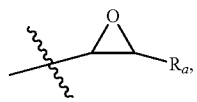

in which $R_a$ is absent or is C1-C3 linear or branched alkyl or C1-C3 linear or branched heteroalkyl comprising an O, N, or S atom.

In some embodiments, the therapeutic agent component is

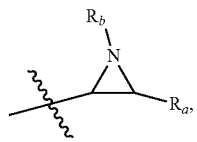

in which $R_a$ is as defined above and $R_b$ is R or —PS($NR_{c1}R_{c2}$), wherein $R_{c1}$ and $R_{c2}$ independently are C1-C6 linear or branched alkyl or C1-C6 cycloalkyl, and R is as defined above.

In some embodiments, the therapeutic agent component is

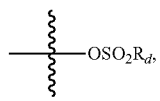

in which $R_d$ is
(a) C1-C8 linear or branched alkyl, optionally substituted with
(i) 1, 2, 3, 4, 5, 6, 7, 8, or 9 fluorine atoms; and/or
(ii) 1, 2, or 3 substituents independently selected from the Group One Substituents; or
(b) phenyl, optionally substituted with 1, 2, or 3 substituents independently selected from the group consisting of C1-C6 linear or branched alkyl, optionally substituted with
(i) 1, 2, 3, 4, 5, or 6 fluorine atoms; and/or
(ii) 1 or 2 substituents independently selected from the Group Two Substituents.

In some embodiments, the therapeutic agent component is

in which X is Cl, Br, or I.

In some embodiments, the therapeutic agent component is temozolomide or a temozolomide analog,

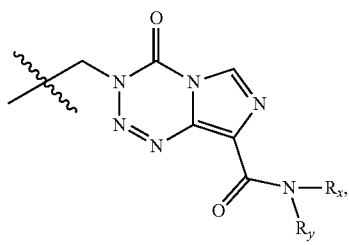

in which $R_x$ and $R_y$ independently are H or C1-C3 linear or branched alkyl.

In some embodiments, the therapeutic agent component is 5-fluorouracil or a 5-fluorouracil analog:

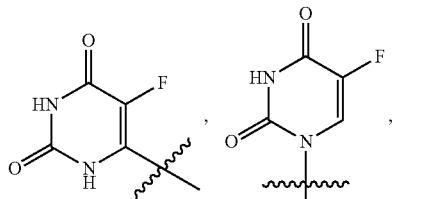

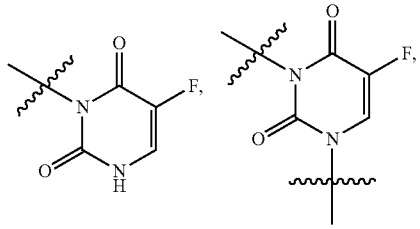

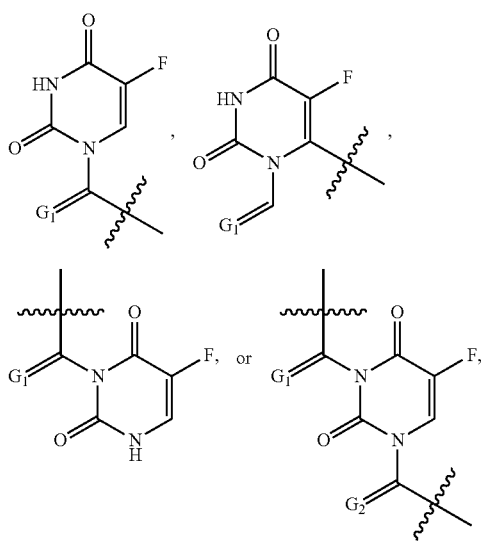

in which $G_1$ and $G_2$ independently are selected from the group consisting of O, S, and NR.

In some embodiments, the therapeutic agent component is diclofenac or an analog of diclofenac:

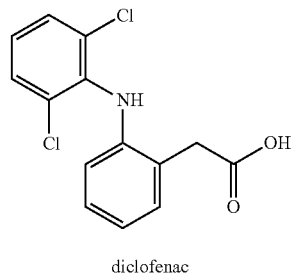 [SMILES: O=C(O)Cc1ccccc1Nc1c(Cl)cccc1Cl]

diclofenac

In some embodiments, a diclofenac component has the structure

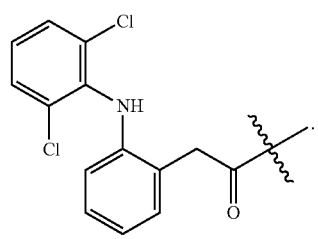 [SMILES: *C(=O)Cc1ccccc1Nc1c(Cl)cccc1Cl]

In some embodiments, a diclofenac component has the structure

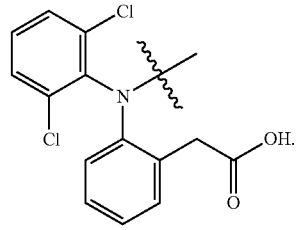 [SMILES: *N(c1ccccc1CC(=O)O)c1c(Cl)cccc1Cl]

In some embodiments, a diclofenac component has the structure

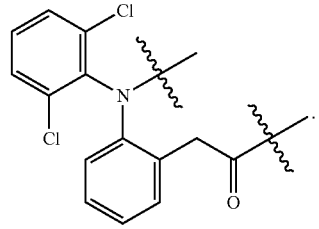 [SMILES: *C(=O)Cc1ccccc1N(*)c1c(Cl)cccc1Cl]

Conjugates comprising a diclofenac component can be administered alone or, for example, as part of a diclofenac-containing product, such as MOBIZOX® (diclofenac, paracetamol, and chlozoxazone), SOLARAZE® (diclofenac sodium), VOLTAREN® (diclofenac sodium), VOLITRA® (benzyl alcohol, capsaicin, diclofenac diethylamine, linseed oil, menthol, methyl salicylate), VOLITRA® MR (diclofenac, thiocolchicoside), VOLITRA® PLUS (diclofenac dethylamine, linseed oil, methyl salicylate, menthol, eucalyptus oil), VOLITRA® S (diclofenac sodium ip, serratiopeptidase), FLEXURA® D (diclofenac potassium bp, metaxalone), MOBISWIFT® D (diclofenac, methoxolone), THIOACT® D (thiocochicoside, diclofenac sodium ip).

In some embodiments, the therapeutic agent component is celecoxib (e.g., CELEBREX®) or an analog of celecoxib:

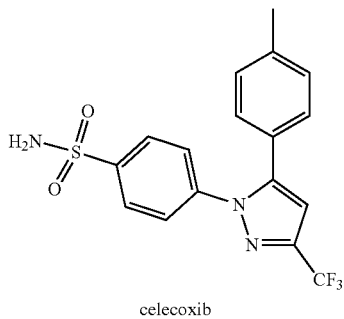 [SMILES: Cc1ccc(-c2cc(C(F)(F)F)nn2-c2ccc(S(N)(=O)=O)cc2)cc1]
celecoxib

In some embodiments, a celecoxib component has the structure

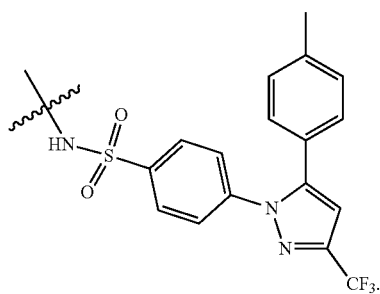 [SMILES: *NS(=O)(=O)c1ccc(-n2nc(C(F)(F)F)cc2-c2ccc(C)cc2)cc1]

In some embodiments, the therapeutic agent component is gemcitabine (e.g., GEMZAR®) or an analog of gemcitabine:

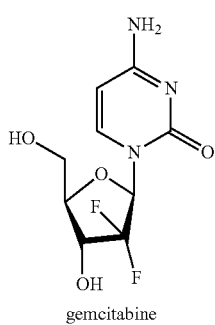
gemcitabine

In some embodiments, a gemcitabine component has the structure

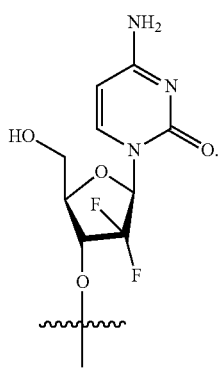

In some embodiments, a gemcitabine component has the structure

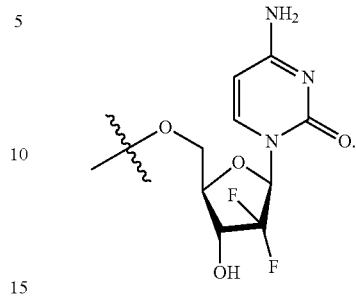

In some embodiments, a gemcitabine component has the structure

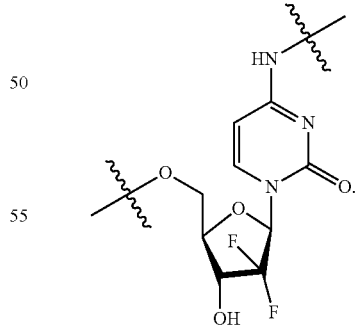

In some embodiments, a gemcitabine component has the structure

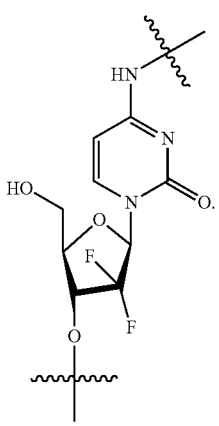

In some embodiments, a gemcitabine component has the structure

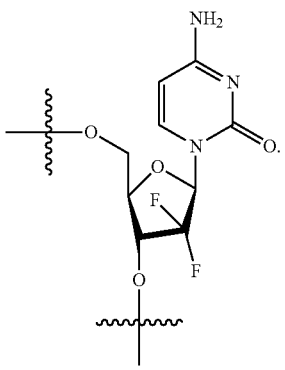

In some embodiments, a gemcitabine component has the structure

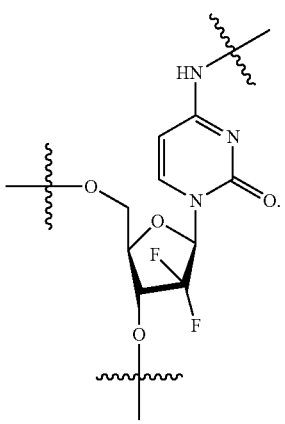

In some embodiments, the therapeutic agent component is or emtricitabine (e.g., DESCOVY®, BIKTARVY®, EMTRIVA®) or an analog of emtricitabine:

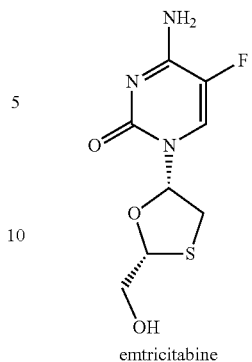

In some embodiments, an emtricitabine component has the structure

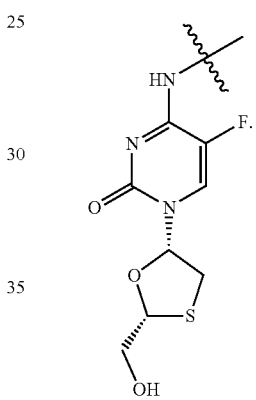

In some embodiments, an emtricitabine component has the structure

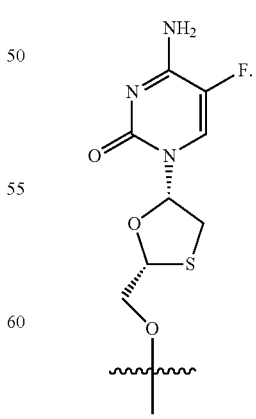

In some embodiments, an emtricitabine component has the structure

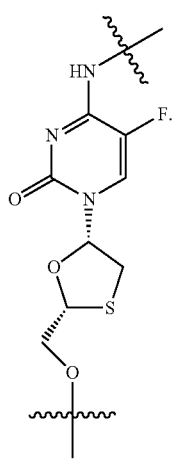

In some embodiments, the therapeutic agent component is entecavir (e.g., BARACLUDE®) or an analog of entecavir:

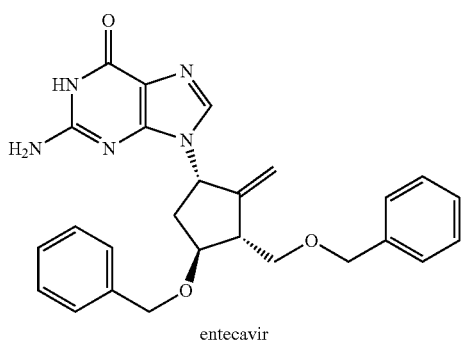 [SMILES: C=C1[C@H](COCc2ccccc2)[C@@H](OCc2ccccc2)C[C@@H]1n1cnc2c(=O)[nH]c(N)nc21]

entecavir

In some embodiments an entecavir component has the structure:

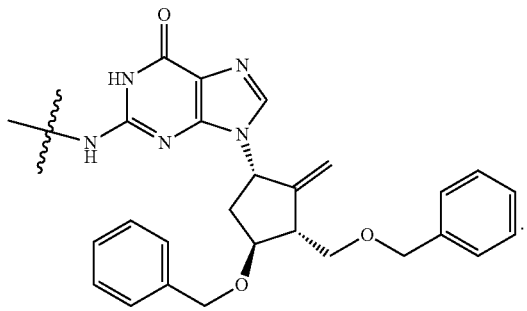 [SMILES: *Nc1nc2c(ncn2[C@H]2C[C@H](OCc3ccccc3)[C@@H](COCc3ccccc3)C2=C)c(=O)[nH]1]

In some embodiments, the therapeutic agent component is axitinib (e.g., INLYTA®) or an analog of axitinib:

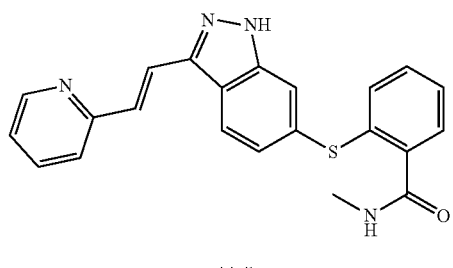

axitinib

In some embodiments, an axitinib component has the structure

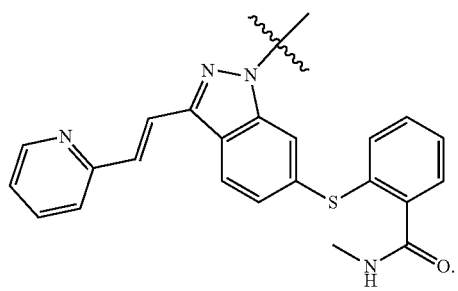 [SMILES: *n1nc(/C=C/c2ccccn2)c2ccc(Sc3ccccc3C(=O)NC)cc21]

In some embodiments, the therapeutic agent component is batimastat or an analog of batimastat:

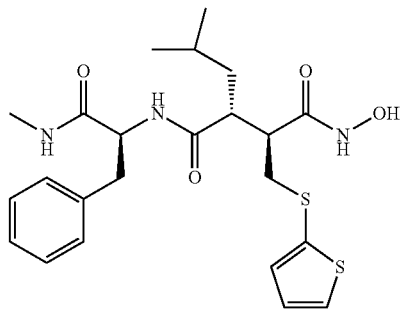

batimastat

In some embodiments, a batimastat component has the structure

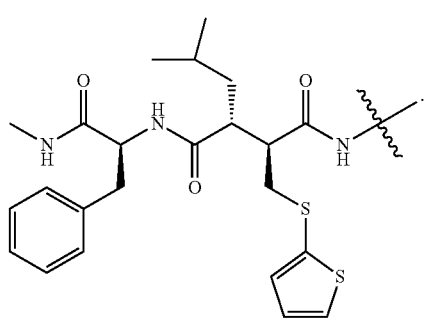 [SMILES: *NC(=O)[C@@H](CSc1cccs1)[C@@H](CC(C)C)C(=O)N[C@@H](Cc1ccccc1)C(=O)NC]

In some embodiments, the therapeutic agent component is bosutinib (e.g., BOSULIF®) or an analog of bosutinib:

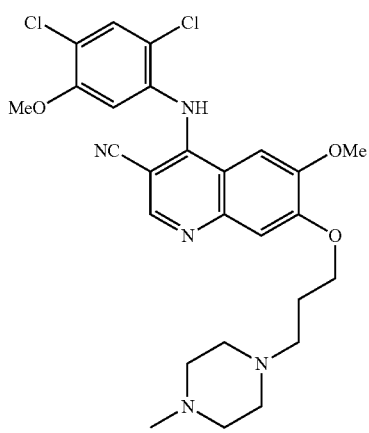

bosutinib

In some embodiments, a bosutinib component has the structure

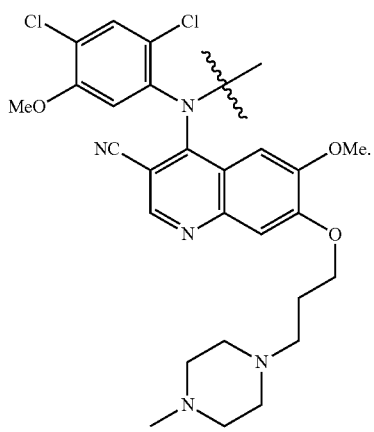 [SMILES: *N(c1cc(OC)c(Cl)cc1Cl)c1c(C#N)cnc2cc(OCCCN3CCN(C)CC3)c(OC)cc12]

In some embodiments, the therapeutic agent component is crizotinib (e.g., XALKORI®) or an analog of crizotinib:

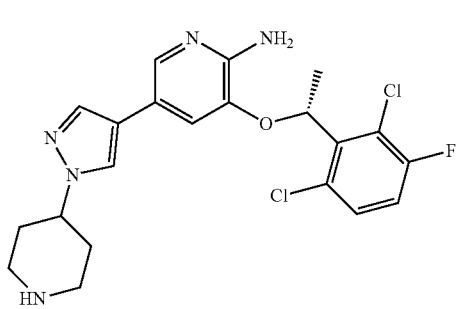

crizotinib

In some embodiments, a crizotinib component has the structure

In some embodiments, a crizotinib component has the structure

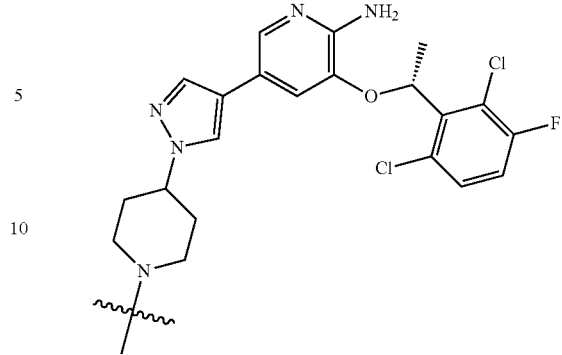

In some embodiments, a crizotinib component has the structure

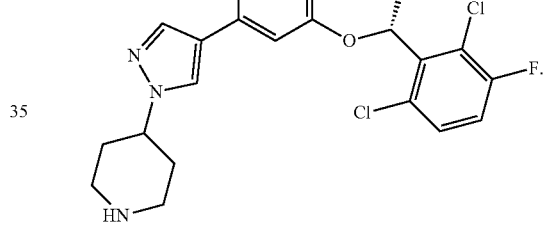

In some embodiments, a crizotinib component has the structure

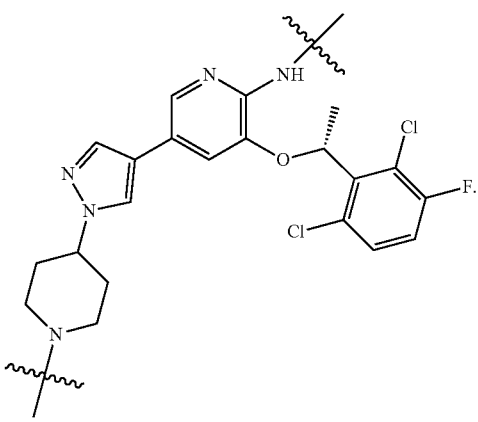 [SMILES: *Nc1ncc(-c2cnn(C3CCN(*)CC3)c2)cc1O[C@H](C)c1c(Cl)ccc(F)c1Cl]

In some embodiments, the therapeutic agent component is erlotinib (e.g., TARCEVA®) or an analog of erlotinib:

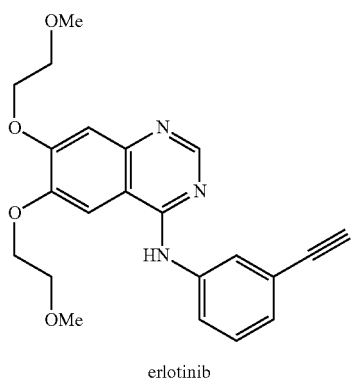 [SMILES: C#Cc1cccc(Nc2ncnc3cc(OCCOC)c(OCCOC)cc23)c1]

erlotinib

In some embodiments, an erlotinib component has the structure

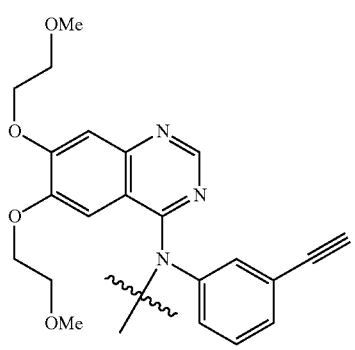

In some embodiments, the therapeutic agent component is gefitinib (e.g., IRESSA®) or an analog of gefitinib:

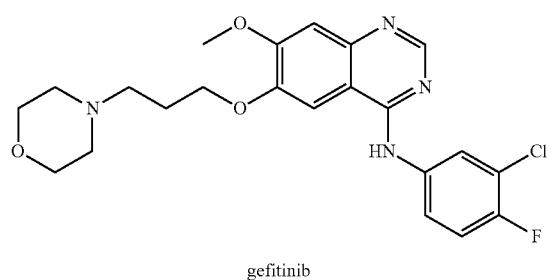 [SMILES: COc1cc2ncnc(Nc3ccc(F)c(Cl)c3)c2cc1OCCCN1CCOCC1]

gefitinib

In some embodiments, a gefitinib component has the structure

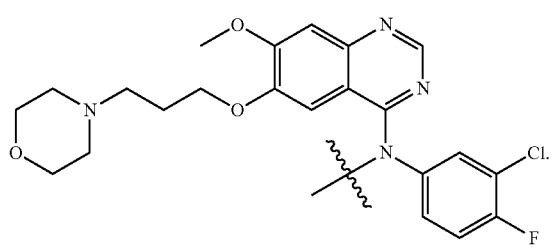 [SMILES: *N(c1ccc(F)c(Cl)c1)c1ncnc2cc(OC)c(OCCCN3CCOCC3)cc12]

In some embodiments, the therapeutic agent component is everolimus (e.g., ZORTRESS®, AFINITOR DISPERZ®, AFINITOR®) or an analog of everolimus:

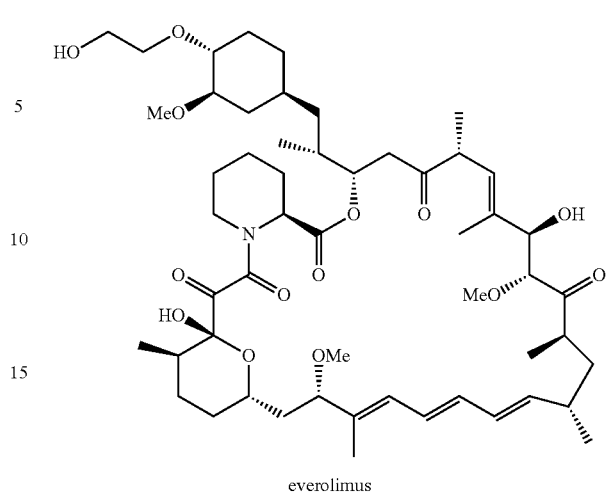

everolimus

In some embodiments, an everolimus component has the structure

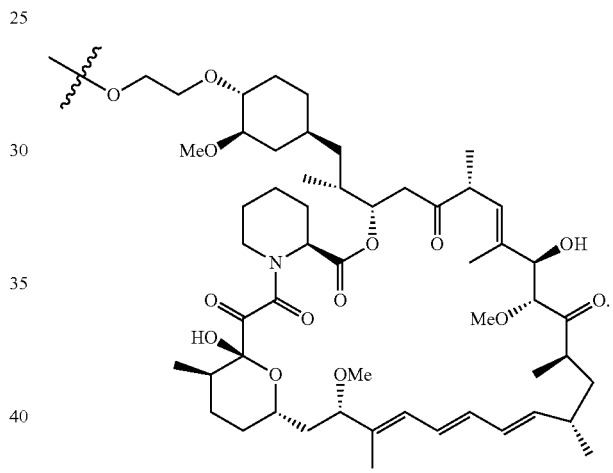

In some embodiments, an everolimus component has the structure

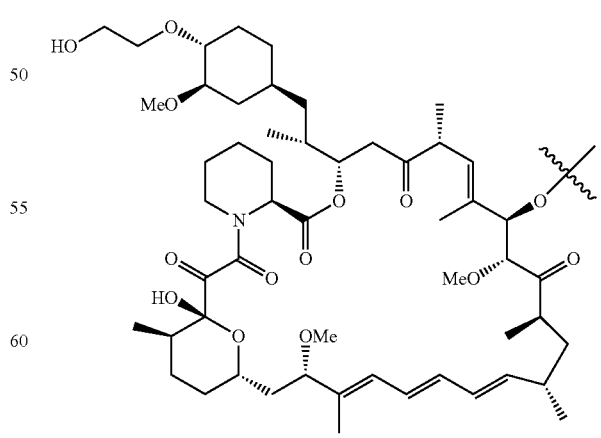

In some embodiments, an everolimus component has the structure

In some embodiments, an everolimus component has the structure

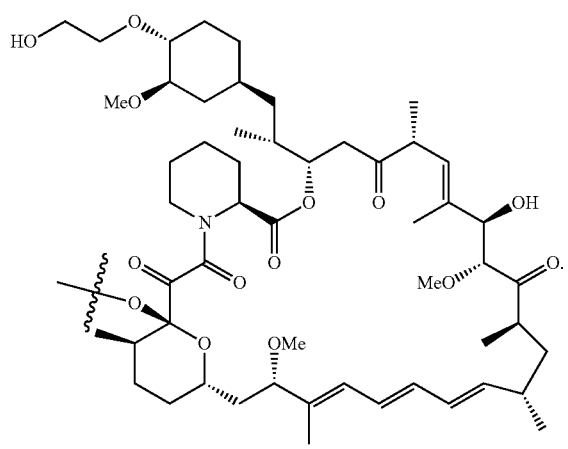 [SMILES: *O[C@@]12O[C@@H](CC[C@H]1C)C[C@H](OC)/C(C)=C/C=C/C=C/[C@@H](C)C[C@@H](C)C(=O)[C@H](OC)[C@H](O)/C(C)=C/[C@@H](C)C(=O)C[C@@H]([C@H](C)C[C@@H]1CC[C@@H](OCCO)[C@H](OC)C1)OC(=O)[C@@H]1CCCCN1C(=O)C2=O]

In some embodiments, an everolimus component has the structure

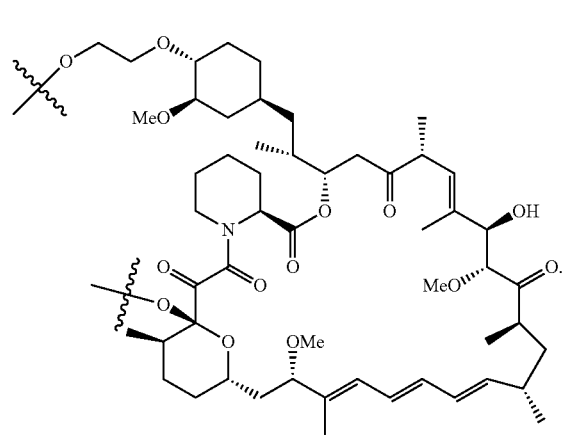 [SMILES: *OCCO[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O*)(O3)C(=O)C(=O)N3CCCC[C@H]3C(=O)O2)C[C@H]1OC]

In some embodiments, an everolimus component has the structure

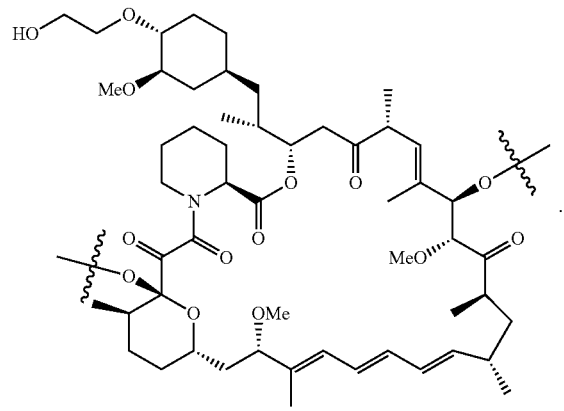 [SMILES: *O[C@@H]1/C(C)=C/[C@@H](C)C(=O)C[C@@H]([C@H](C)C[C@@H]2CC[C@@H](OCCO)[C@H](OC)C2)OC(=O)[C@@H]2CCCCN2C(=O)C(=O)[C@]2(O*)O[C@@H](CC[C@H]2C)C[C@H](OC)/C(C)=C/C=C/C=C/[C@@H](C)C[C@@H](C)C(=O)[C@@H]1OC]

In some embodiments, an everolimus component has the structure

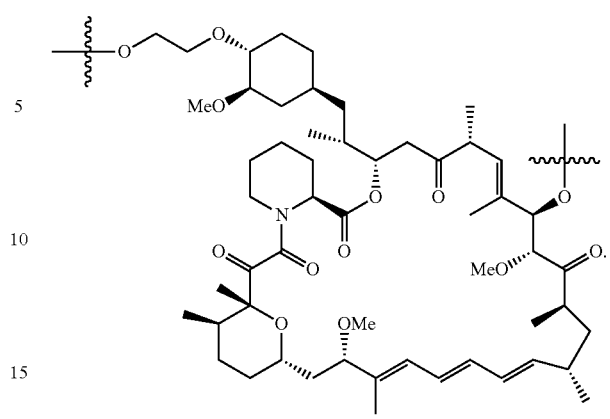

In some embodiments, an everolimus component has the structure

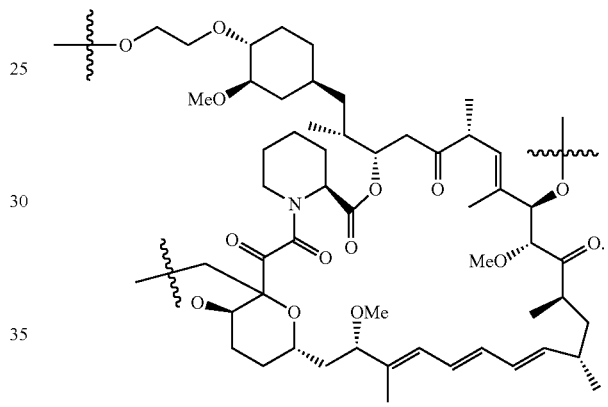

In some embodiments, the therapeutic agent component is temsirolimus (e.g., TORISEL®) or an analog of temsirolimus:

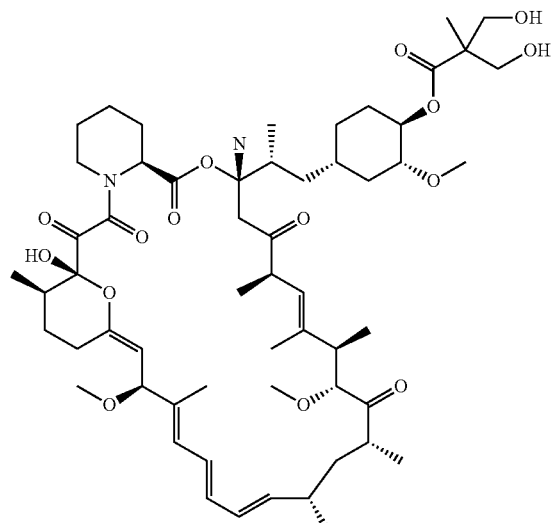

temsirolimus

In some embodiments, a temsirolimus component has one of the following structures, in which each arrow indicates a point where a linker as described below can be attached.
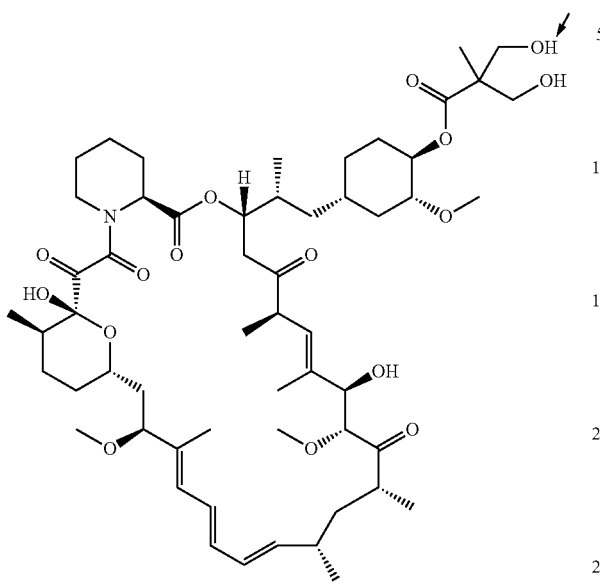
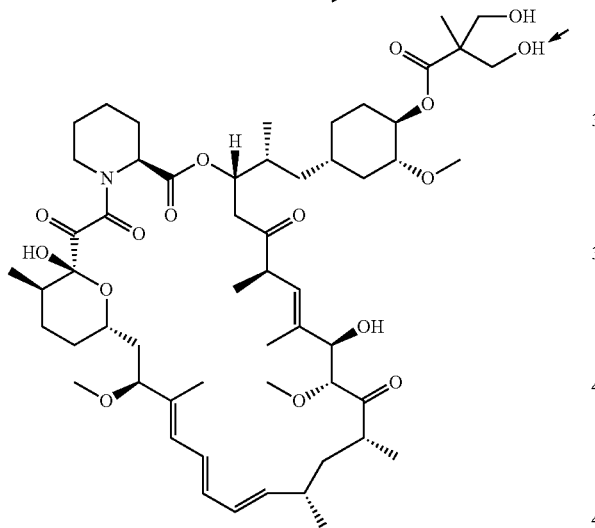
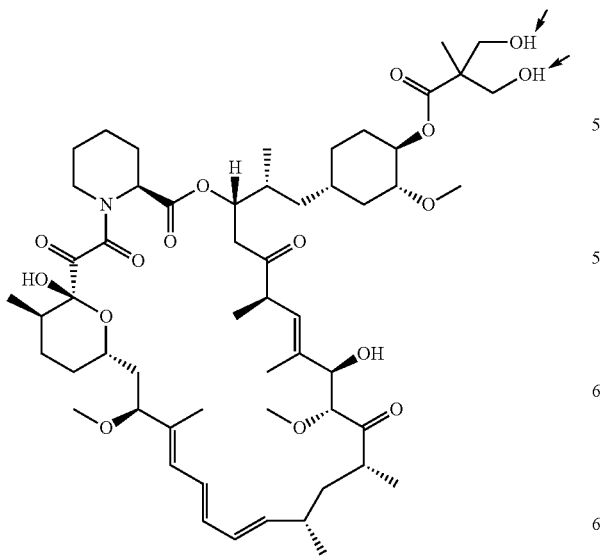
-continued
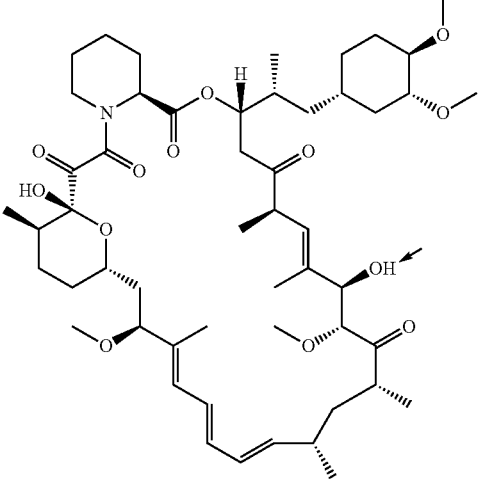
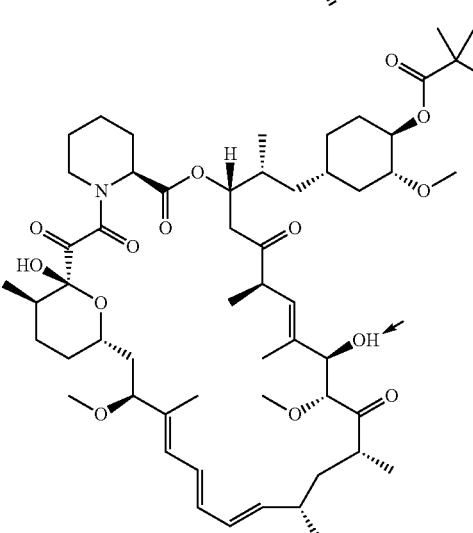
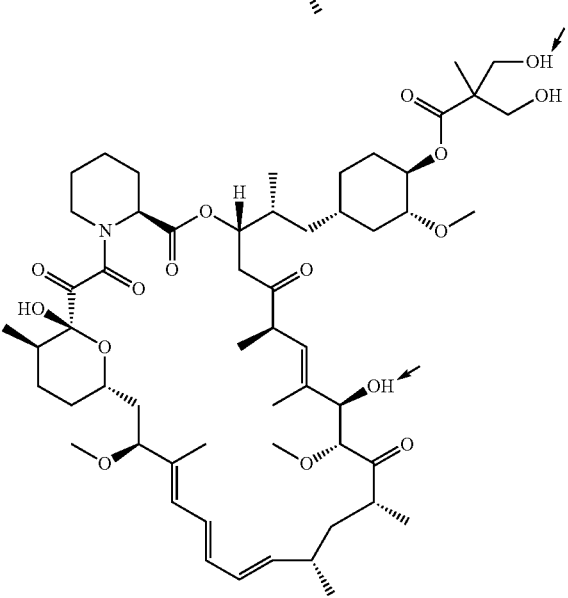

37
-continued
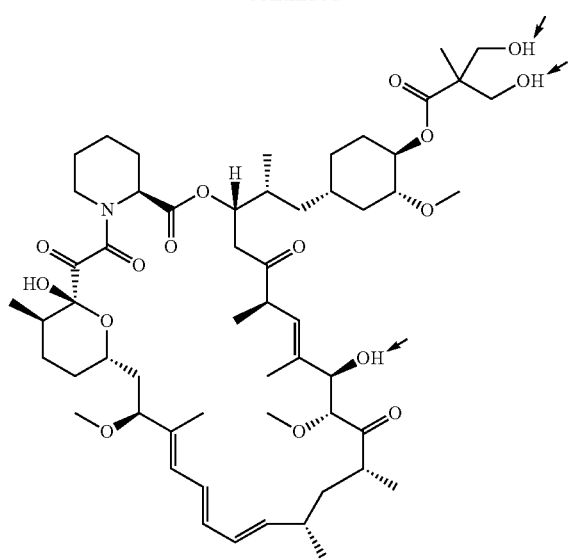
38
-continued
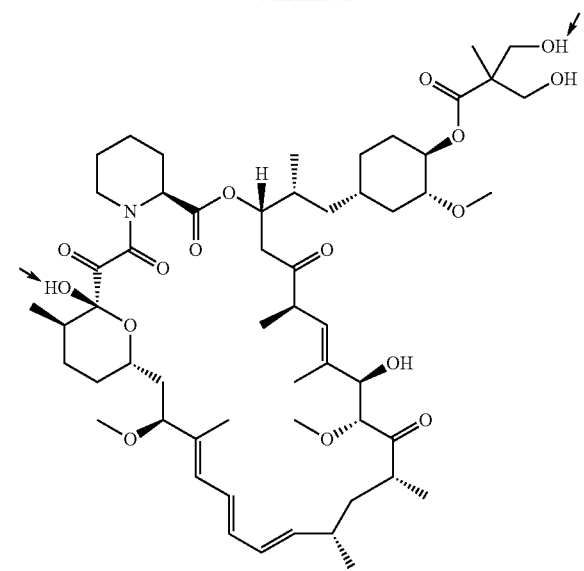

-continued
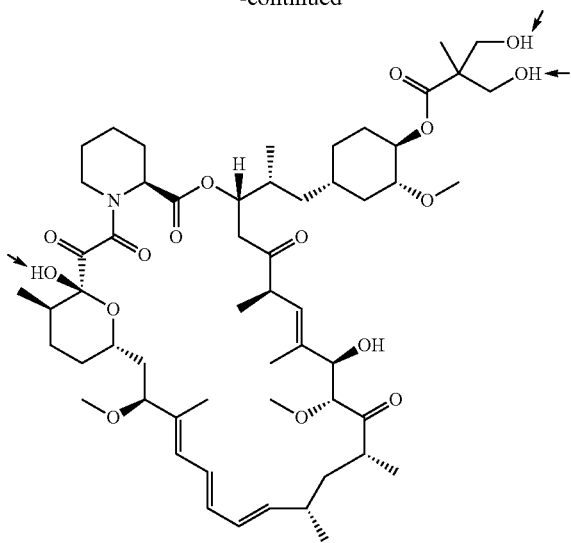
In some embodiments, the therapeutic agent component is ganetespib or an analog of ganetespib:
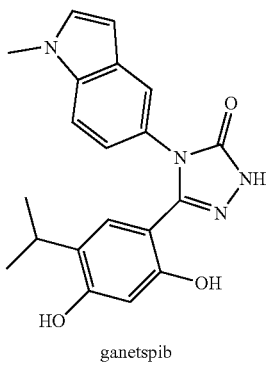 [SMILES: CC(C)c1cc(-c2n[nH]c(=O)n2-c2ccc3c(ccn3C)c2)c(O)cc1O]
ganetspib
In some embodiments, a ganetespib component has the structure
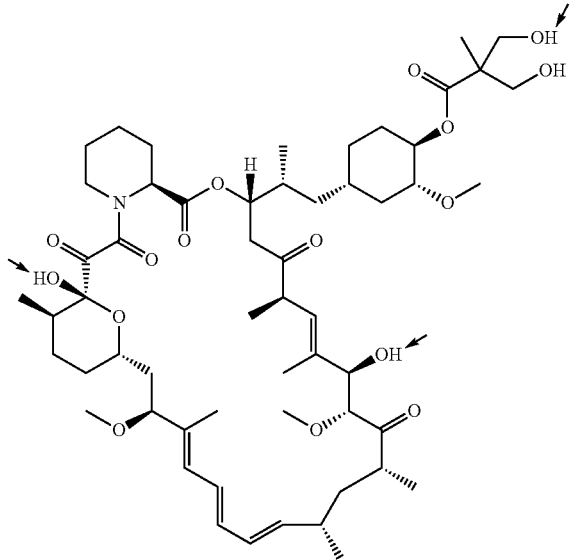
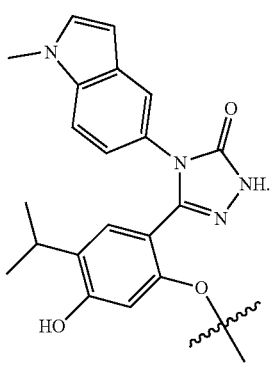 [SMILES: *Oc1cc(O)c(C(C)C)cc1-c1n[nH]c(=O)n1-c1ccc2c(ccn2C)c1]
In some embodiments, a ganetespib component has the structure
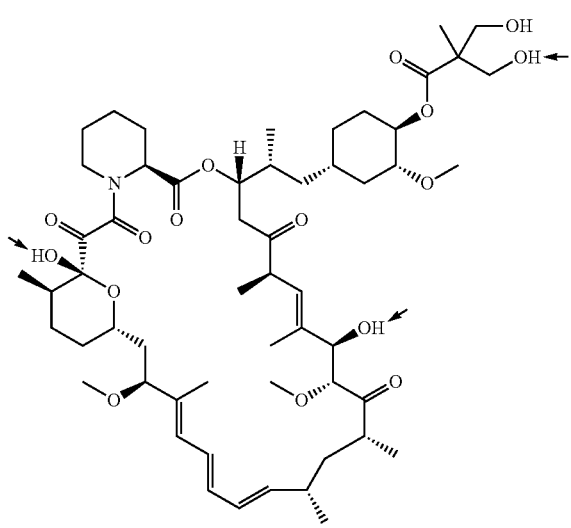
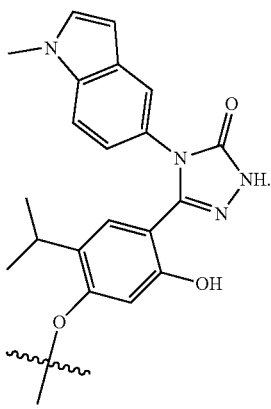 [SMILES: *Oc1cc(O)c(-c2n[nH]c(=O)n2-c2ccc3c(ccn3C)c2)cc1C(C)C]
In some embodiments, a ganetespib component has the structure

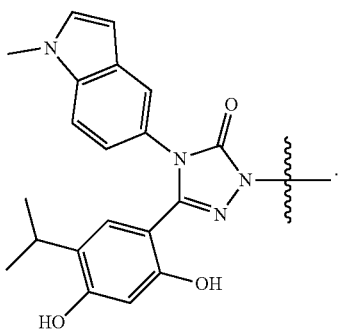 [SMILES: *n1nc(-c2cc(C(C)C)c(O)cc2O)n(-c2ccc3c(ccn3C)c2)c1=O]

In some embodiments, a ganetespib component has the structure

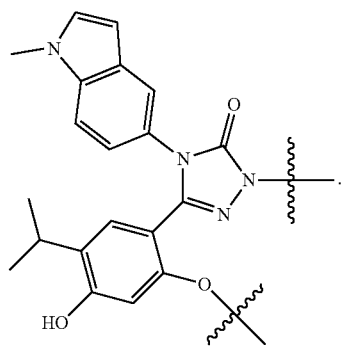

In some embodiments, a ganetespib component has the structure

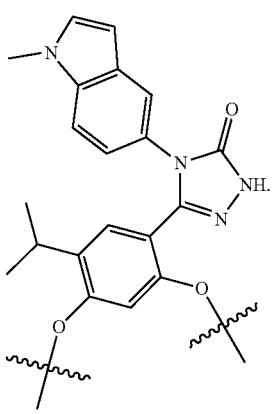 [SMILES: *Oc1cc(O*)c(C(C)C)cc1-c1n[nH]c(=O)n1-c1ccc2c(ccn2C)c1]

In some embodiments, a ganetespib component has the structure

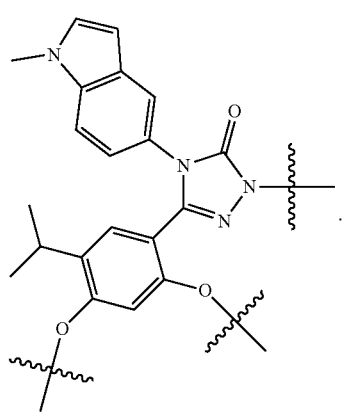

In some embodiments, a ganetespib component has the structure

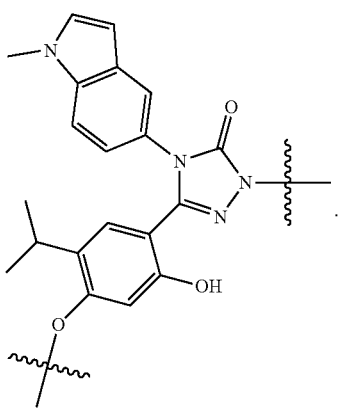 [SMILES: *Oc1cc(O)c(-c2nn(*)c(=O)n2-c2ccc3c(ccn3C)c2)cc1C(C)C]

In some embodiments, a ganetespib component has the structure

In some embodiments, the therapeutic agent component is glasdegib (e.g., GLASDEGIB®) or an analog of glasdegib:

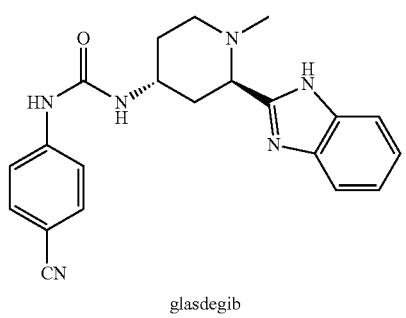 [SMILES: CN1CC[C@@H](NC(=O)Nc2ccc(C#N)cc2)C[C@@H]1c1nc2ccccc2[nH]1]

glasdegib

In some embodiments, a glasdegib component has the structure

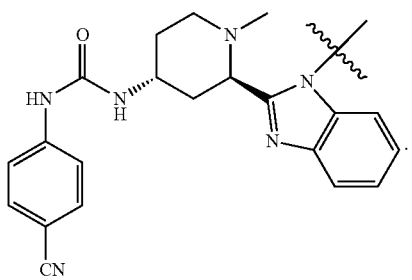 [SMILES: *n1c([C@H]2C[C@H](NC(=O)Nc3ccc(C#N)cc3)CCN2C)nc2ccccc21]

In some embodiments, the therapeutic agent component is imatinib (e.g., GLEEVEC®) or an analog of imatinib:

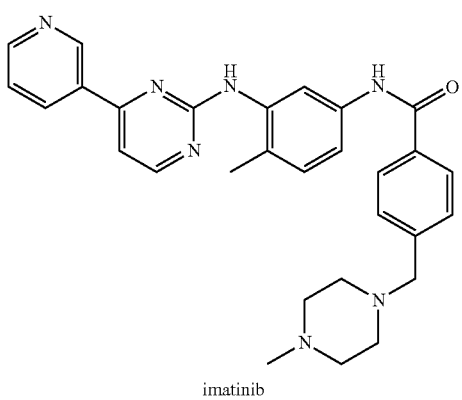 [SMILES: Cc1ccc(NC(=O)c2ccc(CN3CCN(C)CC3)cc2)cc1Nc1nccc(-c2cccnc2)n1]

imatinib

In some embodiments, an imatinib component has the structure

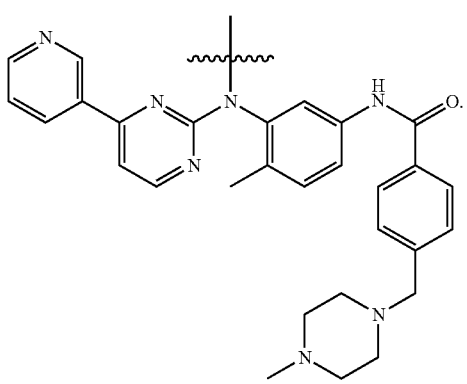 [SMILES: *N(c1nccc(-c2cccnc2)n1)c1cc(NC(=O)c2ccc(CN3CCN(C)CC3)cc2)ccc1C]

In some embodiments, an imatinib component has the structure

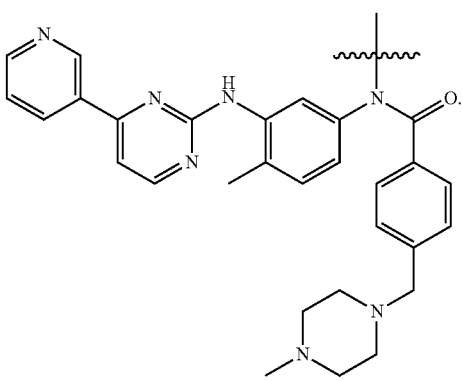 [SMILES: *N(C(=O)c1ccc(CN2CCN(C)CC2)cc1)c1ccc(C)c(Nc2nccc(-c3cccnc3)n2)c1]

In some embodiments, an imatinib component has the structure

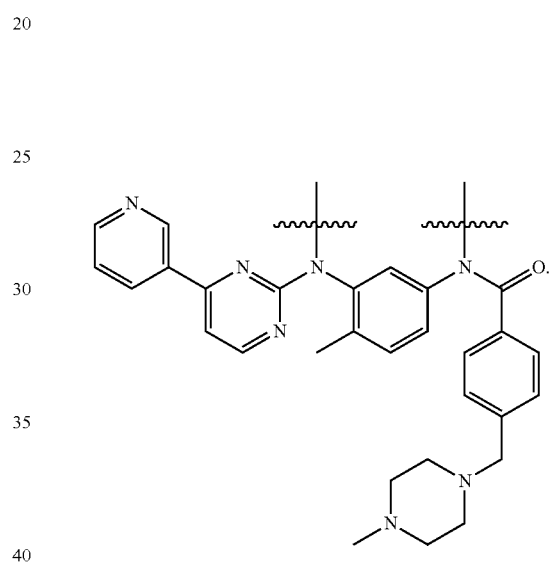

In some embodiments, the therapeutic agent component is lapatinib (e.g., TYKERB®) or an analog of lapatinib:

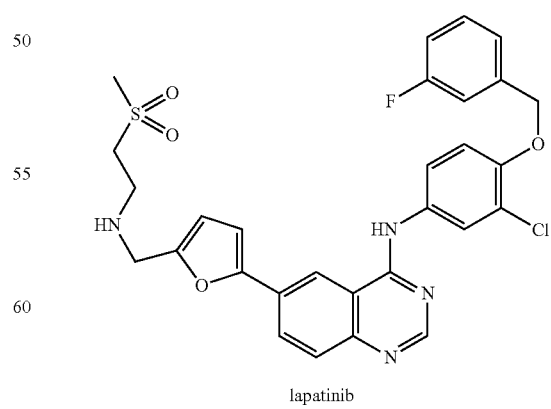

lapatinib

In some embodiments a lapatinib component has the structure

In some embodiments a lapatinib component has the structure

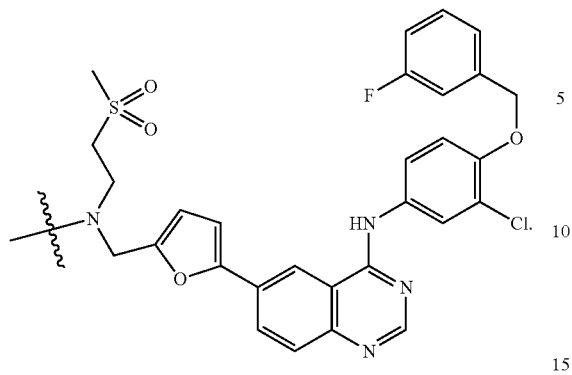

In some embodiments, a navitoclax component has the structure

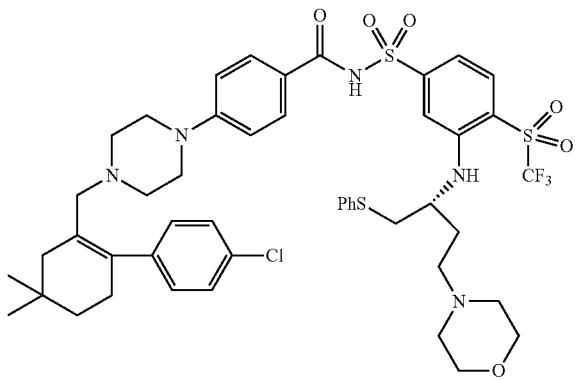

navitoclax

In some embodiments a lapatinib component has the structure

In some embodiments, a navitoclax component has the structure.

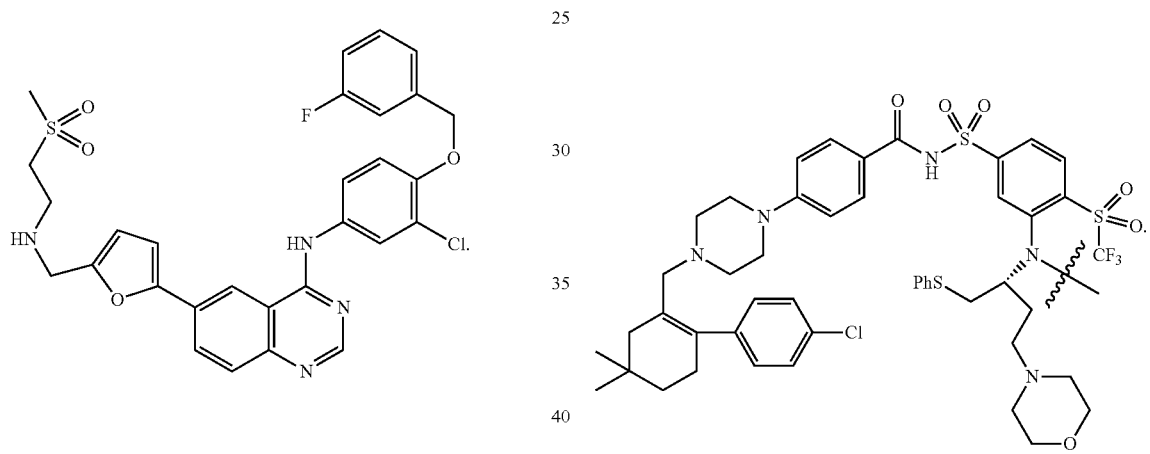

In some embodiments, the therapeutic agent component is navitoclax or an analog of navitoclax:

In some embodiments, a navitoclax component has the structure

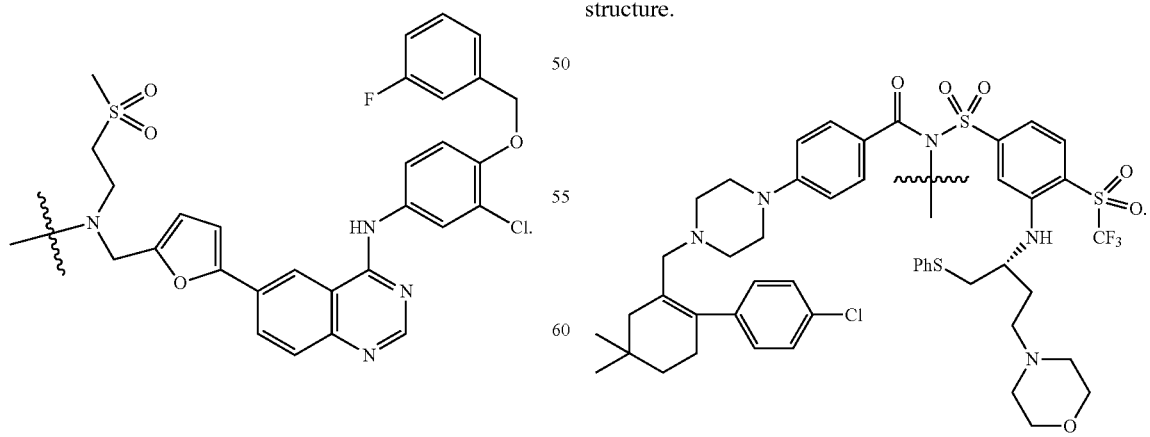

In some embodiments, the therapeutic agent component is nilotinib (e.g., TASIGNA®) or an analog of nilotinib:

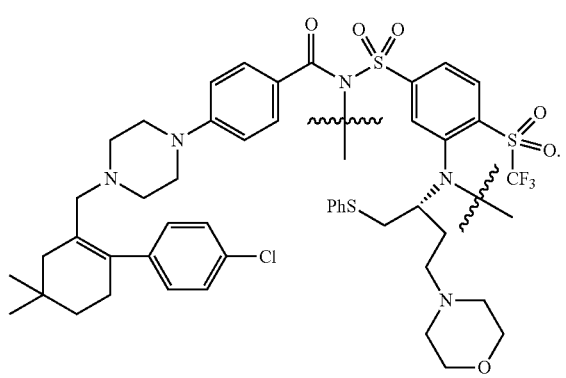

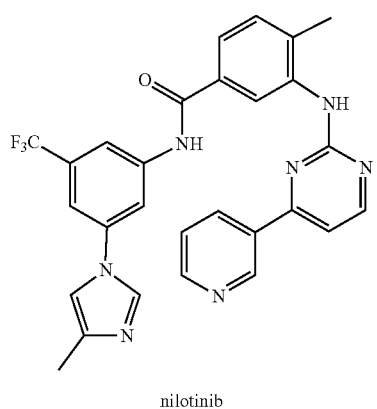 [SMILES: Cc1cn(-c2cc(NC(=O)c3ccc(C)c(Nc4nccc(-c5cccnc5)n4)c3)cc(C(F)(F)F)c2)cn1]

nilotinib

In some embodiments, a nilotinib component has the structure

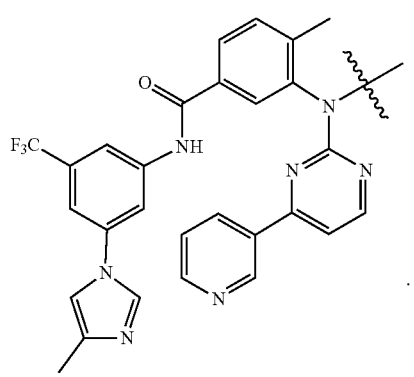 [SMILES: *N(c1nccc(-c2cccnc2)n1)c1cc(C(=O)Nc2cc(-n3cnc(C)c3)cc(C(F)(F)F)c2)ccc1C]

In some embodiments, a nilotinib component has the structure

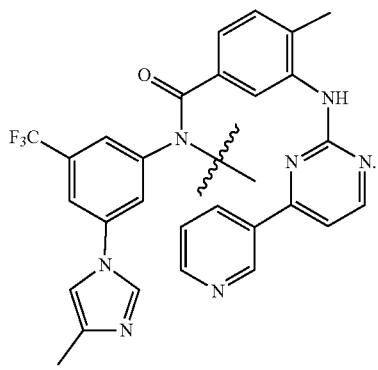 [SMILES: *N(C(=O)c1ccc(C)c(Nc2nccc(-c3cccnc3)n2)c1)c1cc(-n2cnc(C)c2)cc(C(F)(F)F)c1]

In some embodiments, a nilotinib component has the structure

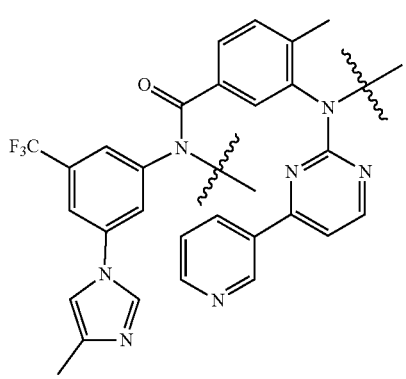 [SMILES: *N(C(=O)c1ccc(C)c(N(*)c2nccc(-c3cccnc3)n2)c1)c1cc(-n2cnc(C)c2)cc(C(F)(F)F)c1]

In some embodiments, the therapeutic agent component is pazopanib (e.g., OPDIVO®, VOTRIENT®) or an analog of pazopanib:

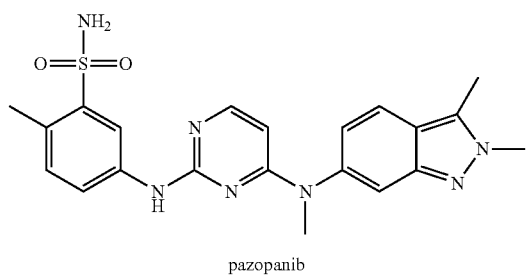

pazopanib

In some embodiments, a pazopanib component has the structure structure

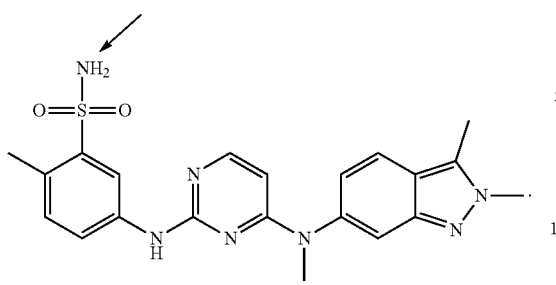

In some embodiments, a pazopanib component has the structure

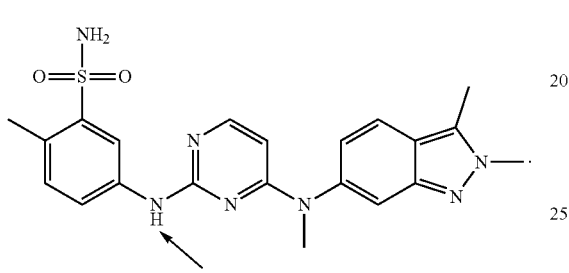

In some embodiments, a pazopanib component has the structure

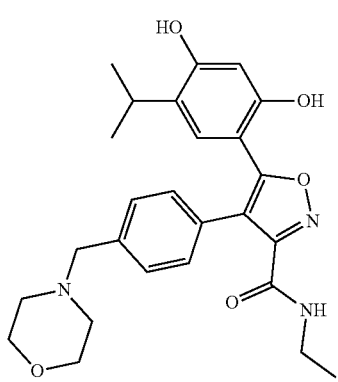 [SMILES: CCNC(=O)c1noc(-c2cc(C(C)C)c(O)cc2O)c1-c1ccc(CN2CCOCC2)cc1]

In some embodiments, the therapeutic agent component is luminespib or an analog of luminespib:

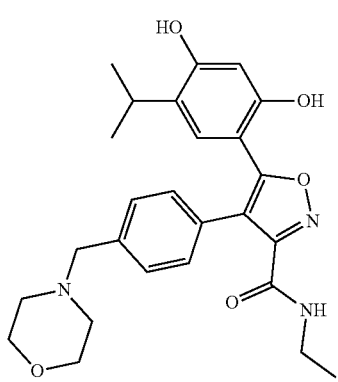 [SMILES: CCNC(=O)c1noc(-c2cc(C(C)C)c(O)cc2O)c1-c1ccc(CN2CCOCC2)cc1]

In some embodiments, a luminespib component has the structure

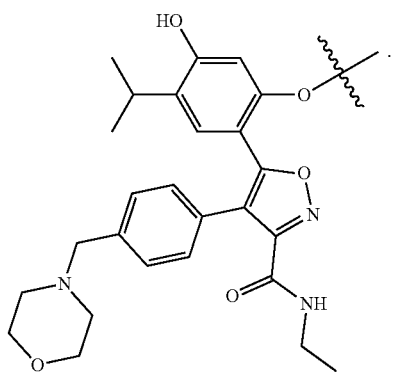 [SMILES: *Oc1cc(O)c(C(C)C)cc1-c1onc(C(=O)NCC)c1-c1ccc(CN2CCOCC2)cc1]

In some embodiments, a luminespib component has the structure

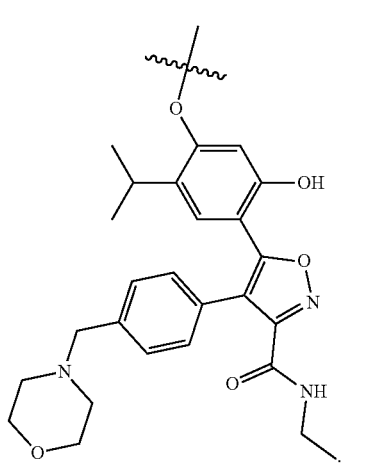 [SMILES: *Oc1cc(O)c(-c2onc(C(=O)NCC)c2-c2ccc(CN3CCOCC3)cc2)cc1C(C)C]

In some embodiments, a luminespib component has the structure

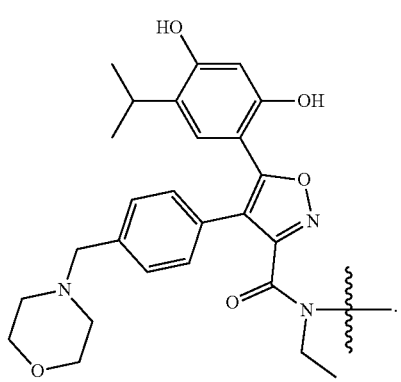 [SMILES: *N(CC)C(=O)c1noc(-c2cc(C(C)C)c(O)cc2O)c1-c1ccc(CN2CCOCC2)cc1]

In some embodiments, a luminespib component has the structure

In some embodiments, a luminespib component has the structure

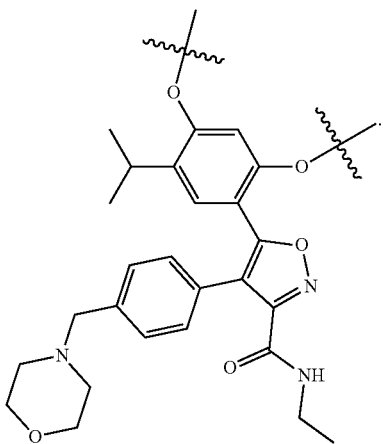 [SMILES: *Oc1cc(O*)c(C(C)C)cc1-c1onc(C(=O)NCC)c1-c1ccc(CN2CCOCC2)cc1]

In some embodiments, a luminespib component has the structure

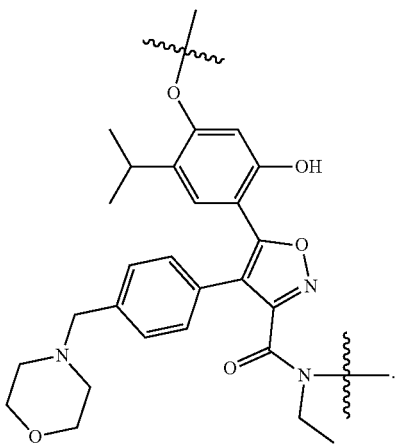 [SMILES: *Oc1cc(O)c(-c2onc(C(=O)N(*)CC)c2-c2ccc(CN3CCOCC3)cc2)cc1C(C)C]

In some embodiments, a luminespib component has the structure

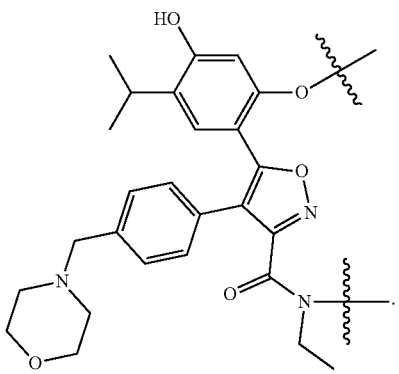 [SMILES: *Oc1cc(O)c(C(C)C)cc1-c1onc(C(=O)N(*)CC)c1-c1ccc(CN2CCOCC2)cc1]

In some embodiments, the therapeutic agent component is obatoclax or an analog of obatoclax:

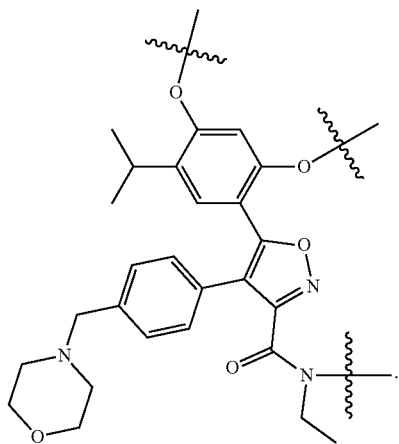 [SMILES: *Oc1cc(O*)c(C(C)C)cc1-c1onc(C(=O)N(*)CC)c1-c1ccc(CN2CCOCC2)cc1]

obatoclax (GX15-070)

In some embodiments, an obatoclax component has the structure

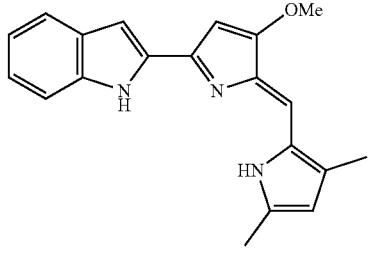

In some embodiments, an obatoclax component has the structure

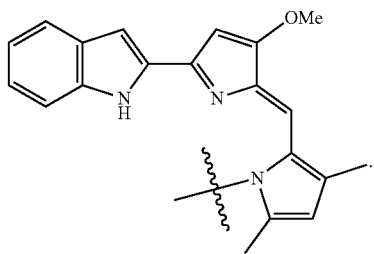 [SMILES: *n1c(C)cc(C)c1/C=C1\N=C(c2cc3ccccc3[nH]2)C=C1OC]

In some embodiments, an obatoclax component has the structure

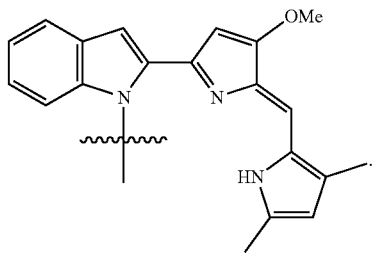 [SMILES: *n1c(C2=N/C(=C\c3[nH]c(C)cc3C)C(OC)=C2)cc2ccccc21]

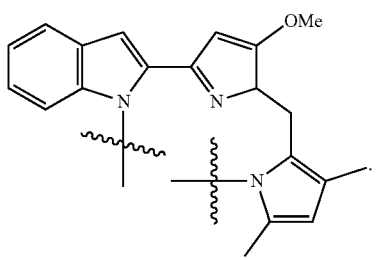 [SMILES: *n1c(C)cc(C)c1CC1N=C(c2cc3ccccc3n2*)C=C1OC]

In some embodiments, the therapeutic agent component is ruxolitinib (e.g., JAKAFI®) or an analog of ruxolitinib:

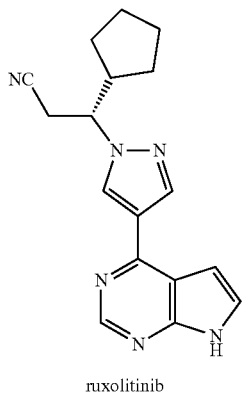 [SMILES: N#CC[C@H](C1CCCC1)n1cc(-c2ncnc3[nH]ccc23)cn1]

ruxolitinib

In some embodiments, a ruxolitinib component has the structure

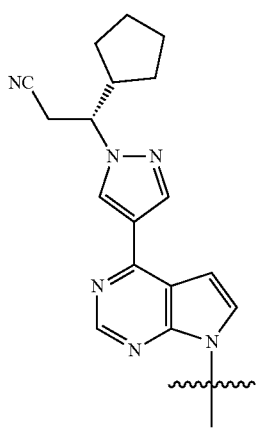

In some embodiments, the therapeutic agent component is saridegib (e.g., ODOMZO®) or an analog of saridegib:

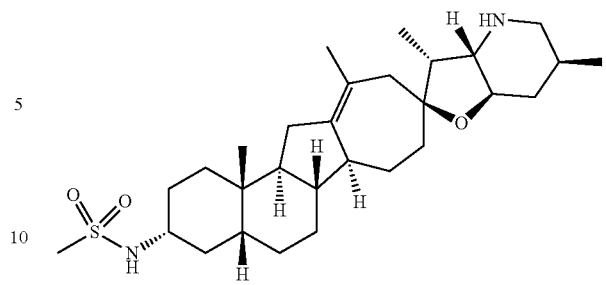

saridegib

In some embodiments, a saridegib component has the structure

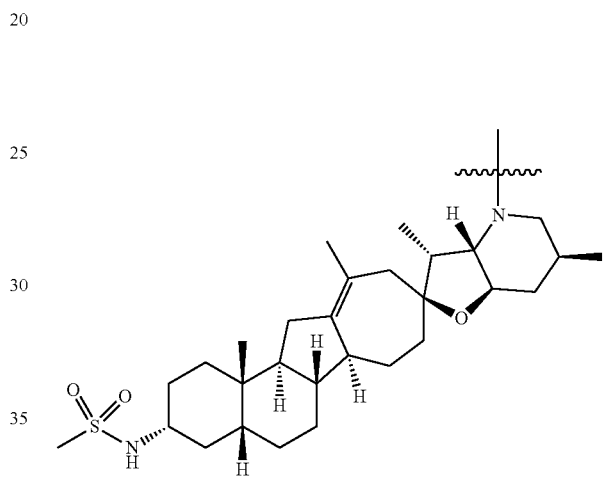

In some embodiments, a saridegib component has the structure

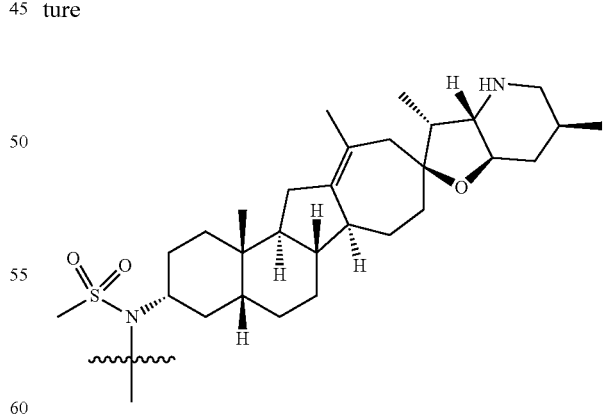

In some embodiments, a saridegib component has the structure

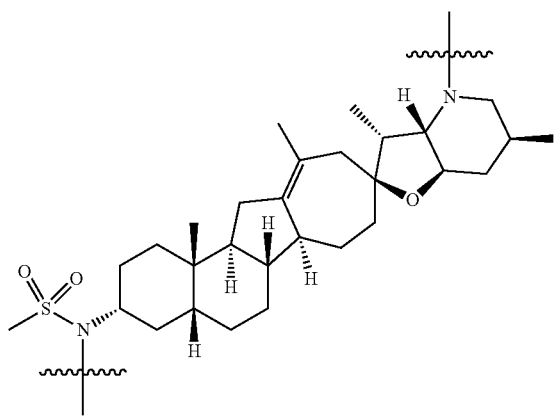

In some embodiments, the therapeutic agent component is sunitinib (e.g., SUTENT®) or an analog of sunitinib:

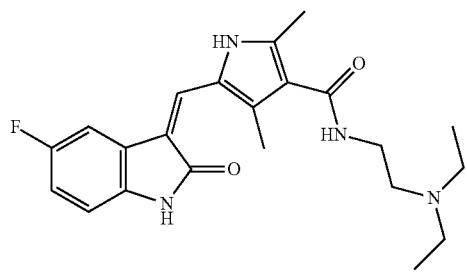

sunitinib

In some embodiments, a sunitinib component has the structure:

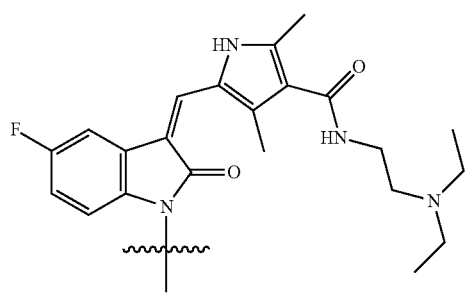

In some embodiments, a sunitinib component has the structure

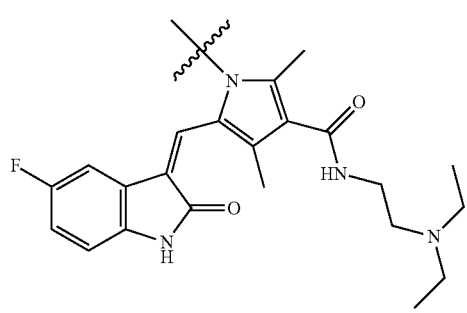

In some embodiments, a sunitinib component has the structure

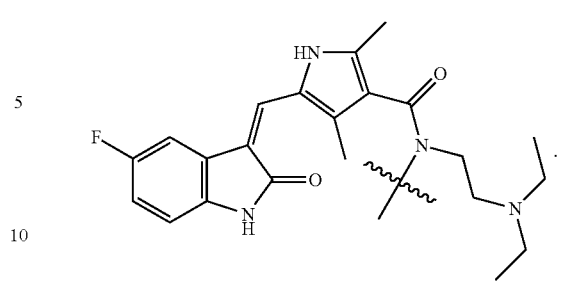

In some embodiments, a sunitinib component has the structure

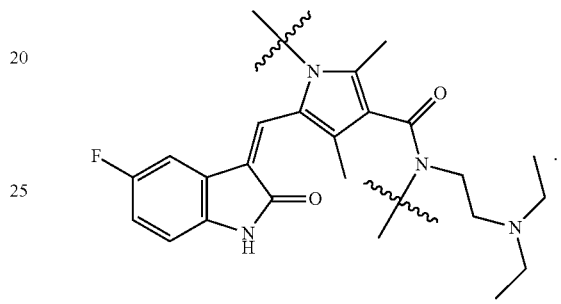

In some embodiments, a sunitinib component has the structure

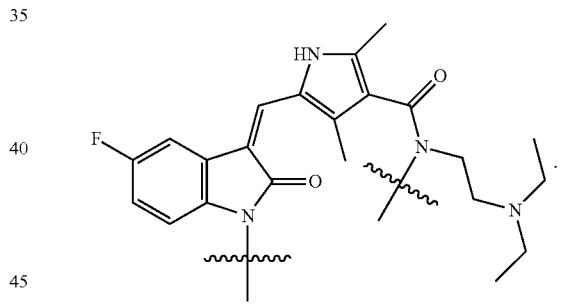

In some embodiments, a sunitinib component has the structure

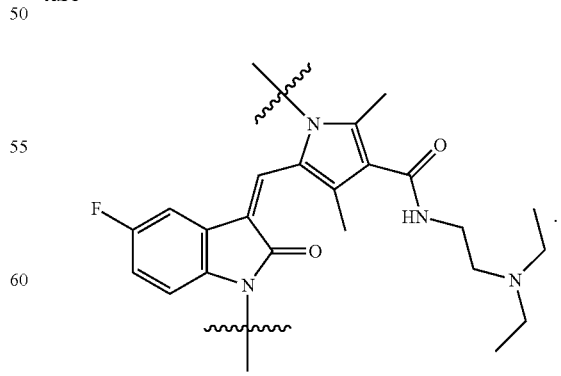

In some embodiments, a sunitinib component has the structure

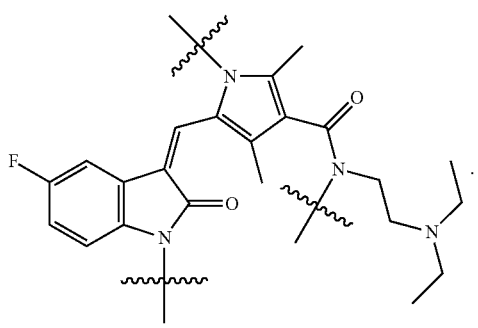 [SMILES: *N(CCN(CC)CC)C(=O)c1c(C)c(/C=C2\C(=O)N(*)c3ccc(F)cc32)n(*)c1C]

In some embodiments, the therapeutic agent component is trametinib (e.g., MEKINIST®) or an analog of trametinib:

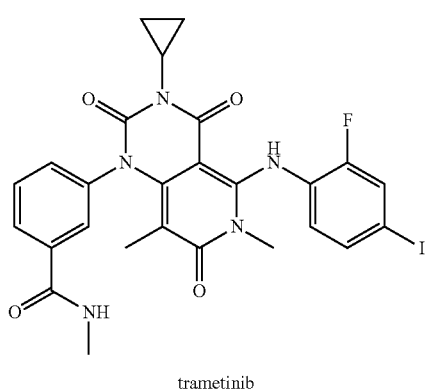 [SMILES: CNC(=O)c1cccc(-n2c(=O)n(C3CC3)c(=O)c3c(Nc4ccc(I)cc4F)n(C)c(=O)c(C)c32)c1]

trametinib

In some embodiments, a trametinib component has the structure

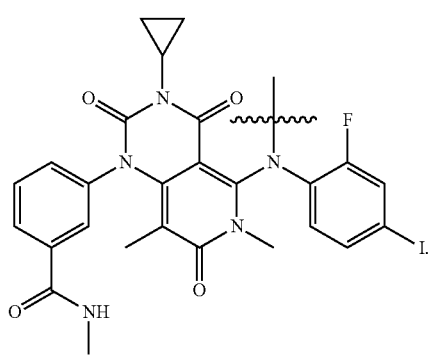 [SMILES: *N(c1ccc(I)cc1F)c1c2c(=O)n(C3CC3)c(=O)n(-c3cccc(C(=O)NC)c3)c2c(C)c(=O)n1C]

In some embodiments, a trametinib component has the structure

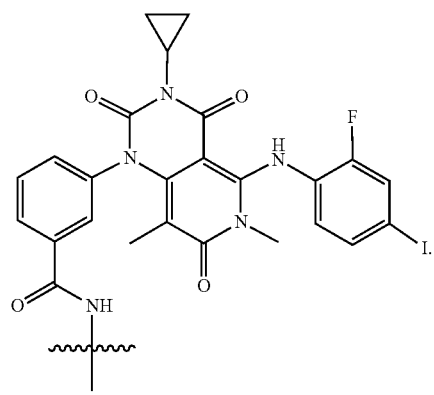 [SMILES: *NC(=O)c1cccc(-n2c(=O)n(C3CC3)c(=O)c3c(Nc4ccc(I)cc4F)n(C)c(=O)c(C)c32)c1]

In some embodiments, a trametinib component has the structure

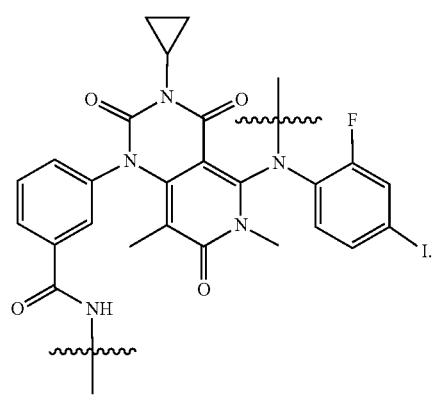 [SMILES: *NC(=O)c1cccc(-n2c(=O)n(C3CC3)c(=O)c3c(N(*)c4ccc(I)cc4F)n(C)c(=O)c(C)c32)c1]

In some embodiments, the therapeutic agent component is warfarin (e.g., COUMADIN®, JANTOVEN®) or an analog of warfarin:

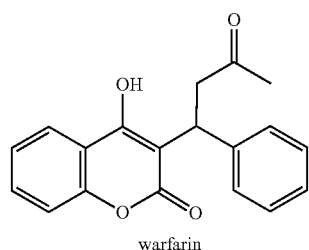 [SMILES: CC(=O)CC(c1ccccc1)c1c(O)c2ccccc2oc1=O]

warfarin

In some embodiments, a warfarin component has the structure

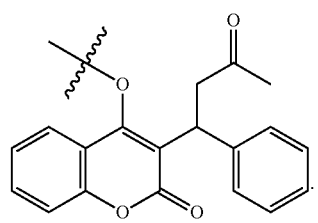 [SMILES: *Oc1c(C(CC(C)=O)c2ccccc2)c(=O)oc2ccccc12]

In some embodiments, the therapeutic agent component is daclatasvir (e.g., DAKLINZA®) or an analog of daclatasvir:

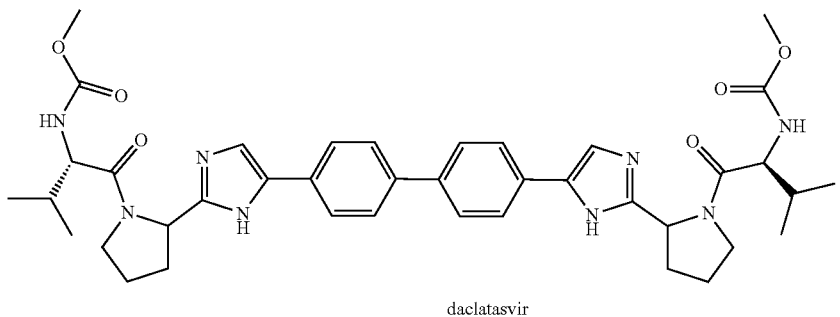 [SMILES: COC(=O)N[C@H](C(=O)N1CCCC1c1ncc(-c2ccc(-c3ccc(-c4cnc(C5CCCN5C(=O)[C@@H](NC(=O)OC)C(C)C)[nH]4)cc3)cc2)[nH]1)C(C)C]

daclatasvir

As daclatasvir is a symmetrical drug, many multi-conjugate structures are envisioned with up to at least four cannabinoid components linked to the parent drug. In some embodiments, a daclatasvir component has a cannabinoid component linked at one or more of sites (a), (b), (c), (d), (e), and (f), illustrated below, in any combination:

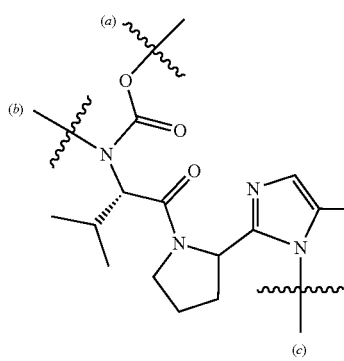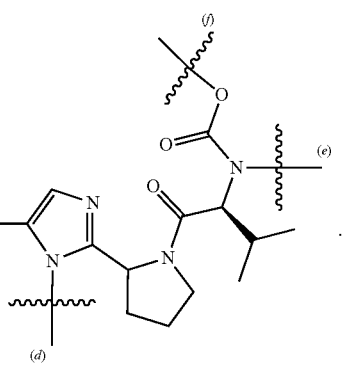

In some embodiments, a cannabinoid component is linked at site (a).

In some embodiments, a cannabinoid component is linked at site (a) and site (b). In some embodiments, a cannabinoid component is linked at site (a) and site (c). In some embodiments, a cannabinoid component is linked at site (a) and site (d). In some embodiments, a cannabinoid component is linked at site (a) and site (e). In some embodiments, a cannabinoid component is linked at site (a) and site (f).

In some embodiments, a cannabinoid component is linked at site (a), site (b), and site (c). In some embodiments, a cannabinoid component is linked at site (a), site (b), and site (d). In some embodiments, a cannabinoid component is linked at site (a), site (b), and site (e). In some embodiments, a cannabinoid component is linked at site (a), site (b), and site (f).

In some embodiments, a cannabinoid component is linked at site (a), site (c), and site (d). In some embodiments, a cannabinoid component is linked at site (a), site (c), and site (e). In some embodiments, a cannabinoid component is linked at site (a), site (c), and site (f).

In some embodiments, a cannabinoid component is linked at site (a), site (d), and site (e). In some embodiments, a cannabinoid component is linked at site (a), site (d), and site (f).

In some embodiments, a cannabinoid component is linked at site (a), site (e), and site (f).

In some embodiments, a cannabinoid component is linked at site (a), site (b), site (c), and site (d). In some embodiments, a cannabinoid component is linked at site (a), site (b), site (c), and site (e). In some embodiments, a cannabinoid component is linked at site (a), site (b), site (c), and site (f).

In some embodiments, a cannabinoid component is linked at site (a), site (d), site (d), and site (e). In some embodiments, a cannabinoid component is linked at site (a), site (d), site (d), and site (f).

In some embodiments, a cannabinoid component is linked at site (a), site (d), site (e), and site (f).

In some embodiments, a cannabinoid component is linked at site (a), site (b), site (c), site (d), and site (e). In some embodiments, a cannabinoid component is linked at site (a), site (b), site (c), site (d), and site (f).

In some embodiments, a cannabinoid component is linked at site (a), site (b), site (c), site (d), site (e), and site (f).

In some embodiments, a cannabinoid component is linked at site (b).

In some embodiments, a cannabinoid component is linked at site (b) and site (c). In some embodiments, a cannabinoid component is linked at site (b) and site (d). In some embodiments, a cannabinoid component is linked at site (b) and site (e). In some embodiments, a cannabinoid component is linked at site (b) and site (f).

In some embodiments, a cannabinoid component is linked at site (b), site (c), and site (d). In some embodiments, a cannabinoid component is linked at site (b), site (c), and site (e). In some embodiments, a cannabinoid component is linked at site (b), site (c), and site (f).

In some embodiments, a cannabinoid component is linked at site (b), site (d), and site (e). In some embodiments, a cannabinoid component is linked at site (b), site (d), and site (f).

In some embodiments, a cannabinoid component is linked at site (b), site (e), and site (f).

In some embodiments, a cannabinoid component is linked at site (b), site (c), site (d), and site (e). In some embodiments, a cannabinoid component is linked at site (b), site (c), site (d), and site (f).

In some embodiments, a cannabinoid component is linked at site (b), site (d), site (e), and site (f).

In some embodiments, a cannabinoid component is linked at site (b), site (c), site (d), site (e), and site (f).

In some embodiments, a cannabinoid component is linked at site (c).

In some embodiments, a cannabinoid component is linked at site (c) and site (d). In some embodiments, a cannabinoid component is linked at site (c) and site (e). In some embodiments, a cannabinoid component is linked at site (c) and site (f).

In some embodiments, a cannabinoid component is linked at site (c), site (d), and site (e). In some embodiments, a cannabinoid component is linked at site (c), site (d), and site (f).

In some embodiments, a cannabinoid component is linked at site (c), site (e), and site (f).

In some embodiments, a cannabinoid component is linked at site (c), site (d), site (e), and site (f).

In some embodiments, a cannabinoid component is linked at site (d).

In some embodiments, a cannabinoid component is linked at site (d) and site (e). In some embodiments, a cannabinoid component is linked at site (d) and site (f).

In some embodiments, a cannabinoid component is linked at site (d), site (e), and site (f).

In some embodiments, a cannabinoid component is linked at site (e).

In some embodiments, a cannabinoid component is linked at site (e) and site (f).

In some embodiments, a cannabinoid component is linked at site (f).

In some embodiments, the therapeutic agent component is etoposide (e.g., ETOPOPHOS®, TOPOSAR®) or an analog of etoposide:

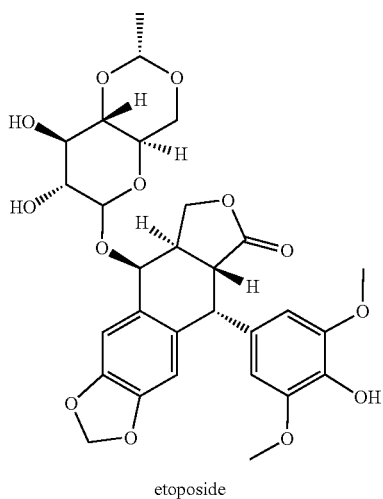

etoposide

In some embodiments, an etoposide component has the structure

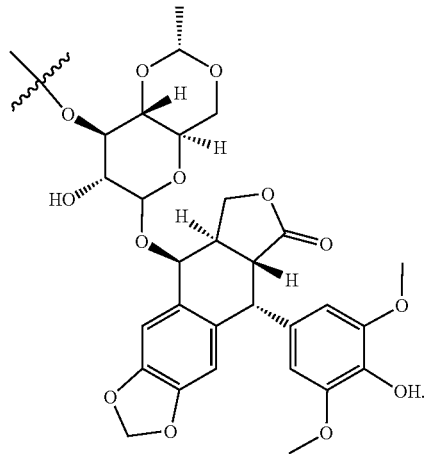

In some embodiments, an etoposide component has the structure

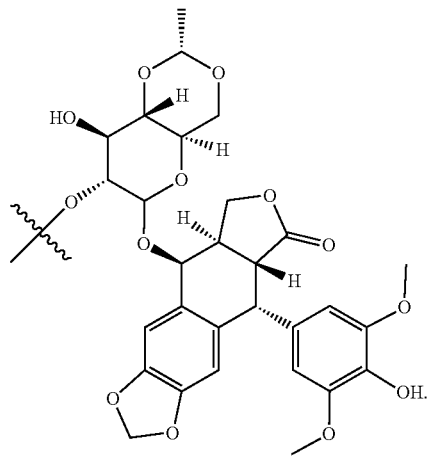

In some embodiments, an etoposide component has the structure

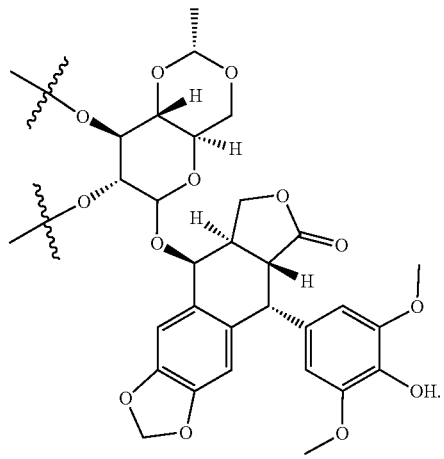

In some embodiments, an etoposide component has the structure

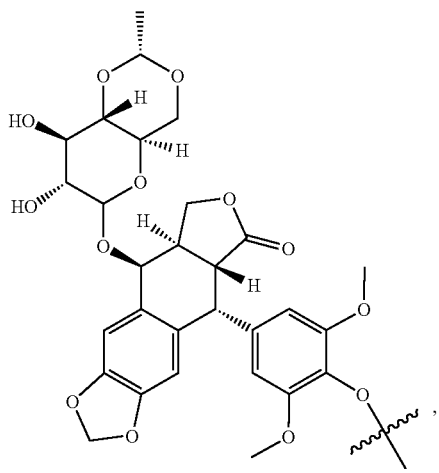

In some embodiments, an etoposide component has the structure

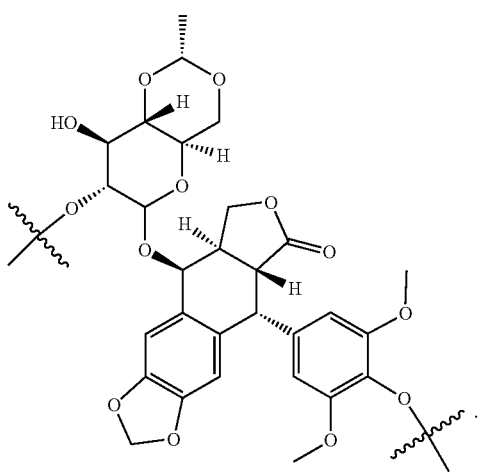

In some embodiments, an etoposide component has the structure

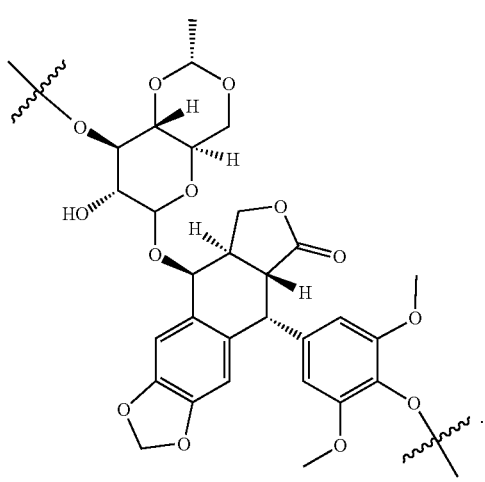

In some embodiments, an etoposide component has the structure

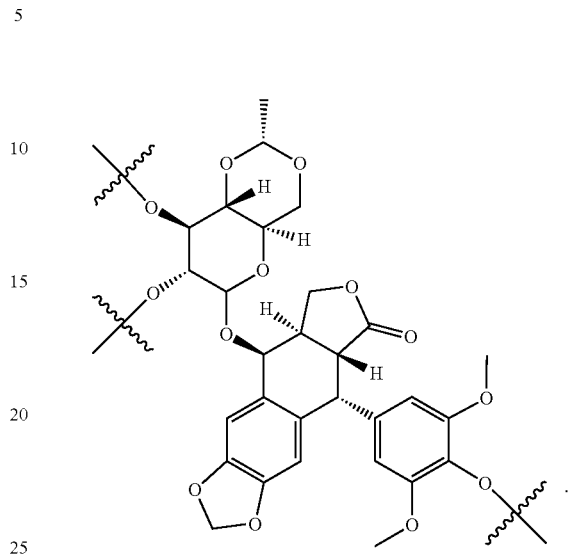

In some embodiments, the therapeutic agent component is atazanavir (e.g., REYATAZ®) or an analog of atazanavir:

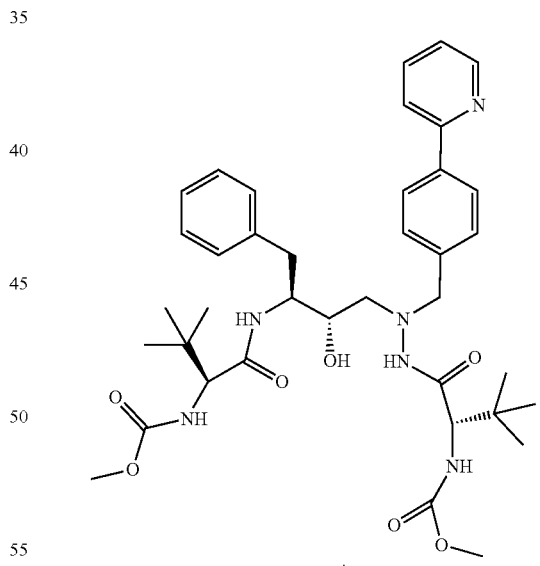

atazanavir

Either or both carbamates in atazanavir may be linked to a cannabinoid component in addition to the OH group or, potentially, the NH hydrazinyl group. In some embodiments, an atazanavir component has the structure

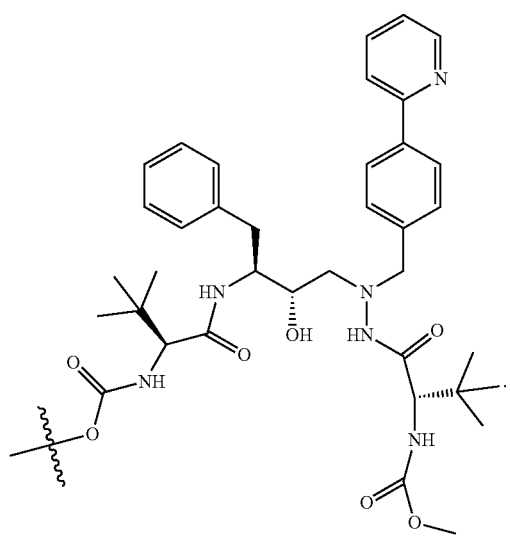 [SMILES: *OC(=O)N[C@H](C(=O)N[C@@H](Cc1ccccc1)[C@@H](O)CN(Cc1ccc(-c2ccccn2)cc1)NC(=O)[C@@H](NC(=O)OC)C(C)(C)C)C(C)(C)C]
In some embodiments, an atazanavir component has the structure
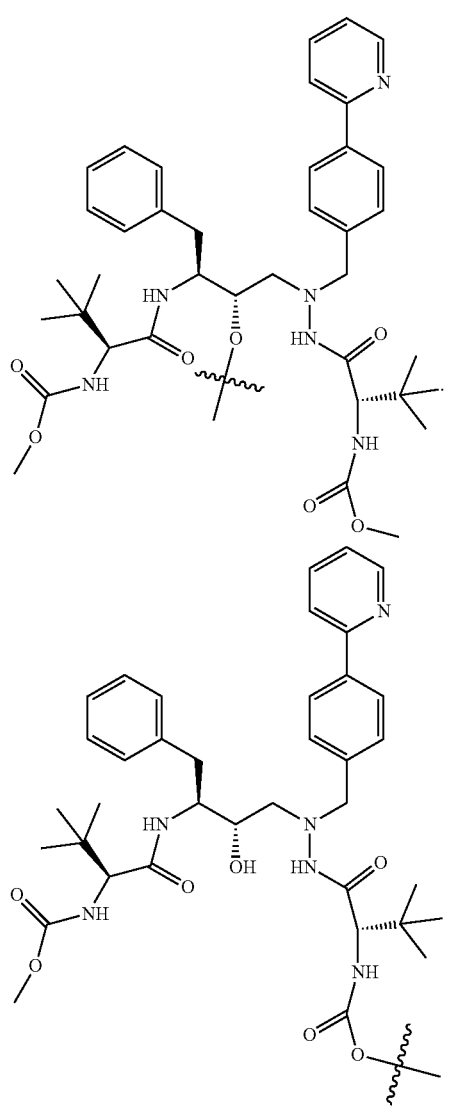
In some embodiments, an atazanavir component has the structure
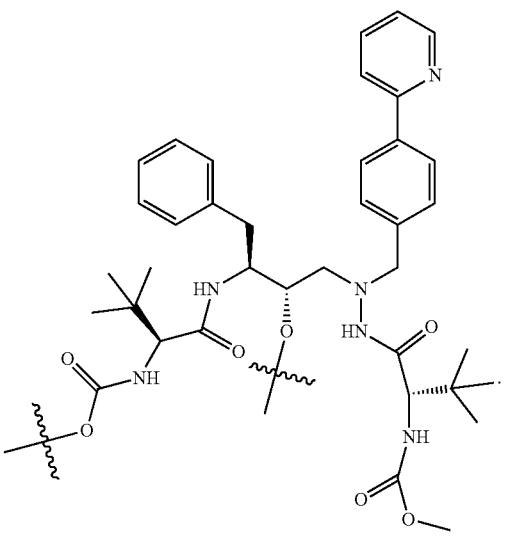 [SMILES: *OC(=O)N[C@H](C(=O)N[C@@H](Cc1ccccc1)[C@H](CN(Cc1ccc(-c2ccccn2)cc1)NC(=O)[C@@H](NC(=O)OC)C(C)(C)C)O*)C(C)(C)C]
In some embodiments, an atazanavir component has the structure
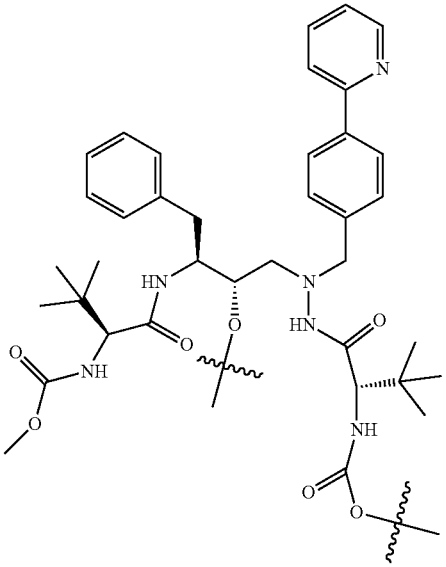
In some embodiments, an atazanavir component has the structure

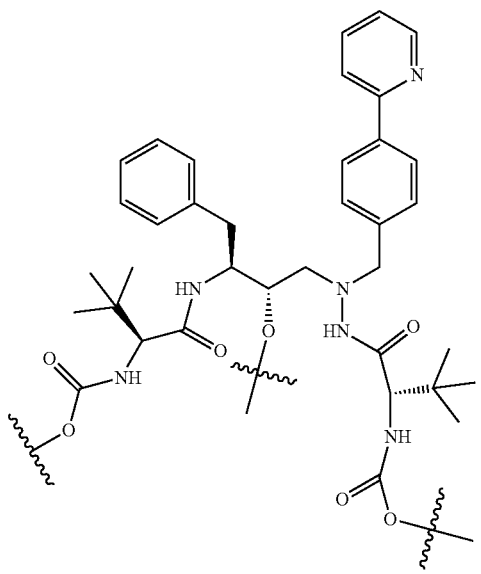
In some embodiments, the therapeutic agent component is pravastatin (e.g., PRAVACHOL®) or an analog of pravastatin:
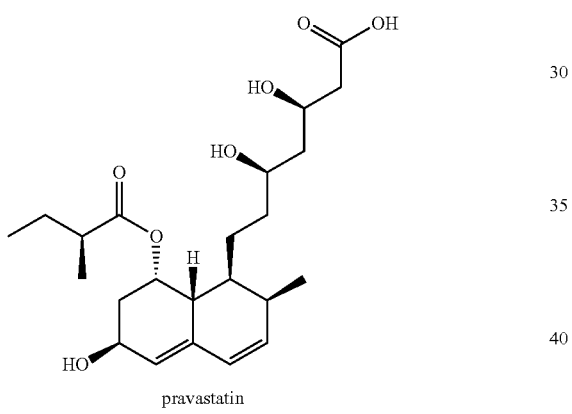
pravastatin
Any or all of the three hydroxyl groups and the carboxylic acid group can be linked to a cannabinoid component. In some embodiments, a pravastatin component has one of the following structures
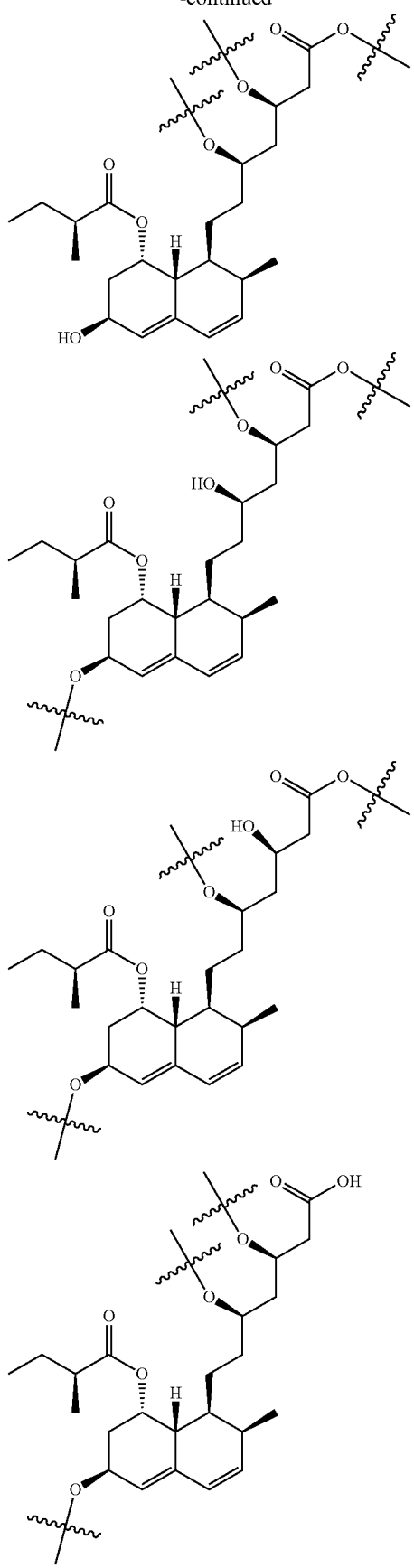

-continued
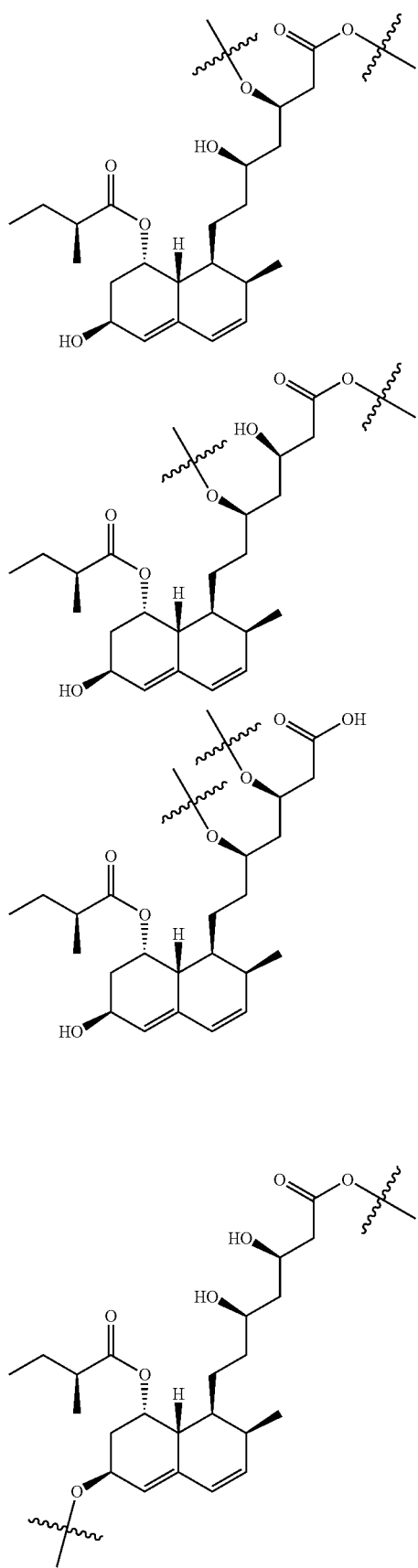
-continued
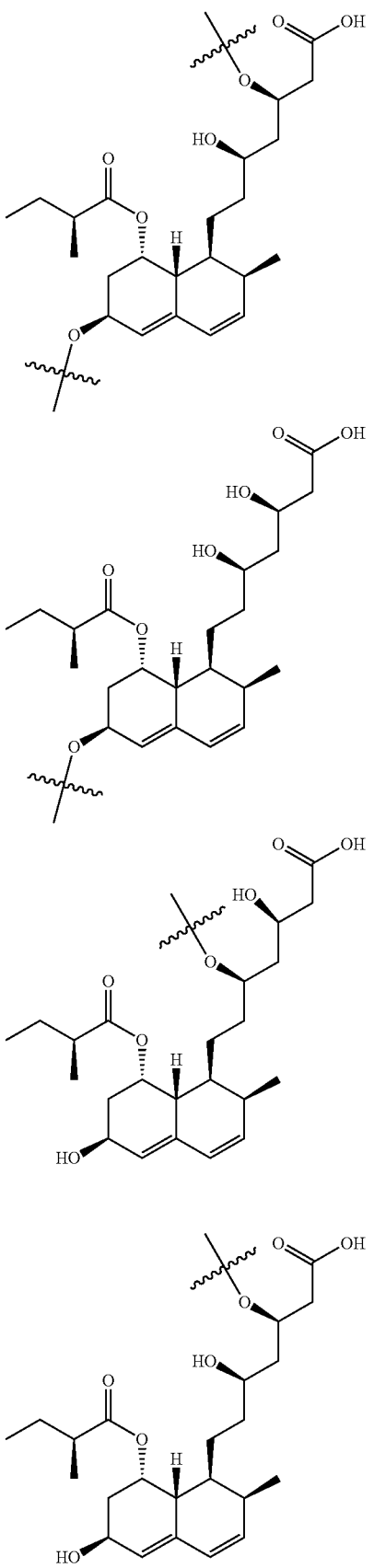

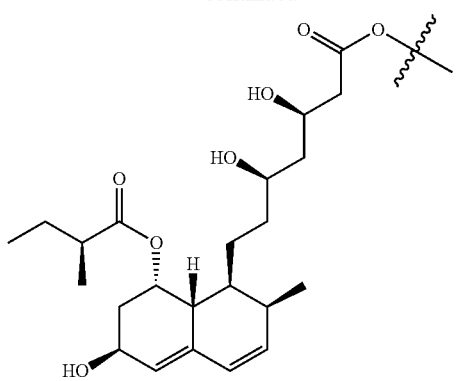

In some embodiments, the therapeutic agent component is dasatinib (e.g., SPRYCEL®) or an analog of dasatinib:

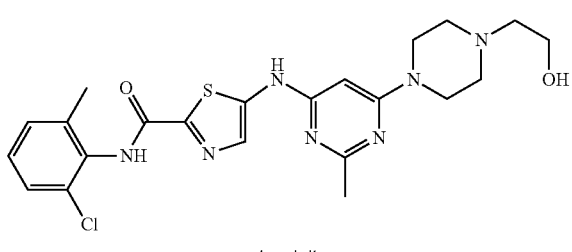

dasatinib

In some embodiments, a dasatinib component has the structure

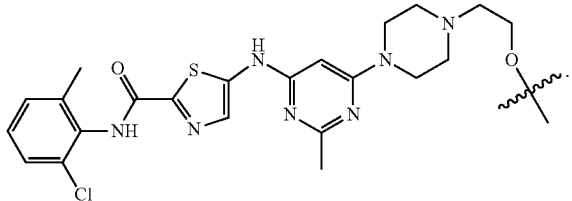 [SMILES: *OCCN1CCN(c2cc(Nc3cnc(C(=O)Nc4c(C)cccc4Cl)s3)nc(C)n2)CC1]

In some embodiments, a dasatinib component has the structure

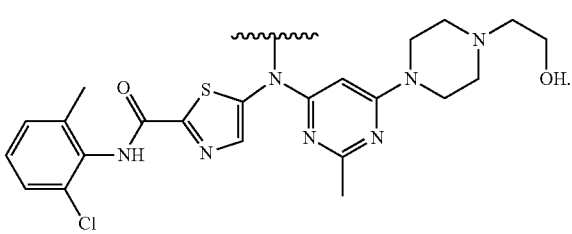 [SMILES: *N(c1cc(N2CCN(CCO)CC2)nc(C)n1)c1cnc(C(=O)Nc2c(C)cccc2Cl)s1]

In some embodiments, a dasatinib component has the structure

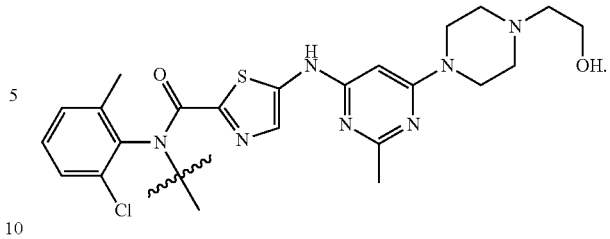

In some embodiments, a dasatinib component has the structure

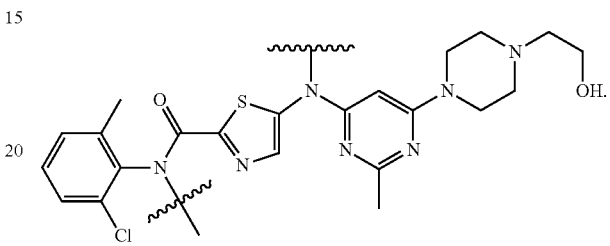

In some embodiments, a dasatinib component has the structure

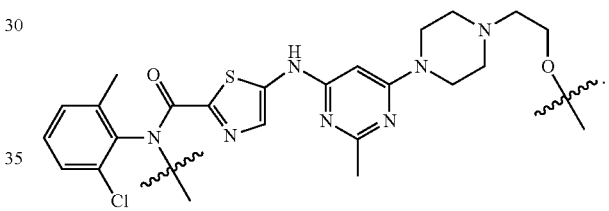

In some embodiments, a dasatinib component has the structure

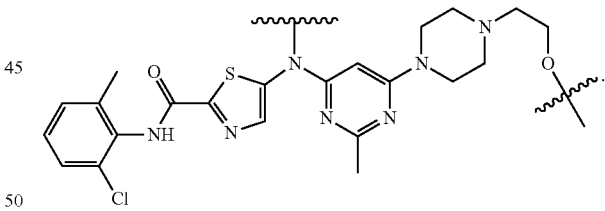

In some embodiments, a dasatinib component has the structure

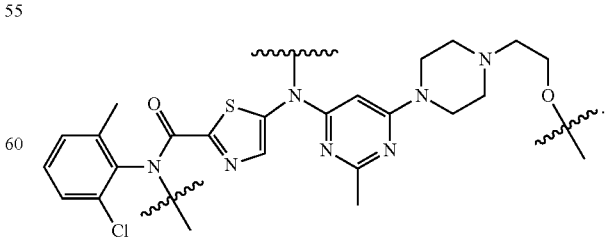

In some embodiments, the therapeutic agent component is didanosine (e.g., VIDEX®) or an analog of didanosine:

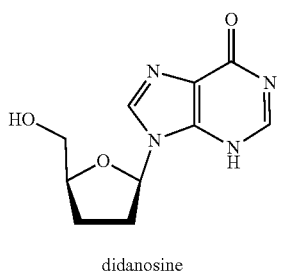

didanosine

In some embodiments, a didanosine component has the structure

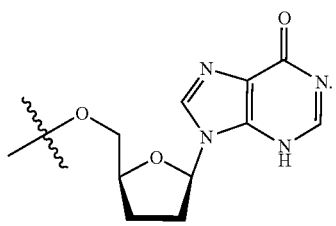

In some embodiments, a didanosine component has the structure

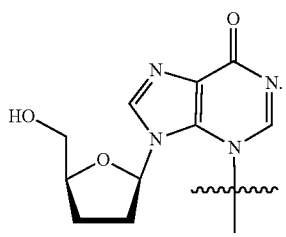

In some embodiments, a didanosine component has the structure

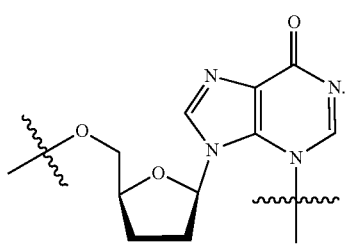

In some embodiments, the therapeutic agent component is stavudine (e.g. ZERIT®) or an analog of stavudine:

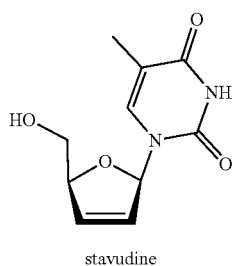 [SMILES: Cc1cn([C@H]2C=C[C@@H](CO)O2)c(=O)[nH]c1=O]

stavudine

In some embodiments, a stavudine component has the structure

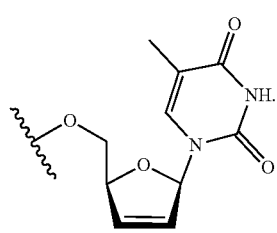 [SMILES: *OC[C@@H]1C=C[C@H](n2cc(C)c(=O)[nH]c2=O)O1]

In some embodiments, a stavudine component has the structure

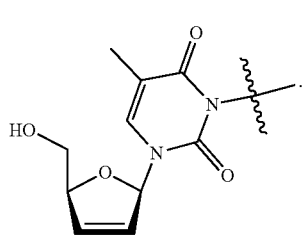 [SMILES: *n1c(=O)c(C)cn([C@H]2C=C[C@@H](CO)O2)c1=O]

In some embodiments, a stavudine component has the structure

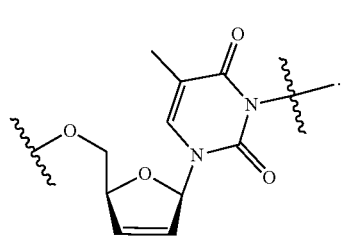 [SMILES: *OC[C@@H]1C=C[C@H](n2cc(C)c(=O)n(*)c2=O)O1]

Additional therapeutic agents can be conjugated as described above. Examples are shown in Table 1.

TABLE 1

| Therapeutic agent(s) | Example Brand Name(s) | Therapeutic Use(s) | Conjugation Options |
|---|---|---|---|
| Aceclofenac | ACECLOFENAC ® | musculoskeletal system | NH and/or COOH group |
| Aceclofenac + Paracetamol | ALTRAFLAM-P ® | anti-inflammatory, analgesic, anti-pyretic | Aceclofenac, NH and/or COOH group Paracetamol (acetaminophen), NH and/or OH |
| Aceclofenac + Rabeprazole sodium | ALTRADAY ® | anti-inflammatory, analgesic + anti-peptic ulcerant | Aceclofenac, NH and/or COOH group |

TABLE 1-continued

| Therapeutic agent(s) | Example Brand Name(s) | Therapeutic Use(s) | Conjugation Options |
|---|---|---|---|
| Aclidinium bromide | BRETARIS ® | respiratory system | OH |
| Almotriptan | AMIGNUL ® | nervous system | NH |
| Ambroxol + Theophylline | ACEBROPHYLLINE ® | respiratory system | Ambroxol, OH and/or NH and/or $NH_2$; theophylline, the NH group |
| Amcinonide | AMCIDERM ® | dermatological | OH |
| Amlodipine | ASTUDAL ® | cardiovascular system | $NH_2$ and/or replace methyl ester with cannabinoid ester |
| Amlodipine + Atorvastatin | ASTUCOR ® | cardiovascular system | Amlodipine, NH and/or $NH_2$; atorvastatin, NH and/or OH and/or COOH |
| Amlodipine + Atenolol | AMLOBET ® | cardiology | Amlodipine, NH and/or $NH_2$; Atenolol, NH and/or OH and/or $NH_2$ |
| Amlodipine + Metoprolol | CARDIBETA ® AM | anti-hypertensive | Amlodipine, NH and/or $NH_2$ |
| Amlodipine + Olmesartan medoxiomil | OLMEZEST ® AM | cardiology | Amlodipine, NH and/or $NH_2$ |
| Amlodipine + Metoprolol tartrate | PROLOMET ® AM 50 | cardiology | Amlodipine, NH and/or $NH_2$ |
| Amlodipine + Lorsartan potassium | REPLACE-A ® | cardiology | Amlodipine, NH and/or $NH_2$ |
| Amlodipine + Telmisartan | TELEACT ® AM | anti-hypertensive | Amlodipine, NH and/or $NH_2$ |
| Amlodipine + Telmisartan + Hydrochlorthiazide | TELEACT ® TRIO | anti-hypertensive | Amlodipine, NH and/or $NH_2$ |
| Amlodipine + Lorsartan potassium usp + Hydrochlorothiazide ip | TRILOPACE ® | cardiology | Amlodipine, NH and/or $NH_2$ |
| Arginin + Ornithin + Vitamin B6 | POLILEVO ® | alimentary tract and metabolism | amino acids at either or both $NH_2$ and/or COOH; conjugate Vit B6 at either or both OH and/or P-OH |
| Atenolol | ATENOLOL ® | cardiovascular system | NH and/or OH and/or $NH_2$ |
| Atenolol + Clortalidone | BLOKIUM-DIU ® | cardiovascular system | either component at NH and/or OH |
| Atenolol + Nifedipine usp | BETATROP ® | cardiology | Atenolol, NH and/or OH and/or $NH_2$ |
| Atenolol + Lercanidipine usp | LOTENSYL-AT ® | cardiology | Atenolol, NH and/or OH and/or $NH_2$ |
| Atenolol + Losartan potassium usp | REPALOL ® H | cardiology | Atenolol, NH and/or OH and/or $NH_2$ |
| Atenolol + Lorsartan potassium | REPALOL ® | cardiology | Atenolol, NH and/or OH and/or $NH_2$ |
| Azelaic acid | FINACEA ® | inflammatory papules and pustules of mild to moderate rosacea. | at either or both end OH groups |
| Balsalazide | PREMID ® | alimentary tract and metabolism | OH and/or NH and/or either or both COOH groups |
| Betamethasone | DIPROVATE ® PLUS | topical steroid | at any 1, 2, or 3 OH groups |
| Betamethasone dipropionate | DIPROVATE ® RD | topical steroid | at any 1, 2, or 3 OH groups |
| Betamethasone dipropionate + Salicylic acid | DIPROVATE ® PLUS ES | topical steroid + keratolytic | Betamethasone, at any 1, 2, or 3 OH groups; Salicyclic acid, the acid and/or at the OH group |
| Betamethasone dipropionate + Neomycin sulphate | DIPROVATE ® PLUS N | topical steroid | Betamethasone, at any 1, 2, or 3 OH groups |
| Betamethasone dipropionate + Gentamicin | DIPROVATE ® PLUS G | topical steroid | Betamethasone, at any 1, 2, or 3 OH groups |
| Calcipotriene | DOVONEX ® | plaque psoriasis | at any 1, 2, or 3 OH groups |
| Calcipotriene + Betamethasone dipropionate | ENSTILAR ®, TALCONEX ® | plaque psoriasis | Betamethasone, at any 1, 2, or 3 OH groups; calcipotriene at any 1, 2, or 3 OH groups |
| Calcitonin | CALCITONINA ® | systemic hormonal preparations | at any 1 or more NH groups |
| Candesartan cilexetil | PARAPRES ® | cardiovascular system | at acid and/or at NH on tetrazole |
| Candesartan cilexetil + Hydrochlorothiazide | PARAPRES ® PLUS | cardiovascular system | Candesartan cilexetil, at acid and/or at NH on tetrazole; Hydrochlorothiazide, at either or both NH and/or $NH_2$ |
| Capecitabine | CAXETA ® | cancer | either or both OH and/or NH |
| Carbocisteine | MUCOACTIOL ® | respiratory system | $NH_2$ and/or either or both of the two acid groups |
| Carboxymethylcysteine | CARBOXIMETILCISTEINE ® | respiratory system | $NH_2$ and/or either of two acid groups |
| Carfilzomib | KYPROLIS ® | cancer; proteosome inhibitor | any 1, 2, 3, or 4 NH groups |
| Centella asiatica + Metronidazole + Miconazole | BLASTOESTIMULINA ÓVULOS ® | genitourinary system and sex hormones | Metronidazole, at OH |
| Centella asiatica + Neomycin | BLASTOESTIMULINA ® | dermatological | Neomycin, any one or more OH and/or $NH_2$ groups |
| Ciclopirox + Hydroxypropyl chitosan | CICLOPOLI ® | dermatological | Ciclopirox, OH |
| Ciclopirox olamine | SELERGO ® | dermatological | Ciclopirox, OH |
| Cinitapride | CIDINE ® | alimentary tract and metabolism | NH and/or $NH_2$ |

TABLE 1-continued

| Therapeutic agent(s) | Example Brand Name(s) | Therapeutic Use(s) | Conjugation Options |
| --- | --- | --- | --- |
| Clebopride | CLEBORIL ® | alimentary tract and metabolism | NH and/or $NH_2$ |
| Clebopride + Simeticone | FLATORIL ® | alimentary tract and metabolism | Clebopride, NH and/or $NH_2$ |
| Clindamycin phosphate + Tretinoin | VELTIN ® | dermatological | Clindamycin, to any 1, 2, or 3 OH and/or to the NH and/or to the acid group of tretinoin. |
| Dapsone | ACZONE ® | dermatological | to either or both acids |
| Delgocitinib (LP0133) | | atopic dermatitis (proposed) | at NH |
| Delta-9-tetrahydrocannabinol (THC) + Cannabidiol (CBD) | SATIVEX ® | nervous system | as described below for cannabinoid components |
| Desonide | DESONATE ® | atopic dermatitis | either or both OH and/or carboxy groups |
| Dihydroergocriptine | ALFA DIHYDROERGOCRYP ® | nervous system | NH or OH |
| Dihydroergocristine mesylate + Piracetam | DIEMIL ® | cardiovascular system | Dihydroergocristine, NH and/or OH; piracetam, $NH_2$ |
| Dihydroergocryptine | ALMIRID-CRIPAR ® | nervous system | OH and/or NH |
| Dimethyl fumarate | SKILARENCE ® | dermatological | by replacing at least one methyl ester as a cannabinoid ester |
| Doxazosin | PROGANDOL ® | cardiovascular system | $NH_2$ |
| Doxycycline hyclate | ACTICLATE ® | dermatological | Acticlate (doxycycline), any 1, 2, 3, 4, or 5 OH groups and/or at the amide |
| Ebastine + Pseudoephedrine | RINO-BACTIL ® | respiratory system | pseudoephedrine, NH and/or OH |
| Eflornithine | VANIQA ® | dermatological | at either or both $NH_2$ and/or to COOH |
| Eplerenone | ELECOR ® | cardiovascular system | by replacing a methyl ester with a cannabinoid ester |
| Erythromycin | AKNE-MYCIN ® | dermatological | at any 1, 2, 3, 4, or 5 OH groups |
| Erythromycin + Tretinoin | AKNEMYCIN ® PLUS | dermatological | Erythromycin, at any 1, 2, 3, 4, or 5 OH groups; tretinoin, at its acid |
| Erythromycin + Zinc acetate dihydrate | ZINERYT ® | dermatological | Erythromycin, at any 1, 2, 3, 4, or 5 OH groups |
| Etodolac | LODINE ® | dermatological | via acid group |
| Fluprednidon-21-acetate + Salicylic acid | SALI-DECODERM ® | dermatological | Fluprednidon-$_2$1-acetate, either or both OH groups; salicylic acid at the acid and/or at the OH group |
| Fluprednidene acetate | DECODERM ® | dermatological | either or both OH groups |
| Fluprednidene acetate + Estradiol | CRINOHERMAL ® | genitourinary system and sex hormones | conjugate either or both components at either or both OH groups |
| Fluprednidene acetate + Miconazole nitrate | DECODERM ® TRI CREAM | dermatological | Fluprednidene, either or both OH groups |
| Flurandrenolide USP | CORDRAN ® | dermatological | either or both OH groups |
| Flurbiprofen | CEBUTID ® | musculoskeletal system | acid |
| Gelatin powder + Biotin | GELACET PULVER ® | alimentary tract and metabolism | Biotin at acid and/or possible NH |
| Gentamicin sulfate | REFOBACIN ® | dermatological | any 1, 2, or 3 OH groups and/or any 1, 2, 3, or 4 $NH_2$ groups and/or one NH group |
| Ginko biloba + Coenzyme Q10 + Vitamin B2 + Commiphora mirra | CLEVIA ® | alimentary tract and metabolism | Vitamin $B_2$, NH and/or any 1, 2, 3, or 4 OH groups |
| Glucosamine | CODEROL ® | musculoskeletal system | $NH_2$ and/or any 1, 2, 3, or 4 OH groups |
| Hyaluronic acid + Hop extract + Liposomes + Vitamin E | GYNOMUNAL ® | genitourinary system and sex hormones | vitamin E via the OH group |
| Hydrocortisone + Urea | HYDRODEXAN ® | dermatological | any 1, 2, or 3 OH groups |
| Hydrocortisone acetate | | dermatological | either or both OH groups |
| Hydrocortisone butyrate | LATICORT ® | dermatological | either or both OH groups |
| Ibrutinib | IMBRUVICA ® | B cell cancers | $NH_2$ |
| Ingenol mebutate | PICATO ® | topical treatment of actinic keratosis. | any 1, 2, or 3 OH groups |
| Isotretinoin | AKNENORMIN ® | dermatological | at its acid |
| Lorazepam | SERENASE ® | nervous system | OH and/or NH |
| Meptazinol | MEPTID ® | nervous system | OH |
| Methocarbamol | ROBAXIN ® | musculoskeletal system | OH and/or via the carbamate |
| Minocycline | AKNEMIN ® | anti-infective for systemic use | any 1, 2, 3, 4, or 5 OH groups and/or at the amide |
| Mometasone furoate | IVOXEL ® | dermatological | OH |
| Mupirocin | MUPIDERM ® | dermatological | any 1, 2, or 3 OH groups and/or at COOH |
| Naproxen sodium salt | SYNFLEX ® | musculoskeletal system | COOH |
| Nifuratel + Nystatin | DAFNEGIL ® | genitourinary system and sex hormones | nystatin, COOH and/or $NH_2$, and/or any 1, 2, 3, 4, 5, 6, 7, 8, 9, or 10 OH groups |
| Noretisterone | ELASTOLABO ® | genitourinary system and sex hormones | OH |
| Nystatin | CANDIO-HERMAL ® | dermatological | COOH and/or $NH_2$, and/or any 1, 2, 3, 4, 5, 6, 7, 8, 9, or 10 OH groups |

TABLE 1-continued

| Therapeutic agent(s) | Example Brand Name(s) | Therapeutic Use(s) | Conjugation Options |
| --- | --- | --- | --- |
| Octopirox | MYFUNGAR ® | dermatological | N-OH moiety |
| Paracetamol | FEBRECTAL ® | nervous system | Paracetamol (acetaminophen), NH and/or OH |
| Paracetamol + Codein + Ascorbic acid | ALGIDOL ® | nervous system | Paracetamol, OH and/or NH; codeine, OH; ascorbic acid, any 1, 2, 3, or 4 OH groups |
| Phenol-methanal-urea polycondensate | TANNOSYNT LOTION ® | dermatological | OH of phenol |
| Pidotimod | POLIMOD ® | immunostimulant | acid and/or the amide |
| Piketoprofen | CALMATEL ® | musculoskeletal system | NH |
| Piracetam | METADIEMIL ® | cardiovascular system, nervous system | $NH_2$ |
| Piroctone olamine + Climbazol | LYGAL DUO ® | dermatological | N-OH |
| Potassium azeloyl diglycinate + Vitamin E + Hydroxypropyl chitosan | ROZERO ® | dermatological | Potassium azeloyl diglycinate via either or both acid groups; vitamin E via the OH group |
| Prednisolon + Piroctone olamine | LYGAL ® | dermatological | Prednisolon, any 1, 2, or 3 OH groups; piroctone, N-OH |
| Pyrithion-zink | DE-SQUAMAN HERMAL ® | dermatological | conjugate via the SH or OH form |
| Retapamulin | ALTABAX ® | dermatological | OH |
| Retinol (Vitamin A) | GELACET ® | alimentary tract and metabolism | OH |
| Rosuvastatin | CRESTOR ® | cardiovascular system | COOH and/or either or both of two OH groups |
| Salicyclic acid | SPEELAC ® | anti-acne | acid and/or at OH group |
| Salicylic acid; Sodium lactate; Glycerine; Titanium dioxide; Triclosan; E.D.T.A./ Codex; Basil extract; Mint Oil/Menthol; Tea tree oil; Olive oil/Oleivem | SOTRET ® SOAP | anti-acne | Salicyclic acid, the acid and/or at the OH group |
| Sarecycline | SEYSARA ® | dermatological | any 1, 2, 3, or 4 OH groups and/or COOH |
| Silodosin | SILODYX ® | genitourinary system and sex hormones | OH and/or NH and/or $NH_2$ |
| Sitagliptin | TESAVEL ® | alimentary tract and metabolism | $NH_2$ |
| Sitagliptin + Metformin | EFFICIB ® | alimentary tract and metabolism | Sitagliptin, $NH_2$; metformin, NH and/or $NH_2$ |
| Sorafenib tosylate | | anti-cancer | urea |
| Sulfamethoxazole | SOLTRIM ® | anti-infective for systemic use | $NH_2$ and/or NH |
| Tacalcitol | CURATODERM ® | dermatological | any 1, 2, or 3 OH groups |
| Tacrolimus | PROTOPIC ® | severe atopic dermatitis | any 1, 2, or 3 OH groups |
| Tannic acid | TANNO-HERMAL ® | dermatological | conjugate to any OH group or combination of OH groups |
| Tazoretene | TAZORAC ® | dermatological | by replacing ethy ester with a cannabinoid ester |
| Tolterodine 1-tartrate | UROTROL ® | genitourinary system and sex hormones | OH |
| Triamterene | PRESTOLE ® | cardiovascular system | any 1, 2, or 3 $NH_2$ groups |
| Ucp peptide | THIOMUCASE ® | dermatological | $NH_2$ |
| Urea | AQEO ® | dermatological | $NH_2$ |
| Urea + Lauromacrogols | BALNEUM ® LOTION | dermatological | Urea, at $NH_2$ |
| Urea + Polidocanol | OPTIDERM ® CRÈME | dermatological | $NH_2$ |
| Urea + Sodium laureth | BALNEUM INTENSIV ® | dermatological | Urea, at $NH_2$ |
| Venlafaxine hydrochloride | DOBUPAL ® | nervous system | OH |
| Vitamin B1 + Vitamin B6 + Vitamin B12 | HIDROXIL ® | alimentary tract and metabolism | Vitamin B1, OH and/or $NH_2$; vitamin B6, OH and/or P-OH |
| Vitamin C | FEMINELLA VAGI C ® | genitourinary system and sex hormones | any 1, 2, 3, or 4 OH groups |
| Xanthinol furosemide + Triamterene | SALIDUR ® | cardiovascular system | Furosemide, conjugate via the acid and/or the NH and/or $NH_2$ groups; Triamterene, any 1, 2, or 3 $NH_2$ groups |
| Acamprosate calcium | ACAMPROL ® | Neurology and Psychiatry | S-OH or NH |
| Entacapone | ADCAPONE ® | Neurology and Psychiatry | OH |
| Methyl phenidate hydrochloride vsp | ADDWIZE ® | Neurology and Psychiatry | NH |
| S-Adenosyl methionine | ADESAM ® | Neurology and Psychiatry | OH and/or acid and/or one or both $NH_2$ |
| Adefovir | ADHEB ® | Anti-viral | Conjugate as phosphate cannabinoid ester |
| Adefovir dipivoxil | ADFOVIR ® | Infections | Conjugate as phosphate cannabinoid ester |
| Memantine hydrochloride | ADMENTA ® | Neurology and Psychiatry | $NH_2$ |

TABLE 1-continued

| Therapeutic agent(s) | Example Brand Name(s) | Therapeutic Use(s) | Conjugation Options |
|---|---|---|---|
| Doxorubicin hydrochloride | ADVADOX ® | Anti-cancer | any of 1, 2, 3, 4, or 5 OH and/or the $NH_2$ |
| Epalrestat | ALDORACE ® | Diabetc neuropathy | to acid |
| Fexofenadine | ALTIVA ® | Anti-histamine | either or both OH or to acid |
| Amisulpride | AMIVAL ® | Anti-psychotic | $NH_2$ or NH |
| Amitriptyline ip, Chloridiazepoxide ip | AMIXIDE ® | Neurology and Psychiatry | chloridiazepoxide, to NH |
| Amlodipine, Atenolol ip | AMLOBET ® | Cardiology | Amlodipine, $NH_2$; atenolol, OH and/or NH and/or $NH_2$ |
| Amlodipine | AMLOSUN ® | Cardiology | $NH_2$ |
| Bicalutamide | ANDROBLOK ® | Cancer | OH |
| Oxazepam | ANXOZAP ® | Neurology and Psychiatry | OH |
| Hydrolchlorothiazide ip | AQUAZIDE ® | Cardiology | NH or $NH_2$ |
| Aripiprazole | ARPIZOL ® | Neurology and Psychiatry | NH |
| Atomoxetine | ATTENTROL ® | Neurology and Psychiatry | NH |
| Atorvastatin | AZTOR ® | Cardiology | either of both OH groups and/or COOH and/or NH groups |
| Atorvastatin, Aspirin ip | AZTOR ® | Cardiology | Atorvastatin, either or both of two OH groups and/or COOH and/or NH groups |
| Atorvastatin, Ezetimibe | AZTOR ® | Cardiology | Atorvastatin, either or both of two OH groups and/or COOH and/or NH groups |
| Mycophenolate | BAXMUNE ® | Immunosupressant | OH or COOH |
| Propranolol hydrochloride Ip | BETACAP ® | Neurology and Psychiatry | OH or NH |
| Propranolol hydrochloride Ip, Flunarizine | BETACAP ® PLUS | Neurology and Psychiatry | Propanolol, OH or NH |
| Nifedipine usp, Atenolol bp | BETATROP ® | Cardiology | Nifedipine, NH or replace a methyl ester with a cannabinoid ester; atenolol, OH and/or NH and/or $NH_2$ |
| Betahistine hydrochloride | BETAVERT ® | Nausea | NH |
| Brimonidine tartrate, Timolol, Benzalkonium chloride | BRIMOLOL ® | Opthalmology | Brimonidine, NH; timolol, NH and/or OH |
| Brimonidine tartrate, Oxychloro complex | BRIMOSUN ® | Opthalmology | Brimonidine, NH |
| Brimonidine tartrate | BRIMOSUN ®-P | Opthalmology | NH |
| Bortezomib | VELCADE ® | multiple myeloma and mantle cell lymphoma | NH or link as a borate ester. |
| Paclitaxel | ABRAXANE ® | lung, ovarian, and breast cancer, Kaposi sarcoma | any OH and/or any NH |
| Docetaxel | DOCEFREZ ®, TAXOTERE ® | breast, lung, prostate, stomach, and head and neck cancer | any OH and/or any NH |
| Efavirenz | SUSTIVA ® | HIV | NH |
| Irinotecan | ONIVYDE ®, CAMPTOSAR ® | cancer of the colon or rectum | OH |
| Tenofovir | VEMLIDY ®, VIREAD ® | hepatitis B and HIV infection | link by making a cannabinoid phosphonate ester prodrug |
| Lopinavir | KALETRA ® | HIV | OH and/or any 1, 2, or 3 NH |
| Ritonavir | | | OH and/or either or both NH |
| Lamivudine | EPIVIR ® HBV, EPIVIR ® | hepatitis B and HIV | OH and/or $NH_2$ |
| Zidovudine | RETROVIR ® | HIV | OH and/or NH |
| Nevirapine | VIRAMUNE ® XR, VIRAMUNE ® | HIV | NH |
| Ganciclovir | ZIRGAN ® | cytomegalovirus | either or both OH and/or $NH_2$ |
| Valacyclovir | VALTREX ® | herpes, chicken pox | either or both $NH_2$ |
| Ledipasvir | HARVONI ® (w/ sofubusvir) | hepatitis C | any or all NH |
| Valganciclovir | VALCYTE | cytomegalovirus | OH and/or either or both $NH_2$ |

Type I-C Conjugate Molecules

The cannabinoid conjugate component in a Type I-C conjugate molecule is a "β-lactam antibiotic cannabinoid conjugate component," in which a β-lactam antibiotic component is covalently attached to hydroxy group or a carboxylic acid group of a cannabinoid component via a Type I-C linker.

A "β-lactam antibiotic" as used in this disclosure is molecule that contains a 4-membered lactam ring (β-lactam) and that has antibacterial activity. A "β-lactam antibiotic component" as used in this disclosure is that portion of the β-lactam antibiotic that is present in the β-lactam antibiotic cannabinoid conjugate component and covalently attached to the linker.

In some embodiments, the β-lactam antibiotic component is covalently attached at its 3 position to the cannabinoid conjugate component Type I-C linker. In some of these embodiments, the β-lactam antibiotic component is a cephem component. In some of these embodiments, the β-lactam antibiotic component is a carbacephem component. In some of these embodiments, the β-lactam antibiotic component is a penem component. In some of these embodiments, the β-lactam antibiotic component is a carbapenem component.

In some embodiments, the β-lactam antibiotic component is a monobactam component covalently attached at its 2 position to the first cannabinoid component Type I-C linker.

A number of β-lactam antibiotics can be used to provide the β-lactam antibiotic component.

Cephems and Carbacephems

In some embodiments, the β-lactam antibiotic component is a cephem component. As used in this disclosure, a "cephem component" is a cephem in which the substituent ordinarily present at the 3 position of the molecule is not present, as illustrated below:

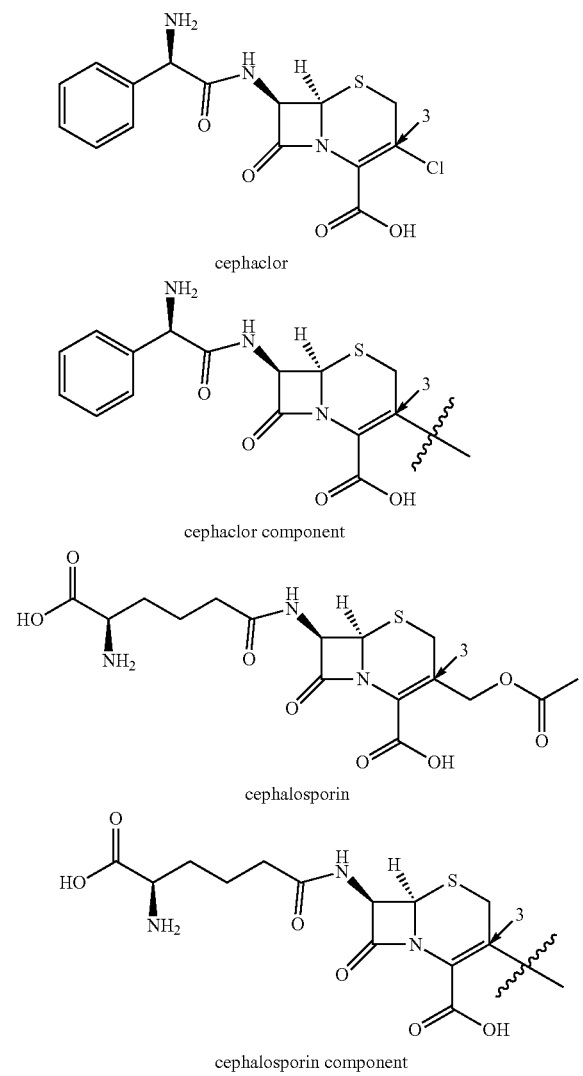

dinir, cefcapene, cefdaloxime, ceftizoxime, cefminoxime, cefotaxime, cefpiramide, cefpodoxime, ceftibuten, cefditoren, cefetamet, cefodizime, cefpimizole, cefsulodin, cefteram ceftiolene, flomoxef, latamoxef, cefepime, cefozopran, cefpirome, cefquinome, ceftaroline fosamil, ceftolozane, ceftobiprole, ceftiofur, cefquinome, and cefovecin. See also, for example, U.S. Pat. Nos. 9,751,894; 7,696,354; 6,150,351.

In some embodiments, the β-lactam antibiotic component is a carbacephem component. As used in this disclosure, a "carbacephem component" is a carbacephem in which the substituent ordinarily present at the 3 position of the molecule is not present, as illustrated below:

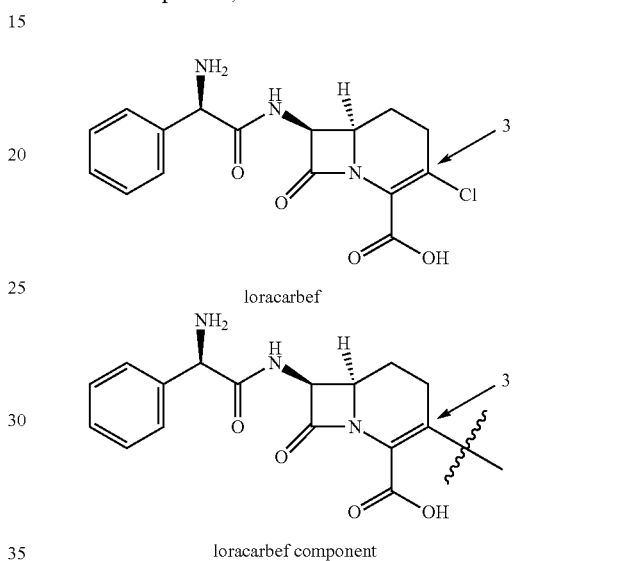

Carbacephems include, but are not limited to, loracarbef. See also, for example, U.S. Pat. Nos. 8,445,476, 4,980,348.

In some embodiments the β-lactam antibiotic component falls within structural Formula (A):

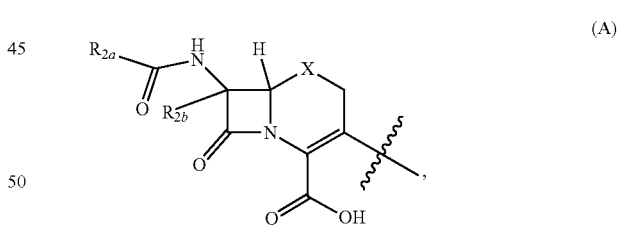

in which X is S, C, or O; $R_{2a}$ is a side chain of a first cephem or a side chain of a first carbacephem; and $R_{2b}$ is H or —OCH$_3$. Cephem side chains include, for example:

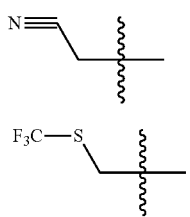

A cephem component can be provided by any of a variety of cephems including, but not limited to, cefazolin, cephalexin, cefadroxil, cefapirin, cefazedone, cefazaflur, cefradine, cefroxadine, ceftezole, cefaloglycin, cephacetrile, cefalonium, cefaloridine, cefalotin, cefatrizine, cefaclor, cefotetan, cephamycin, cefoxitin, cefprozil, cefuorixime, cefuroxime axetil, cefamandole, cefminox, cefonicid, ceforanide, cefotiam, cefbuperazone, cefuzonam, cefmetazole, cefixime, ceftriaxzone, ceftazidime, cefoperazone, cef-

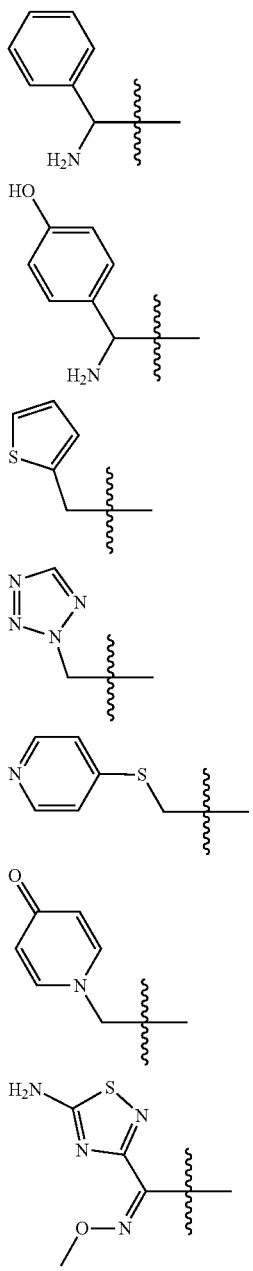

Carbacephem side chains include, for example,

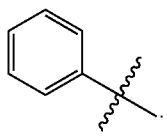

Penems and Carbapenems

In some embodiments, the β-lactam antibiotic component is a penem component. As used in this disclosure, a "penem component" is a penem in which the substituent ordinarily present at the 3 position of the molecule is not present, as illustrated below:

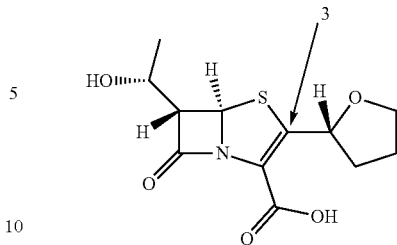

faropenem

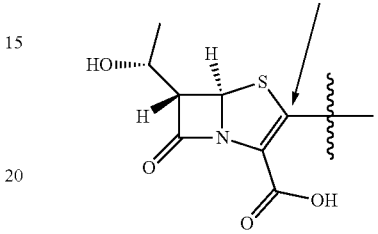

faropenem component

Penems include, but are not limited to, faropenem and ritipenem. See also U.S. Pat. Nos. 6,271,222; 5,757,583.

In other embodiments, the β-lactam antibiotic component is a carbapenem component. As used in this disclosure, a "carbapenem component" is a carbapenem in which the substituent ordinarily present at the 3 position of the molecule is not present, as illustrated below:

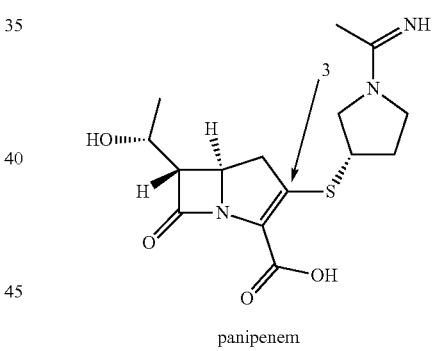

panipenem

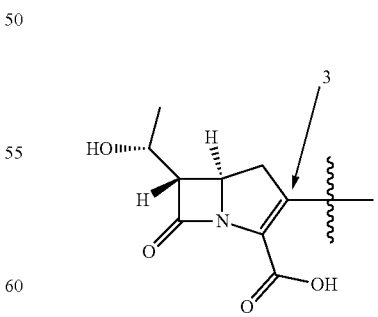

panipenem component

Carbapenems include, but are not limited to, ertapenem, doripenem, imipenem, meropenem, biapenem, and panipenem. See also U.S. Pat. Nos. 9,937,151; 8,318,716.

In some embodiments the β-lactam antibiotic component falls within structural Formula (B):

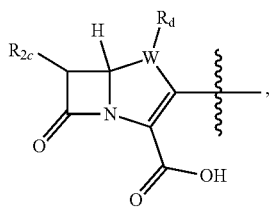

(B)

in which W is S or C; and $R_{2c}$ is a side chain of a first penem or a side chain of a first carbapenem; and when W is C, $R_{2a}$ is H, —$CH_3$, or phenyl, wherein the phenyl is optionally substituted with 1, 2, 3, or 4 groups independently selected from the group consisting of halide, trifluoromethyl, C1-C6 linear or branched alkyl optionally substituted with 1, 2, 3, 4, 5, 6, 7, 8, or 9 fluorine atoms, and C1-C6 linear or branched heteroalkyl containing 1, 2, or 3 atoms independently selected from O, N, and S and optionally substituted with 1, 2, 3, 4, 5, 6, 7, 8, or 9 fluorine atoms.

In some embodiments, the side chain of the penem or carbapenem is

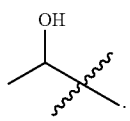 [SMILES: *C(C)O]

In some embodiments, $R_d$ is β-methyl.

Monobactams

In some embodiments, the β-lactam antibiotic component is a monobactam component. As used in this disclosure, "monobactam component" is a monobactam in which the substituent ordinarily present at the 2 position of the molecule is not present, as illustrated by the example below.

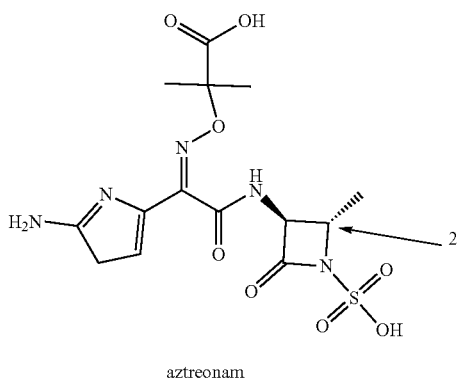

aztreonam

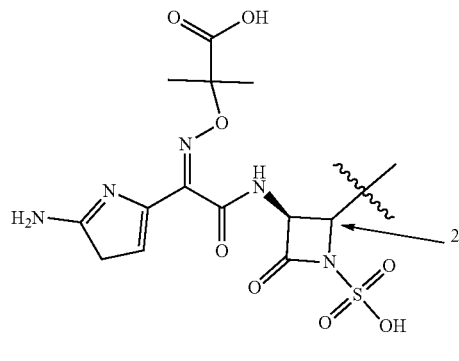

aztreonam component

Monobactams include, but are not limited to, aztreonam, tigemonam, carumonam, and nocardicin A. See also, for example, U.S. Pat. No. 9,174,978.

In some embodiments the β-lactam antibiotic component falls within structural Formula (C):

(C)

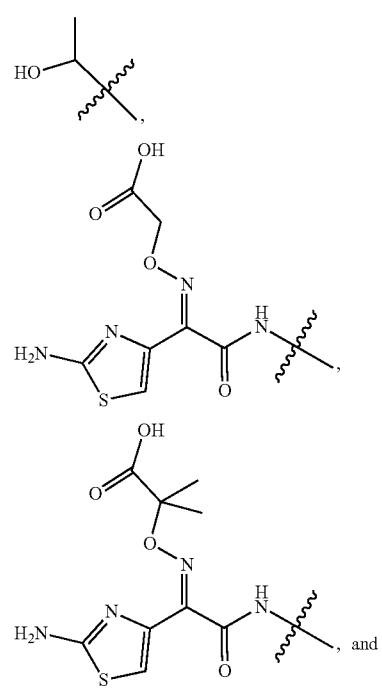

in which $R_{M3}$ is a position 3 monobactam substituent, and $R_{M1}$ is a position 1 monobactam substituent.

Examples of $R_{M3}$ include

, and

-continued

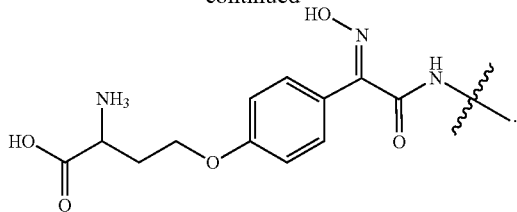

Examples of $R_{M1}$ include

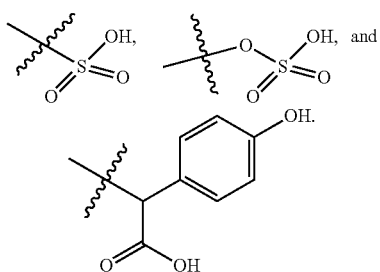

Type I-C Linkers

Type I-C linkers used to connect a β-lactam antibiotic component and a cannabinoid component are typically two to 10 atoms in length and are functionalized to facilitate release of the cannabinoid when the β-lactam antibiotic engages its biological target. When a β-lactam antibiotic component is provided by a cephem, carbacephem, penem, or carbapenem, the linker is covalently attached to the 3 position of the β-lactam antibiotic component; e.g.:

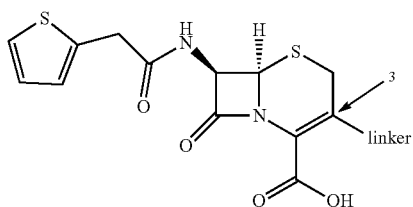

When a β-lactam antibiotic component is provided by a monobactam, the linker is covalently attached to the 2 position of the monobactam component; e.g.:

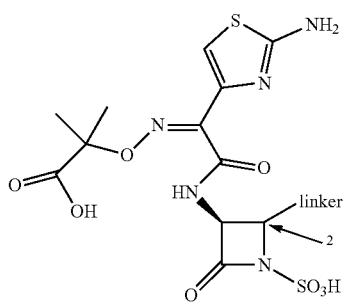

A variety of linkers can be used in Type I-C cannabinoid conjugate components, including ethers, acetals, alkenes, propenyl amines, carbamates, carbonates, xanthates, aminals, propenyl carbamates, propenyl thiocarbamates, propenyl carbonates, propenyl thiocarbonates, S-alkyl thiocarbonates, thiocarbamates, thiocarbonates, and thiohemiacetal ethers.

Figure 1:
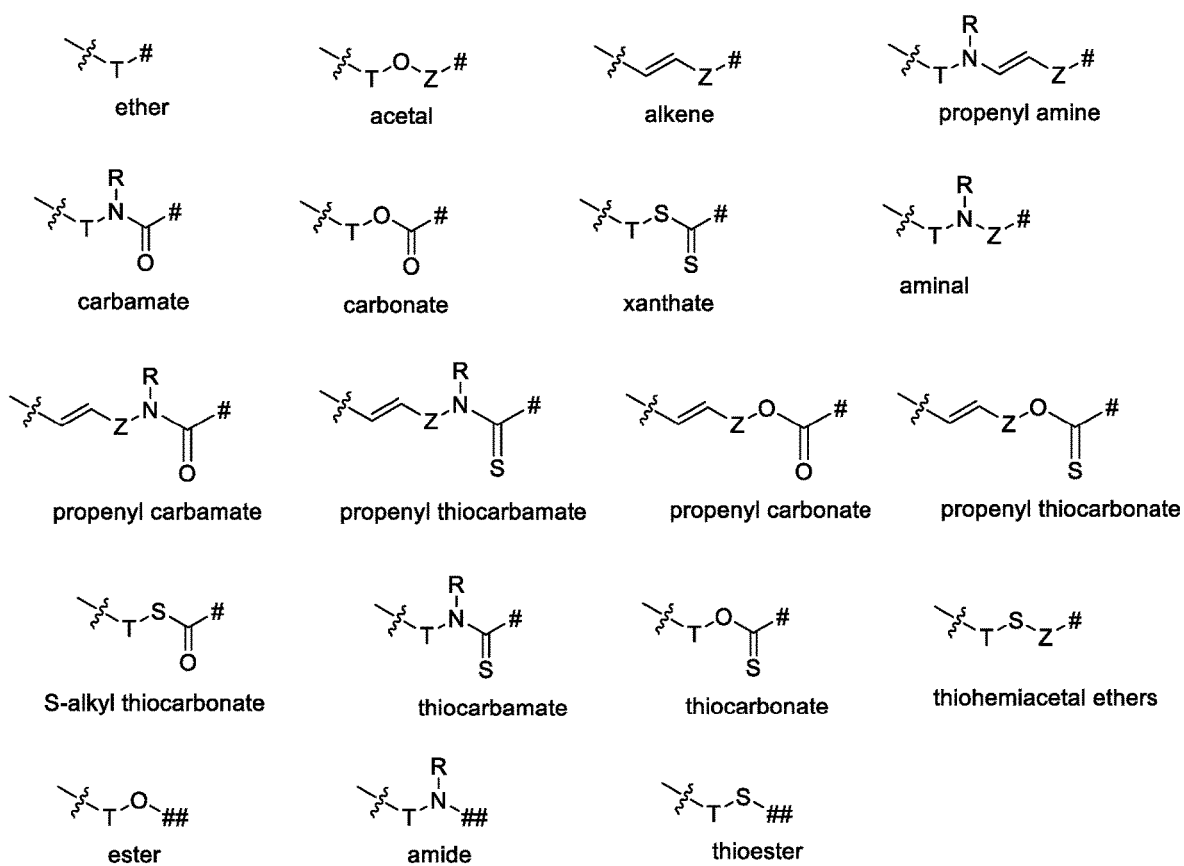
FIG. 1. Group AB Linkers, in which # indicates a site of covalent attachment to the oxygen atom from the OH of a cannabinoid component, ## in cases such as ester, amide, and thioester indicates the site of covalent attachment to the carbon atom of a carbonyl component of a carboxylic acid-bearing cannabinoid component, and  marks a bond by which the linker is covalently attached to the β-lactam antibiotic component and in which T is absent or is —CH$_2$, —CHCH$_3$, or —CH-phenyl, and Z is CR$_{1A}$R$_{2A}$; and R$_{1A}$ and R$_{2A}$ independently are R.

When a β-lactam antibiotic component is provided by a cephem, carbacephem, penem, or carbapenem, the Type I-C linker can be selected from the group of linkers shown in FIG. 1 ("Group AB Linkers").

Figure 2:
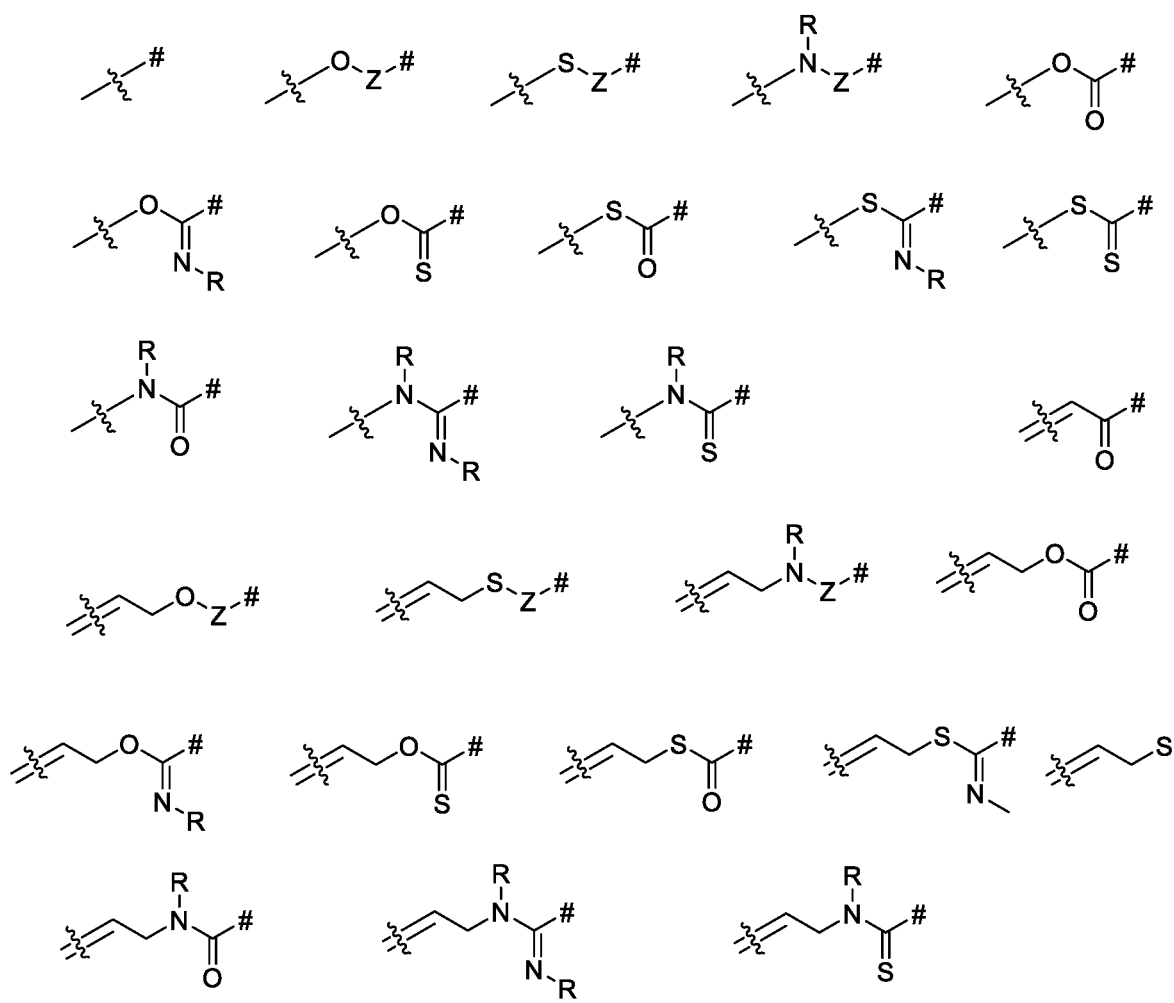
FIG. 2. Group C linkers, in which #, ##, Z, and R are as defined for Group AB linkers.

When a β-lactam antibiotic component is provided by a monobactam, the Type I-C linker by which the β-lactam antibiotic component is covalently attached to the cannabinoid component can be selected from the group of linkers shown in FIG. 2 ("Group C Linkers").

In some embodiments, in which the cannabinoid component has at least two hydroxy groups, at least one hydroxy group and at least one carboxylic acid group, or at least two carboxylic acid groups, a second β-lactam antibiotic component can be covalently attached to the second hydroxy group by means of a second linker such that the conjugate molecule contains a first β-lactam antibiotic component and a second β-lactam antibiotic component covalently attached to the cannabinoid component by means of a first linker and a second linker, respectively.

In some embodiments, the first β-lactam antibiotic component is a cephem component. In some embodiments, the first β-lactam antibiotic component is a carbacephem component. In some embodiments, the first β-lactam component is a penem component. In some embodiments, the first β-lactam component is a carbapenem component. In some embodiments, the first β-lactam component is a monobactam component. In any of these embodiments, the second β-lactam antibiotic component can be carbapenem component, a cephem component, a carbacephem component, or a monobactam component. That is, the two β-lactam antibiotic components can be the same or different, in any combination.

The first and second linkers, too, can be the same or different. In some embodiments, the first and second linkers independently are selected from Group AB linkers. In some embodiments, the first and second linkers independently are selected from Group C linkers. In some embodiments, the first linker is selected from Group AB linkers and the second linker is selected from Group C linkers.

Examples of Type I-C Cannabinoid Conjugate Components

Examples of Type I-C cannabinoid conjugate components comprising cephem, carbacephem, penem, carbapenem, and beta-methyl carbapenem components are shown below. For simplicity, the illustrated cannabinoid component is a cannabidiol component covalently linked to a single β-lactam antibiotic. In each case, "$R_{3A}$" is a side chain of a cephem or carbacephem, and "$R_{3B}$" is a side chain of a penem or carbapenem, and * indicates a point of attachment to linker $L_{cc}$.

Type I-C Cannabinoid Conjugate Components with Ether Linkages:

Cephem

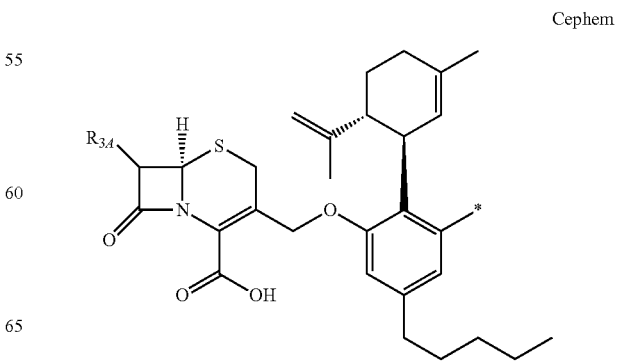

Carbacephem
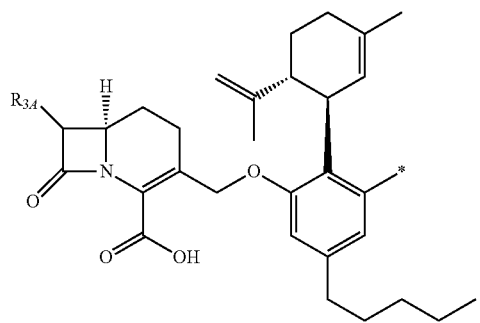
Penem
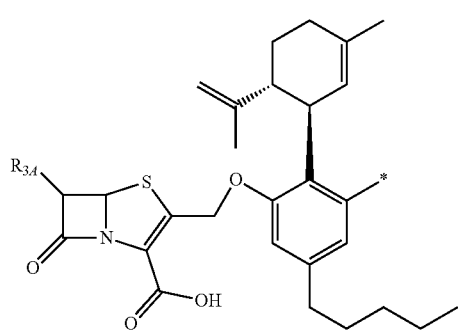
Carbapenem
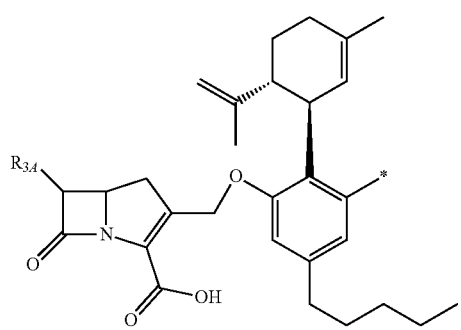
Beta-methyl Carbapenem
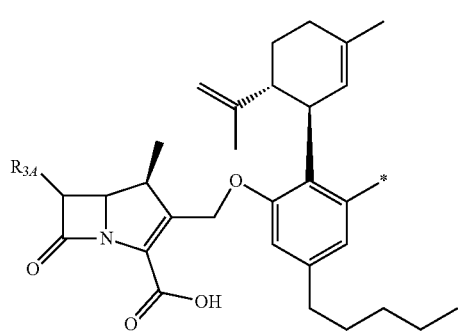
Type I-C Cannabinoid Conjugate Components with Acetal Linkages:
Cephem
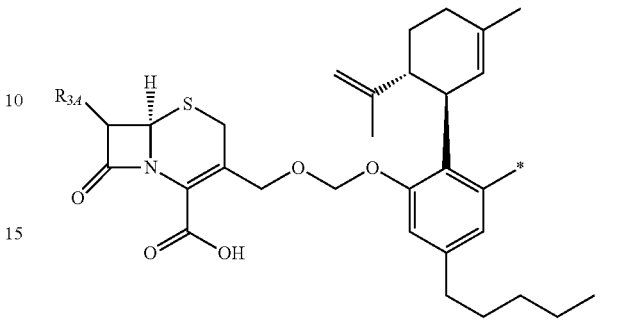
Carbacephem
Penem

Carbapenem
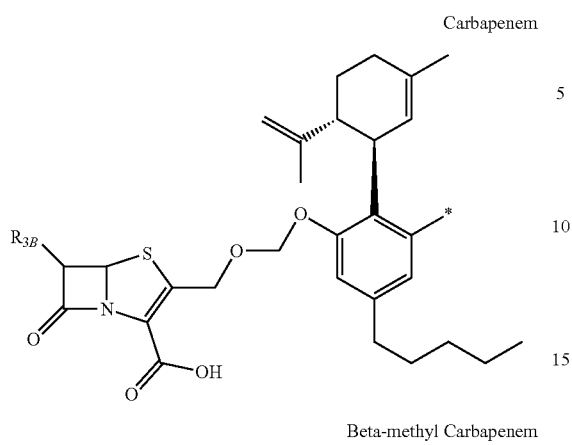
Beta-methyl Carbapenem
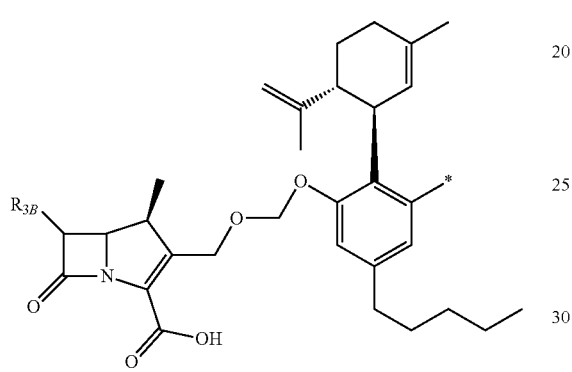
Type I-C Cannabinoid Conjugate Components with Alkene Linkages:
Cephem
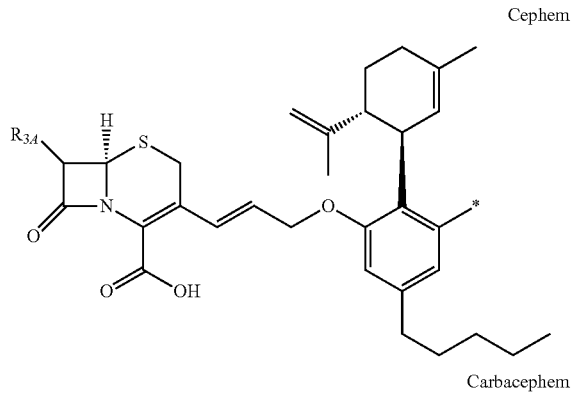
Carbacephem
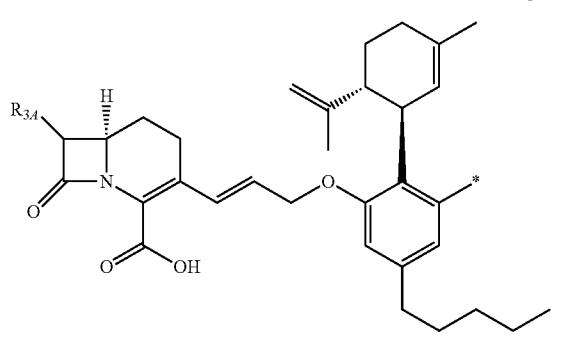
Penem
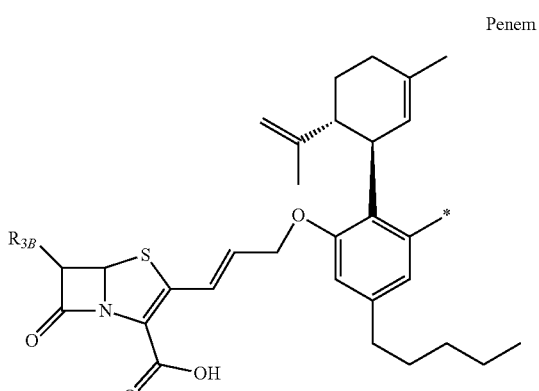
Carbacephem
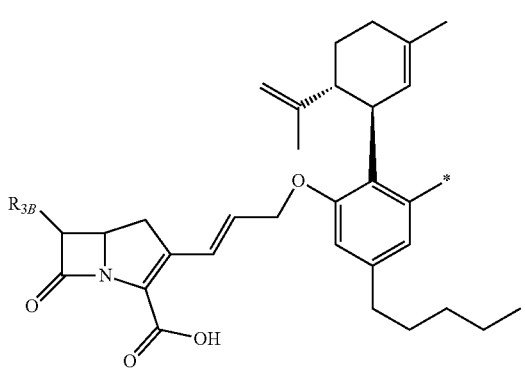
Beta-metyl Carbapenem
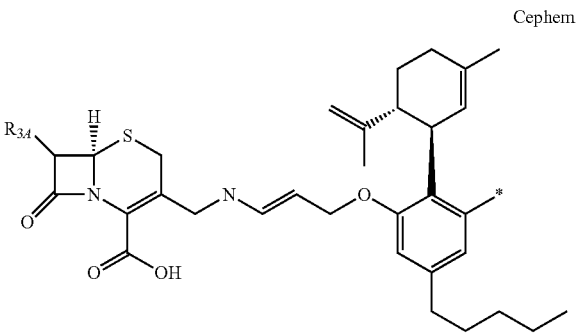
Type I-C Cannabinoid Conjugate Components with Propenyl Amine Linkages:
Cephem

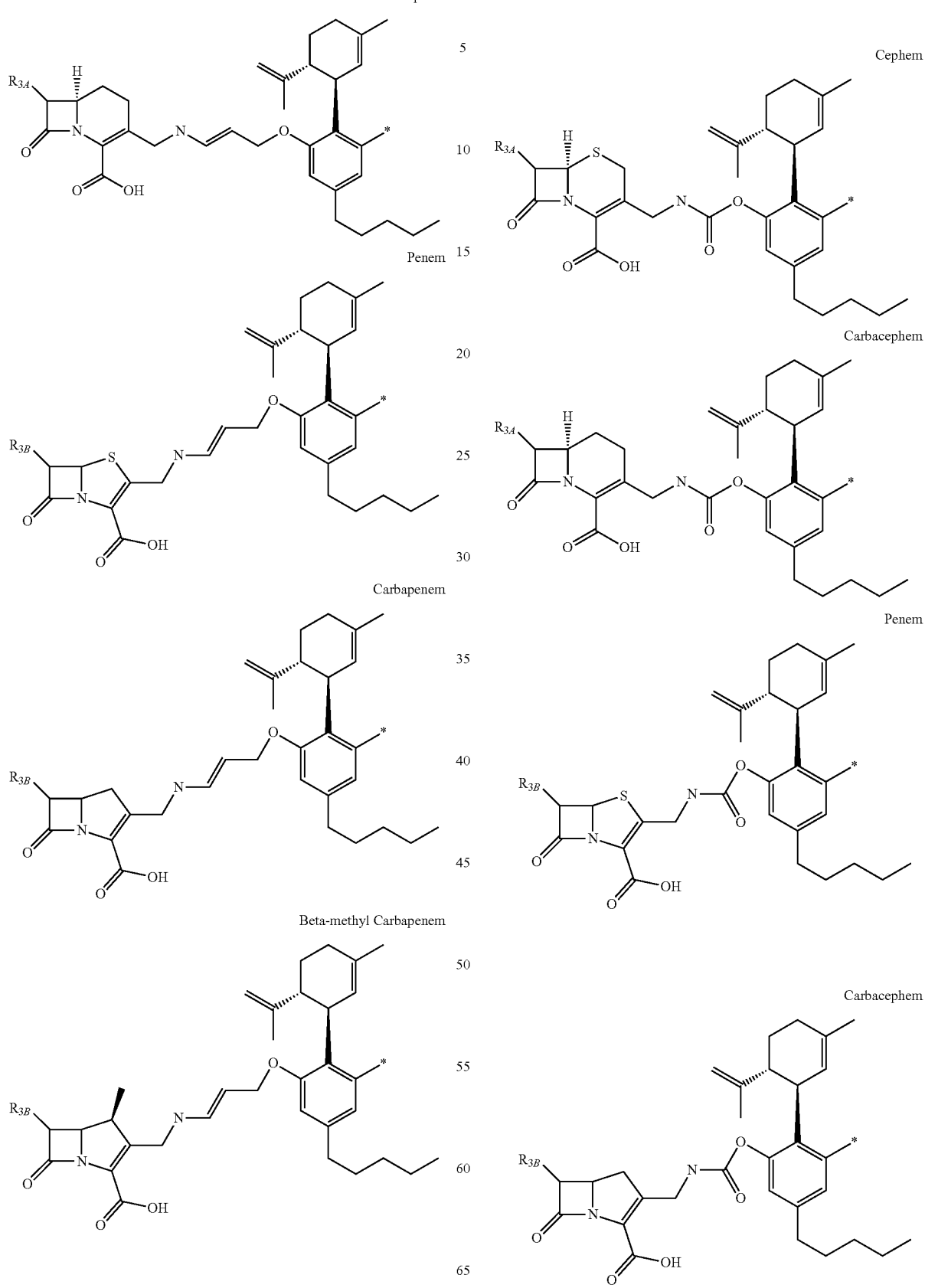
Type I-C Cannabinoid Conjugate Components with Carbamate Linkages:

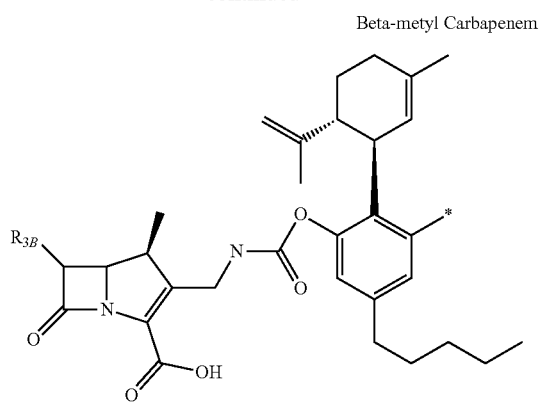
Beta-metyl Carbapenem
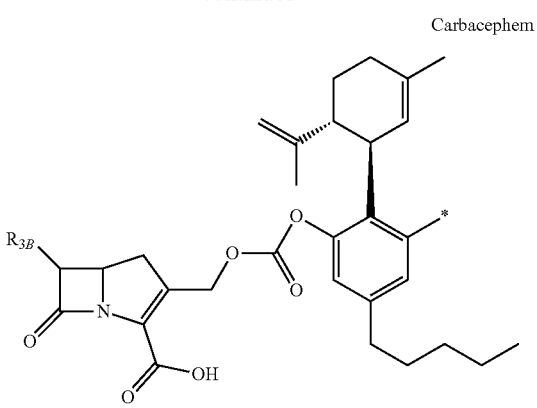
Carbacephem
Type I-C Cannabinoid Conjugate Components with Carbonate Linkages:
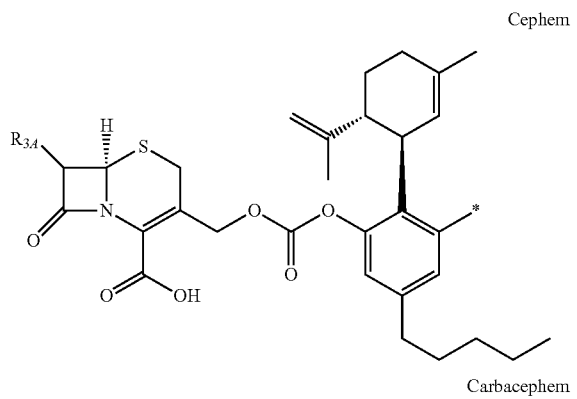
Cephem
Beta-metyl Carbapenem
Type I-C Cannabinoid Conjugate Components with Xanthate Linkages:
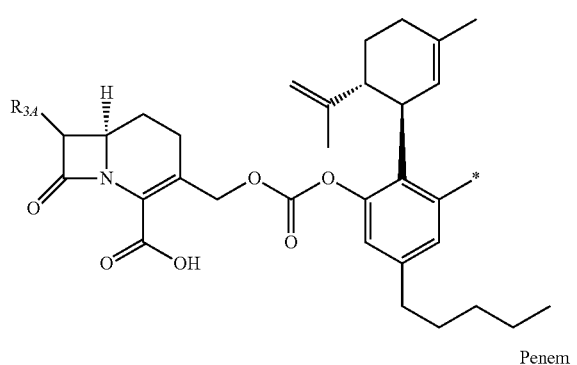
Carbacephem
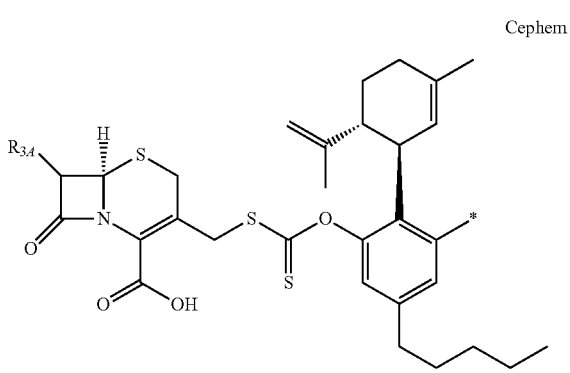
Cephem
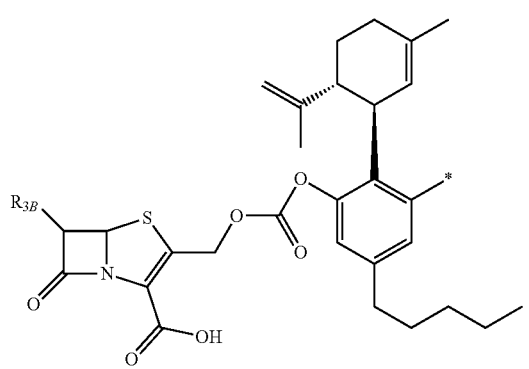
Penem
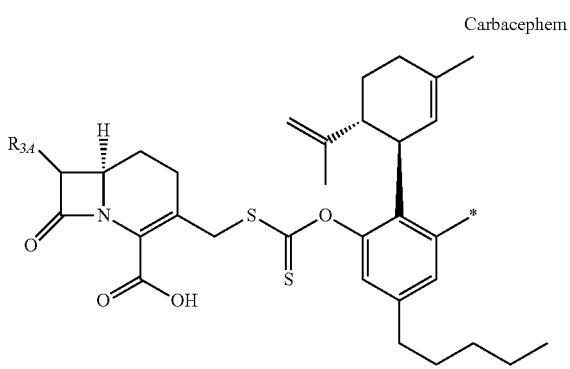
Carbacephem Penem
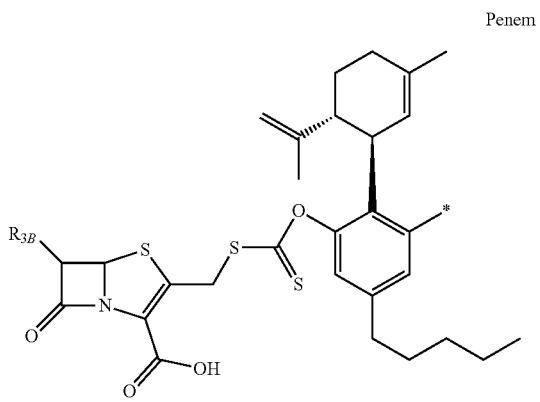
Carbacephem
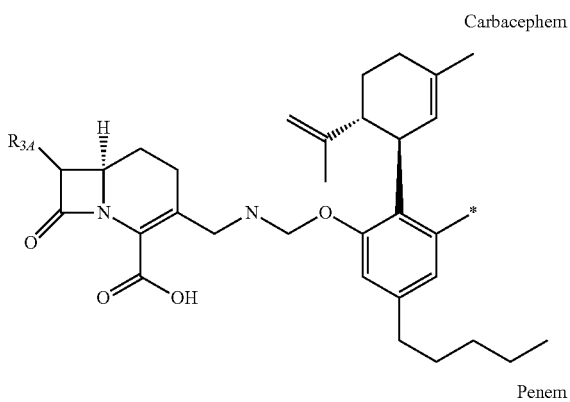
Carbacephem
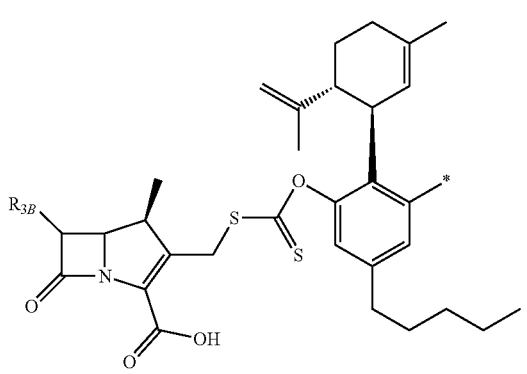
Penem
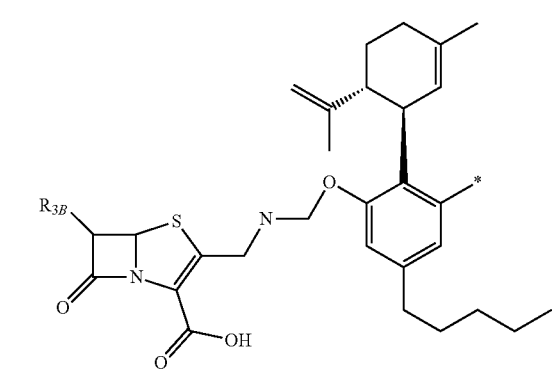
Beta-metyl Carbapenem
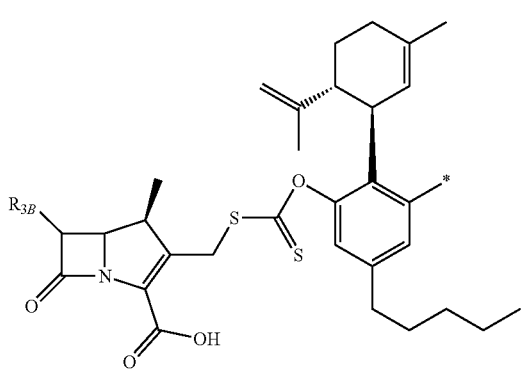
Penem
Type I-C Cannabinoid Conjugate Components with Aminal Linkages:
Cephem
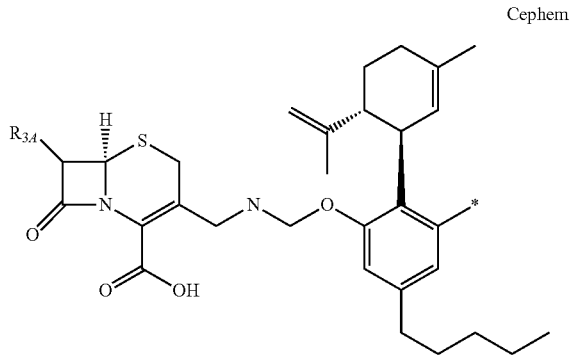
Carbapenem
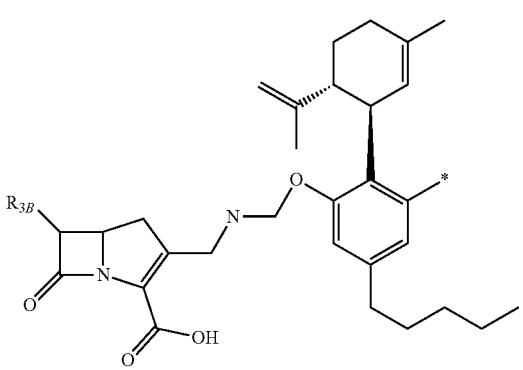

101
-continued
Penem
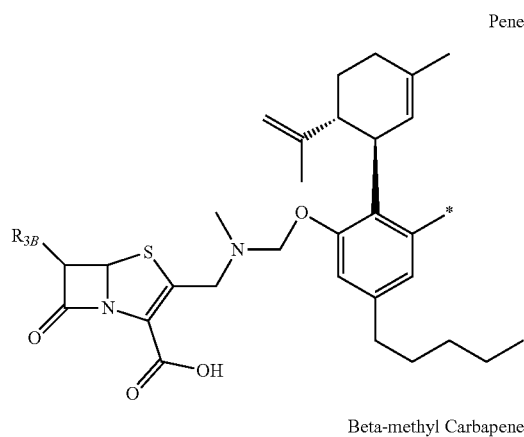
Beta-methyl Carbapenem
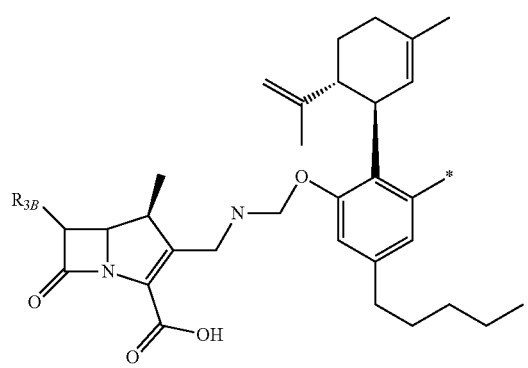
Type I-C Cannabinoid Conjugate Components with Propenyl Carbamate Linkages:
Cephem
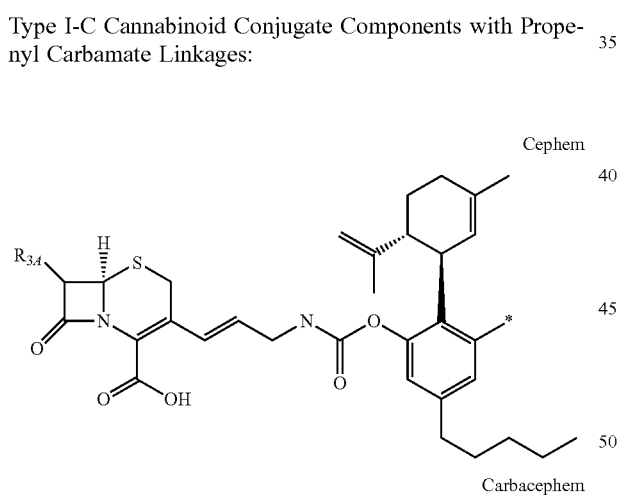
Carbacephem
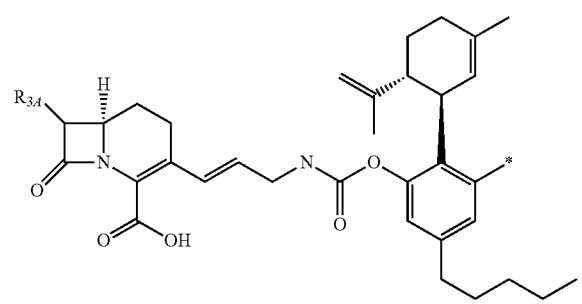
102
-continued
Penem
Carbapenem
Beta-methyl Carbapenem
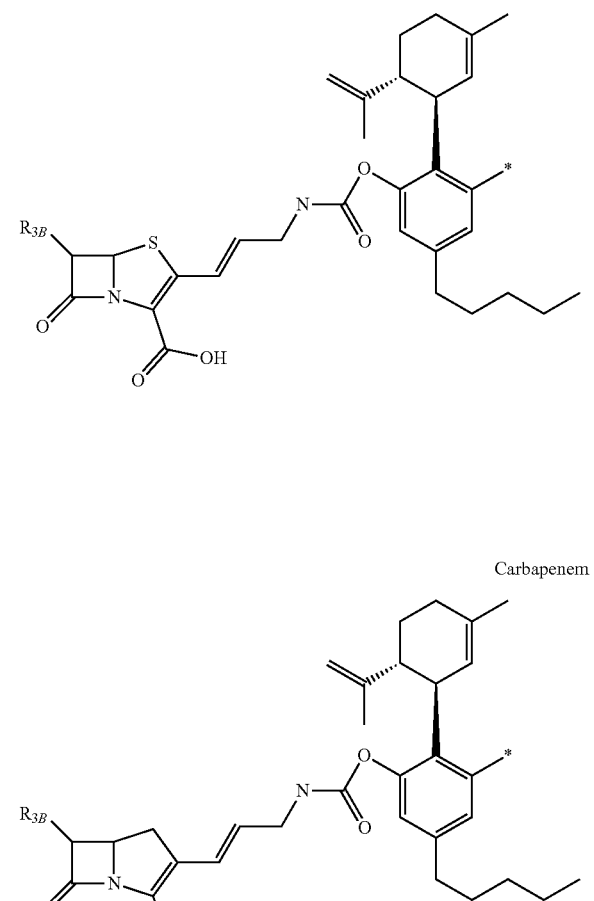
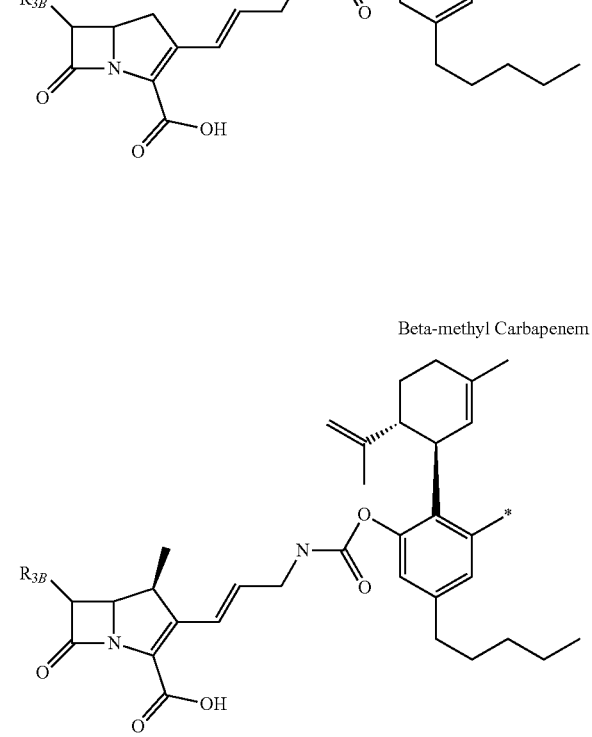
Type I-C Cannabinoid Conjugate Components with Propenyl Thiocarbamate Linkages:

Cephem
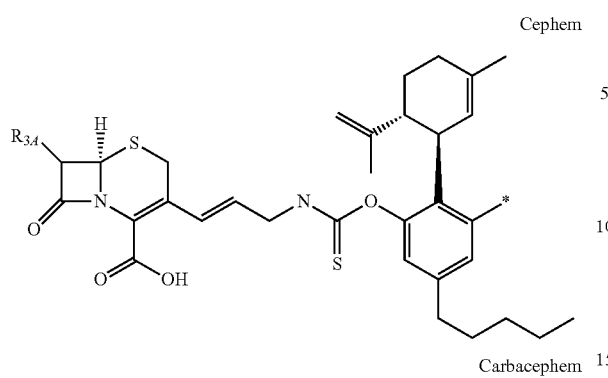
Carbacephem
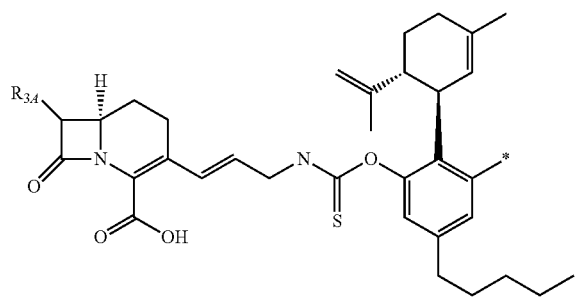
Penem
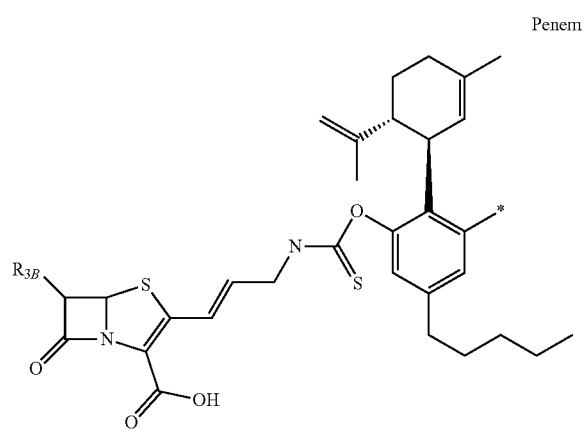
Carbapenem
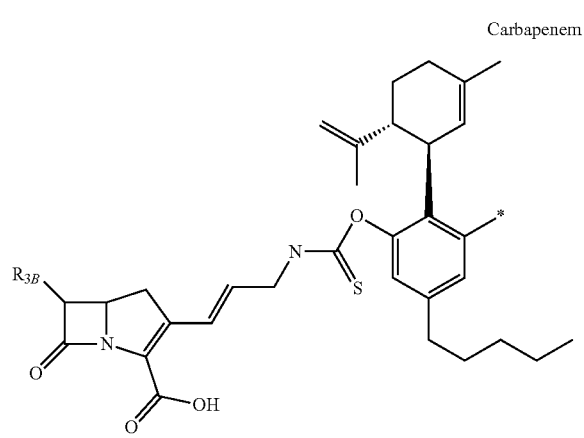
Beta-methyl Carbapenem
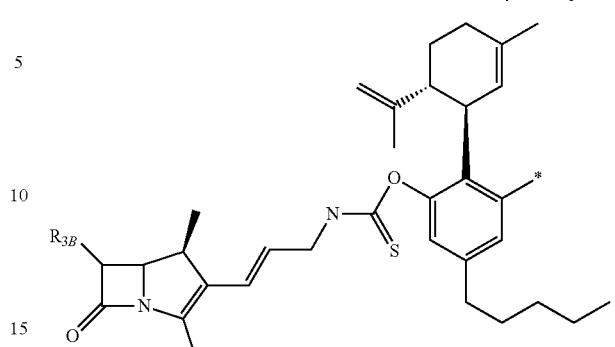
Type I-C Cannabinoid Conjugate Components with Propenyl Carbonate Linkages:
Cephem
Carbacephem
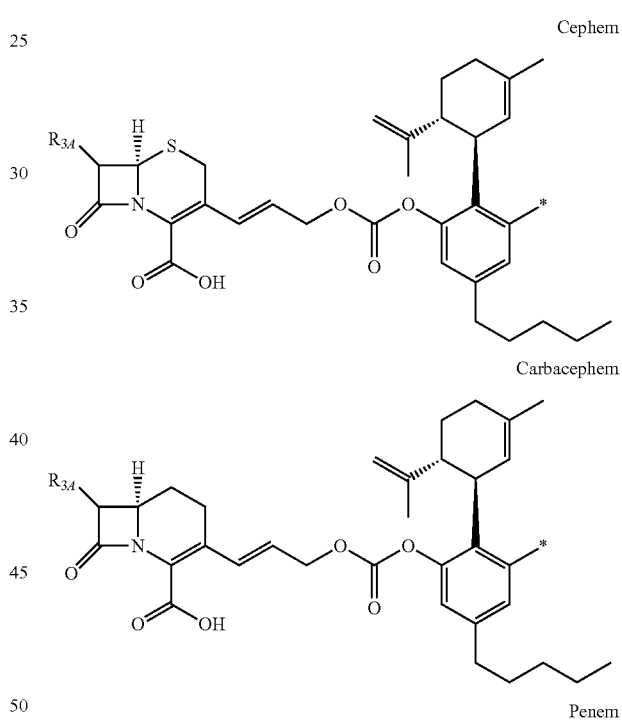
Penem
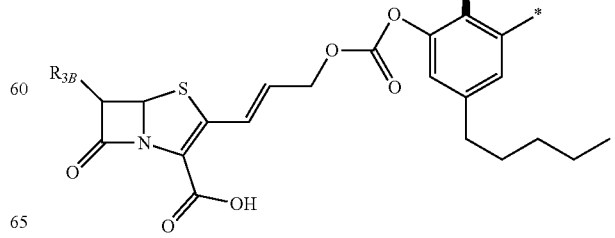

Type I-C Cannabinoid Conjugate Components with Propenyl Thiocarbonate Linkages:

Type I-C Cannabinoid Conjugate Components with Thiocarbamate Linkages:

Cephem
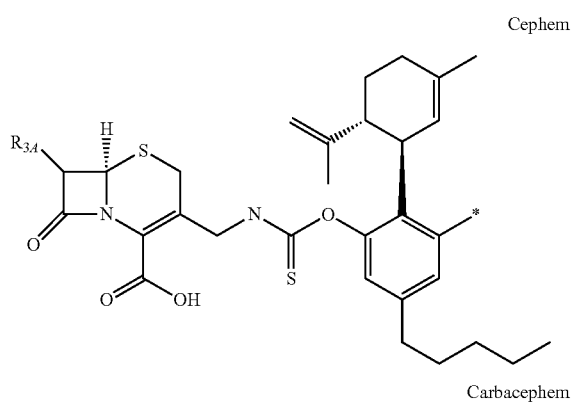
Carbacephem
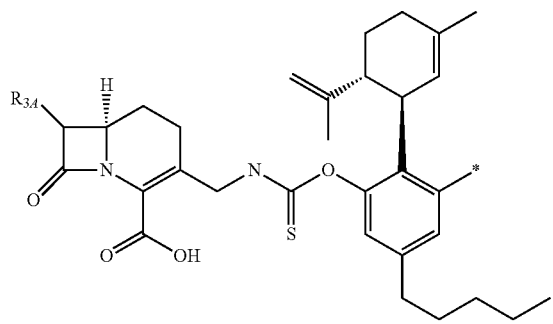
Penem
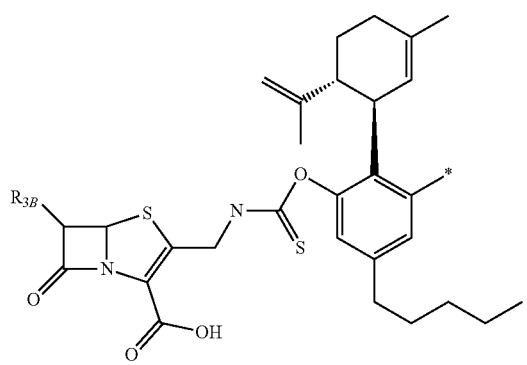
Carbapenem
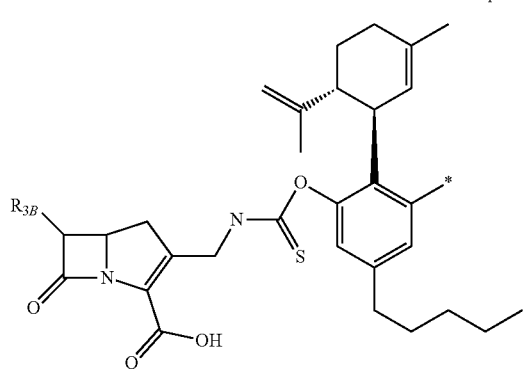
Beta-methyl Carbapenem
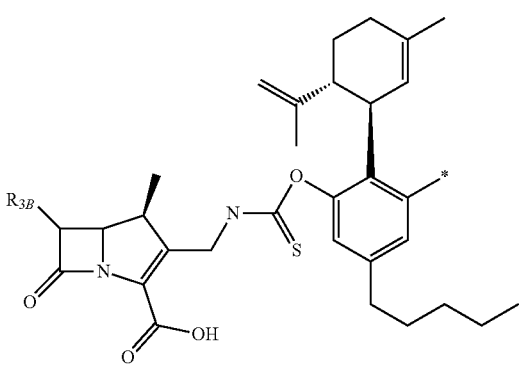
Type I-C Cannabinoid Conjugate Components with S-Alkylthiocarbonate Linkages:
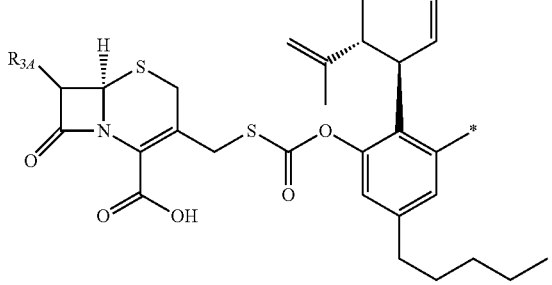
Cephem
Carbacephem
Cephem -continued
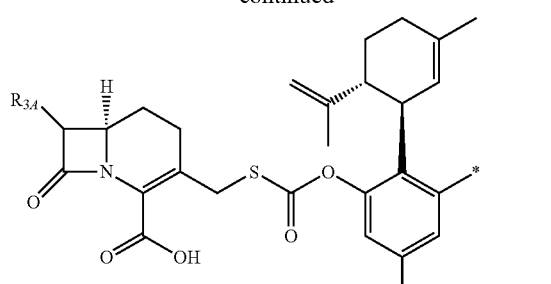
Carbacephem
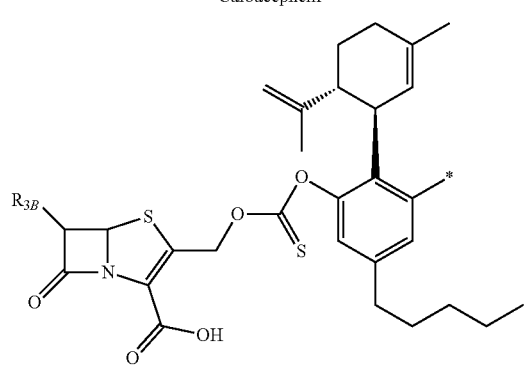
Penem
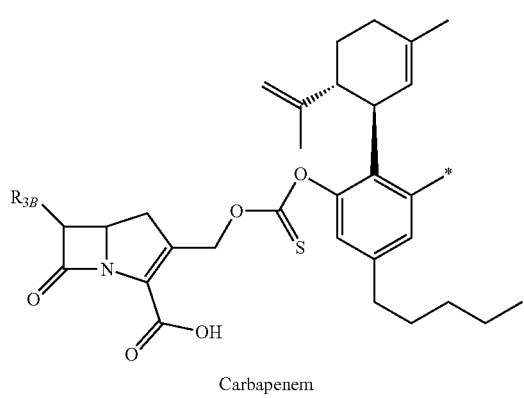
Carbapenem
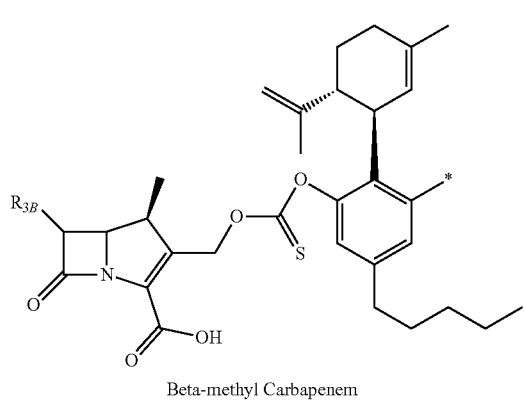
Beta-methyl Carbapenem
-continued
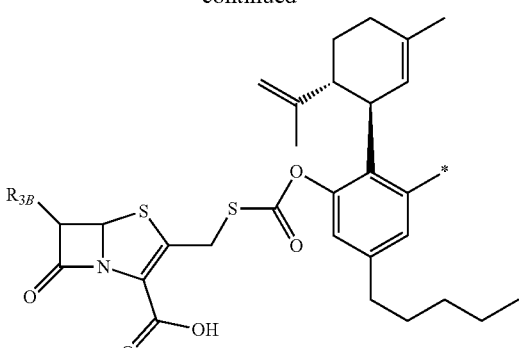
Penem
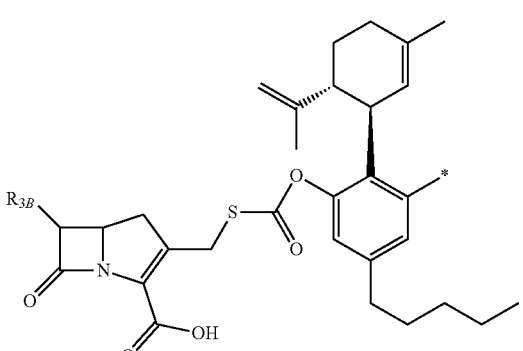
Carbapenem
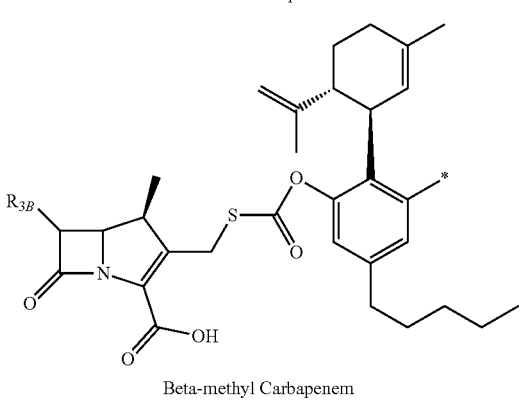
Beta-methyl Carbapenem
Type I-C Cannabinoid Conjugate Components with Thio-hemiacetal Linkages:
Cephem
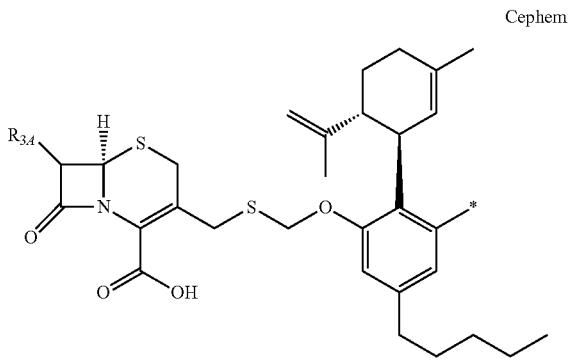

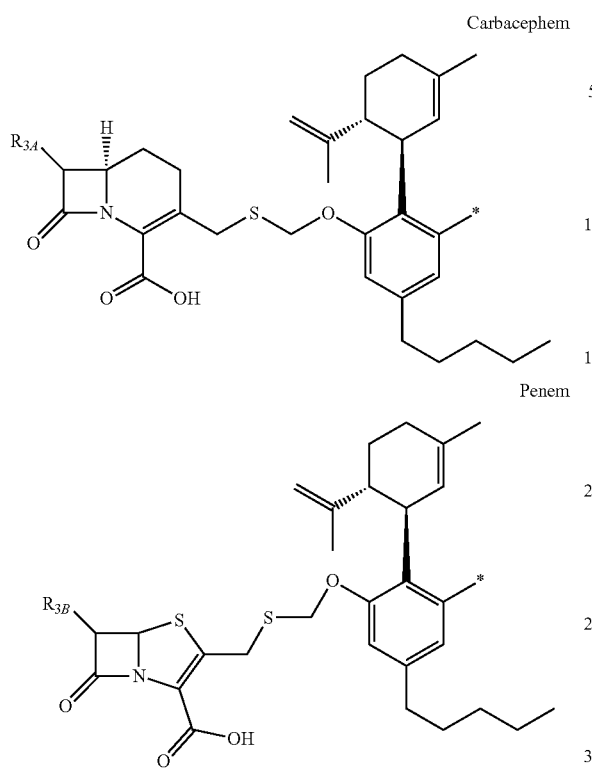
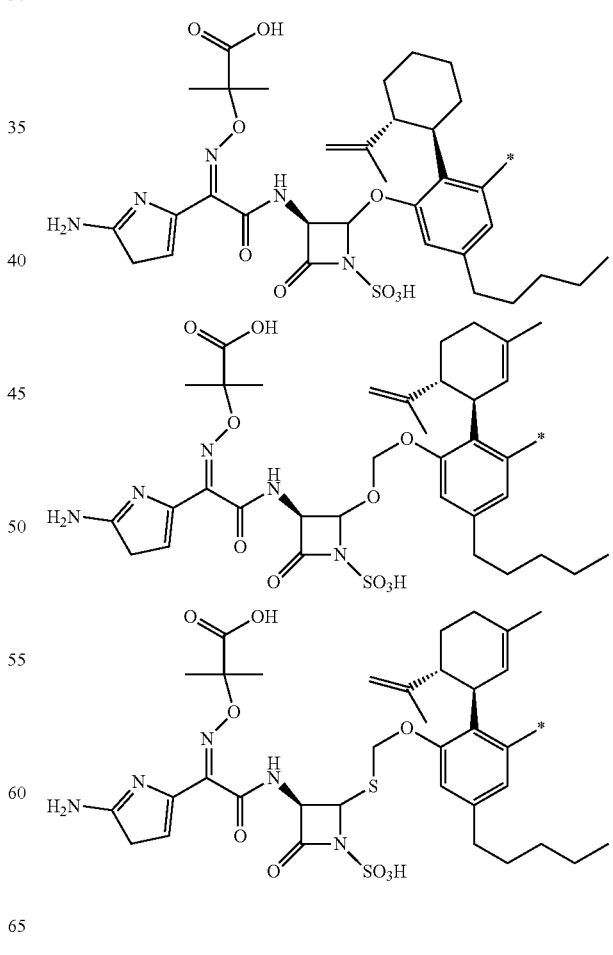
Examples of Type I-C cannabinoid conjugate components comprising a monobactam component are shown below. For simplicity, the cannabinoid component is a cannabidiol component covalently linked to a single aztreonam component, and * indicates a point of attachment to linker $L_{cc}$.

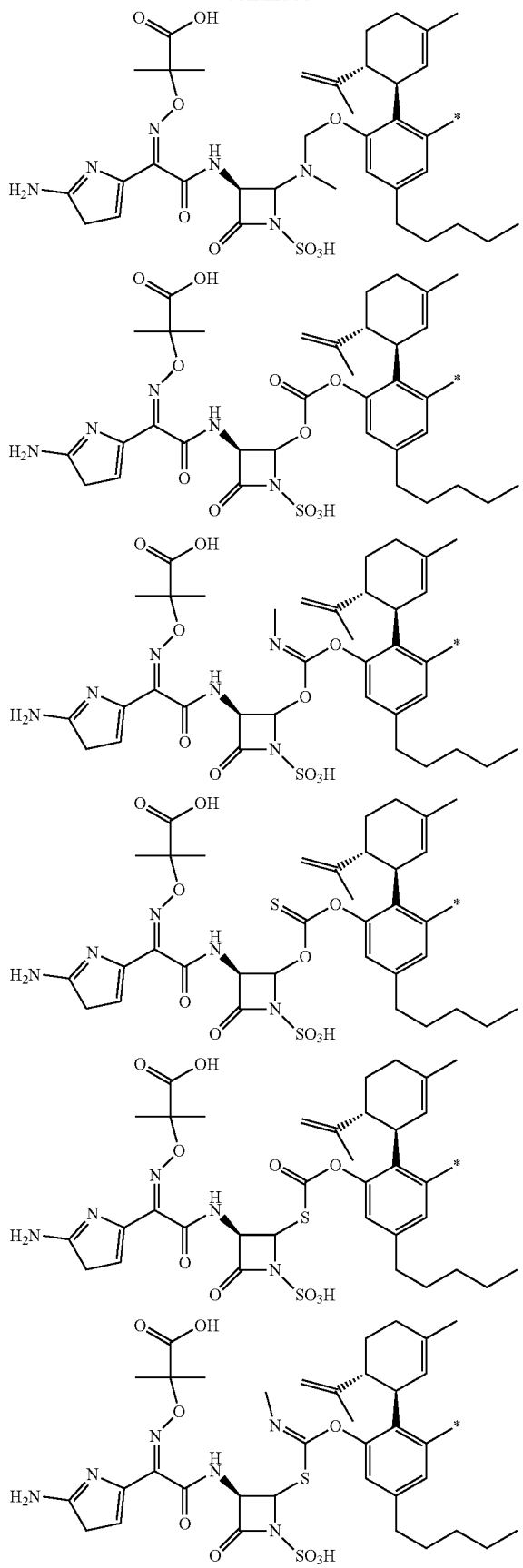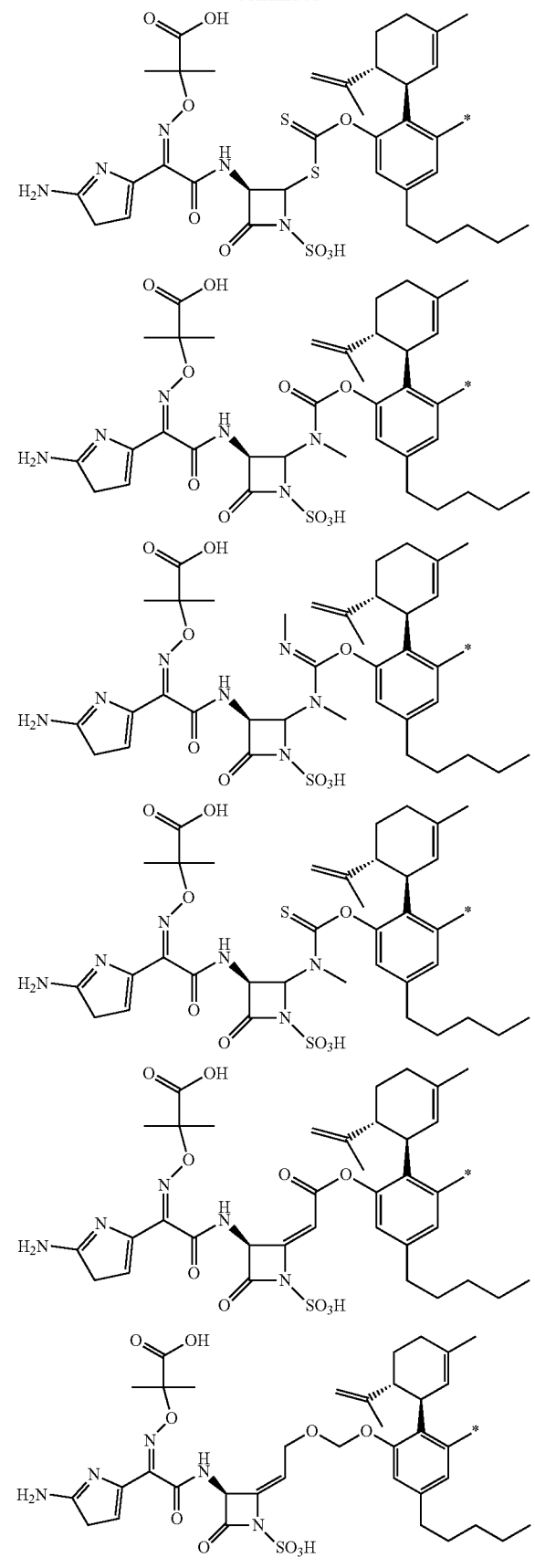

-continued

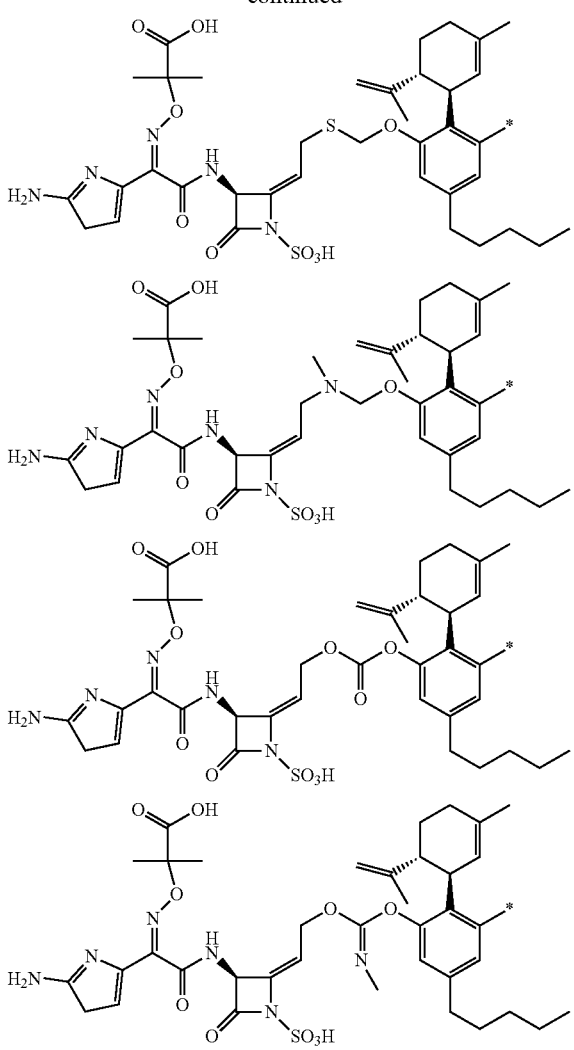

-continued

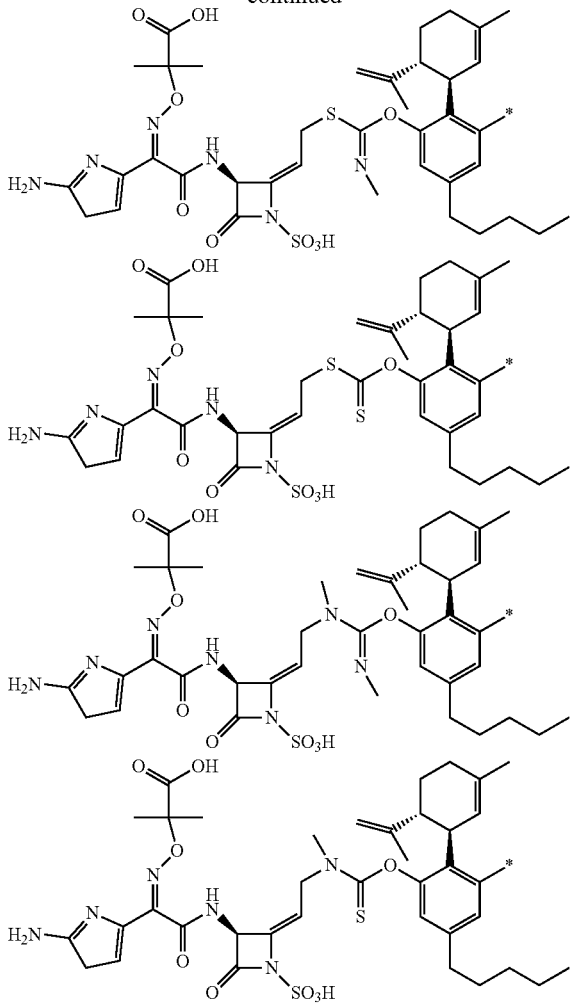

Type II Conjugate Molecules

In some embodiments, conjugate molecules have the formula:

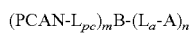  (II)

in which PCAN is a platinum complex anti-neoplastic agent component; $L_{pc}$ is a PCAN linker as described below, which may be absent; B is a target binding component; $L_a$ is an active component linker; and A is an active component. In embodiments in which B is an antibody, m is 1-30; n is 0-29; and the sum of m+n is 1-30.

In Type II conjugate molecules, B, $L_a$, and A are as defined above.

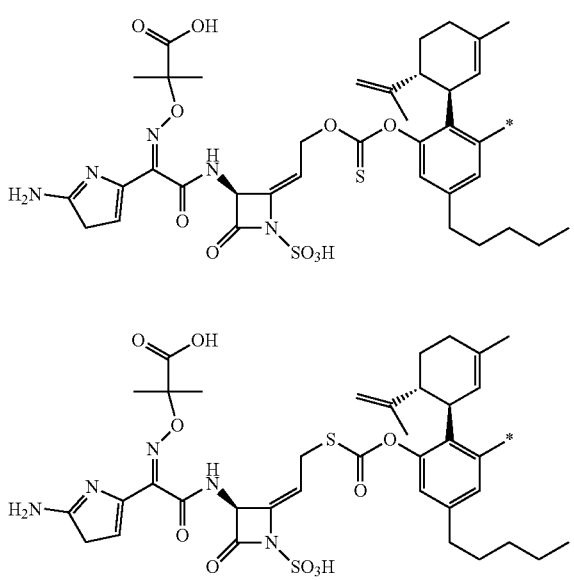

In some embodiments, a cannabinoid component is provided by a cannabigerol, a cannabichromene, a cannabidiol, a tetrahydrocannabinol, a cannabicyclol, a cannabielsoin, a cannabinol, a cannabinodiol, a cannabitriol, a dehydrocannabifuran, a cannabifuran, a cannabichromanon, or a cannabiripsol. In some embodiments, a cannabinoid component is provided by cannabidiol. In some embodiments, a cannabinoid component is provided by cannabigerol.

In embodiments in which m is at least 2, each of the cannabinoid conjugate components independently can be the same or different; and, independently, each of linkers $L_{cc}$ can be the same or different.

In embodiments in which n is at least 2, each of the active agent components can be the same or different; and, independently, each of linkers $L_a$ can be the same or different.

In embodiments in which m is at least 2, each of the platinum complex anti-neoplastic agent components independently can be the same or different; and, independently, each of linkers $L_{pc}$ can be the same or different.

In some embodiments, n is 0; and m is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, n is 1; and m is 1, 2, 3, 4, 5, 6, 7, 8, 9, 10, 11, 12, 13, 14, 15, 16, 17, 18, 19, 20, 21, 22, 23, 24, 25, 26, 27, 28, or 29.

In some embodiments, n is 2; and m is 1, 2, 3, 4, 5, 6, 7, 8, 9, 10, 11, 12, 13, 14, 15, 16, 17, 18, 19, 20, 21, 22, 23, 24, 25, 26, 27, or 28.

In some embodiments, n is 3; and m is 1, 2, 3, 4, 5, 6, 7, 8, 9, 10, 11, 12, 13, 14, 15, 16, 17, 18, 19, 20, 21, 22, 23, 24, 25, 26, or 27.

In some embodiments, n is 4; and m is 1, 2, 3, 4, 5, 6, 7, 8, 9, 10, 11, 12, 13, 14, 15, 16, 17, 18, 19, 20, 21, 22, 23, 24, 25, or 26.

In some embodiments, n is 5; and m is 1, 2, 3, 4, 5, 6, 7, 8, 9, 10, 11, 12, 13, 14, 15, 16, 17, 18, 19, 20, 21, 22, 23, 24, or 25.

In some embodiments, n is 6; and m is 1, 2, 3, 4, 5, 6, 7, 8, 9, 10, 11, 12, 13, 14, 15, 16, 17, 18, 19, 20, 21, 22, 23, or 24.

In some embodiments, n is 7; and m is 1, 2, 3, 4, 5, 6, 7, 8, 9, 10, 11, 12, 13, 14, 15, 16, 17, 18, 19, 20, 21, 22, or 23.

In some embodiments, n is 8; and m is 1, 2, 3, 4, 5, 6, 7, 8, 9, 10, 11, 12, 13, 14, 15, 16, 17, 18, 19, 20, 21, or 22.

In some embodiments, n is 9; and m is 1, 2, 3, 4, 5, 6, 7, 8, 9, 10, 11, 12, 13, 14, 15, 16, 17, 18, 19, 20, or 21.

In some embodiments, n is 10; and m is 1, 2, 3, 4, 5, 6, 7, 8, 9, 10, 11, 12, 13, 14, 15, 16, 17, 18, 19, or 20.

In some embodiments, n is 11; and m is 1, 2, 3, 4, 5, 6, 7, 8, 9, 10, 11, 12, 13, 14, 15, 16, 17, 18, or 19.

In some embodiments, n is 12; and m is 1, 2, 3, 4, 5, 6, 7, 8, 9, 10, 11, 12, 13, 14, 15, 16, 17, or 18.

In some embodiments, n is 13; and m is 1, 2, 3, 4, 5, 6, 7, 8, 9, 10, 11, 12, 13, 14, 15, 16, or 17.

In some embodiments, n is 14; and m is 1, 2, 3, 4, 5, 6, 7, 8, 9, 10, 11, 12, 13, 14, 15, or 16.

In some embodiments, n is 15; and m is 1, 2, 3, 4, 5, 6, 7, 8, 9, 10, 11, 12, 13, 14, or 15.

In some embodiments, n is 16; and m is 1, 2, 3, 4, 5, 6, 7, 8, 9, 10, 11, 12, 13, or 14.

In some embodiments, n is 17; and m is 1, 2, 3, 4, 5, 6, 7, 8, 9, 10, 11, 12, or 13.

In some embodiments, n is 18; and m is 1, 2, 3, 4, 5, 6, 7, 8, 9, 10, 11, or 12.

In some embodiments, n is 19; and m is 1, 2, 3, 4, 5, 6, 7, 8, 9, 10, or 11.

In some embodiments, n is 20; and m is 1, 2, 3, 4, 5, 6, 7, 8, 9, or 10.

In some embodiments, n is 21; and m is 1, 2, 3, 4, 5, 6, 7, 8, or 9.

In some embodiments, n is 22; and m is 1, 2, 3, 4, 5, 6, 7, or 8.

In some embodiments, n is 23; and m is 1, 2, 3, 4, 5, 6, or 7.

In some embodiments, n is 24; and m is 1, 2, 3, 4, 5, or 6.

In some embodiments, n is 25; and m is 1, 2, 3, 4, or 5.

In some embodiments, n is 26; and m is 1, 2, 3, or 4.

In some embodiments, n is 27; and m is 1, 2, or 3.

In some embodiments, n is 28; and m is 1 or 2.

In some embodiments, n is 29. In these embodiments, m is 1.

In embodiments in which B is an antibody, the antibody is an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof.

In some embodiments in which B is an antibody, the antibody is an IgG, an IgE, an IgM, an IgD, an IgA, or an IgY.

In some embodiments in which B is an antibody, the antibody is an IgG1, IgG2 (e.g., IgG2a, IgG2), IgG3, IgG4, IgA1, or IgA2.

In some embodiments in which B is an antibody, the antibody binds to
 i. a cluster of differentiation (CD) antigen;
 ii. a checkpoint inhibitor;
 iii. a vascular target antigen;
 iv. a stromal antigen;
 v. an extracellular matrix antigen;
 vi. a circulating antigen;
 vii. an interleukin;
 viii. an interleukin receptor;
 ix. a growth factor;
 x. a growth factor receptor;
 xi. a drug;
 xii. an adhesion molecule;
 xiii. a tumor necrosis factor;
 xiv. a tumor necrosis factor-related apoptosis-inducing ligand receptor;
 xv. an insulin receptor;
 xvi. a receptor tyrosine kinase;
 xvii. a cytokine receptor;
 xviii. a tropomyosin receptor kinase;
 xix. an integrin;
 xx. an immunoglobulin; or
 xxi. an antigen of an infectious organism.

In some embodiments in which B is an antibody, "B-($L_a$-A)" is an ADC.

In some embodiments in which B is an antibody, the antibody binds to binds to:
 i. an antigen selected from the group consisting of CD2, CD3, CD4, CD11a, CD19, CD20, CD25 (ILR2), CD30, CD33, CD38, CD52, CD139, CD152 (CTLA-4), CD274 (PD-L1), or CD319 (SLAMF);
 ii. an antigen selected from the group consisting of PD-1 and PD-L1 (CD274);
 iii. PSMA;
 iv. Bone Marrow Stromal Antigen 2;
 v. an antigen selected from the group consisting of CI, CIII, CIV, CV, LM, and FN;
 vi. Factor IXa or Factor X;
 vii. an antigen selected from the group consisting of IL-1β, IL-2, IL-5, IL-6, IL-12, IL-17A, and IL-23;
 viii. an antigen selected from the group consisting of ILR2 (CD25), IL-4RA, IL-5RA, IL-6R, and IL-17RA;
 ix. VEGFA;
 x. an antigen selected from the group consisting of EGFR (ErbB1), FGFR, FGFR2, FGFR3, FGFR4, FGFR23, HER2/neu, HER3, (ErbB3), HER4, PDGFRA, VEGFR1, VEGFR2, VEGFR3, EphA1, EphA2, EphA3, EphA4, EphA5, EphA6, EphA7, EphA8, EphB1, EphB2, EphB3, EphB4, EphB5, EphB6, EphB7, HGFR (c-Met), and IGF2R;
 xi. digoxin or dabigatran;
 xii. EpCAM;

xiii. TNF-α or TNF-β;
xiv. TRAIL-R1 or TRAIL-R2;
xv. IR;
xvi. an antigen selected from the group consisting of FLT3, CSF-1R, KIT/SCFR, RON (SEA), AXL (UFO), MER, TYRO3, MUSK, RET, TIE1, DDR1, DDR2, ROR1, ROR2, ROS, LTL, ALK, KLG, and RYK;
xvii. an antigen selected from the group consisting of type I cytokine receptor, type II cytokine receptor, TNF receptors, CCR4, TGF-β receptors, and activin receptors;
xviii. an antigen selected from the group consisting of TRKA, TRKB, and TRKC;
xix. an antigen selected from the group consisting of integrin α4, integrin α4β1, and integrin α4β7;
xx. an IgE;
xxi. an antigen selected from the group of infectious organisms consisting of respiratory syncytial virus, *Bacillus anthracis*, and *Clostridium difficile*; or
xxii. an antigen selected from the group consisting of PSCK9, CGRPR, CRLR, RANKL, GP IIb/IIIa receptor, GD2, BLyS, C5, IRR, and TAG72.

Platinum Complex Anti-Neoplastic Agent (PCAN) Components

Platinum complexes comprise a central platinum atom complexed to leaving and non-leaving ligands. The "non-leaving ligand component" can be a single (bidentate or tridentate) non-leaving ligand or can be two or three individual non-leaving ligands. The "leaving ligand component" can be one or two individual ligands or can be a bidentate leaving ligand.

Both Pt(II) and Pt(IV) complex anti-neoplastic agents are well known in the art. Agents in commercial use include cisplatin, carboplatin, oxaliplatin, eptaplatin, lobaplatin, nedaplatin, and satraplatin. As illustrated below, these agents work by alkylating DNA at the expense of the bond between one or two leaving ligands (circled) and the central platinum atom.

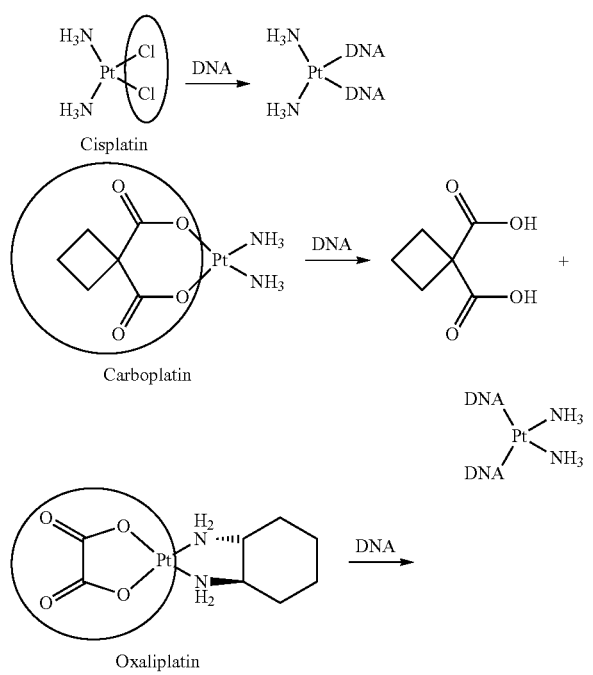

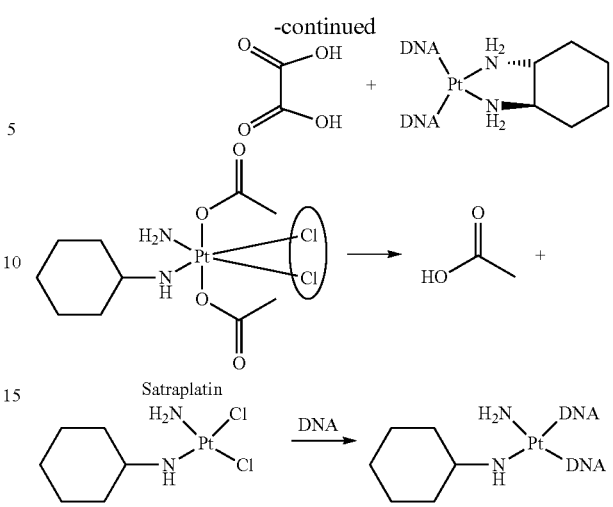

The platinum complex anti-neoplastic agent components ("PCAN components") present in a type (II) conjugate molecule comprise at least one cannabinoid ligand as either a leaving ligand or an axial ligand. After the agent enters the cell, the cannabinoid ligand is released as a cannabinoid, where the cannabinoid can then provide additional therapeutic benefits. These benefits include, but are not limited to, anti-tumor activity (Massi et al., J. Pharmacol. Exp. Ther. 308, 838-45, e-pub 2003; Guindon & Hohmann, Br. J. Pharmacol. 163, 1447-63, 2011; Borrelli et al., Carcinogenesis 35, 2787-97, 2014; McAllister et al., J. Neuroimmune Pharmacol. 10, 255-67, 2015) and inhibition of tumor progression (Velasco et al., Nat. Rev. Cancer 12, 436-44, 2012).

As described in more detail below, a cannabinoid can be attached to a central platinum atom as a leaving ligand or, for Pt(IV) complexes, as an axial ligand. In various embodiments, a Pt(II) PCAN component can incorporate a cannabinoid in place of one leaving ligand or in place of each of two leaving ligands. In various embodiments, a Pt(IV) PCAN component can incorporate a cannabinoid in place of one axial ligand or in place of each of two axial ligands. In addition, a Pt(IV) PCAN component can incorporate a cannabinoid in place of one leaving ligand or in place of each of two leaving ligands. Thus, a Pt(II) PCAN component can incorporate and release one or two cannabinoids; and a Pt(IV) PCAN component can incorporate and release one, two, three, or four cannabinoids. In any particular PCAN component that incorporates two or more cannabinoids, the cannabinoids can be the same or different.

In the description that follows, wherever a leaving ligand, a non-leaving ligand component, or an axial ligand is unspecified in an embodiment of a PCAN component, such ligands can be the ligands of any platinum complex anti-neoplastic agent. See, e.g., Kozubik et al., Metal-Based Drugs, Volume 2008, Article ID 417897, 2008; Johnstone et al., Chem. Rev. 116, 3436-86, 2016; Intini et al., Inorg. Chem. 56, 1483-97, 2017; Neumann et al., ChemMedChem. 2014 June; 9(6):1150-3, 2014; Tolan et al., Appl. Organometal Chem. 33:e4763, 2019; Jia et al., Molecules 24, 581, 2019; Zhou et al., Chem. Commun. 54, 2788-91, 2018; Li et al., Bioinorganic Chemistry and Applications Volume 2018, Article ID 8276139; Ndagi et al., Drug Design, Development and Therapy 11, 599-616, 2017; Monroe et al., 2018; U.S. Pat. Nos. 7,268,244; 7,759,488; 9,227,991; 9,593,139; 9,771,387; 10,053,478.

For simplicity, PCAN components are depicted in this disclosure without indicating any stereochemistry. It is well known, however, that both cannabinoids and platinum complexes exhibit a variety of stereochemistries. In this disclosure, unless otherwise indicated, any particular PCAN component structure includes all possible isomers, including isomers of the cannabinoid ligands incorporated into the PCAN component.

In addition, the use of any particular leaving ligand, non-leaving ligand, or cannabinoid ligand in the structural examples below is for simplicity and is not intended to limit any of the ligands of the disclosed PCAN components.

Cannabinoid Ligand

A "cannabinoid ligand" as used in this disclosure is that portion of a cannabinoid that is present in a PCAN component in place of a leaving ligand or an axial ligand. Illustrations are shown in the examples below.

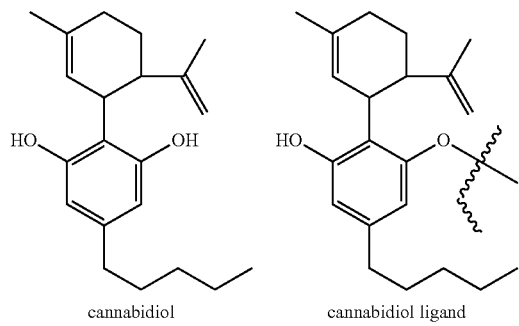
cannabidiol     cannabidiol ligand

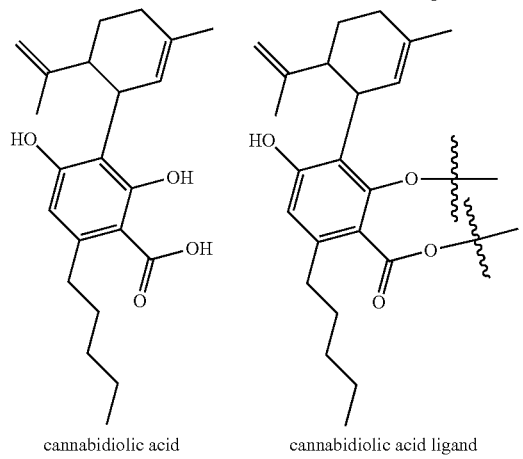
cannabidiolic acid     cannabidiolic acid ligand

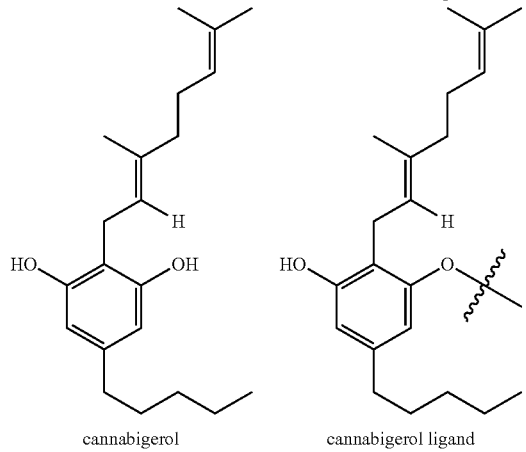
cannabigerol     cannabigerol ligand

A cannabinoid ligand, either a cannabinoid leaving ligand or a cannabinoid axial ligand, can be provided by any cannabinoid that contains a hydroxy group (aromatic or aliphatic) or a carboxyl group by which the cannabinoid can be attached to the central platinum atom, either directly or via a linker. The cannabinoid can be a naturally occurring molecule, either isolated or synthesized, or a modified version of a naturally occurring molecule. See, for example, Morales et al., Frontiers in Pharmacology June 2017 review, 1-18.

Examples of cannabinoids include, but are not limited to, the cannabinoids described above in connection with cannabinoid components.

PCAN Components Comprising a Cannabinoid Leaving Ligand

In some embodiments, a PCAN component comprises (a) a central platinum atom; (b) a non-leaving ligand component; and (c) a leaving ligand component, which comprises a first cannabinoid leaving ligand attached to the central platinum atom via an oxygen atom of (i) a first hydroxy group of the first cannabinoid ligand or of (ii) a first carboxy group of the first cannabinoid ligand. Non-limiting examples are shown below, in which * indicates a point of attachment to linker $L_{pc}$.

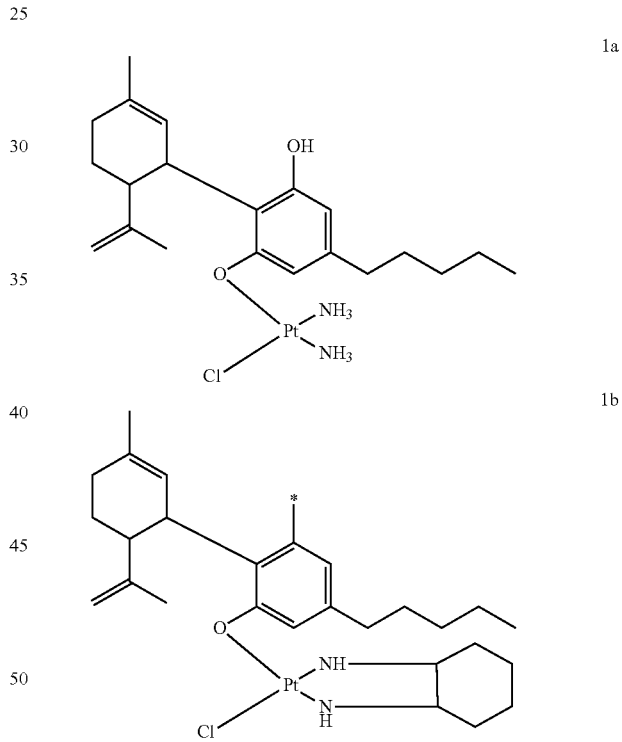

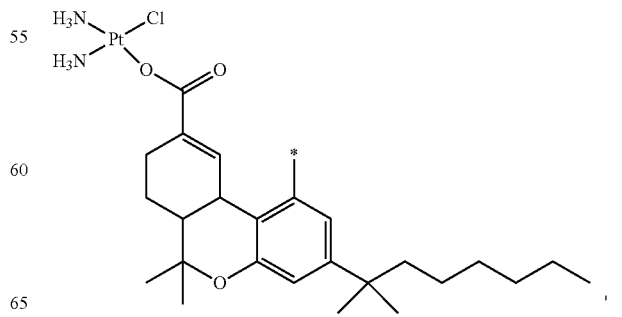

In some embodiments, the leaving ligand component comprises a second cannabinoid ligand ("second cannabinoid leaving ligand"). The first and second cannabinoid leaving ligands can be the same or different. Non-limiting examples are shown below, in which * indicates a point of attachment to linker $L_{pc}$.

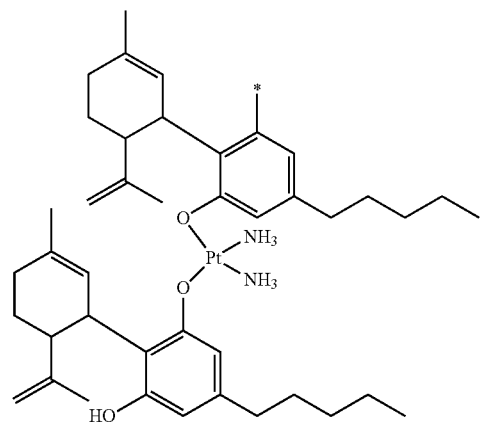

1c

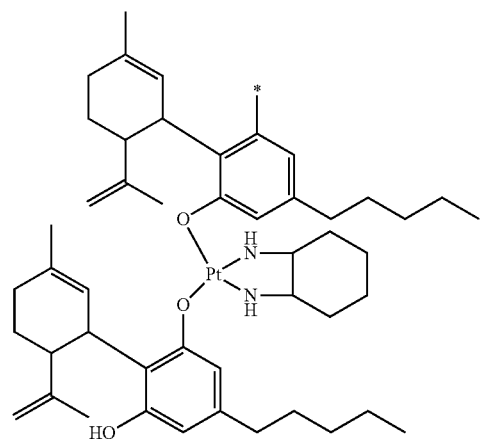

1d

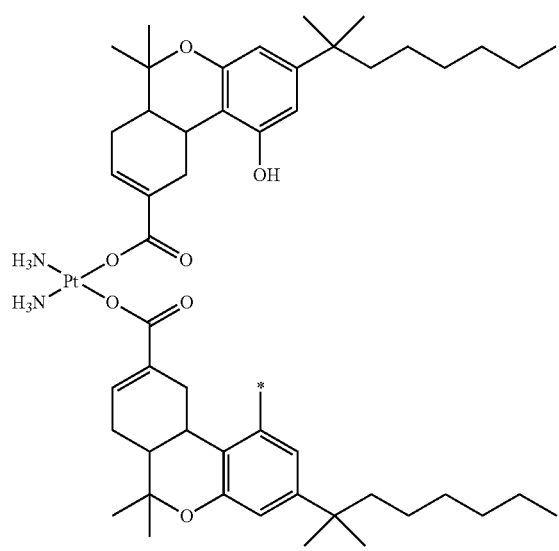

In some embodiments, the cannabinoid ligand component is a bidentate cannabinoid ligand ("bidentate cannabinoid leaving ligand"). A non-limiting example is shown below, in which in which * indicates a point of attachment to linker $L_{pc}$.

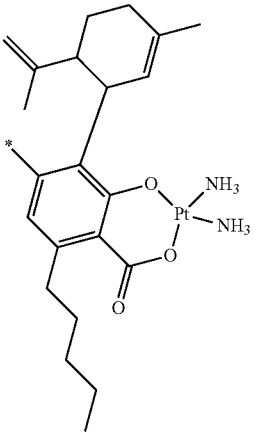

2a

In some embodiments, the PCAN component further comprises (d) a first axial ligand and a second axial ligand. Non-limiting examples of these embodiments are shown below, in which ● represents an axial ligand and * indicates a point of attachment to linker $L_{pc}$.

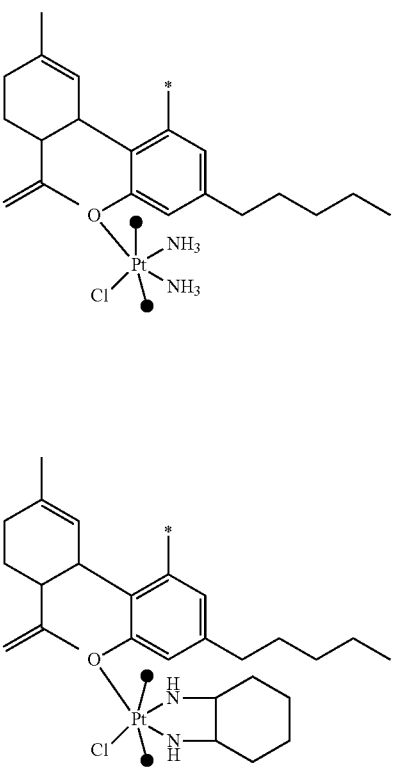

2b

-continued

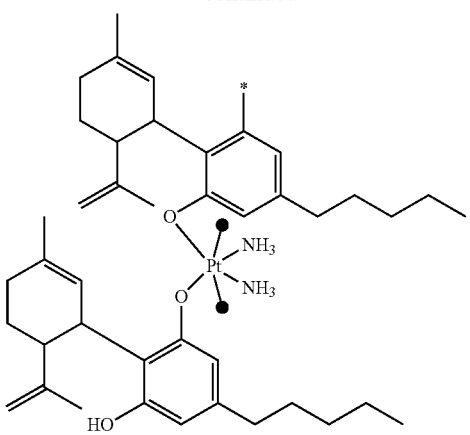

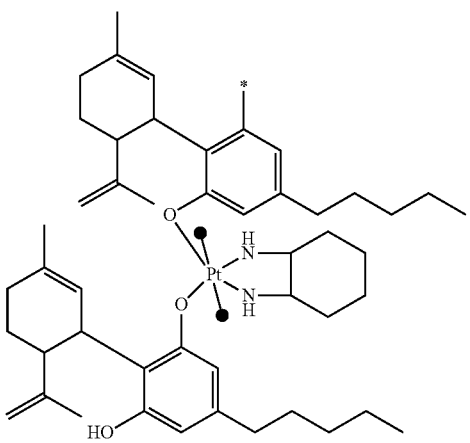

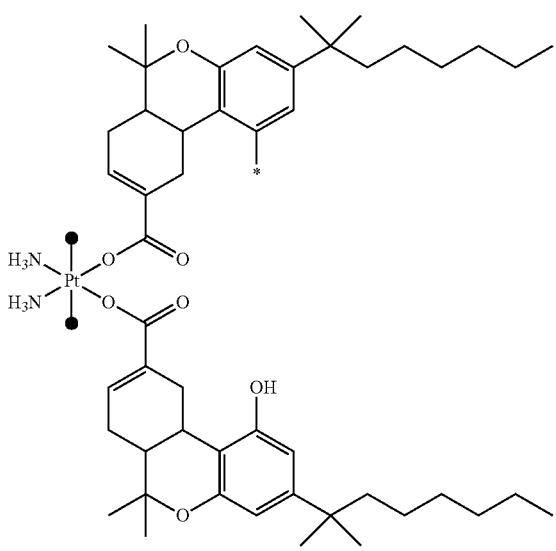

-continued

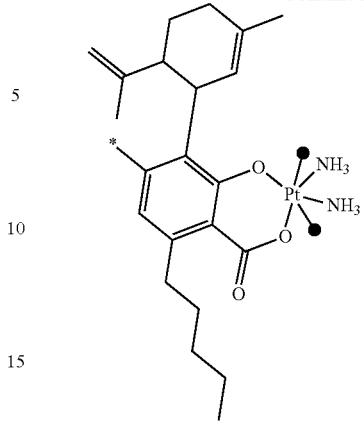

In some embodiments, a cannabinoid leaving ligand is attached to the central platinum atom by a linker. In the linkers described below,  is the point of attachment of a cannabinoid leaving ligand and * is the point of attachment to the central platinum atom. In some embodiments, a first cannabinoid leaving ligand is connected to the central platinum atom by a linker. In some embodiments, a first and a second cannabinoid leaving ligand are connected to the central platinum atom by a linker. The linkers, which can be the same or different, are described below.

In some embodiments, the linker is

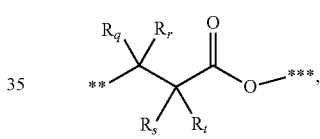

in which:
(a) $R_q$, $R_r$, $R_s$, and $R_t$ independently are selected from the group consisting of (i) H, (ii) C1-C6 linear or branched alkyl, (iii) C1-C6 linear or branched heteroalkyl having 1, 2, or 3 heteroatoms independently selected from O, S, and N; (iv) C3-C6 cycloalkyl;

(v) a 3- to 9-membered cycloheteroalkyl having 1, 2, or 3 heteroatoms independently selected from O, N, and S; (vi) phenyl; and (vii) a 5- to 10-membered heteroaromatic comprising 1, 2, 3, 4, 5, or 6 heteroatoms independently selected from O, N, and S; or (b) when any two of $R_q$, $R_r$, $R_s$, and $R_t$ independently are (i) C1-C6 linear or branched alkyl or (ii) C1-C6 linear or branched heteroalkyl having 1, 2, or 3 heteroatoms independently selected from O, S, and N, then the two of $R_q$, $R_r$, $R_s$, and $R_t$, together with the carbons to which they are attached, form a 3-6-membered ring.

In some embodiments, the linker is

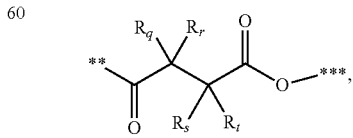

in which , *, $R_q$, $R_r$, $R_s$, and $R_t$ are as defined above.

Figure 3A:
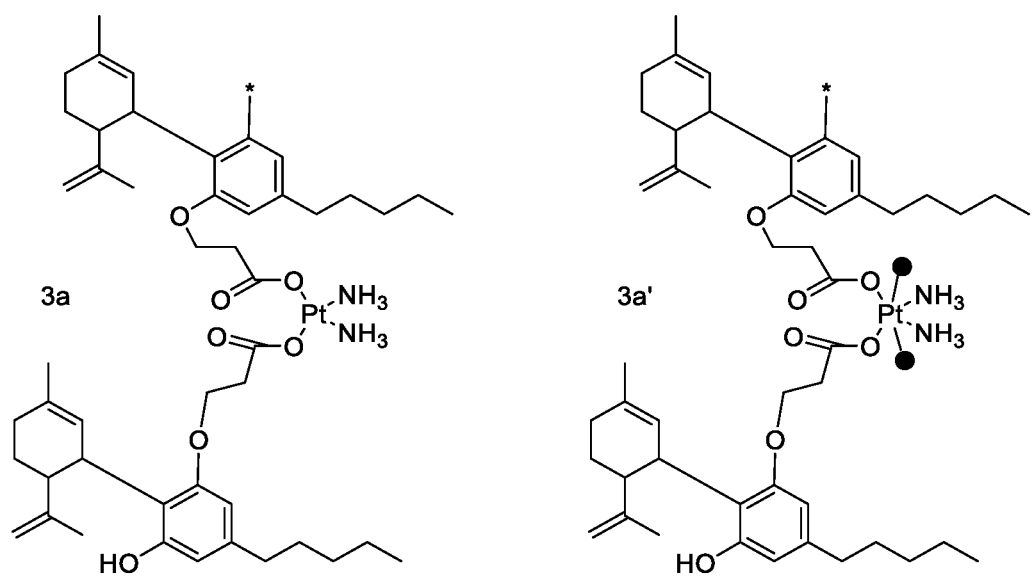
FIGS. 3A-B. Non-limiting examples of Platinum Complex Anti-Neoplastic (PCAN) components comprising a cannabinoid leaving ligand, in which * is the point of attachment to linker L$_{pc}$.
Figure 3B:
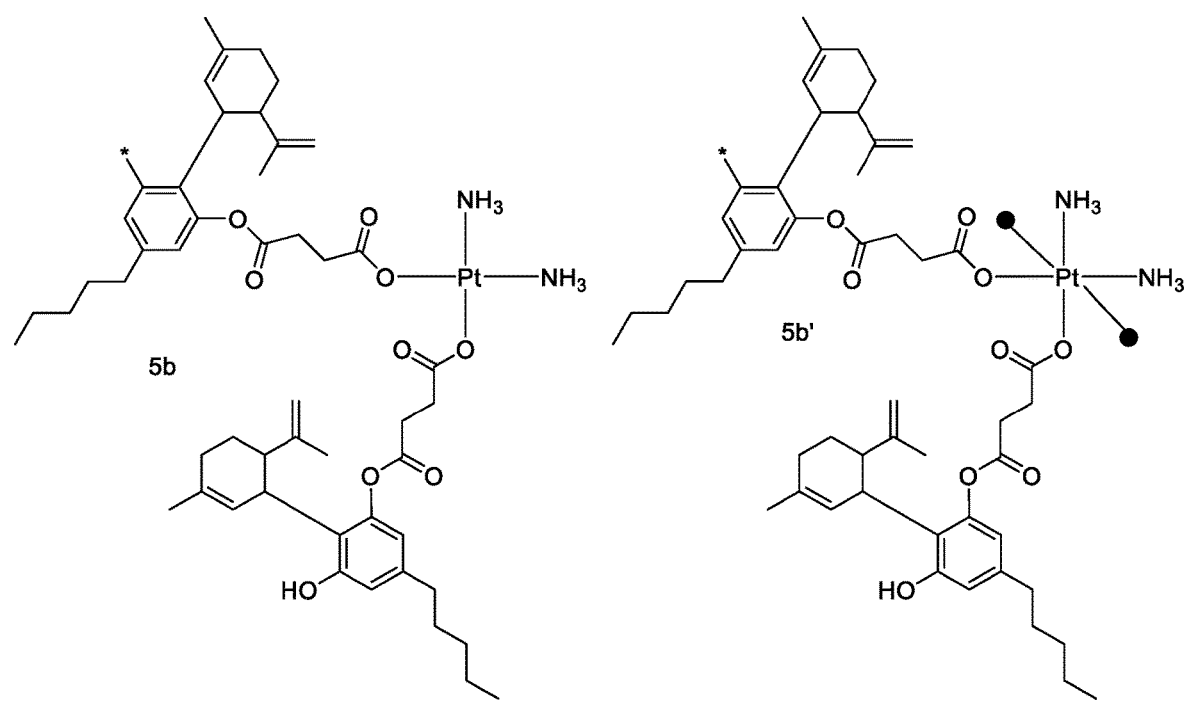

Non-limiting examples are shown in FIGS. 3A and 3B.

Platinum Complex Anti-Neoplastic Agents Comprising a Cannabinoid Axial Ligand

In some embodiments, a PCAN component comprises (a) a central platinum atom; (b) a non-leaving ligand component; (c) a leaving ligand component; and (d) a first axial ligand and a second axial ligand. In these embodiments, at least the first axial ligand is a first cannabinoid ligand ("first cannabinoid axial ligand") attached to the central platinum atom via an oxygen atom of (i) a first hydroxy group of the first cannabinoid ligand or (ii) a first carboxy group of the first cannabinoid ligand. In some embodiments, the first and second axial ligand are independently chosen cannabinoid ligands attached to the central platinum atom via an oxygen atom of (i) a hydroxy group of the first or second cannabinoid ligand or (ii) a carboxy group of the first or second cannabinoid ligand. In some embodiments, one or both of the leaving ligands is a cannabinoid leaving ligand, as described above. In some embodiments, the leaving ligand component is a bidentate leaving ligand.

Figure 4:
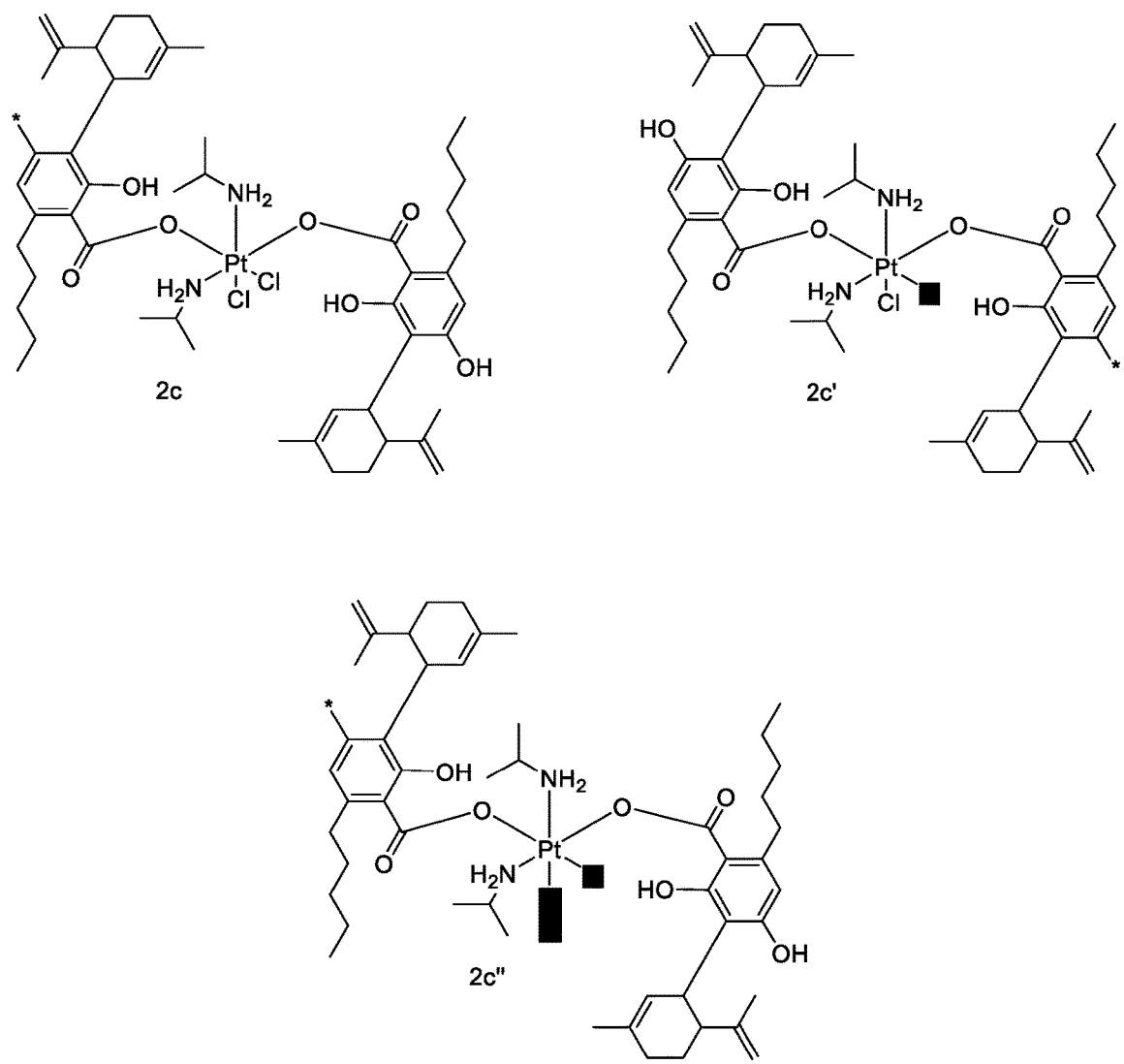
FIG. 4. Non-limiting examples of PCAN agents comprising a cannabinoid axial ligand, in which, for simplicity each cannabinoid axial ligand is a cannabidiol axial ligand.

Non-limiting examples are shown in FIG. 4.

In some embodiments, an axial cannabinoid ligand is attached to the central platinum atom by a linker. In the linkers described below,  is the point of attachment of a cannabinoid axial ligand and * is the point of attachment to the central platinum atom. In some embodiments, a first cannabinoid axial ligand is connected to the central platinum atom by a linker. In some embodiments, a first and a second cannabinoid axial ligand are connected to the central platinum atom by a linker. The linkers, which can be the same or different, are described below.

In some embodiments, the linker is

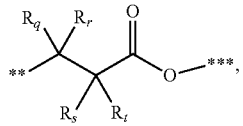

in which $R_q$, $R_r$, $R_s$, and $R_t$ are as defined above.

In some embodiments, the linker is

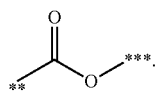

In some embodiments, the linker is

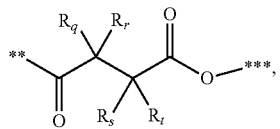

in which $R_q$, $R_r$, $R_s$, and $R_t$ are as defined above.

In some embodiments, the linker is

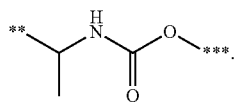

In some embodiments, the linker is

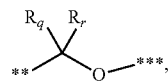

in which $R_q$ and $R_r$ are as defined above.

Non-limiting examples are shown in FIGS. 5A-5E.

Non-Leaving Ligand Component

In some embodiments, the non-leaving ligand component is (i) a first non-leaving ligand and a second non-leaving ligand, as illustrated, for example, by cisplatin, carboplatin, and nedaplatin:

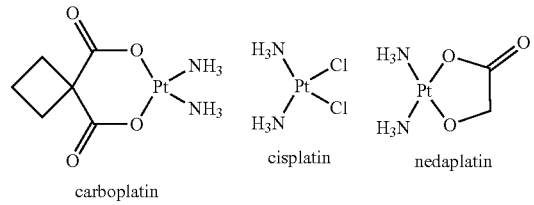

carboplatin     cisplatin     nedaplatin

In some embodiments, the non-leaving ligand component of a PCAN component is a first non-leaving ligand, a second non-leaving ligand, and a third non-leaving ligand, as illustrated, for example, by pyriplatin and phenanthriplatin:

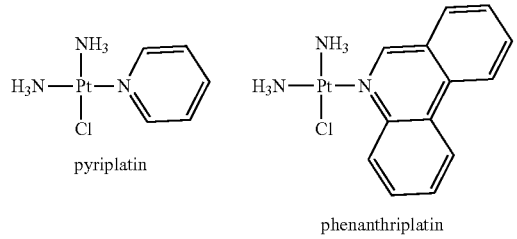

pyriplatin     phenanthriplatin

In some embodiments, the non-leaving ligand component is a bidentate non-leaving ligand, as illustrated, for example, by oxaliplatin, lobaplatin, heptaplatin, and eptaplatin:

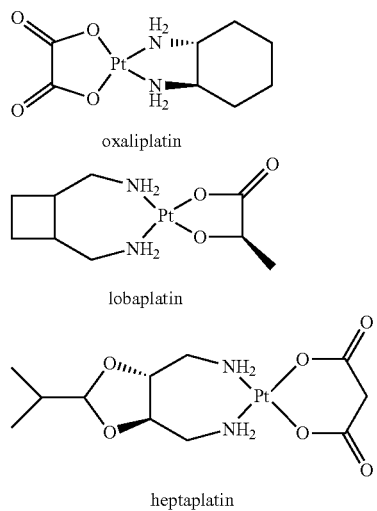

oxaliplatin lobaplatin heptaplatin

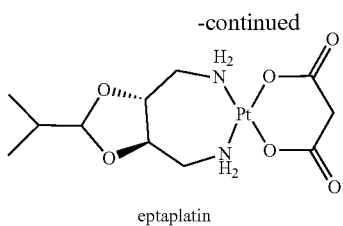

eptaplatin

In some embodiments, the non-leaving ligand component of a PCAN component is a tridentate ligand, as illustrated, for example, by [Pt(dien)Cl]+ and [Pt(Et₂dien)Cl]+:

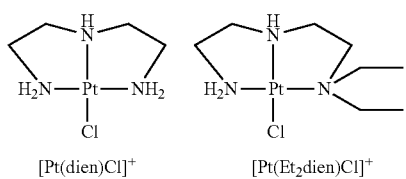

[Pt(dien)Cl]⁺   [Pt(Et₂dien)Cl]⁺

Modified Ligands

In some embodiments, a non-leaving ligand or an axial ligand is modified to comprise a bioactive moiety, for example to alter the pharmacokinetic properties of a PCAN component, to provide a targeting function, or to provide an additional therapeutic effect. Bioactive moieties include, but are not limited to, targeting ligands such as steroid units, carbohydrates, bile acids, peptides (e.g., netropsin, distamycin), and folate units; histone deacetylase inhibitors, p53 agonists, alkylating agents, nonsteroidal anti-inflammatory complexes, and adamantylamine. See, e.g., Johnstone et al., Chem. Rev. 116, 3436-86, 2016; Li et al., Bioinorganic Chemistry and Applications Volume 2018, Article ID 8276139; Kozubik et al., Metal-Based Drugs, Volume 2008, Article ID 417897.

Isomers

As mentioned above, platinum complexes exhibit various forms of stereoisomerism. In some embodiments, a PCAN component is a cis isomer. In some embodiments, a PCAN component is a trans isomer. In some embodiments, a PCAN component is a X stereoisomer. In some embodiments, a PCAN component is a δ stereoisomer.

Type III Conjugate Molecules

Type III conjugate molecules have the formula:

(CBN-L_c)_m-B-(L_a-A)_n    (III)

in which CBN is a cannabinoid component; $L_c$ is a cannabinoid component linker; B is a target binding component; $L_a$ is an active component linker; and A is an active component. In embodiments in which B is an antibody, m is 1-30, n is 0-29, and the sum of m+n is 1-30.

In some embodiments, a cannabinoid component is provided by a cannabigerol, a cannabichromene, a cannabidiol, a tetrahydrocannabinol, a cannabicyclol, a cannabielsoin, a cannabinol, a cannabinodiol, a cannabitriol, a dehydrocannabifuran, a cannabifuran, a cannabichromanon, or a cannabiripsol. In some embodiments, a cannabinoid component is provided by cannabidiol. In some embodiments, a cannabinoid component is provided by cannabigerol.

In embodiments in which m is at least two, each of the cannabinoid components can be the same or different; and, independently, each of linkers $L_c$ can be the same or different.

In embodiments in which n is at least 2, each of the active agent components can be the same or different; and, independently, each of linkers $L_a$ can be the same or different.

In some embodiments, n is 0; and m is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, n is 1; and m is 1, 2, 3, 4, 5, 6, 7, 8, 9, 10, 11, 12, 13, 14, 15, 16, 17, 18, 19, 20, 21, 22, 23, 24, 25, 26, 27, 28, or 29.

In some embodiments, n is 2; and m is 1, 2, 3, 4, 5, 6, 7, 8, 9, 10, 11, 12, 13, 14, 15, 16, 17, 18, 19, 20, 21, 22, 23, 24, 25, 26, 27, or 28.

In some embodiments, n is 3; and m is 1, 2, 3, 4, 5, 6, 7, 8, 9, 10, 11, 12, 13, 14, 15, 16, 17, 18, 19, 20, 21, 22, 23, 24, 25, 26, or 27.

In some embodiments, n is 4; and m is 1, 2, 3, 4, 5, 6, 7, 8, 9, 10, 11, 12, 13, 14, 15, 16, 17, 18, 19, 20, 21, 22, 23, 24, 25, or 26.

In some embodiments, n is 5; and m is 1, 2, 3, 4, 5, 6, 7, 8, 9, 10, 11, 12, 13, 14, 15, 16, 17, 18, 19, 20, 21, 22, 23, 24, or 25.

In some embodiments, n is 6; and m is 1, 2, 3, 4, 5, 6, 7, 8, 9, 10, 11, 12, 13, 14, 15, 16, 17, 18, 19, 20, 21, 22, 23, or 24.

In some embodiments, n is 7; and m is 1, 2, 3, 4, 5, 6, 7, 8, 9, 10, 11, 12, 13, 14, 15, 16, 17, 18, 19, 20, 21, 22, or 23.

In some embodiments, n is 8; and m is 1, 2, 3, 4, 5, 6, 7, 8, 9, 10, 11, 12, 13, 14, 15, 16, 17, 18, 19, 20, 21, or 22.

In some embodiments, n is 9; and m is 1, 2, 3, 4, 5, 6, 7, 8, 9, 10, 11, 12, 13, 14, 15, 16, 17, 18, 19, 20, or 21.

In some embodiments, n is 10; and m is 1, 2, 3, 4, 5, 6, 7, 8, 9, 10, 11, 12, 13, 14, 15, 16, 17, 18, 19, or 20.

In some embodiments, n is 11; and m is 1, 2, 3, 4, 5, 6, 7, 8, 9, 10, 11, 12, 13, 14, 15, 16, 17, 18, or 19.

In some embodiments, n is 12; and m is 1, 2, 3, 4, 5, 6, 7, 8, 9, 10, 11, 12, 13, 14, 15, 16, 17, or 18.

In some embodiments, n is 13; and m is 1, 2, 3, 4, 5, 6, 7, 8, 9, 10, 11, 12, 13, 14, 15, 16, or 17.

In some embodiments, n is 14; and m is 1, 2, 3, 4, 5, 6, 7, 8, 9, 10, 11, 12, 13, 14, 15, or 16.

In some embodiments, n is 15; and m is 1, 2, 3, 4, 5, 6, 7, 8, 9, 10, 11, 12, 13, 14, or 15.

In some embodiments, n is 16; and m is 1, 2, 3, 4, 5, 6, 7, 8, 9, 10, 11, 12, 13, or 14.

In some embodiments, n is 17; and m is 1, 2, 3, 4, 5, 6, 7, 8, 9, 10, 11, 12, or 13.

In some embodiments, n is 18; and m is 1, 2, 3, 4, 5, 6, 7, 8, 9, 10, 11, or 12.

In some embodiments, n is 19; and m is 1, 2, 3, 4, 5, 6, 7, 8, 9, 10, or 11.

In some embodiments, n is 20; and m is 1, 2, 3, 4, 5, 6, 7, 8, 9, or 10.

In some embodiments, n is 21; and m is 1, 2, 3, 4, 5, 6, 7, 8, or 9.

In some embodiments, n is 22; and m is 1, 2, 3, 4, 5, 6, 7, or 8.

In some embodiments, n is 23; and m is 1, 2, 3, 4, 5, 6, or 7.

In some embodiments, n is 24; and m is 1, 2, 3, 4, 5, or 6.

In some embodiments, n is 25; and m is 1, 2, 3, 4, or 5.
In some embodiments, n is 26; and m is 1, 2, 3, or 4.
In some embodiments, n is 27; and m is 1, 2, or 3.
In some embodiments, n is 28; and m is 1 or 2.
In some embodiments, n is 29. In these embodiments, m is 1.

In embodiments in which B is an antibody, the antibody is an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof.

In some embodiments in which B is an antibody, the antibody is an IgG, an IgE, an IgM, an IgD, an IgA, or an IgY.

In some embodiments in which B is an antibody, the antibody is an IgG1, IgG2 (e.g., IgG2a, IgG2), IgG3, IgG4, IgA1, or IgA2.

In some embodiments in which B is an antibody, the antibody binds to
  i. a cluster of differentiation (CD) antigen;
  ii. a checkpoint inhibitor;
  iii. a vascular target antigen;
  iv. a stromal antigen;
  v. an extracellular matrix antigen;
  vi. a circulating antigen;
  vii. an interleukin;
  viii. an interleukin receptor;
  ix. a growth factor;
  x. a growth factor receptor;
  xi. a drug;
  xii. an adhesion molecule;
  xiii. a tumor necrosis factor;
  xiv. a tumor necrosis factor-related apoptosis-inducing ligand receptor;
  xv. an insulin receptor;
  xvi. a receptor tyrosine kinase;
  xvii. a cytokine receptor;
  xviii. a tropomyosin receptor kinase;
  xix. an integrin;
  xx. an immunoglobulin; or
  xxi. an antigen of an infectious organism.

In some embodiments in which B is an antibody, "B-($L_a$-A)" is an ADC.

In some embodiments in which B is an antibody, the antibody binds to:
  i. an antigen selected from the group consisting of CD2, CD3, CD4, CD11a, CD19, CD20, CD25 (ILR2), CD30, CD33, CD38, CD52, CD139, CD152 (CTLA-4), CD274 (PD-L1), or CD319 (SLAMF);
  ii. an antigen selected from the group consisting of PD-1 and PD-L1 (CD274);
  iii. PSMA;
  iv. Bone Marrow Stromal Antigen 2;
  v. an antigen selected from the group consisting of CI, CIII, CIV, CV, LM, and FN;
  vi. Factor IXa or Factor X;
  vii. an antigen selected from the group consisting of IL-1β, IL-2, IL-5, IL-6, IL-12, IL-17A, and IL-23;
  viii. an antigen selected from the group consisting of ILR2 (CD25), IL-4RA, IL-5RA, IL-6R, and IL-17RA;
  ix. VEGFA;
  x. an antigen selected from the group consisting of EGFR (ErbB1), FGFR, FGFR2, FGFR3, FGFR4, FGFR23, HER2/neu, HER3, (ErbB3), HER4, PDGFRA, VEGFR1, VEGFR2, VEGFR3, EphA1, EphA2, EphA3, EphA4, EphA5, EphA6, EphA7, EphA8, EphB1, EphB2, EphB3, EphB4, EphB5, EphB6, EphB7, HGFR (c-Met), and IGF2R;
  xi. digoxin or dabigatran;
  xii. EpCAM;
  xiii. TNF-α or TNF-β;
  xiv. TRAIL-R1 or TRAIL-R2;
  xv. IR;
  xvi. an antigen selected from the group consisting of FLT3, CSF-1R, KIT/SCFR, RON (SEA), AXL (UFO), MER, TYRO3, MUSK, RET, TIE1, DDR1, DDR2, ROR1, ROR2, ROS, LTL, ALK, KLG, and RYK;
  xvii. an antigen selected from the group consisting of type I cytokine receptor, type II cytokine receptor, TNF receptors, CCR4, TGF-β receptors, and activin receptors;
  xviii. an antigen selected from the group consisting of TRKA, TRKB, and TRKC;
  xix. an antigen selected from the group consisting of integrin α4, integrin α4β1, and integrin α4β7;
  xx. an IgE;
  xxi. an antigen selected from the group of infectious organisms consisting of respiratory syncytial virus, *Bacillus anthracis*, and *Clostridium difficile*; or
  xxii. an antigen selected from the group consisting of PSCK9, CGRPR, CRLR, RANKL, GP IIb/IIIa receptor, GD2, BLyS, C5, IRR, and TAG72.

Type III-A Conjugate Molecules

Type III-A conjugate molecules have the formula:

$$(CBN-L_c)_m\text{-}B \qquad (\text{III-A})$$

in which CBN, $L_c$, and B are as defined above, and m is at least 1. In embodiments in which B is an antibody, m is 1-30.

In some embodiments, a cannabinoid component is provided by a cannabigerol, a cannabichromene, a cannabidiol, a tetrahydrocannabinol, a cannabicyclol, a cannabielsoin, a cannabinol, a cannabinodiol, a cannabitriol, a dehydrocannabifuran, a cannabifuran, a cannabichromanon, or a cannabiripsol. In some embodiments, a cannabinoid component is provided by cannabidiol. In some embodiments, a cannabinoid component is provided by cannabigerol.

In embodiments in which m is at least two, each of the cannabinoid components can be the same or different; and, independently, each of linkers $L_c$ can be the same or different.

In embodiments in which B is an antibody, the antibody is an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof.

In some embodiments in which B is an antibody, the antibody is an IgG, an IgE, an IgM, an IgD, an IgA, or an IgY.

In some embodiments in which B is an antibody, the antibody is an IgG1, IgG2 (e.g., IgG2a, IgG2), IgG3, IgG4, IgA1, or IgA2.

In some embodiments in which B is an antibody, the antibody binds to
  i. a cluster of differentiation (CD) antigen;
  ii. a checkpoint inhibitor;
  iii. a vascular target antigen;
  iv. a stromal antigen;
  v. an extracellular matrix antigen;
  vi. a circulating antigen;
  vii. an interleukin;
  viii. an interleukin receptor;
  ix. a growth factor;
  x. a growth factor receptor;
  xi. a drug;

xii. an adhesion molecule;
xiii. a tumor necrosis factor;
xiv. a tumor necrosis factor-related apoptosis-inducing ligand receptor;
xv. an insulin receptor;
xvi. a receptor tyrosine kinase;
xvii. a cytokine receptor;
xviii. a tropomyosin receptor kinase;
xix. an integrin;
xx. an immunoglobulin; or
xxi. an antigen of an infectious organism.

In some embodiments in which B is an antibody, the antibody binds to binds to:
i. an antigen selected from the group consisting of CD2, CD3, CD4, CD11a, CD19, CD20, CD25 (ILR2), CD30, CD33, CD38, CD52, CD139, CD152 (CTLA-4), CD274 (PD-L1), or CD319 (SLAMF);
ii. an antigen selected from the group consisting of PD-1 and PD-L1 (CD274);
iii. PSMA;
iv. Bone Marrow Stromal Antigen 2;
v. an antigen selected from the group consisting of CI, CIII, CIV, CV, LM, and FN;
vi. Factor IXa or Factor X;
vii. an antigen selected from the group consisting of IL-1β, IL-2, IL-5, IL-6, IL-12, IL-17A, and IL-23;
viii. an antigen selected from the group consisting of ILR2 (CD25), IL-4RA, IL-5RA, IL-6R, and IL-17RA;
ix. VEGFA;
x. an antigen selected from the group consisting of EGFR (ErbB1), FGFR, FGFR2, FGFR3, FGFR4, FGFR23, HER2/neu, HER3, (ErbB3), HER4, PDGFRA, VEGFR1, VEGFR2, VEGFR3, EphA1, EphA2, EphA3, EphA4, EphA5, EphA6, EphA7, EphA8, EphB1, EphB2, EphB3, EphB4, EphB5, EphB6, EphB7, HGFR (c-Met), and IGF2R;
xi. digoxin or dabigatran;
xii. EpCAM;
xiii. TNF-α or TNF-β;
xiv. TRAIL-R1 or TRAIL-R2;
xv. IR;
xvi. an antigen selected from the group consisting of FLT3, CSF-1R, KIT/SCFR, RON (SEA), AXL (UFO), MER, TYRO3, MUSK, RET, TIE1, DDR1, DDR2, ROR1, ROR2, ROS, LTL, ALK, KLG, and RYK;
xvii. an antigen selected from the group consisting of type I cytokine receptor, type II cytokine receptor, TNF receptors, CCR4, TGF-β receptors, and activin receptors;
xviii. an antigen selected from the group consisting of TRKA, TRKB, and TRKC;
xix. an antigen selected from the group consisting of integrin α4, integrin α4β1, and integrin α4β7;
xx. an IgE;
xxi. an antigen selected from the group of infectious organisms consisting of respiratory syncytial virus, *Bacillus anthracis*, and *Clostridium difficile*; or
xxii. an antigen selected from the group consisting of PSCK9, CGRPR, CRLR, RANKL, GP IIb/IIIa receptor, GD2, BLyS, C5, IRR, and TAG72.

Type III-B Conjugate Molecules

Type III-B conjugate molecules have the formula

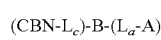

(III-B)

in which CBN, $L_c$, $L_a$, and A are as defined above, "B-($L_a$-A)" is an ADC.

In some embodiments, the cannabinoid component is provided by a cannabigerol, a cannabichromene, a cannabidiol, a tetrahydrocannabinol, a cannabicyclol, a cannabielsoin, a cannabinol, a cannabinodiol, a cannabitriol, a dehydrocannabifuran, a cannabifuran, a cannabichromanon, or a cannabiripsol. In some embodiments, a cannabinoid component is provided by cannabidiol. In some embodiments, the cannabinoid component is provided by cannabigerol.

In some embodiments, the antibody is an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof.

In some embodiments in which B is an antibody, the antibody is an IgG, an IgE, an IgM, an IgD, an IgA, or an IgY.

In some embodiments in which B is an antibody, the antibody is an IgG1, IgG2 (e.g., IgG2a, IgG2), IgG3, IgG4, IgA1, or IgA2.

In some embodiments, the antibody binds to
i. a cluster of differentiation (CD) antigen;
ii. a checkpoint inhibitor;
iii. a vascular target antigen;
iv. a stromal antigen;
v. an extracellular matrix antigen;
vi. a circulating antigen;
vii. an interleukin;
viii. an interleukin receptor;
ix. a growth factor;
x. a growth factor receptor;
xi. a drug;
xii. an adhesion molecule;
xiii. a tumor necrosis factor;
xiv. a tumor necrosis factor-related apoptosis-inducing ligand receptor;
xv. an insulin receptor;
xvi. a receptor tyrosine kinase;
xvii. a cytokine receptor;
xviii. a tropomyosin receptor kinase;
xix. an integrin;
xx. an immunoglobulin; or
xxi. an antigen of an infectious organism.

In some embodiments, the antibody binds to binds to:
i. an antigen selected from the group consisting of CD2, CD3, CD4, CD11a, CD19, CD20, CD25 (ILR2), CD30, CD33, CD38, CD52, CD139, CD152 (CTLA-4), CD274 (PD-L1), or CD319 (SLAMF);
ii. an antigen selected from the group consisting of PD-1 and PD-L1 (CD274);
iii. PSMA;
iv. Bone Marrow Stromal Antigen 2;
v. an antigen selected from the group consisting of CI, CIII, CIV, CV, LM, and FN;
vi. Factor IXa or Factor X;
vii. an antigen selected from the group consisting of IL-1β, IL-2, IL-5, IL-6, IL-12, IL-17A, and IL-23;
viii. an antigen selected from the group consisting of ILR2 (CD25), IL-4RA, IL-5RA, IL-6R, and IL-17RA;
ix. VEGFA;
x. an antigen selected from the group consisting of EGFR (ErbB1), FGFR, FGFR2, FGFR3, FGFR4, FGFR23, HER2/neu, HER3, (ErbB3), HER4, PDGFRA, VEGFR1, VEGFR2, VEGFR3, EphA1, EphA2, EphA3, EphA4, EphA5, EphA6, EphA7, EphA8, EphB1, EphB2, EphB3, EphB4, EphB5, EphB6, EphB7, HGFR (c-Met), and IGF2R;
xi. digoxin or dabigatran;
xii. EpCAM;
xiii. TNF-α or TNF-β;
xiv. TRAIL-R1 or TRAIL-R2;
xv. IR;
xvi. an antigen selected from the group consisting of FLT3, CSF-1R, KIT/SCFR, RON (SEA), AXL (UFO), MER, TYRO3, MUSK, RET, TIE1, DDR1, DDR2, ROR1, ROR2, ROS, LTL, ALK, KLG, and RYK;
xvii. an antigen selected from the group consisting of type I cytokine receptor, type II cytokine receptor, TNF receptors, CCR4, TGF-β receptors, and activin receptors;
xviii. an antigen selected from the group consisting of TRKA, TRKB, and TRKC;
xix. an antigen selected from the group consisting of integrin α4, integrin α4β1, and integrin α4β7;
xx. an IgE;
xxi. an antigen selected from the group of infectious organisms consisting of respiratory syncytial virus, *Bacillus anthracis*, and *Clostridium difficile*; or
an antigen selected from the group consisting of PSCK9, CGRPR, CRLR, RANKL, GP IIb/IIIa receptor, GD2, BLyS, C5, IRR, and TAG72.

Type III-C Conjugate Molecules

Type III-C conjugate molecules have the formula $$(CBN\text{-}L_c)\text{-}B\text{-}(L_a\text{-}A)_n \qquad (III\text{-}C)$$

in which CBN, $L_c$, B, $L_a$, and A are as defined above. In embodiments in which B is an antibody, n is 2-29.

In some embodiments, the cannabinoid component is provided by a cannabigerol, a cannabichromene, a cannabidiol, a tetrahydrocannabinol, a cannabicyclol, a cannabielsoin, a cannabinol, a cannabinodiol, a cannabitriol, a dehydrocannabifuran, a cannabifuran, a cannabichromanon, or a cannabiripsol. In some embodiments, a cannabinoid component is provided by cannabidiol. In some embodiments, the cannabinoid component is provided by cannabigerol.

In some embodiments in which B is an antibody, the antibody is an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof.

In some embodiments in which B is an antibody, the antibody is an IgG, an IgE, an IgM, an IgD, an IgA, or an IgY.

In some embodiments in which B is an antibody, the antibody is an IgG1, IgG2 (e.g., IgG2a, IgG2), IgG3, IgG4, IgA1, or IgA2.

In some embodiments, the antibody binds to
i. a cluster of differentiation (CD) antigen;
ii. a checkpoint inhibitor;
iii. a vascular target antigen;
iv. a stromal antigen;
v. an extracellular matrix antigen;
vi. a circulating antigen;
vii. an interleukin;
viii. an interleukin receptor;
ix. a growth factor;
x. a growth factor receptor;
xi. a drug;
xii. an adhesion molecule;
xiii. a tumor necrosis factor;
xiv. a tumor necrosis factor-related apoptosis-inducing ligand receptor;
xv. an insulin receptor;
xvi. a receptor tyrosine kinase;
xvii. a cytokine receptor;
xviii. a tropomyosin receptor kinase;
xix. an integrin;
xx. an immunoglobulin; or
xxi. an antigen of an infectious organism.

In some embodiments, in which B is an antibody, the antibody binds to binds to:
i. an antigen selected from the group consisting of CD2, CD3, CD4, CD11a, CD19, CD20, CD25 (ILR2), CD30, CD33, CD38, CD52, CD139, CD152 (CTLA-4), CD274 (PD-L1), or CD319 (SLAMF);
ii. an antigen selected from the group consisting of PD-1 and PD-L1 (CD274);
iii. PSMA;
iv. Bone Marrow Stromal Antigen 2;
v. an antigen selected from the group consisting of CI, CIII, CIV, CV, LM, and FN;
vi. Factor IXa or Factor X;
vii. an antigen selected from the group consisting of IL-1β, IL-2, IL-5, IL-6, IL-12, IL-17A, and IL-23;
viii. an antigen selected from the group consisting of ILR2 (CD25), IL-4RA, IL-5RA, IL-6R, and IL-17RA;
ix. VEGFA;
x. an antigen selected from the group consisting of EGFR (ErbB1), FGFR, FGFR2, FGFR3, FGFR4, FGFR23, HER2/neu, HER3, (ErbB3), HER4, PDGFRA, VEGFR1, VEGFR2, VEGFR3, EphA1, EphA2, EphA3, EphA4, EphA5, EphA6, EphA7, EphA8, EphB1, EphB2, EphB3, EphB4, EphB5, EphB6, EphB7, HGFR (c-Met), and IGF2R;
xi. digoxin or dabigatran;
xii. EpCAM;
xiii. TNF-α or TNF-β;
xiv. TRAIL-R1 or TRAIL-R2;
xv. IR;
xvi. an antigen selected from the group consisting of FLT3, CSF-1R, KIT/SCFR, RON (SEA), AXL (UFO), MER, TYRO3, MUSK, RET, TIE1, DDR1, DDR2, ROR1, ROR2, ROS, LTL, ALK, KLG, and RYK;
xvii. an antigen selected from the group consisting of type I cytokine receptor, type II cytokine receptor, TNF receptors, CCR4, TGF-β receptors, and activin receptors;
xviii. an antigen selected from the group consisting of TRKA, TRKB, and TRKC;
xix. an antigen selected from the group consisting of integrin α4, integrin α4β1, and integrin α4β7;
xx. an IgE;
xxi. an antigen selected from the group of infectious organisms consisting of respiratory syncytial virus, *Bacillus anthracis*, and *Clostridium difficile*; or
xxii. an antigen selected from the group consisting of PSCK9, CGRPR, CRLR, RANKL, GP IIb/IIIa receptor, GD2, BLyS, C5, IRR, and TAG72.

Type III-D Conjugate Molecules

Type III-D conjugate molecules have the formula:

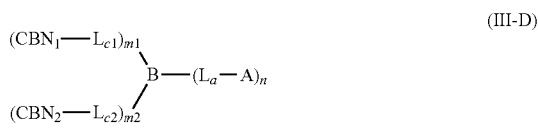

in which $CBN_1$ is a first cannabinoid component; Lei is a first cannabinoid component linker; $CBN_2$ is a second cannabinoid component; $L_{c2}$ is a second cannabinoid component linker; B is a target binding component; $L_a$ is an active component linker; A is an active component; and m1 and m2 each are at least 1. In embodiments in which B is an antibody, m1 and m2 independently are 1-30; n is 0-29; and the sum of m1, m2, and n is 2-30.

In some embodiments in which m1 and m2 are each 1, and the first and second cannabinoid components are the same. In some embodiments in which m1 and m2 are each 1, at least the first and the second cannabinoid components are different.

In some embodiments, the first and second cannabinoid components independently are provided by a cannabigerol, a cannabichromene, a cannabidiol, a tetrahydrocannabinol, a cannabicyclol, a cannabielsoin, a cannabinol, a cannabinodiol, a cannabitriol, a dehydrocannabifuran, a cannabifuran, a cannabichromanon, or a cannabiripsol. In some embodiments, the first and second cannabinoid components independently are provided by cannabidiol. In some embodiments, the first and second cannabinoid components independently are provided by cannabigerol.

In some embodiments, at least the first and second cannabinoid components are the same. In some embodiments, at least the first and second cannabinoid components are different.

In some embodiments in which B is an antibody, the antibody is an anti-idiotypic (anti-Id) antibody, a camelized antibody, a chimeric antibody, a disulfide-linked Fvs (sdFv), a F(ab') fragment, a Fab fragment, a human antibody, a humanized antibody, a murine antibody, an intrabody, a monoclonal antibody, a bispecific antibody, a multispecific antibody, or a single-chain Fv (scFv), or an epitope binding fragment thereof.

In some embodiments in which B is an antibody, the antibody is an IgG, an IgE, an IgM, an IgD, an IgA, or an IgY.

In some embodiments in which B is an antibody, the antibody is an IgG1, IgG2 (e.g., IgG2a, IgG2), IgG3, IgG4, IgA1, or IgA2.

In some embodiments, the antibody binds to
i. a cluster of differentiation (CD) antigen;
ii. a checkpoint inhibitor;
iii. a vascular target antigen;
iv. a stromal antigen;
v. an extracellular matrix antigen;
vi. a circulating antigen;
vii. an interleukin;
viii. an interleukin receptor;
ix. a growth factor;
x. a growth factor receptor;
xi. a drug;
xii. an adhesion molecule;
xiii. a tumor necrosis factor;
xiv. a tumor necrosis factor-related apoptosis-inducing ligand receptor;
xv. an insulin receptor;
xvi. a receptor tyrosine kinase;
xvii. a cytokine receptor;
xviii. a tropomyosin receptor kinase;
xix. an integrin;
xx. an immunoglobulin; or
xxi. an antigen of an infectious organism.

In some embodiments, in which B is an antibody, the antibody binds to binds to:

i. an antigen selected from the group consisting of CD2, CD3, CD4, CD11a, CD19, CD20, CD 25 (ILR2), CD30, CD33, CD38, CD52, CD139, CD152 (CTLA-4), CD274 (PD-L1), or CD319 (SLAMF);
ii. an antigen selected from the group consisting of PD-1 and PD-L1 (CD274);
iii. PSMA;
iv. Bone Marrow Stromal Antigen 2;
v. an antigen selected from the group consisting of CI, CIII, CIV, CV, LM, and FN;
vi. Factor IXa or Factor X;
vii. an antigen selected from the group consisting of IL-1β, IL-2, IL-5, IL-6, IL-12, IL-17A, and IL-23;
viii. an antigen selected from the group consisting of ILR2 (CD25), IL-4RA, IL-5RA, IL-6R, and IL-17RA;
ix. VEGFA;
x. an antigen selected from the group consisting of EGFR (ErbB1), FGFR, FGFR2, FGFR3, FGFR4, FGFR23, HER2/neu, HER3, (ErbB3), HER4, PDGFRA, VEGFR1, VEGFR2, VEGFR3, EphA1, EphA2, EphA3, EphA4, EphA5, EphA6, EphA7, EphA8, EphB1, EphB2, EphB3, EphB4, EphB5, EphB6, EphB7, HGFR (c-Met), and IGF2R;
xi. digoxin or dabigatran;
xii. EpCAM;
xiii. TNF-α or TNF-β;
xiv. TRAIL-R1 or TRAIL-R2;
xv. IR;
xvi. an antigen selected from the group consisting of FLT3, CSF-1R, KIT/SCFR, RON (SEA), AXL (UFO), MER, TYRO3, MUSK, RET, TIE1, DDR1, DDR2, ROR1, ROR2, ROS, LTL, ALK, KLG, and RYK;
xvii. an antigen selected from the group consisting of type I cytokine receptor, type II cytokine receptor, TNF receptors, CCR4, TGF-β receptors, and activin receptors;
xviii. an antigen selected from the group consisting of TRKA, TRKB, and TRKC;
xix. an antigen selected from the group consisting of integrin α4, integrin α4β1, and integrin α4β7;
xx. an IgE;
xxi. an antigen selected from the group of infectious organisms consisting of respiratory syncytial virus, *Bacillus anthracis*, and *Clostridium difficile*; or
xxii. an antigen selected from the group consisting of PSCK9, CGRPR, CRLR, RANKL, GP IIb/IIIa receptor, GD2, BLyS, C5, IRR, and TAG72.

In some embodiments, each of Lei and $L_c2$ is the same linker. In some embodiments, each of Lei and $L_c2$ is a different linker.

Methods of Synthesis

The disclosed conjugate molecules can be synthesized using methods well known in the art. Examples of methods for synthesizing cannabinoid conjugate components are provided in the working examples, below.

Pharmaceutically Acceptable Salts

The disclosed conjugate molecules can form salts. "Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19.

Pharmaceutical Compositions

Pharmaceutical compositions comprise one or more of the conjugate molecules described above, or a pharmaceutically acceptable salt of the conjugate molecule, together with a pharmaceutically acceptable vehicle, such as water, or a buffered aqueous solution. Pharmaceutical compositions can be provided as lyophilized powders containing, e.g., sodium chloride and mannitol, to be reconstituted using water for injection.

In some embodiments, a pharmaceutical composition comprises both cis and trans isomers. In some embodiments, a pharmaceutical composition comprises substantially only cis isomers or substantially only trans isomers. A pharmaceutical composition comprises "substantially only" cis isomers or substantially only trans isomers when the relevant isomer is below a detectable level as measured by a conventional analytical method such as spectroscopy or chromatography.

In some embodiments, a pharmaceutical composition comprises both λ and δ stereoisomers. In some embodiments, a pharmaceutical composition comprises substantially only λ stereoisomers or substantially only δ stereoisomers. A pharmaceutical composition comprises "substantially only" λ stereoisomers or substantially only δ stereoisomers when the relevant stereoisomer is below a detectable level as measured by a conventional analytical method such as spectroscopy or chromatography.

Delivery Vehicles

In some embodiments, a pharmaceutical composition includes a delivery vehicle for the conjugate molecule. Delivery vehicles include, but are not limited to, a carbon nanotube, a carbon nanoparticle, a PEGylated nanosized graphene oxide, a gold nanoparticle, a nanosized metalorganic framework, a nanoparticle comprising polysiloxane, a polymeric micellar nanoparticle, a block copolymer micelle nanoparticle, and a liposome. See, e.g., Johnstone et al., Chem. Rev. 116, 3436-86, 2016.

Therapeutic Methods

The disclosed conjugate molecules have a variety of therapeutic uses depending on which therapeutic agent component(s) are included in a conjugate molecule. "Treat" as used in this disclosure means reducing or inhibiting the progression of one or more symptoms of the disorder or disease for which the conjugate molecule is administered, such as inflammation or pain.

Suitable administration routes include, but are not limited to, intravenous, intraperitoneal, intratumoral, intra-arterial, intra-arterial with blood brain barrier disruption, oral, topical, transdermal, inhalation, parenteral, sublingual, buccal, rectal, vaginal, urethral, intranasal, subcutaneous, and intrapleural. The dose of a conjugate molecule can be based on the doses typically used for the various components of the conjugate molecule (e.g., platinum complex anti-neoplastic agents, β-lactam antibiotics). These doses are well known in the art.

1. Hyperproliferative Disorders

Conjugate molecules can be used to treat hyperproliferative disorders, including cancers. For example, treatment of cancer may include inhibiting the progression of a cancer, for example, by reducing proliferation of neoplastic or pre-neoplastic cells; destroying neoplastic or pre-neoplastic cells; or inhibiting metastasis or decreasing the size of a tumor. Cancers that can be treated include, but are not limited to, multiple myeloma (including systemic light chain amyloidosis and Waldenström's macroglobulinemia/lymphoplasmocytic lymphoma), myelodysplastic syndromes, myeloproliferative neoplasms, gastrointestinal malignancies (e.g., esophageal, esophagogastric junction, gallbladder, gastric, colon, pancreatic, hepatobiliary, anal, and rectal cancers), leukemias (e.g., acute myeloid, acute myelogenous, chronic myeloid, chronic myelogenous, acute lymphocytic, acute lymphoblastic, chronic lymphocytic, and hairy cell leukemia), Hodgkin lymphoma, non-Hodgkin's lymphomas (e.g., B-cell lymphoma, hairy cell leukemia, primary cutaneous B-cell lymphoma, and T-cell lymphoma), lung cancer (e.g., small cell and non-small cell lung cancers), basal cell carcinoma, plasmacytoma, breast cancer, bladder cancer, kidney cancer, neuroendocrine tumors, adrenal tumors, bone cancer, soft tissue sarcoma, head and neck cancer, thymoma, thymic carcinoma, cervical cancer, uterine cancers, ovarian cancer (e.g., Fallopian tube and primary peritoneal cancers), vaginal cancer, vulvar cancer, penile cancer, testicular cancer, prostate cancer, melanoma (e.g., cutaneous and uveal melanomas), non-melanoma skin cancers (e.g., basal cell skin cancer, dermatofibrosarcoma protuberans, Merkel cell carcinoma, and squamous cell skin cancer), malignant pleural mesothelioma, central nervous system (CNS) cancers (e.g., astrocytoma, oligodendroglioma, anaplastic glioma, glioblastoma, intra-cranial ependymoma, spinal ependymoma, medulloblastoma, CNS lymphoma, spinal cord tumor, meningioma, brain metastases, leptomeningeal metastases, metastatic spine tumors), and occult primary cancers (i.e., cancers of unknown origin).

Conjugate molecules described in this disclosure can be administered in conjunction with one or more other cancer therapies such as chemotherapies, immunotherapies, tumor-treating fields (TTF; e.g., OPTUNE® system), radiation therapies (XRT), and other therapies (e.g., hormones, autologous bone marrow transplants, stem cell reinfusions). "In conjunction with" includes administration together with, before, or after administration of the one or more other cancer therapies.

Chemotherapies include, but are not limited to, FOLFOX (leucovorin calcium, fluorouracil, oxaliplatin), FOLFIRI (leucovorin calcium, fluorouracil, irinotecan), FOLFIRINOX (leucovorin calcium, fluorouracil, irinotecan, oxaliplatin), irinotecan (e.g., CAMPTOSAR®), capecitabine (e.g., XELODA®), gemcitabine (e.g., GEMZAR®), paclitaxel (e.g., ABRAXANE®), dexamethasone, lenalidomide (e.g., REVLIMID®), pomalidomide (e.g., POMALYST®), cyclophosphamide, regorafenib (e.g., STIVARGA®), erlotinib (e.g., TARCEVA®), ixazomib (e.g., NINLARO®), bevacizumab (e.g., AVASTIN®), bortezomib (e.g., VELCADE®, NEOMIB®), cetuximab (e.g., ERBITUX®), daratumumab (e.g., DARZALEX®), elotumumab (e.g., EMPLICITI™), carfilzomib (e.g., KYPRO- LIS®), palbociclib (e.g., IBRANCE®), fulvestrant (e.g., FASLODEX®), carboplatin, cisplatin, taxol, nab paclitaxel (e.g., ABRAXANE®), 5-fluorouracil, RVD (lenalidomide, bortezomib, dexamethasone), pomolidomide (e.g., POMALYST®), temozolomide (e.g., TEMODAR®), pCV (procarbazine, lomustine, vincristine), methotrexate (e.g., TREXALL®, RASUVO®, XATMEP®), carmustine (e.g., BICNU®, GLIADEL WAFER®), etoposide (e.g., ETOPOPHOS®, TOPOSAR®), sunitinib (e.g., SUTENT®), everolimus (e.g., ZORTRESS®, AFINITOR®), rituximab (e.g., RITUXAN®, MABTHERA®), r-MPV (vincristine, procarbazine, rituximab), cytarabine (e.g., DEPOCYT®, CYTOSAR-U®), thiotepa (e.g., TEPADINA®), busulfan (e.g., BUSULFEX®, MYLERAN®), TBC (thiotepa, busulfan, cyclophosphamide), ibrutinib (e.g., IMBRUVICA®), topotecan (e.g., HYCAMTIN®), pemetrexed (e.g., ALIMTA®), vemurafenib (e.g., ZELBORAF®), cobimetinib (e.g., COTELLIC®), dabrafenib (e.g., TAFINLAR®), trametinib (e.g., MEKINIST®), alectinib (e.g., ALECENSA®), lapatinib (e.g., TYKERB®), neratinib (e.g., NERLYNX®), ceritinib (e.g., ZYKADIA®), brigatinib (e.g., ALUNBRIG®), afatinib (e.g., GILOTRIF®, GIOTRIF®), gefitinib (e.g., IRESSA®), osimertinib (e.g., TAGRISSO®, TAGRIX®), and crizotinib (e.g., XALKORI®).

Immunotherapies include, but are not limited to, checkpoint inhibitors, including monoclonal antibodies such as ipilimumab (e.g., YERVOY®), nivolumab (e.g., OPDIVO®), pembrolizumab (e.g., KEYTRUDA®); cytokines; cancer vaccines; and adoptive cell transfer.

In some embodiments, one or more conjugate molecules described above are administered to a patient with a cancer, including any of those cancers listed above. In some embodiments, as described below, the patient has colon cancer, rectal cancer, pancreatic cancer, multiple myeloma, or glioblastoma multiforme and the conjugate molecule(s) are administered in conjunction with an additional therapy appropriate for the particular cancer.

A conjugate molecule having a hydroxyurea component can be used to treat chronic myeloid leukemia, ovarian cancer, and squamous cell cancers of the head and neck, as well as to reduce episodes of pain and the need for blood transfusions in patients with sickle cell anemia.

A conjugate molecule having a temozolomide component can be used to treat brain cancers (e.g., astrocytoma, glioblastoma multiforme).

A conjugate molecule having a physostigmine-based carbamate component can be used to treat glaucoma and to reverse central and peripheral anticholinergia. A conjugate molecule having a rivastigmine-based carbamate component can be used to treat confusion or dementia in, for example, in patients with Alzheimer's disease or Parkinson's disease.

The disclosed conjugate molecules can be used to treat these and other disorders in the same way the therapeutic agent components of the molecules are used, and these methods are well known. For example, conjugate molecules containing entecavir, emtricitabine, daclatasvir, atazanavir, didanosine, and/or stavudine can be used to treat viral infections; conjugate molecules containing diclofenac or celecoxib components can be used as anti-inflammatory agents; conjugate molecules containing a warfarin component can be used as anticoagulants; and conjugate molecules containing pravastatin components can be used to treat cardiovascular disorders. An advantage of conjugate molecules, however, is that the cannabinoid can be delivered directly to the site of action of the therapeutic agent, where the released cannabinoid can provide further therapeutic benefits. The therapeutic benefits and potential benefits of cannabinoids are well known. For example, see Dzierzanowski, Cancers 11, 129-41, 2019 (oncology and palliative care); Urits et al., Pain Ther. 8, 41-51, 2019 (pain); Hillen et al., Ther. Adv. Drug Safety 10, 1-23 2019 (neuropsychiatric symptoms in dementia).

2. Additional Therapeutic Uses of Type I-C Conjugate Molecules

Type I-C conjugate molecules have a variety of therapeutic uses depending on which β-lactam antibiotic component(s) are included in a conjugate molecule.

For example, in addition to treating bacterial infections (including chronic lung infections in cystic fibrosis; e.g., Kirkby et al., Core Evidence 6, 59-66, 2011), β-lactam antibiotics have been proposed for the treatment of type I diabetes (e.g., US 2014/0234282, US 2007/0060561); treatment of cancer (e.g., US 2006/0160787); as neuroprotective compounds (e.g., US 2007/0238717); and as proteasome inhibitors, for treatment of, e.g., Alzheimer's disease, cachexia and muscle-wasting diseases, allergies, and inflammation (in connection with rheumatoid arthritis, scleroderma, rheumatic fever, inflammatory bowel disease, myasthenia gravis, multiple sclerosis, Guillain-Barre syndrome, conjunctiva of the eye, systemic lupus erythematosus, encephalitis, Adult Respiratory Distress Syndrome, psoriasis, emphysema, and muscular dystrophy (e.g., US 2007/0060561).

The disclosed conjugate molecules can be used to treat these and other disorders in the same way the β-lactam antibiotic components of the molecules are used, and these methods are well known. An advantage of conjugate molecules, however, is that the cannabinoid can be delivered directly to the site of infection where it can provide further therapeutic benefits. The therapeutic benefits and potential benefits of cannabinoids are well known. For example, see Dzierzanowski, Cancers 11, 129-41, 2019 (oncology and palliative care); Urits et al., Pain Ther. 8, 41-51, 2019 (pain); Hillen et al., Ther. Adv. Drug Safety 10, 1-23 2019 (neuropsychiatric symptoms in dementia).

In addition, *C. sativa* extracts have microbicidal activity in vitro against gram-positive bacteria (e.g., *Bacillus subtilis, Bacillus pumilus, Staphylococcus aureus, Micrococcus flavus, Clostridium sporogens, Enterococcus faecium*, and *Streptococcus salivarius*); gram-negative bacteria (e.g., *Proteus vulgaris, Bordetella bronchioseptica, Pectobacterium carotovorum*, and *Pseudomonas savastonoi*); and fungi (e.g., *Aspergillus niger*). See Elphick, Gene 399, 65-71, 2007; Wasim et al., J. Pharm. Sci. 8, 29-38, 1995; Nissen et al., Fitoterapia 81, 413-19, 2010; and Hernandez-Cervantes et al., Neuroimmunomodulation 24, 183-99, 2017. See also Appendino et al., J. Nat. Prod. 71, 1427-30, 2008.

EXAMPLES: β-LACTAM ANTIBIOTIC CANNABINOID CONJUGATE COMPONENTS

The following synthetic methods are general. They can be used to make these examples or related β-lactam antibiotic cannabinoid conjugate components using alternative building blocks, intermediates, or reagents. Alternative reagent systems and conditions to achieve desired transformations can be used. Alternative protecting group strategies can be used. Standard purification techniques can be used at any stage of a synthesis. For simplicity, cannabidiol (CBD) is used as a representative cannabinoid.

Example 1. Ether-Linked β-Lactam Antibiotic Cannabinoid Conjugate Components

Cephem Conjugates

Cephem ether linked β-lactam antibiotic cannabinoid conjugate components are synthesized according to the following Scheme. The CAS numbers for the two key building blocks is shown. Reaction conditions follow standard conditions for amine acylation in the first step to attach the cephem side chain, for alkylation of a phenol group of a cannabinoid in the second step with optional use of a catalyst or enhancer such as NaI, followed by standard removal of the p-methoxybenzyl protecting group in the third step to furnish the product. A di-alkylated product may also be obtained.

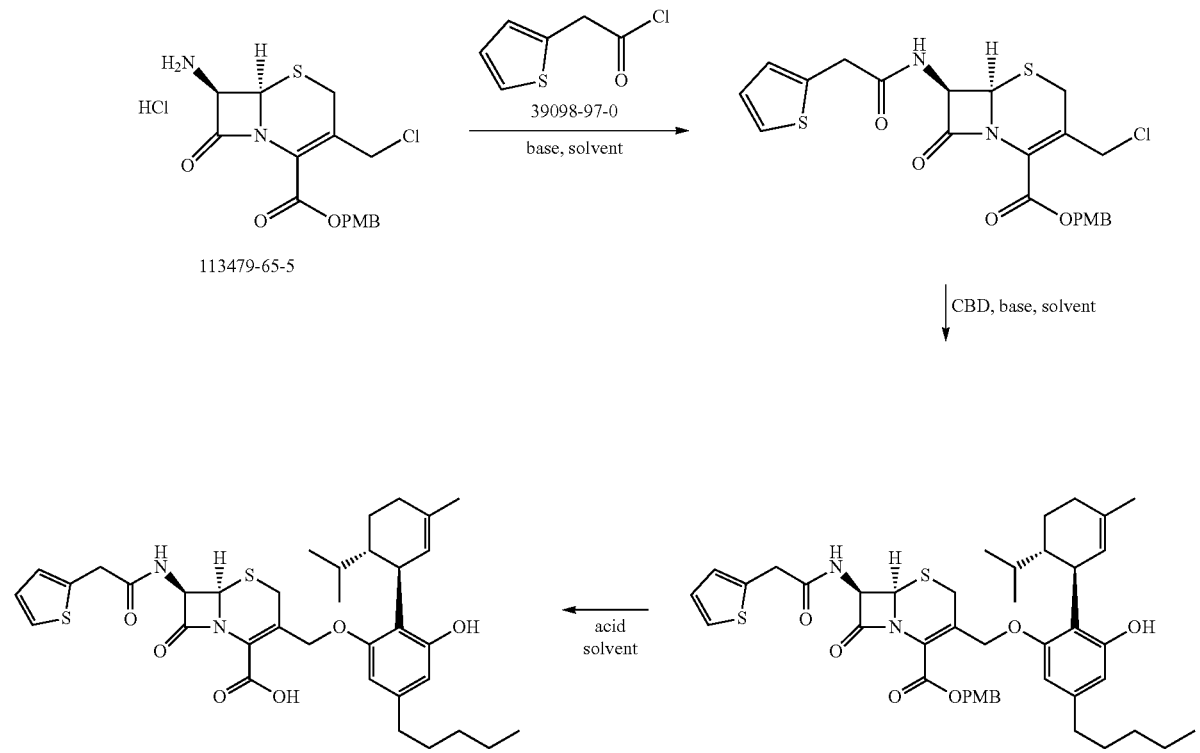

Carbacephem Conjugates

Carbacephem ether linked β-lactam antibiotic cannabinoid conjugate components are synthesized according to the following Scheme. The general starting material [177472-75-2] was reported in racemic form as [54296-34-3] (Journal of the American Chemical Society (1974), 96(24), 7584) and is elaborated to the iodide intermediate after installing a side chain of choice using a previously reported process (WO 96/04247). Alkylation of CBD with the iodide followed by deprotection, both steps under standard conditions, provides the desired product.

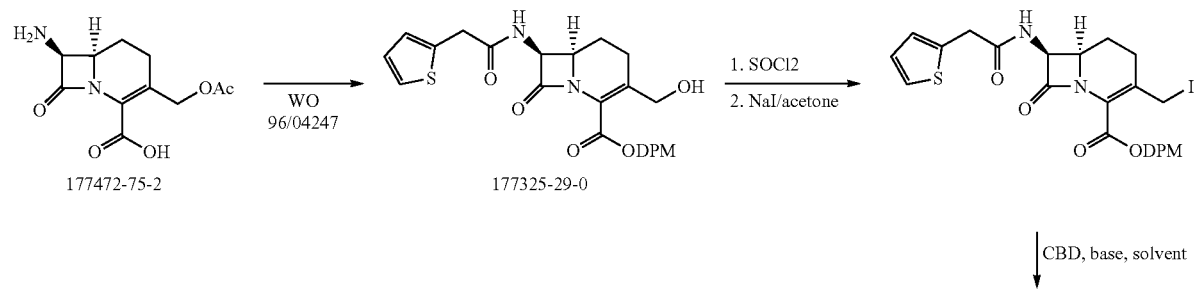

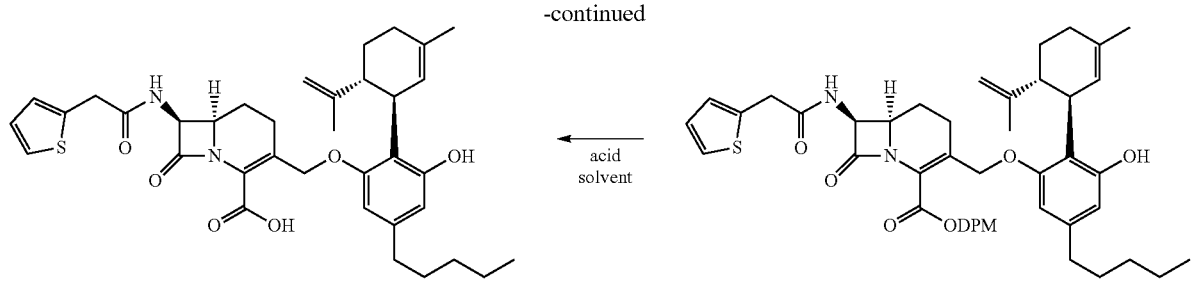

← acid solvent

Penem Conjugates

Penem ether linked β-lactam antibiotic cannabinoid conjugate components are synthesized according to the following Scheme. The starting material [145354-22-9], prepared as reported (Journal of Organic Chemistry, 58(1), 272-4; 1993), is reacted with CBD under standard alkylating conditions. The silyl ether TBS protecting group is then removed followed by deallylation under known conditions to give the desired product.

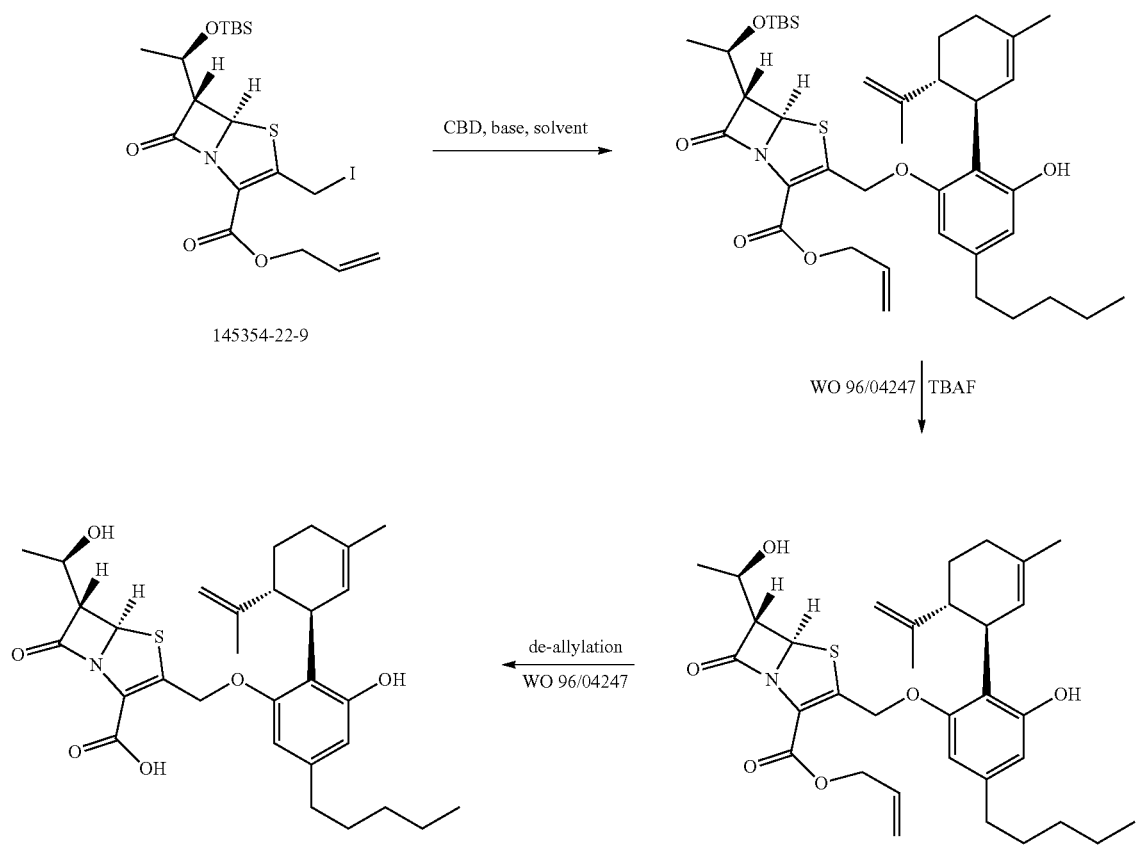

Carbapenem Conjugates

Carbapenem ether linked β-lactam antibiotic cannabinoid conjugate components are synthesized according to the following Scheme. The starting material [136324-03-3] is reacted with CBD under standard alkylating conditions. The silyl ether TES protecting group is then removed followed by removal of the p-methoxybenzyl ester protecting group under known conditions to give the desired product.

147 148

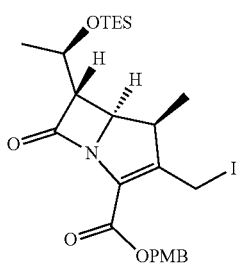

136324-03-3

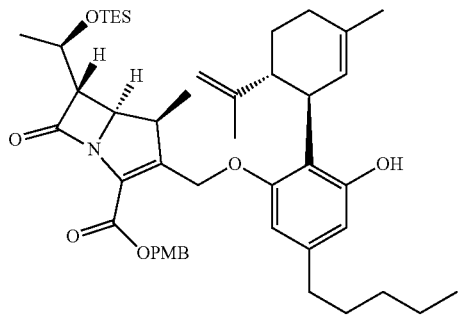

silyl ether protecting group removal

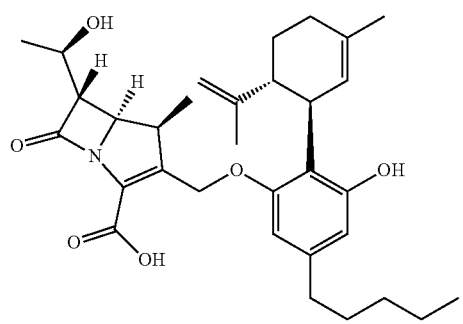

← deprotection
acid, solvent

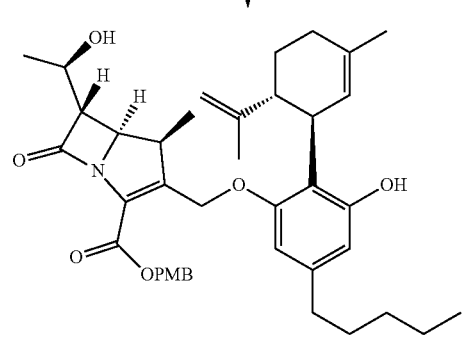

Example 2. Carbonate-Linked β-Lactam Antibiotic Cannabinoid Conjugate Components Cephem Conjugates Cephem carbonate linked β-lactam antibiotic cannabinoid conjugate components are synthesized according to the following Scheme. The starting material is acylated with a side chain of choice and then the acid is protected as described previously (WO 96/04247). The resulting alcohol is then treated with phosgene and the adduct reacted with CBD in the presence of base to form the carbonate-linked intermediate, which is then deprotected with acid to deliver the desired product.

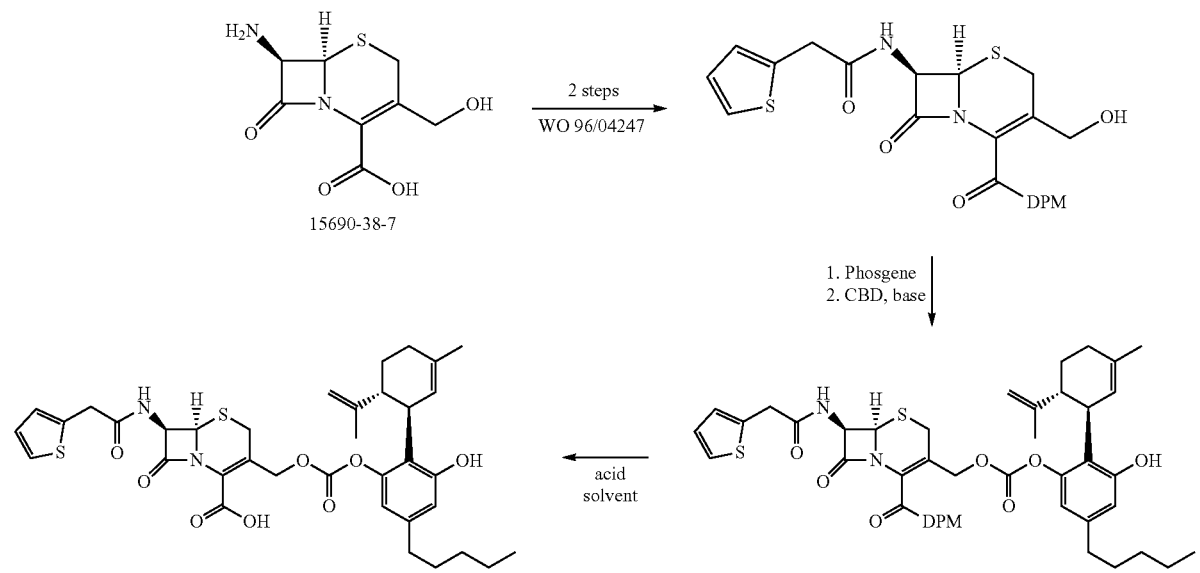

Carbacephem Conjugates

Carbacephem carbonate linked β-lactam antibiotic cannabinoid conjugate components are synthesized according to the following Scheme. The starting material is acylated with a side chain of choice and then the acid is protected as described previously (WO 96/04247). The resulting alcohol is then treated with phosgene and the adduct reacted with CBD in the presence of base to form the carbonate-linked intermediate, which is then deprotected with acid to deliver the desired product.

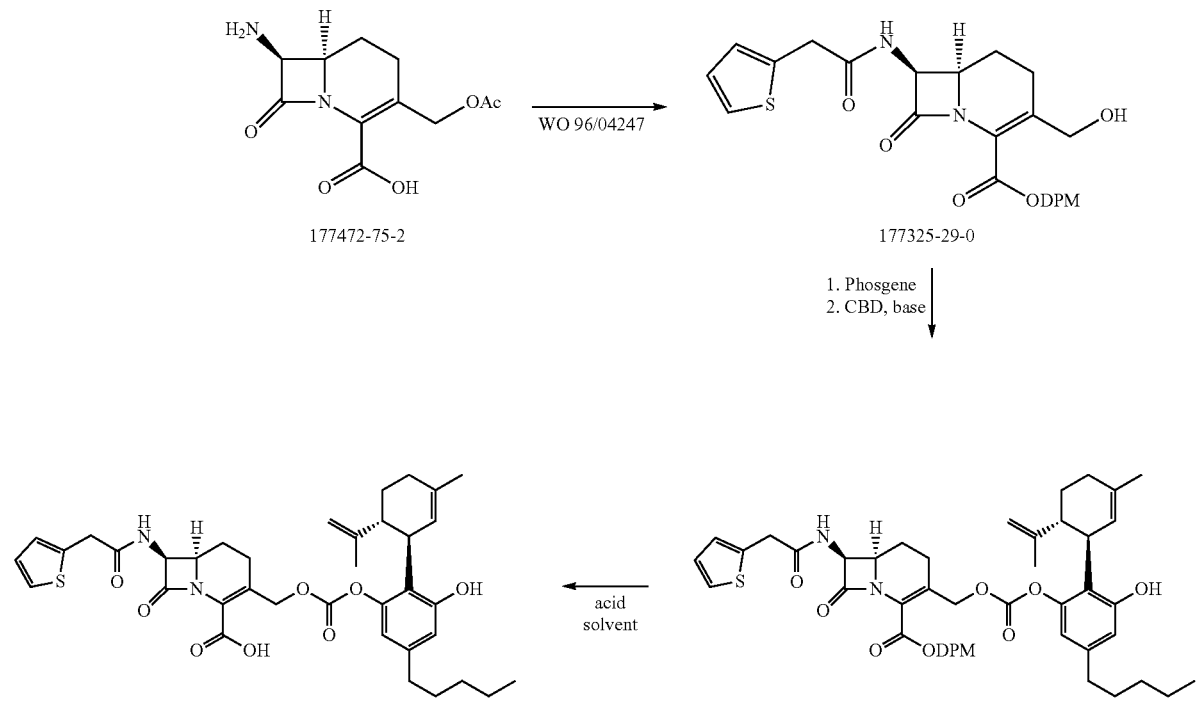

Penem Conjugates

Penem carbonate linked β-lactam antibiotic cannabinoid conjugate components are synthesized according to the following Scheme. The starting material [88585-78-8], prepared as reported (U.S. Pat. No. 4,631,150), is reacted with phosgene and the intermediate reacted with CBD under standard basic conditions. The silyl ether TBS protecting group is then removed followed by deallylation under known conditions to give the desired product.

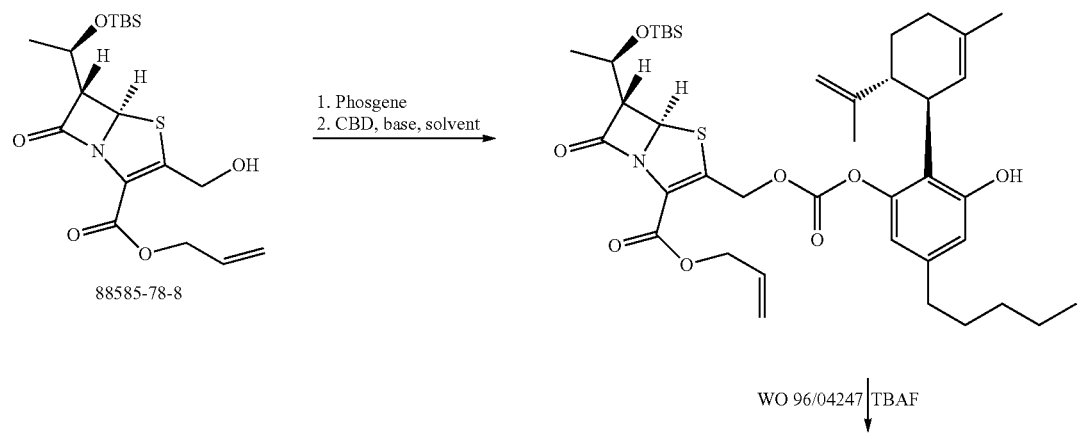

151

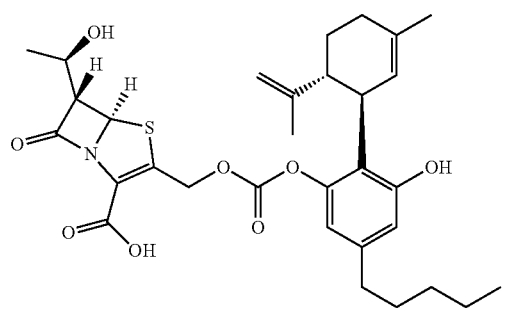

152

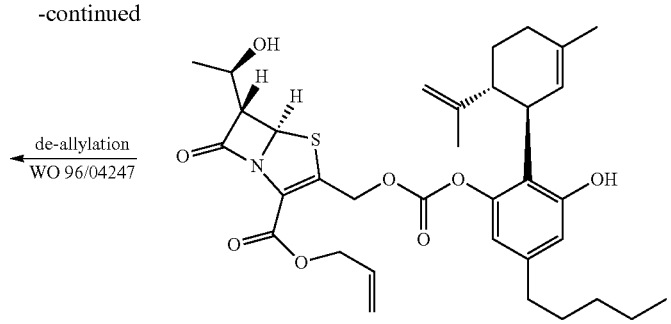

-continued de-allylation
WO 96/04247

Carbapenem Conjugates

Carbapenem carbonate linked β-lactam antibiotic cannabinoid conjugate components are synthesized according to the following Scheme. The starting material [118990-99-1], prepared as reported (Journal of Antibiotics (1988), 41(6), 780-7), is reacted with phosgene and the intermediate reacted with CBD under standard basic conditions. Deallylation under known conditions gives the desired product.

Example 3. Thiocarbonate-Linked β-Lactam Antibiotic Cannabinoid Conjugate Components Cephem Conjugates Cephem thiocarbonate linked β-lactam antibiotic cannabinoid conjugate components are synthesized according to the following Scheme. The starting material is acylated with a side chain of choice and then the acid is protected as described previously (WO 96/04247). The resulting alcohol

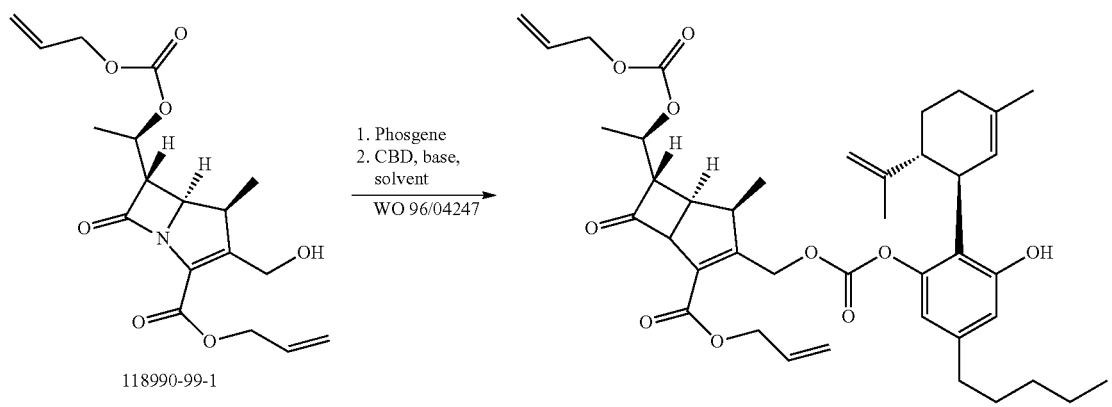

118990-99-1

1. Phosgene
2. CBD, base, solvent

WO 96/04247 deallylation
WO 96/04247

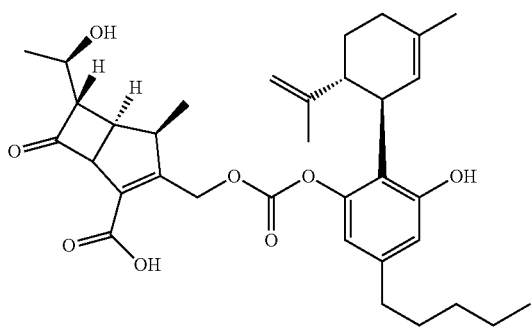

is then treated with thiophosgene and the adduct reacted with CBD in the presence of base to form the thiocarbonate product which is then deprotected with acid to deliver the desired product.

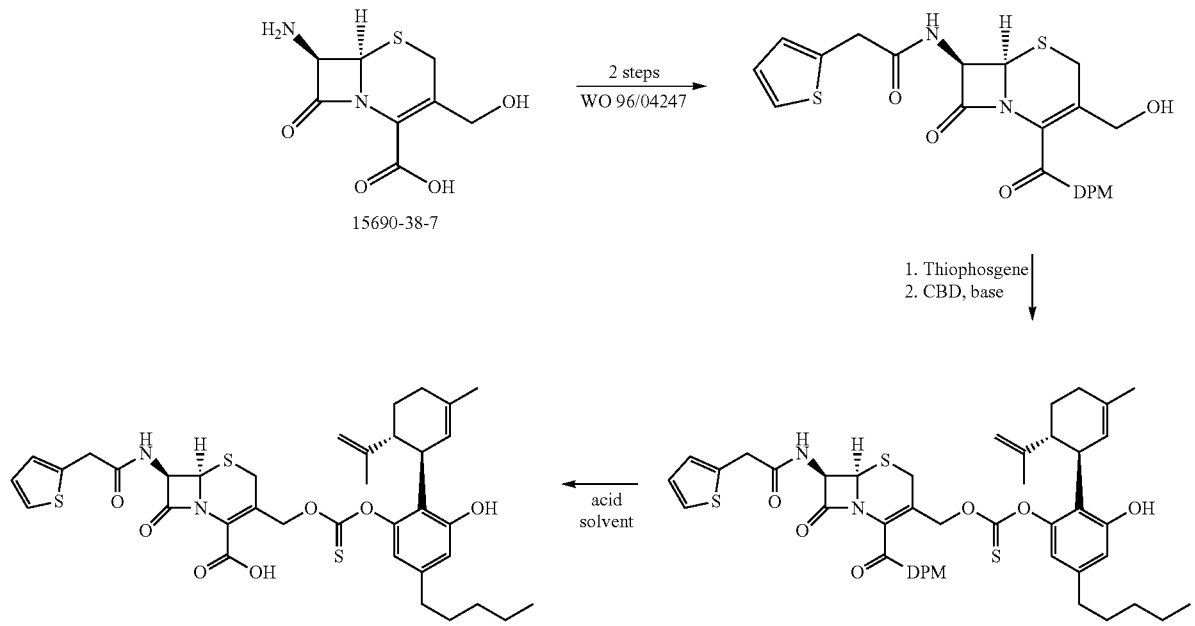

Carbacephem Conjugates

Carbacephem thiocarbonate linked β-lactam antibiotic cannabinoid conjugate components are synthesized according to the following Scheme. The starting material is acylated with a side chain of choice and then the acid is protected as described previously (WO 96/04247). The resulting alcohol is then treated with thiophosgene and the adduct reacted with CBD in the presence of base to form the thiocarbonate product which is then deprotected with acid to deliver the desired product.

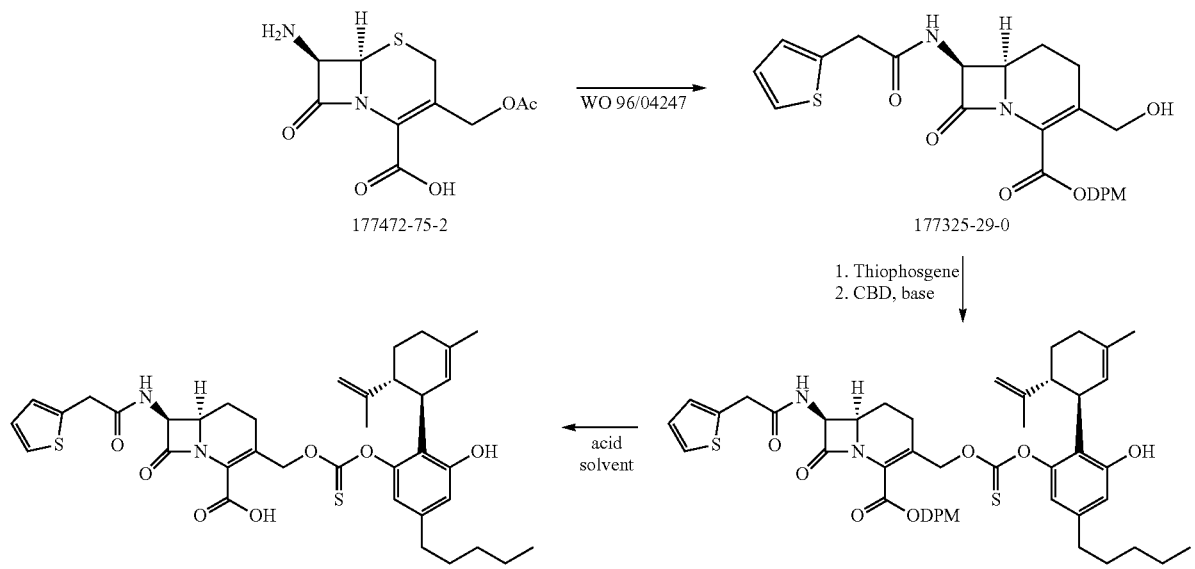

Penem Conjugates

Penem thiocarbonate linked β-lactam antibiotic cannabinoid conjugate components are synthesized according to the following Scheme. The starting material [88585-78-8], prepared as reported (U.S. Pat. No. 4,631,150), is reacted with thiophosgene and the intermediate reacted with CBD under standard basic conditions. The silyl ether TBS protecting group is then removed followed by deallylation under known conditions to give the desired

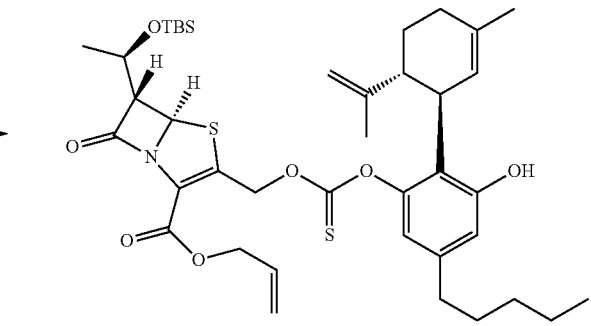
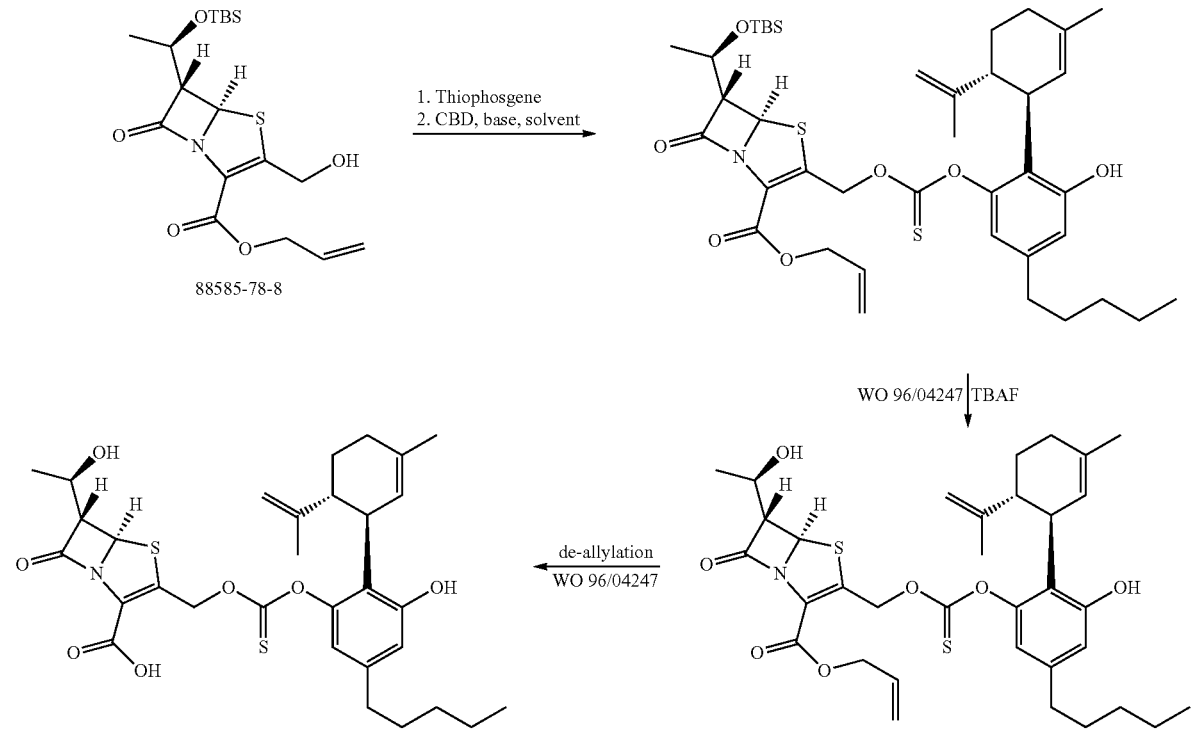

Carbapenem Conjugates

Carbapenem thiocarbonate linked β-lactam antibiotic cannabinoid conjugate components are synthesized according to the following Scheme. The starting material [118990-99-1], prepared as reported (Journal of Antibiotics (1988), 41(6), 780-7), is reacted with thiophosgene and the intermediate reacted with CBD under standard basic conditions. Deallylation under known conditions gives the desired product.

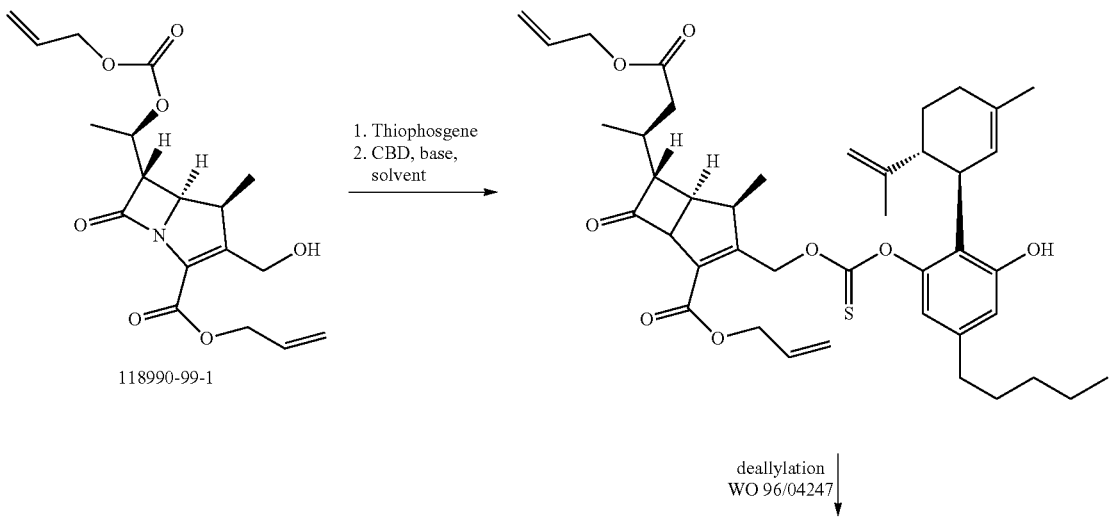

-continued

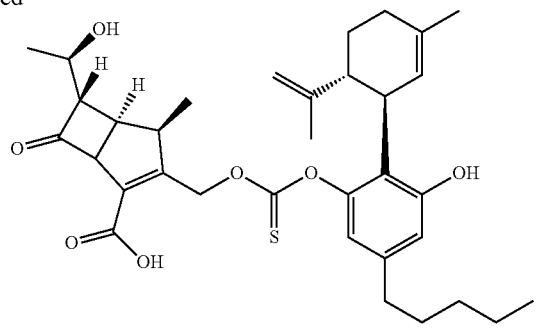

Example 4. Carbamate-Linked β-Lactam Antibiotic Cannabinoid Conjugate Components

Cephem Conjugates

Cephem carbamate linked β-lactam antibiotic cannabinoid conjugate components are synthesized according to the following Scheme. The starting material [6187-87-7] is acylated with a side chain of choice. The acetate group is then converted to the iodide with TMS-I as has been reported for similar molecules (WO 96/04247). The iodide is then converted to the azide which is then reduced to the amine, both steps under standard conditions. Reaction of the amine with phosgene followed by addition of CBD forms the carbamate linkage. Deprotection of the t-butyl ester under standard conditions gives the desired product.

Carbacephem Conjugates

Carbacephem carbamate linked β-lactam antibiotic cannabinoid conjugate components are synthesized according to the following Scheme. The starting material [177472-75-2] has been previously described (WO 96/04247; Journal of the American Chemical Society (1974), 96(24), 7584). It is converted to the t-butyl ester under established isobutylene conditions, and then is acylated with a side chain of choice. The acetate group is then converted to the iodide with TMS-I as has been reported for similar molecules (WO 96/04247). The iodide is then converted to the azide, which is then reduced to the amine, both steps under standard conditions. Reaction of the amine with phosgene followed by addition of CBD forms the carbamate linkage. Deprotection of the t-butyl ester under standard conditions gives the desired product.

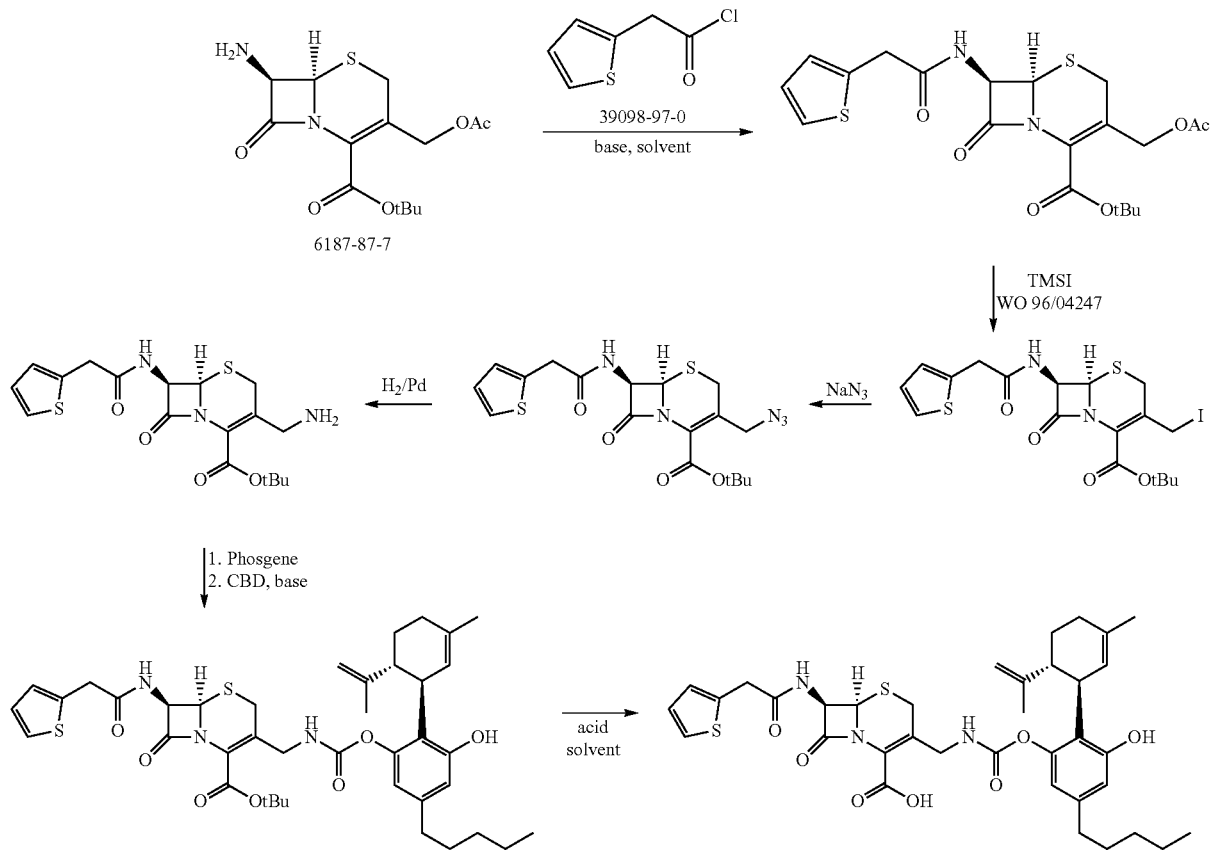

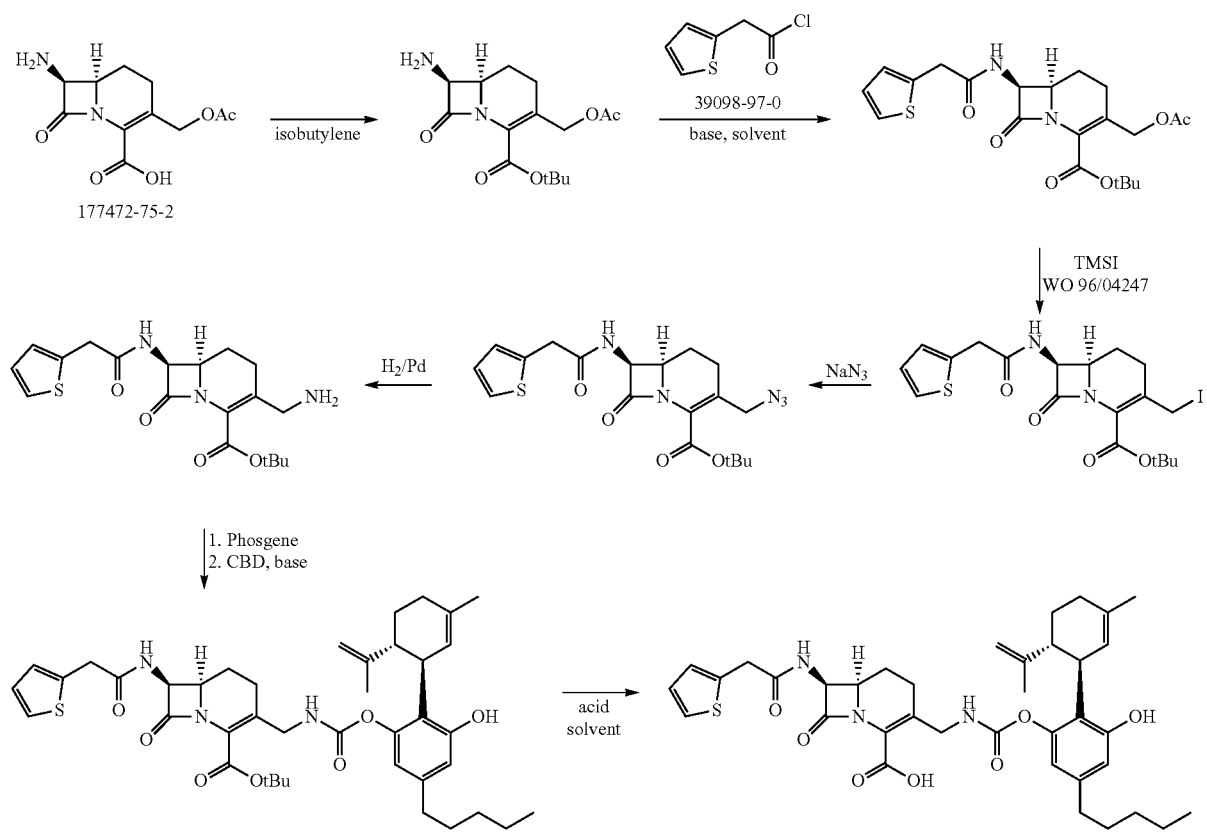

Penem Conjugates

Penem carbamate linked β-lactam antibiotic cannabinoid conjugate components are synthesized according to the following Scheme. The starting material [83572-65-0] has been previously described (Journal of Antibiotics (1982), 35(9), 1248-51). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide, which is then reduced to the amine, both steps under standard conditions. Reaction of the amine with phosgene followed by addition of CBD forms the carbamate linkage. Removal of the TBDMS ether and t-butyl ester protecting groups under standard conditions gives the desired product.

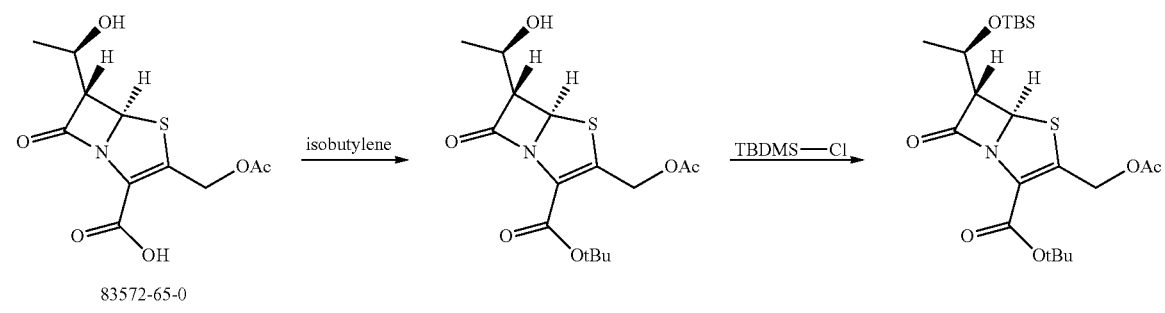

161 162

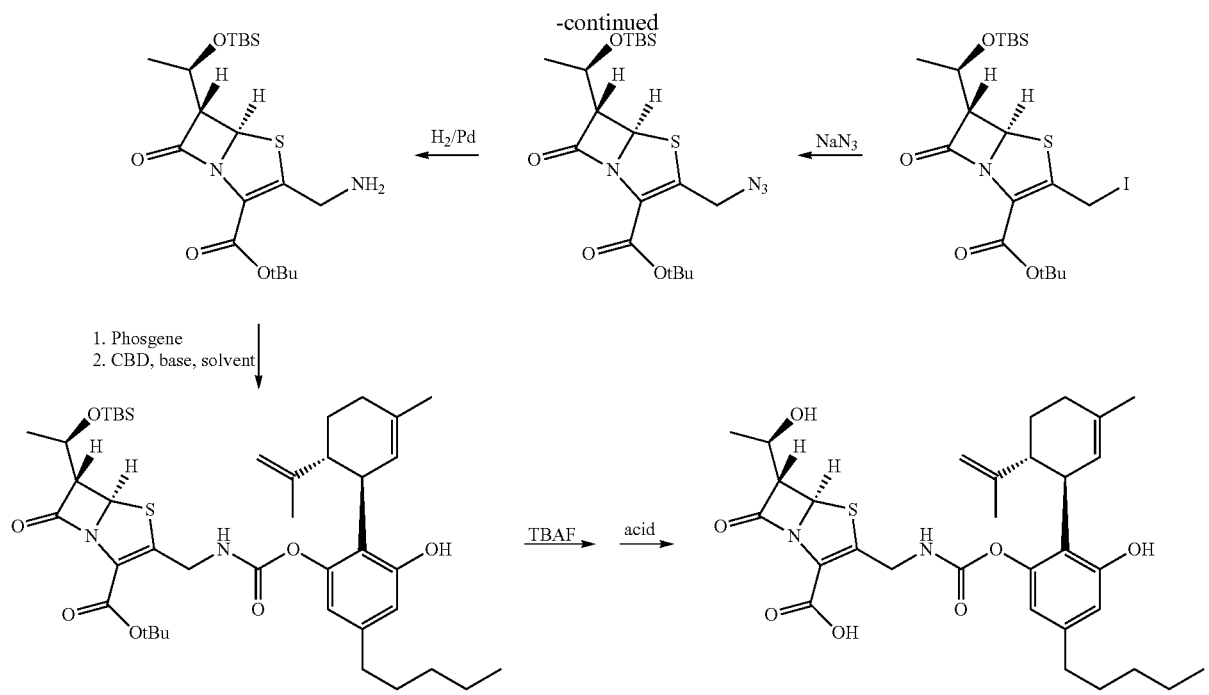

Carbapenem Conjugates

Carbapenem carbamate linked β-lactam antibiotic cannabinoid conjugate components are synthesized according to the following Scheme. The starting material [112064-40-1] has been previously described (Journal of Antibiotics (1988), 41(6), 780-7). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide which is then reduced to the amine, both steps under standard conditions. Reaction of the amine with phosgene followed by addition of CBD forms the carbamate linkage. Removal of the TBDMS ether and t-butyl ester protecting groups under standard conditions gives the desired product.

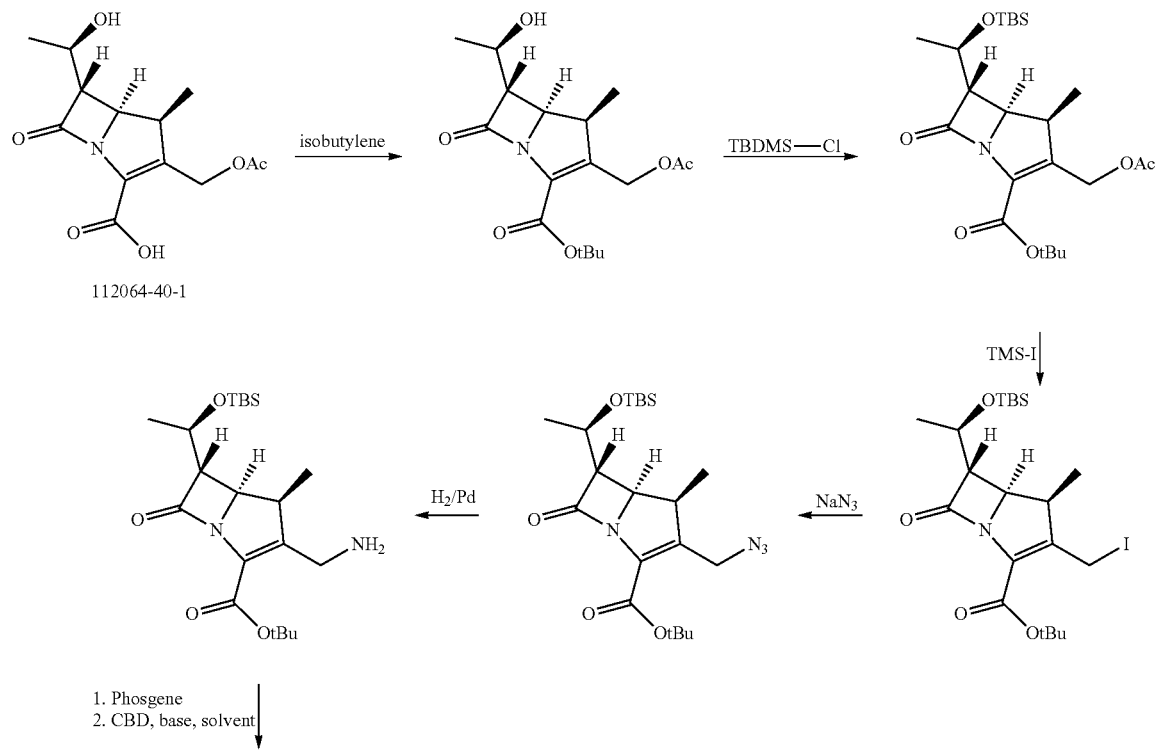

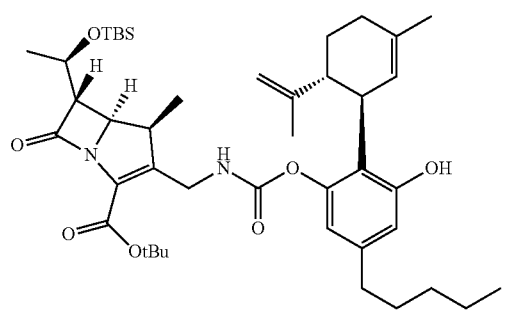
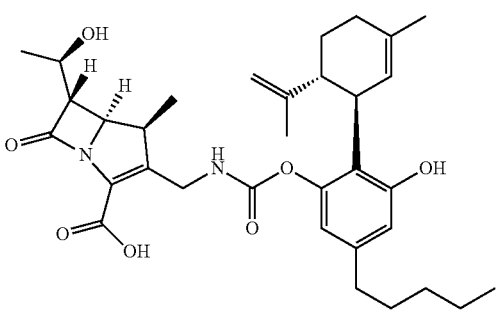

Example 5. Thiocarbamate-Linked β-Lactam Antibiotic Cannabinoid Conjugate Components

Cephem Conjugates

Cephem thiocarbamate linked β-lactam antibiotic cannabinoid conjugate components are synthesized according to the following Scheme. The starting material [6187-87-7] is acylated with a side chain of choice. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of CBD forms the thiocarbamate linkage. Deprotection of the t-butyl ester under standard conditions gives the desired product.

Carbacephem Conjugates

Carbacephem thiocarbamate linked β-lactam antibiotic cannabinoid conjugate components are synthesized according to the following Scheme. The starting material [177472-75-2] has been previously described (WO 96/04247; Journal of the American Chemical Society (1974), 96(24), 7584). It is converted to the t-butyl ester under established isobutylene conditions, and then is acylated with a side chain of choice. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of CBD forms the thiocarbamate linkage. Deprotection of the t-butyl ester under standard conditions gives the desired product.

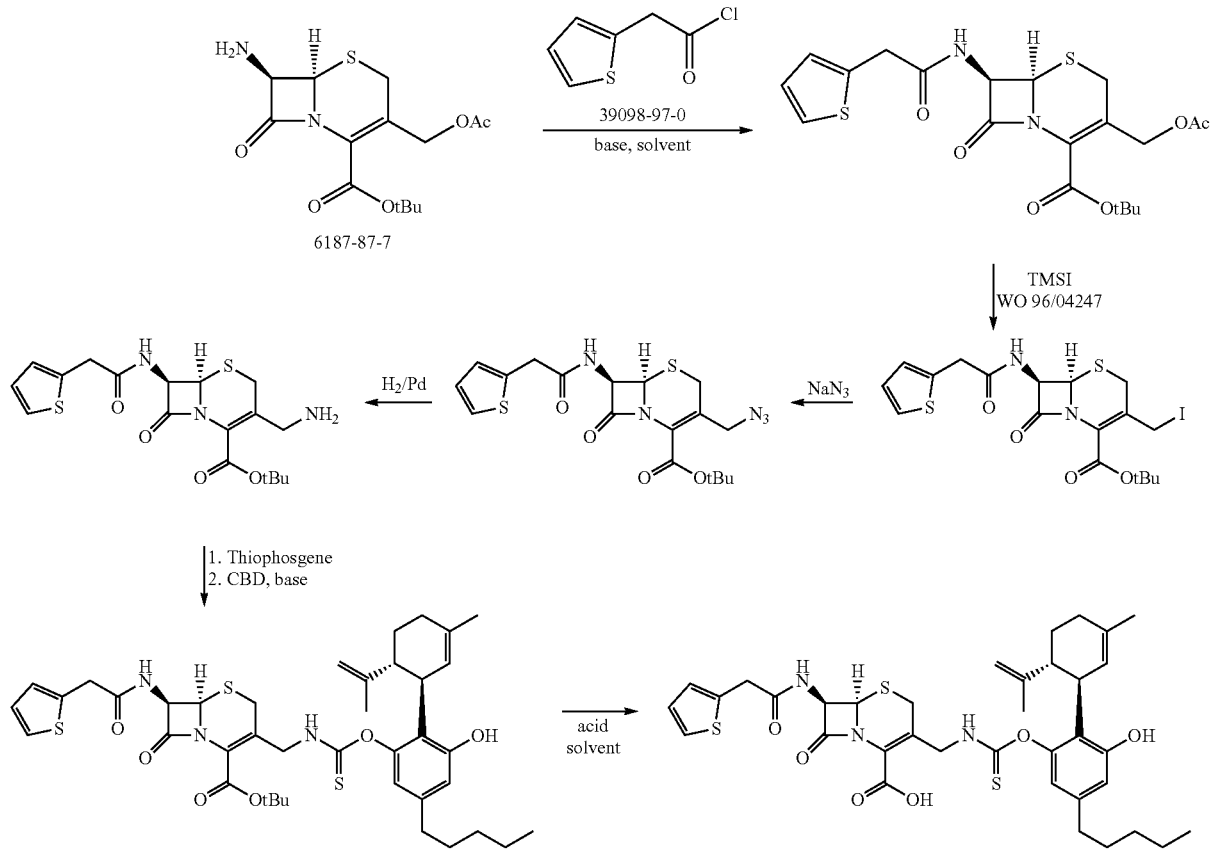

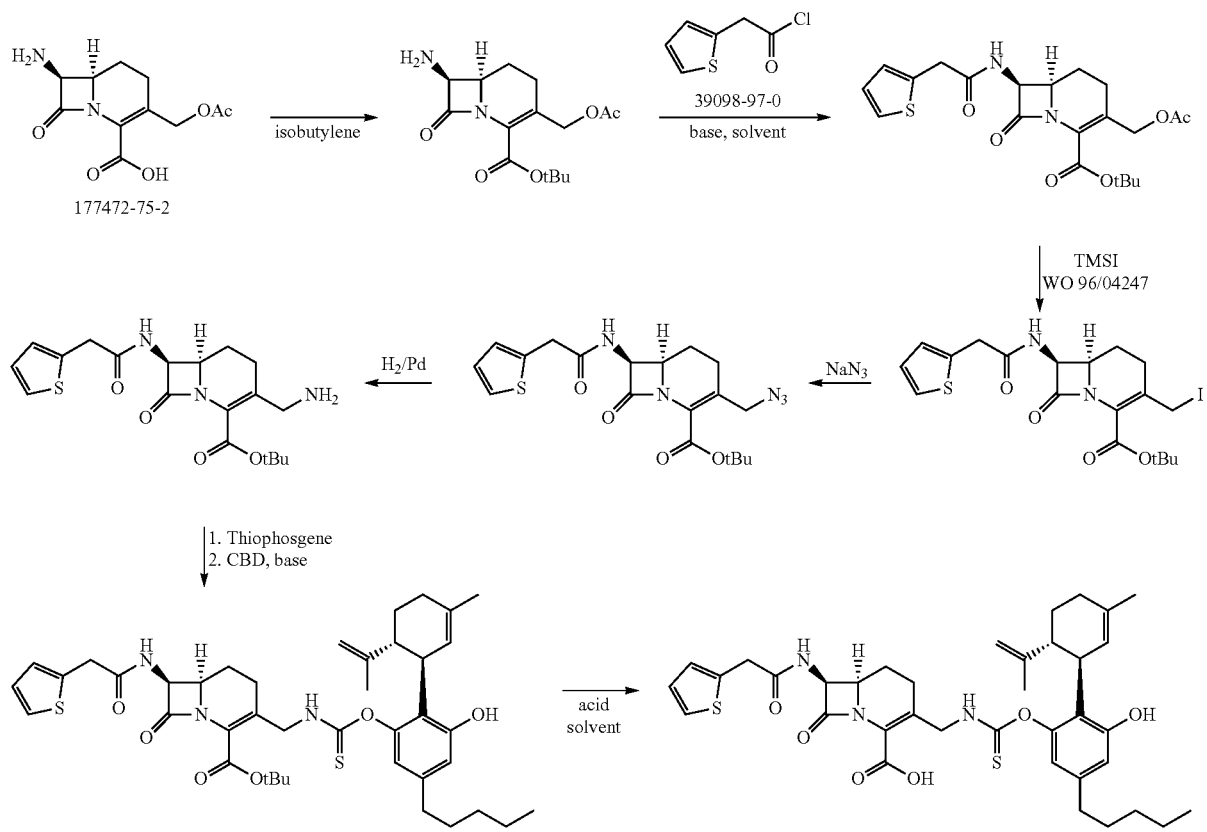

Penem Conjugates

Penem thiocarbamate linked β-lactam antibiotic cannabinoid conjugate components are synthesized according to the following Scheme. The starting material [83572-65-0] has been previously described (Journal of Antibiotics (1982), 35(9), 1248-51). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of CBD forms the thiocarbamate linkage. Removal of the TBDMS ether and t-butyl ester protecting groups under standard conditions gives the desired product.

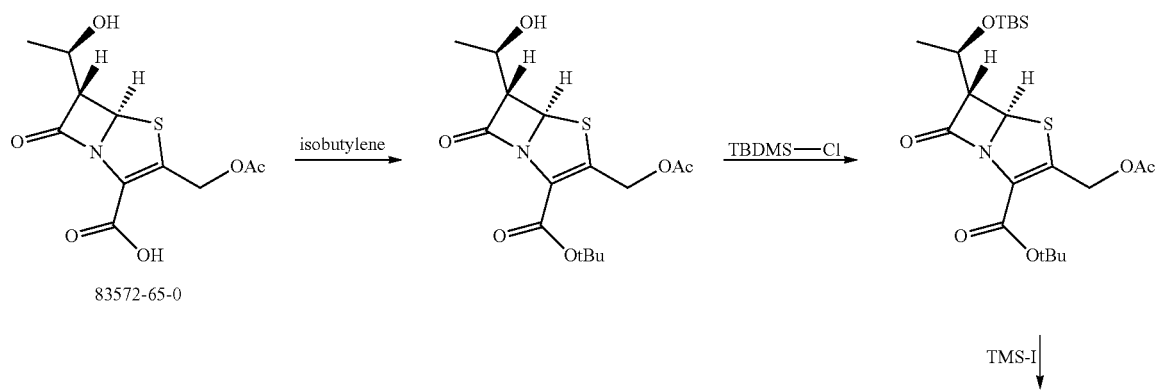

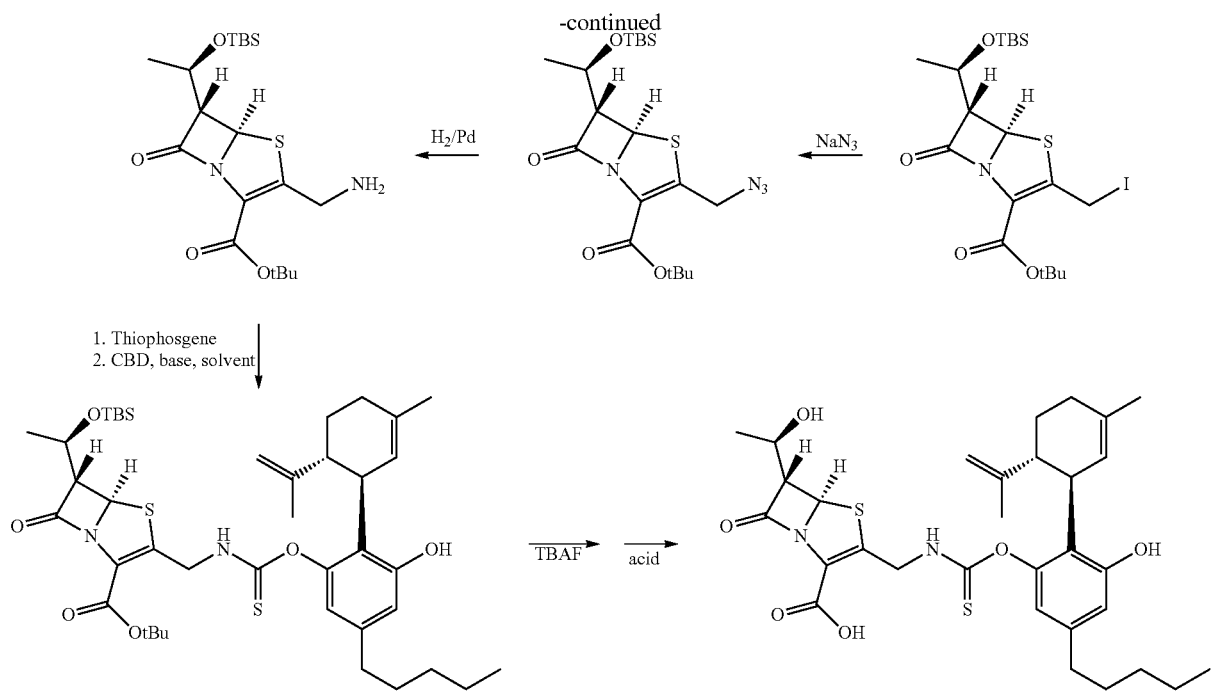

Carbapenem Conjugates

Carbapenem thiocarbamate linked β-lactam antibiotic cannabinoid conjugate components are synthesized according to the following Scheme. The starting material [112064-40-1] has been previously described (Journal of Antibiotics (1988), 41(6), 780-7). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of CBD forms the thiocarbamate linkage. Removal of the TBDMS ether and t-butyl ester protecting groups under standard conditions gives the desired product.

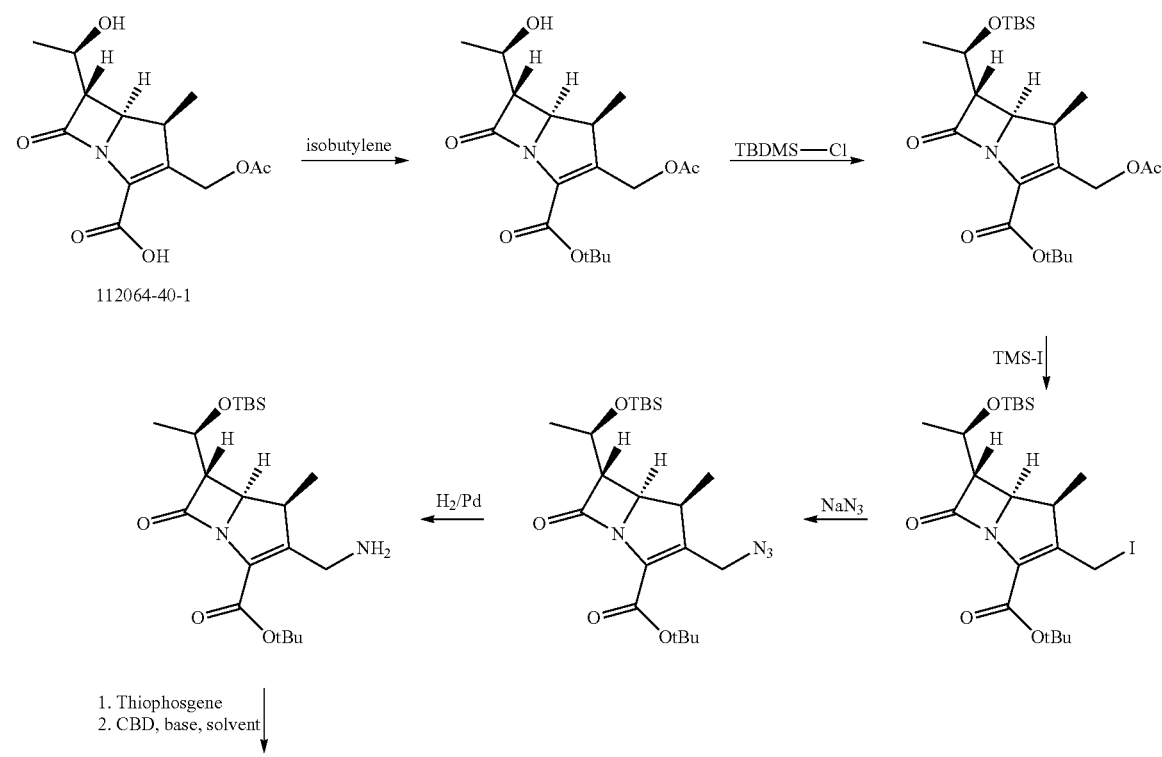

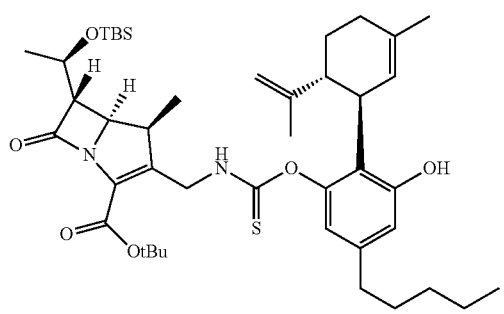

169

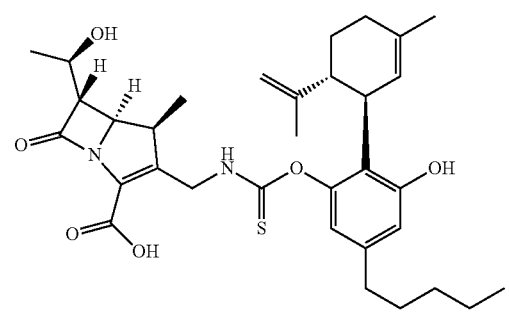

170

-continued

Example 6. Propenylamine-Linked β-Lactam Antibiotic Cannabinoid Conjugate Components

Cephem Conjugates

Cephem propenylamine linked β-lactam antibiotic cannabinoid conjugate components are synthesized according to the following Scheme. The starting material [6187-87-7] is acylated with a side chain of choice. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (in this case CBD) under standard basic conditions. Removal of the t-butyl ester protecting group under acidic conditions generates the desired product.

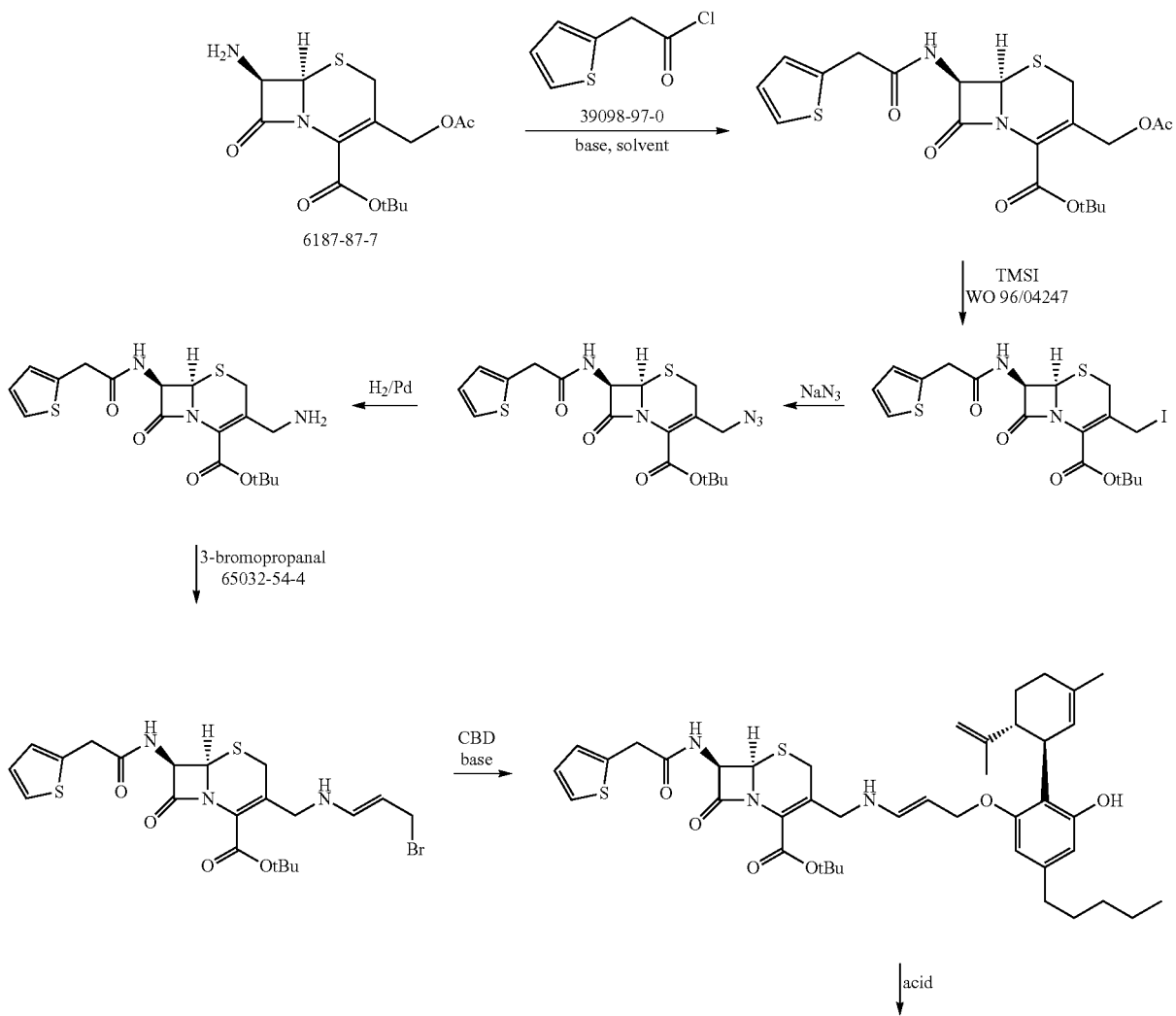

-continued

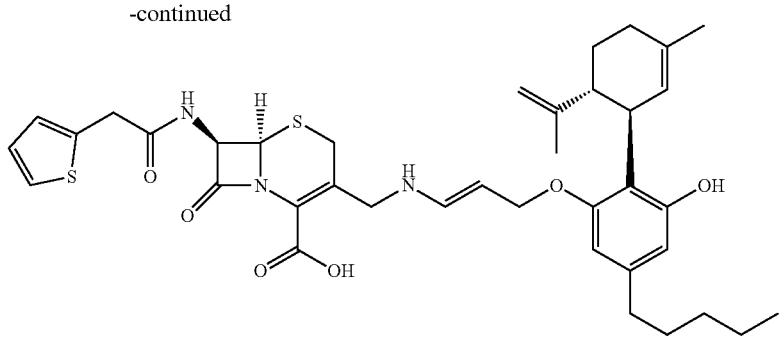

Carbacephem Conjugates

Carbacephem propenylamine linked β-lactam antibiotic cannabinoid conjugate components are synthesized according to the following Scheme. The starting material [177472-75-2] is protected as the t-butyl ester under standard isobutylene conditions and then is acylated with a side chain of choice. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (CBD) under standard basic conditions. Removal of the t-butyl ester protecting group under acidic conditions generates the desired product.

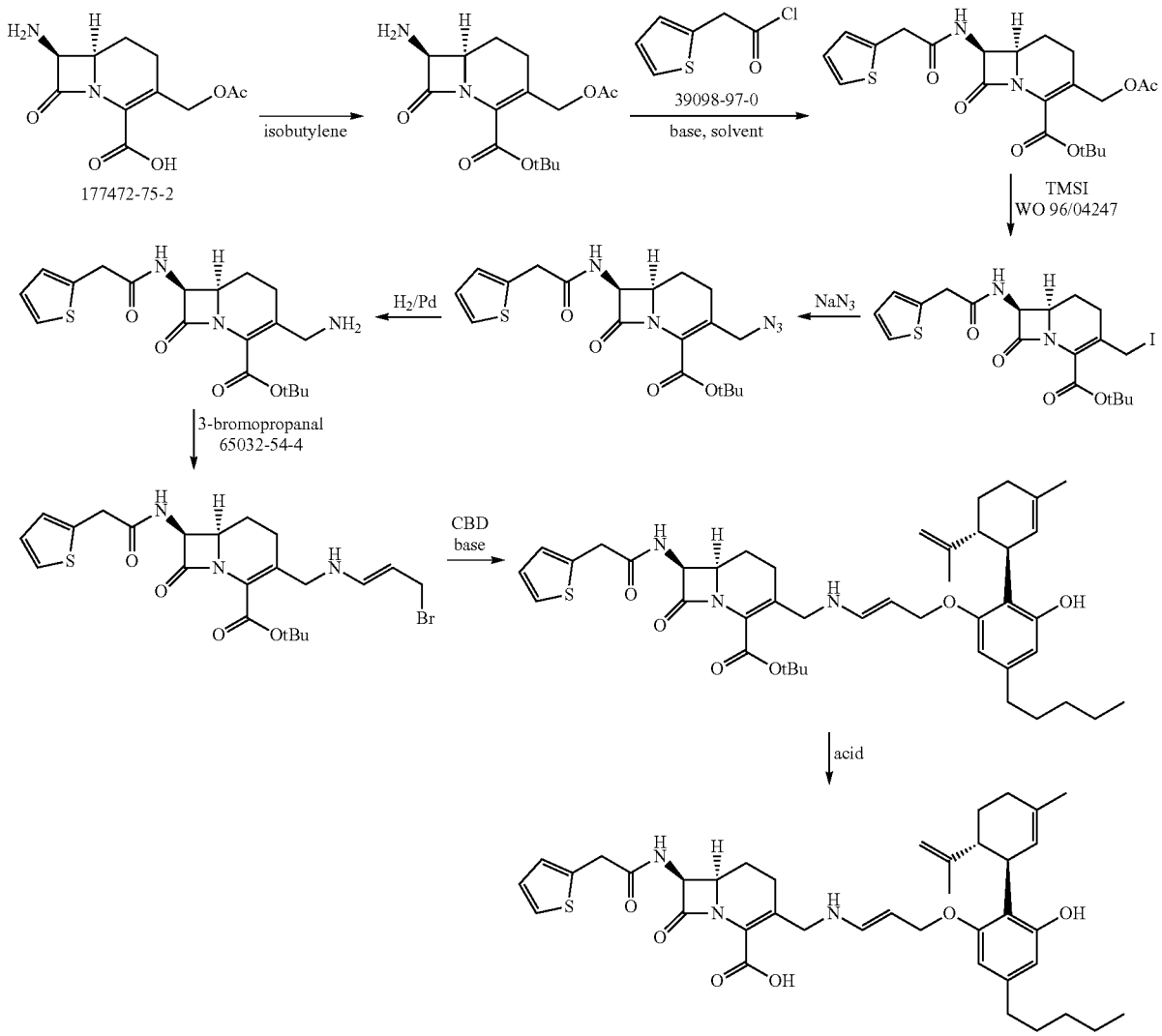

Penem Conjugates

Penem propenylamine linked β-lactam antibiotic cannabinoid conjugate components are synthesized according to the following Scheme. The starting material [83572-65-0] is protected as the t-butyl ester under standard isobutylene conditions and then the secondary alcohol is protected as the TBDMS ether. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (CBD) under standard basic conditions. Removal of the TBDMS ether and t-butyl ester protecting groups under standard conditions gives the desired product.

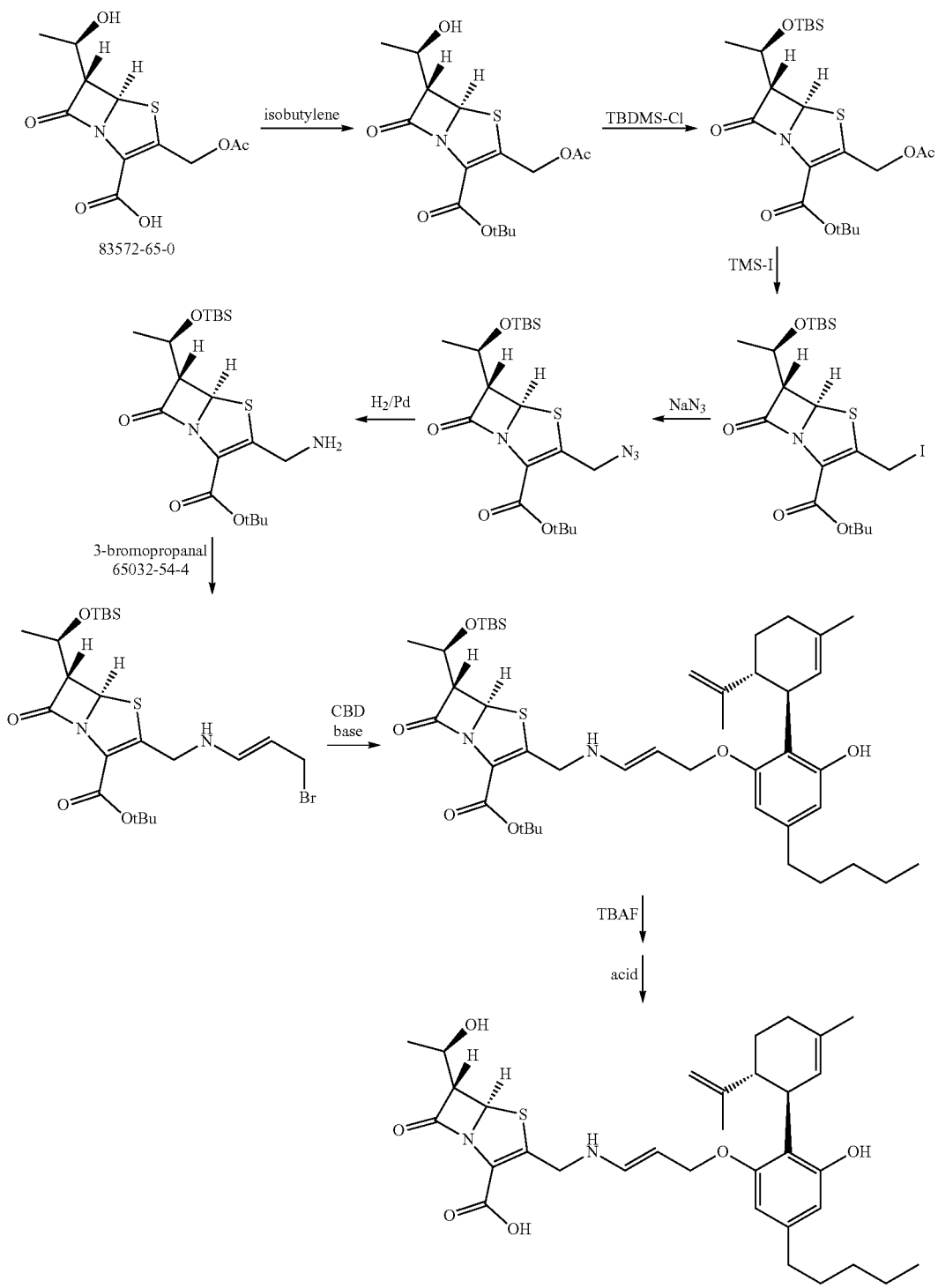

Carbapenem Conjugates

Carbapenem propenylamine linked β-lactam antibiotic cannabinoid conjugate components are synthesized according to the following Scheme. The starting material [112064-40-1] is protected as the t-butyl ester under standard isobutylene conditions and then the secondary alcohol is protected as the TBDMS ether. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (CBD) under standard basic conditions. Removal of the TBDMS ether and t-butyl ester protecting groups under standard conditions gives the desired product.

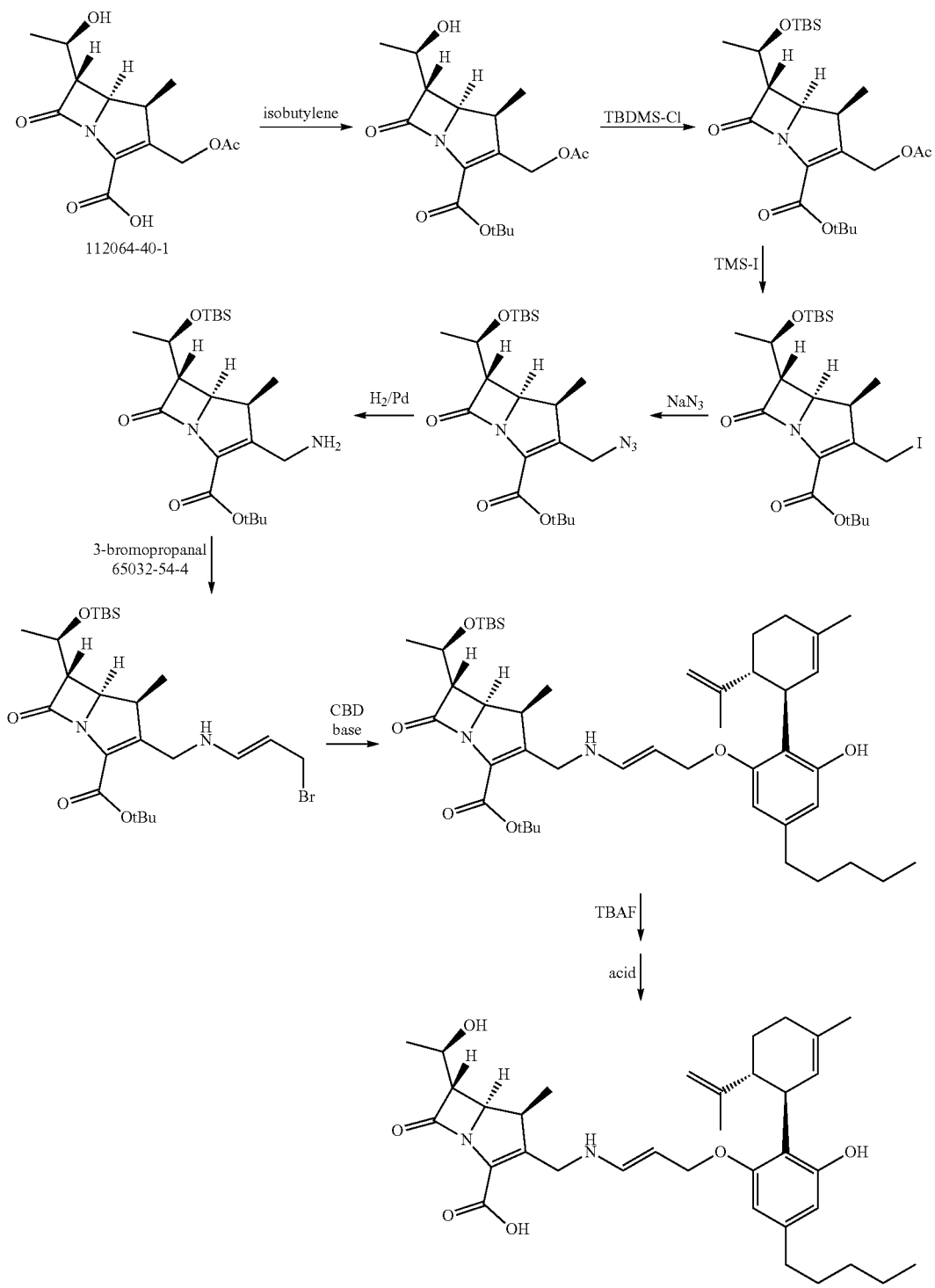

Example 7. Alkene-Linked β-Lactam Antibiotic Cannabinoid Conjugate Components

Cephem Conjugates

Cephem alkene linked β-lactam antibiotic cannabinoid conjugate components are synthesized according to the following Scheme. The starting material [130516-07-3] has been reported previously (Journal of Organic Chemistry (1993), 58(8), 2296-2301). It is reacted with the organostannane under conditions described for related molecules (WO 99/62906) to give the allylic alcohol intermediate. The alcohol is then activated as the mesylate and reacted with the cannabinoid (CBD) under basic conditions to produce the alkene linked intermediate. Removal of the DPM protecting group under standard conditions gives the desired product.

Carbacephem Conjugates

Carbacephem alkene linked β-lactam antibiotic cannabinoid conjugate components are synthesized according to the following Scheme. The starting material [123078-32-0] has been reported previously (Journal of Organic Chemistry, 54(24), 5828-30; 1989). It is reacted with the organostannane under conditions described for related molecules (WO 99/62906) to give the allylic alcohol intermediate. The alcohol is then activated as the mesylate and reacted with the cannabinoid (CBD) under basic conditions to produce the alkene linked intermediate. Removal of the DPM protecting group under standard conditions gives the desired

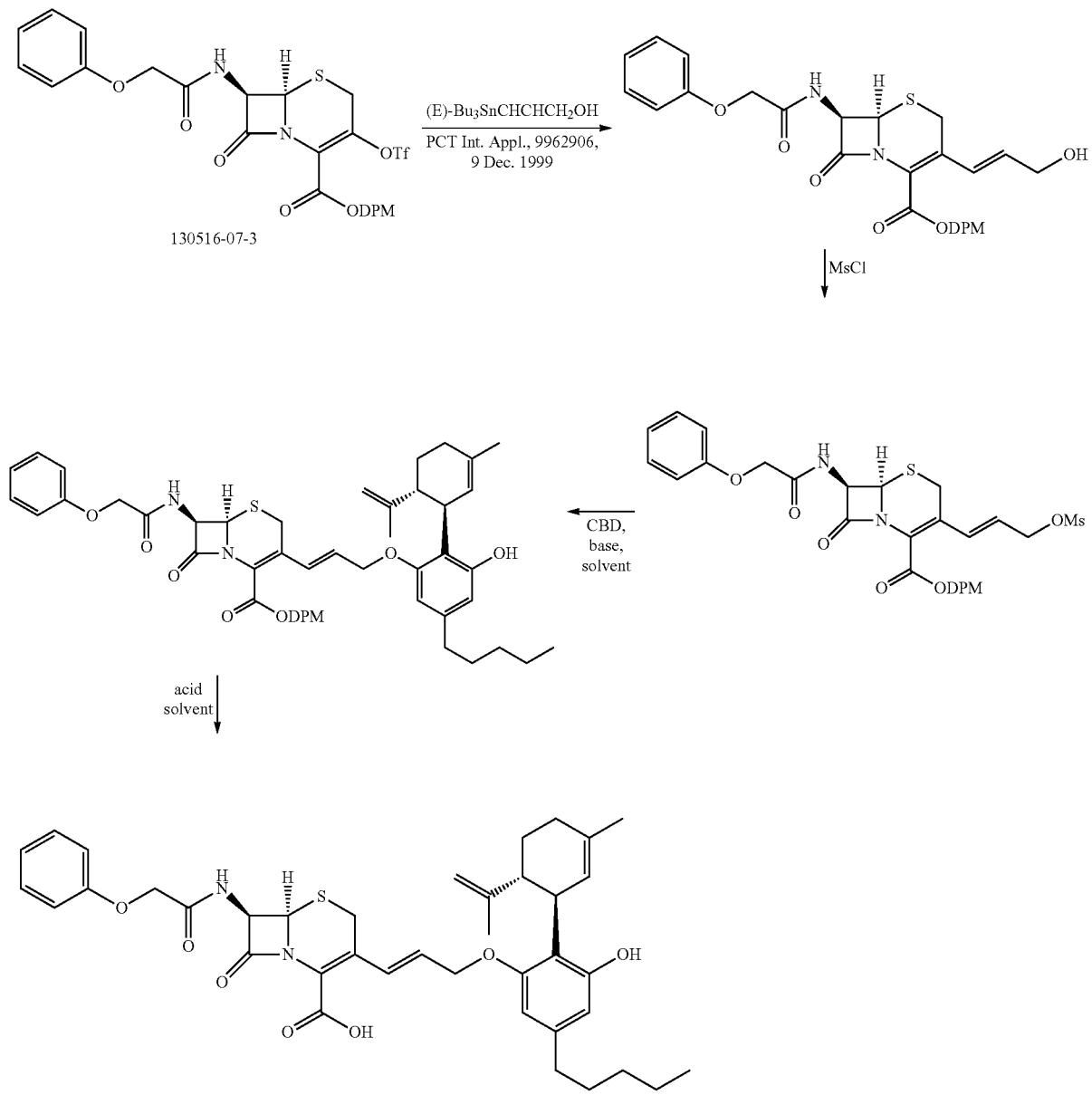

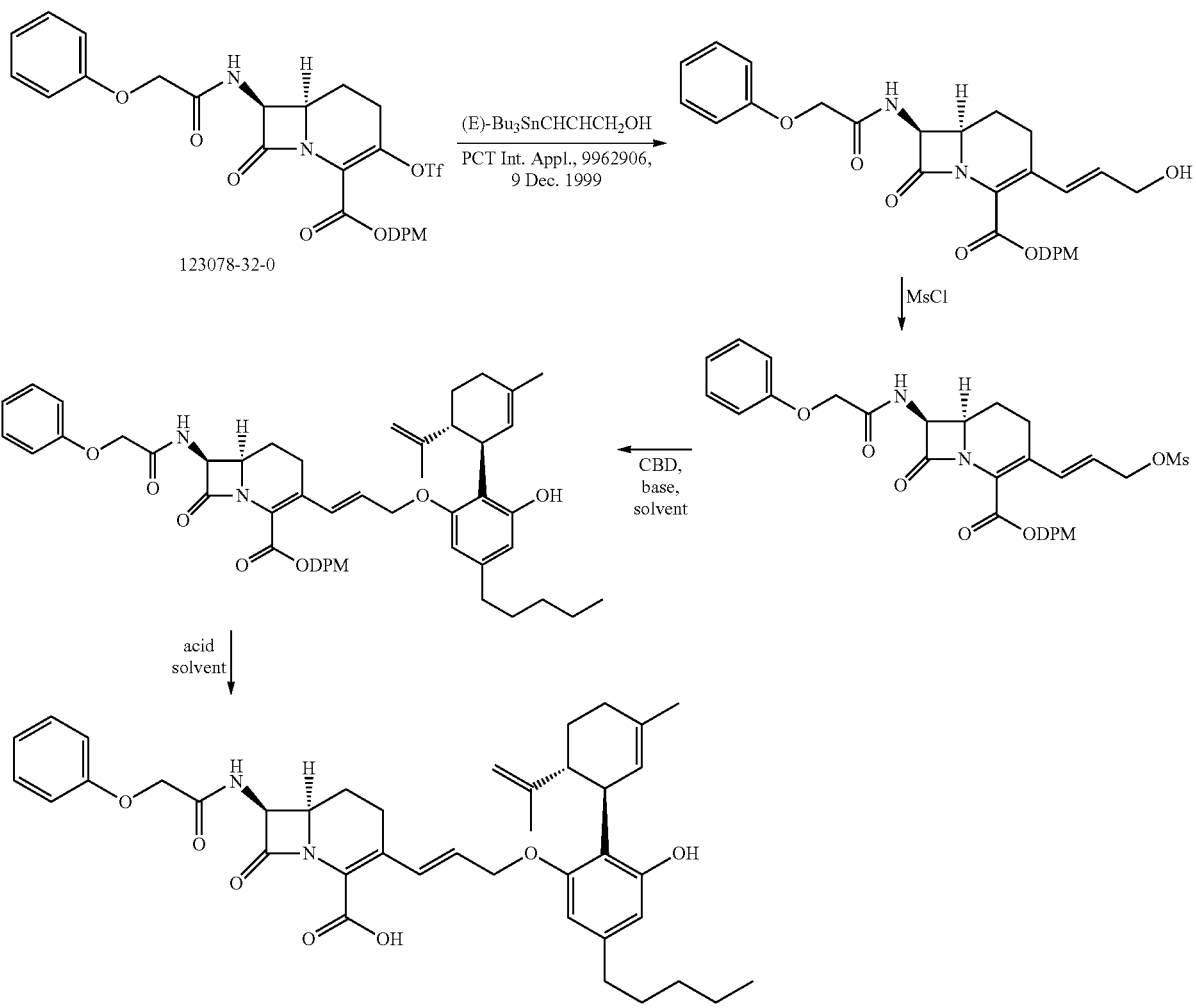

Penem Conjugates

Penem alkene linked β-lactam antibiotic cannabinoid conjugate components are synthesized according to the following Scheme. The starting material [127941-62-2] has been previously reported (U.S. Pat. No. 4,895,940). It is converted to the allylic alcohol intermediate as previously described for similar molecules (WO 99/62906). The alcohol is then activated as the mesylate and reacted with the cannabinoid (CBD) under basic conditions to produce the alkene linked intermediate. Removal of the TBDMS ether and trimethylsilylethyl ester protecting groups is achieved under standard conditions of excess TBAF to give the desired product.

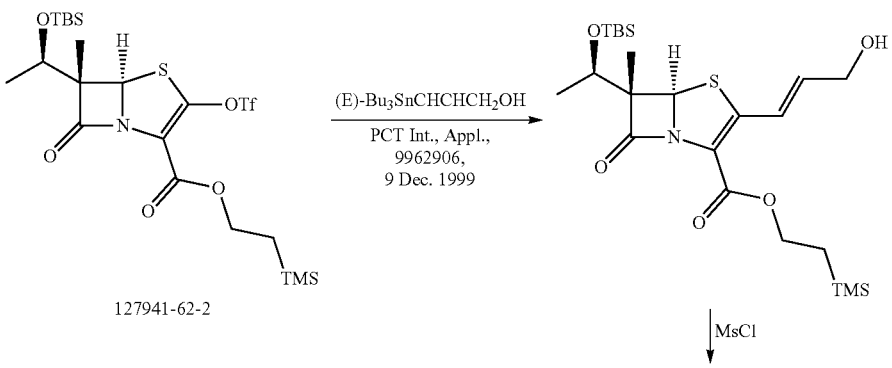

181

-continued

182

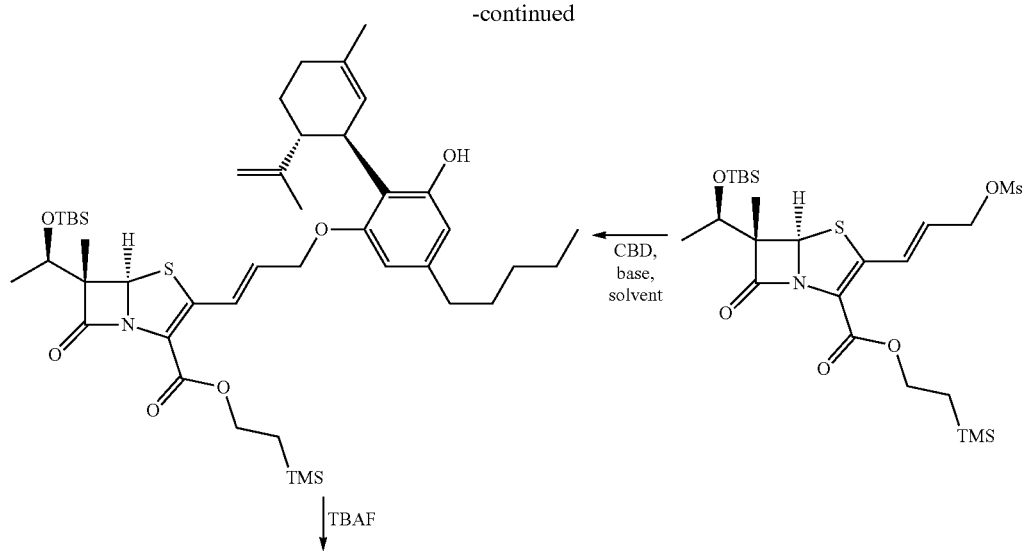

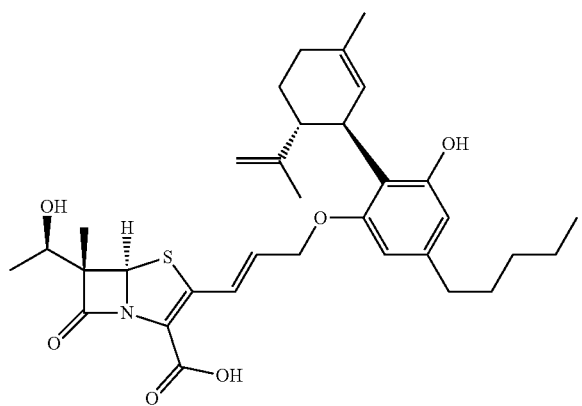

Carbapenem Conjugates

Carbapenem alkene linked β-lactam antibiotic cannabinoid conjugate components are synthesized according to the following Scheme. The starting material [165817-82-3] along with its conversion to the allylic alcohol intermediate has been described previously (WO 99/62906). The alcohol is then activated as the mesylate and reacted with the cannabinoid (CBD) under basic conditions to produce the alkene linked intermediate. Removal of the TES ether and PNB ester groups under standard conditions produces the desired product.

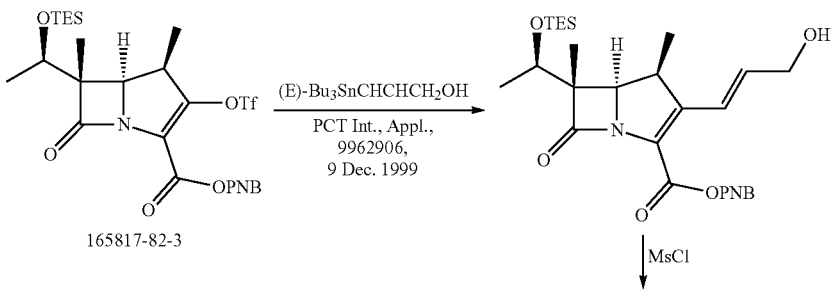

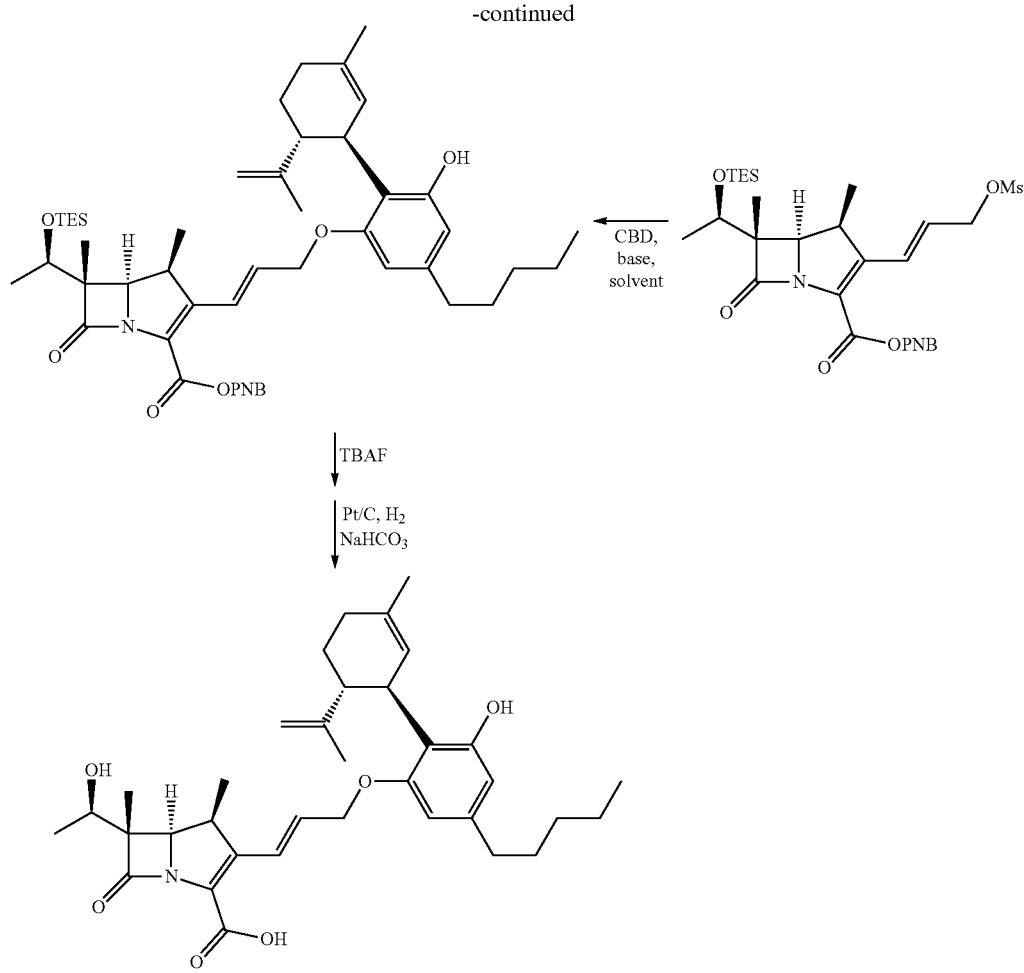

Example 8. Propenyl Carbonate-Linked β-Lactam Antibiotic Cannabinoid Conjugate Components

Cephem Conjugates

Cephem propenyl carbonate linked β-lactam antibiotic cannabinoid conjugate components are synthesized according to the following Scheme. The starting material [130516-07-3] has been reported previously (Journal of Organic Chemistry (1993), 58(8), 2296-2301). It is converted to the allylic alcohol intermediate as previously described for similar molecules (WO 99/62906). This alcohol is reacted with phosgene and the resulting intermediate reacted with the cannabinoid (CBD) under basic conditions to form the carbonate group. Removal of the DPM ester protecting group under standard acidic conditions produces the desired product.

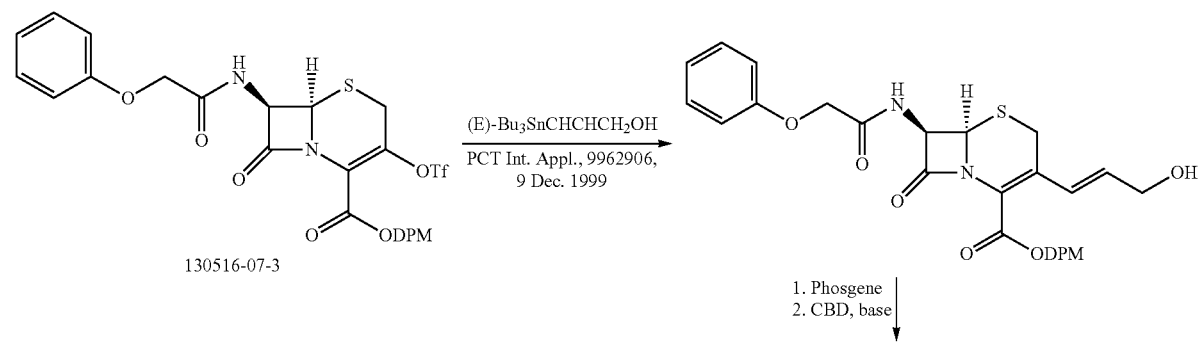

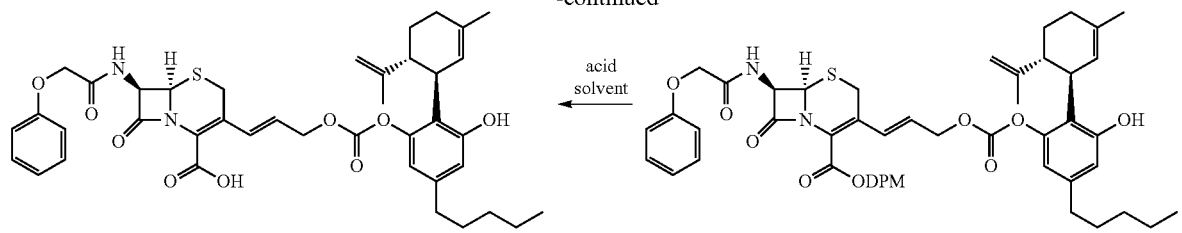

Carbacephem Conjugates

Carbacephem propenyl carbonate linked β-lactam antibiotic cannabinoid conjugate components are synthesized according to the following Scheme. The starting material [123078-32-0] has been reported previously (Journal of Organic Chemistry (1993), 58(8), 2296-2301). It is converted to the allylic alcohol intermediate as previously described for similar molecules (WO 99/62906). This alcohol is reacted with phosgene and the resulting intermediate reacted with the cannabinoid (CBD) under basic conditions to form the carbonate group. Removal of the DPM ester protecting group under standard acidic conditions produces the desired product.

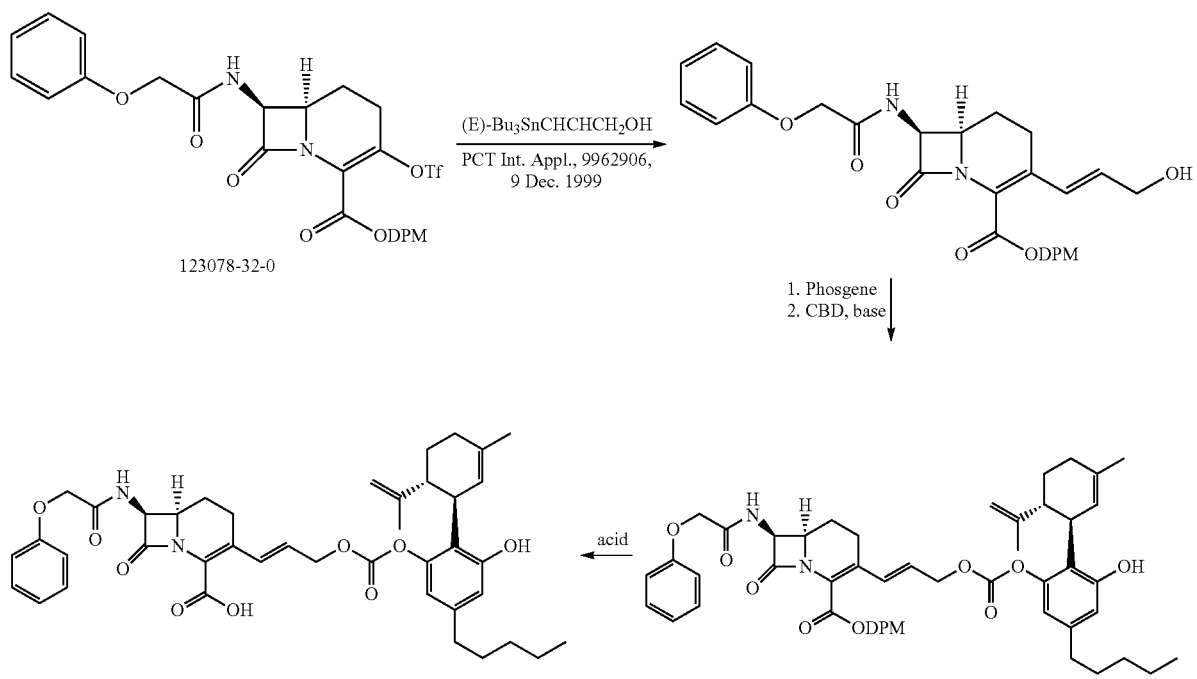

Penem Conjugates

Penem propenyl carbonate linked β-lactam antibiotic cannabinoid conjugate components are synthesized according to the following Scheme. The starting material [127941-62-2] has been previously reported (U.S. Pat. No. 4,895,940). It is converted to the allylic alcohol intermediate as previously described for similar molecules (WO 99/62906). The alcohol is then reacted with phosgene and the resulting intermediate reacted with the cannabinoid (CBD) under basic conditions to form the carbonate group. Removal of the TBDMS ether and trimethylsilylethyl ester protecting groups is achieved under standard conditions of excess TBAF to give the desired product.

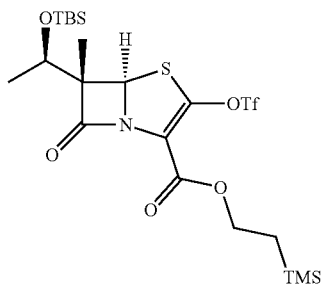

127941-62-2

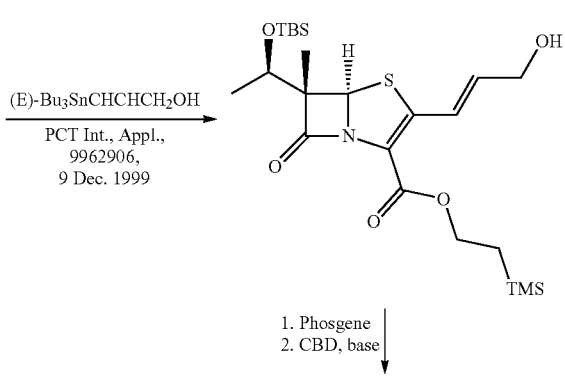

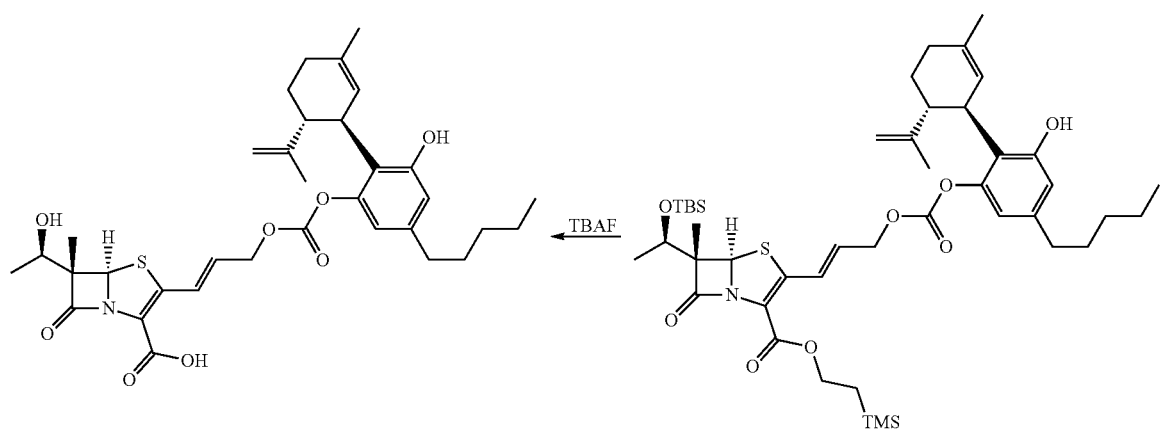

Carbapenem Conjugates

Carbapenem propenyl carbonate linked β-lactam antibiotic cannabinoid conjugate components are synthesized according to the following Scheme. The starting material [165817-82-3] along with its conversion to the allylic alcohol intermediate has been described previously (WO 99/62906). The alcohol is then reacted with phosgene and the resulting intermediate reacted with the cannabinoid (CBD) under basic conditions to form the carbonate group. Removal of the TES ether and PNB ester groups under standard conditions produces the desired product.

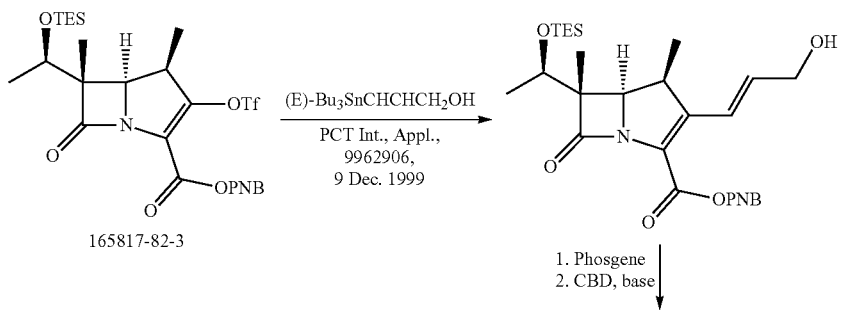

165817-82-3

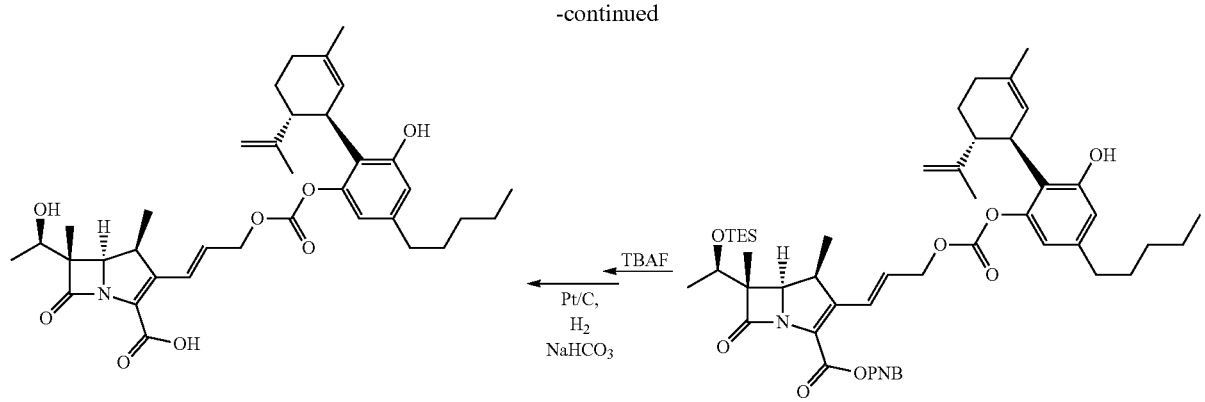

Example 9. Propenyl Thiocarbonate-Linked β-Lactam Antibiotic Cannabinoid Conjugate Components Cephem Conjugates Cephem propenyl thiocarbonate linked β-lactam antibiotic cannabinoid conjugate components are synthesized according to the following Scheme. The starting material [130516-07-3] has been reported previously (Journal of Organic Chemistry (1993), 58(8), 2296-2301). It is converted to the allylic alcohol intermediate as previously described for similar molecules (WO 99/62906). This alcohol is reacted with thiophosgene and the resulting intermediate reacted with the cannabinoid (CBD) under basic conditions to form the thiocarbonate group. Removal of the DPM ester protecting group under standard acidic conditions produces the desired product.

Carbacephem Conjugates

Carbacephem propenyl thiocarbonate linked β-lactam antibiotic cannabinoid conjugate components are synthesized according to the following Scheme. The starting material [12078-32-0] has been reported previously (Journal of Organic Chemistry (1993), 58(8), 2296-2301). It is converted to the allylic alcohol intermediate as previously described for similar molecules (WO 99/62906). This alcohol is reacted with thiophosgene and the resulting intermediate reacted with the cannabinoid (CBD) under basic conditions to form the thiocarbonate group. Removal of the DPM ester protecting group under standard acidic conditions produces the desired product.

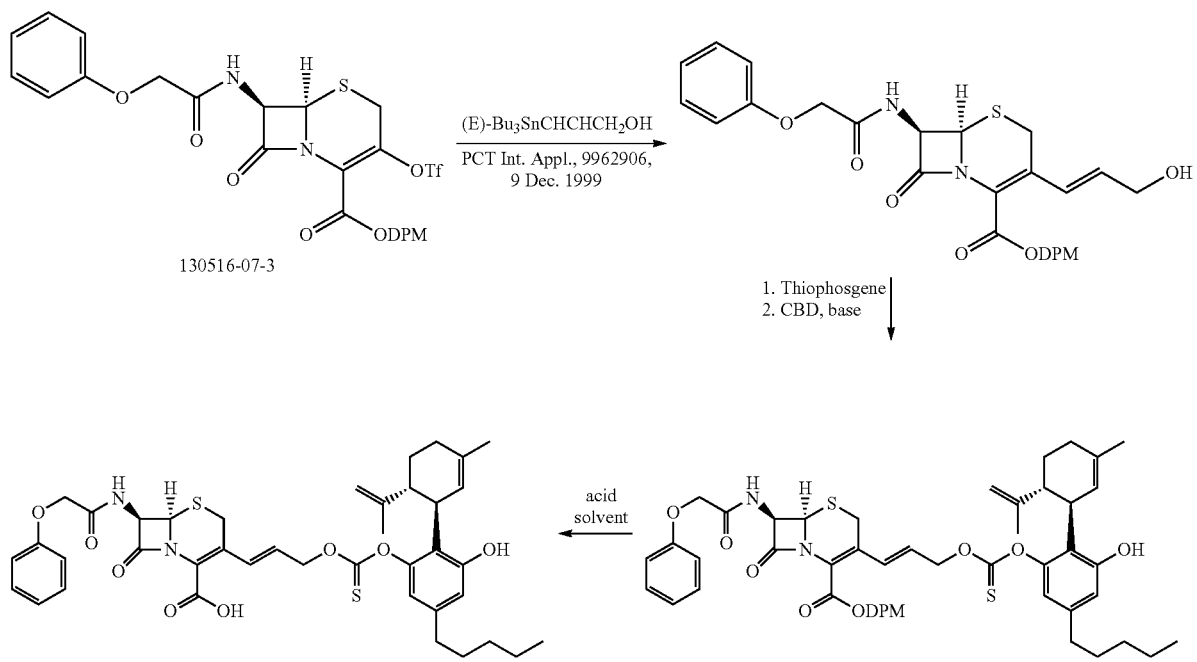

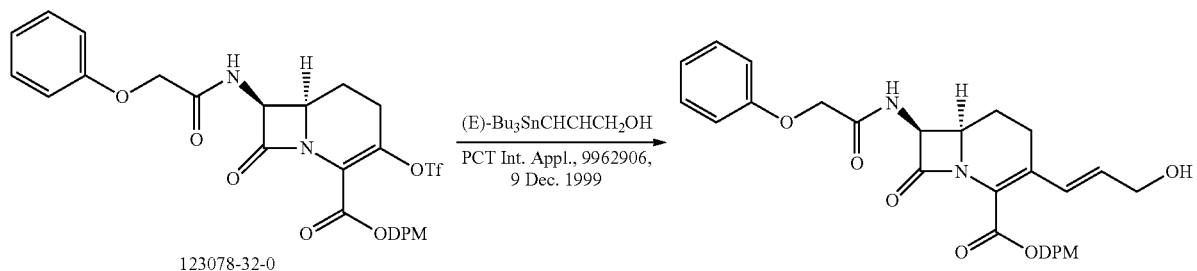

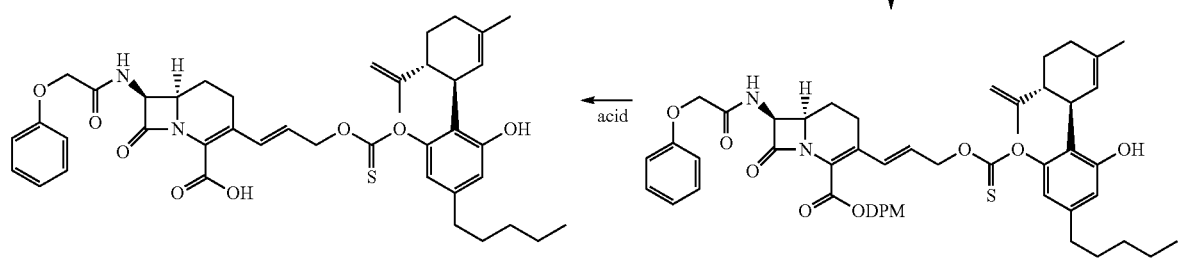

Penem Conjugates

Penem propenyl thiocarbonate linked β-lactam antibiotic cannabinoid conjugate components are synthesized according to the following Scheme. The starting material [127941-62-2] has been previously reported (U.S. Pat. No. 4,895,940). It is converted to the allylic alcohol intermediate as previously described for similar molecules (WO 99/62906). The alcohol is then reacted with thiophosgene and the resulting intermediate reacted with the cannabinoid (CBD) under basic conditions to form the thiocarbonate group. Removal of the TBDMS ether and trimethylsilylethyl ester protecting groups is achieved under standard conditions of excess TBAF to give the desired product.

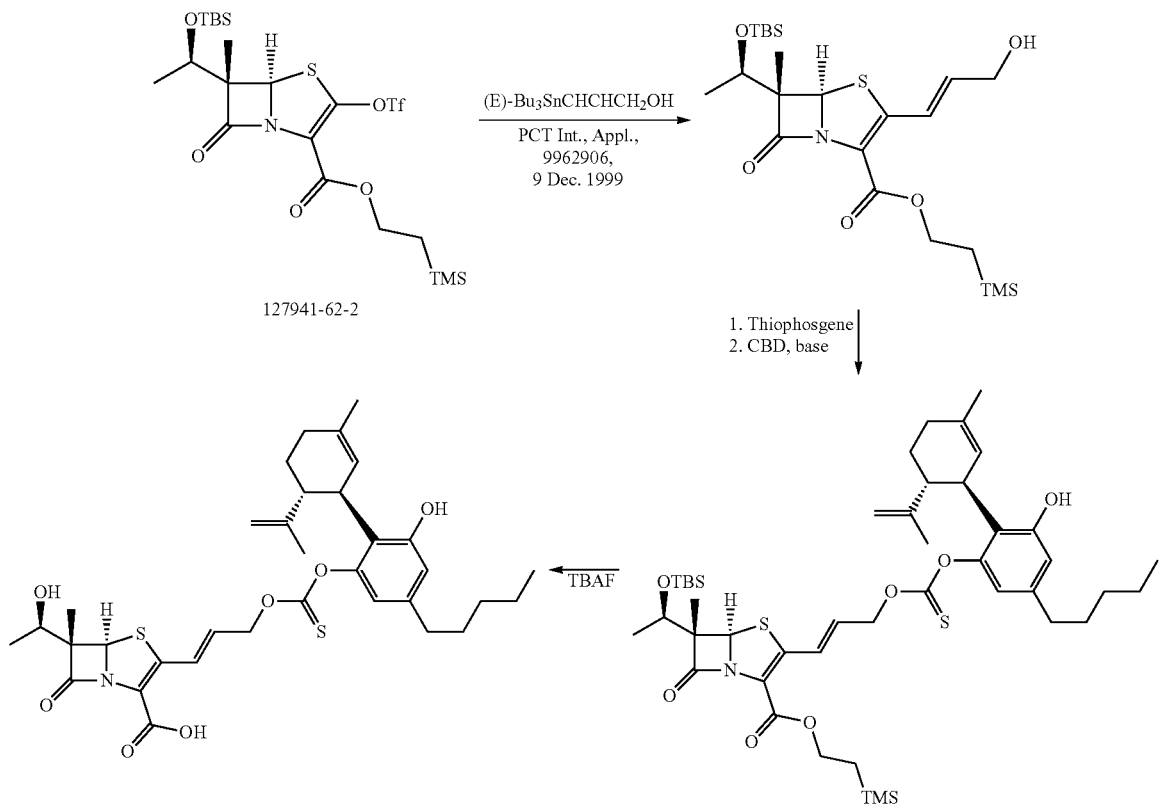

Carbapenem Conjugates

Carbapenem propenyl thiocarbonate linked β-lactam antibiotic cannabinoid conjugate components are synthesized according to the following Scheme. The starting material [165817-82-3] along with its conversion to the allylic alcohol intermediate has been described previously (WO 99/62906). The alcohol is then reacted with thiophosgene and the resulting intermediate reacted with the cannabinoid (CBD) under basic conditions to form the thiocarbonate group. Removal of the TES ether and PNB ester groups under standard conditions produces the desired product.

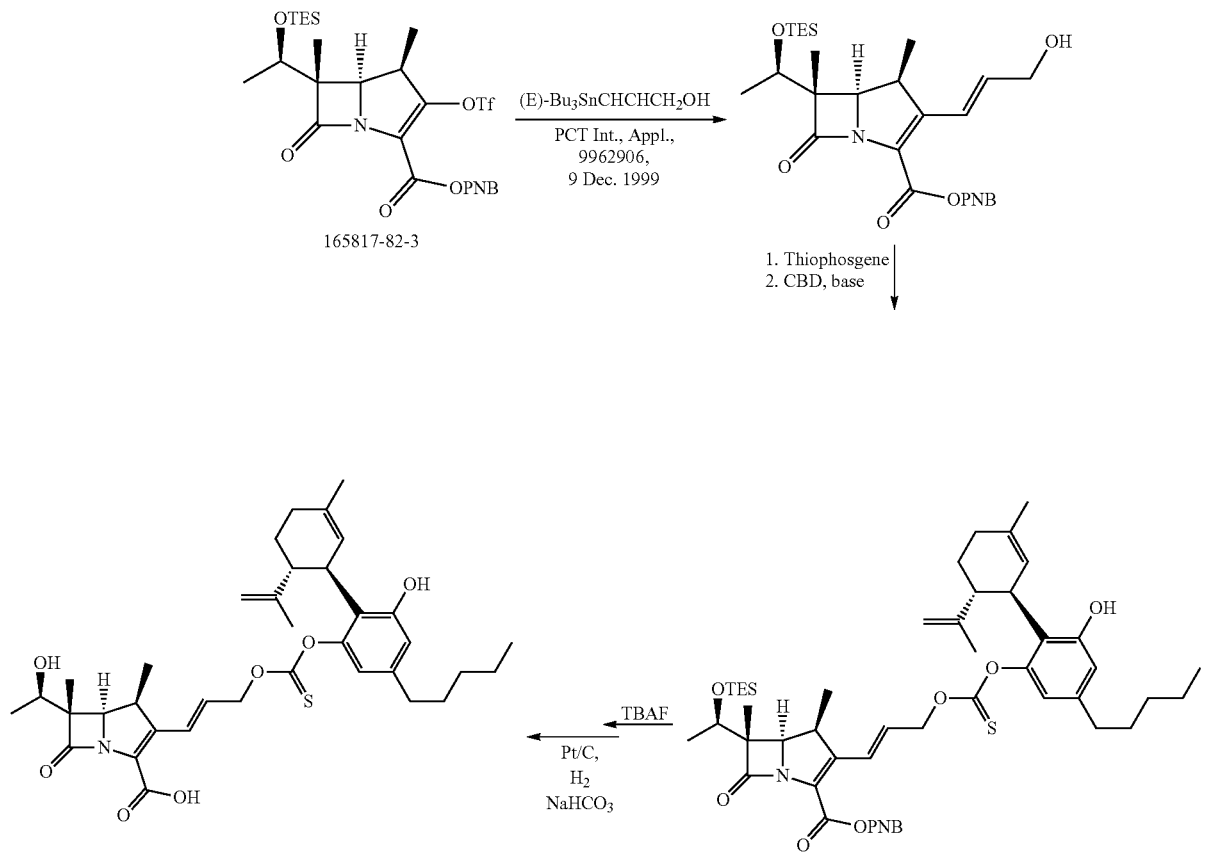

Example 10. Propenyl Carbamate-Linked β-Lactam Antibiotic Cannabinoid Conjugate Components Cephem Conjugates Cephem propenyl carbamate linked β-lactam antibiotic cannabinoid conjugate components are synthesized according to the following Scheme. The starting material [57562-43-3] has been reported (CN 103588788 A 20140219). It is converted under standard conditions to the enol triflate, which is reacted with the BOC-protected aminoorganostannane [139111-44-7](use in similar cephem triflate: Bioorganic & Medicinal Chemistry Letters (2010), 20(15), 4635-4638) followed by BOC removal under standard conditions to give the propenyl amine intermediate. This amine is reacted with phosgene and the resulting intermediate reacted with the cannabinoid (CBD) under basic conditions to form the carbamate group. Removal of the PNB ester group under standard conditions produces the desired product.

195

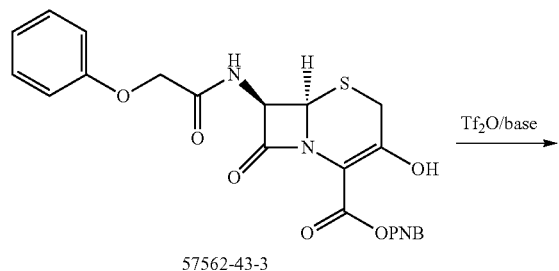

196

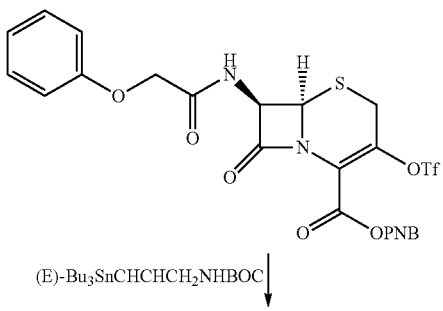

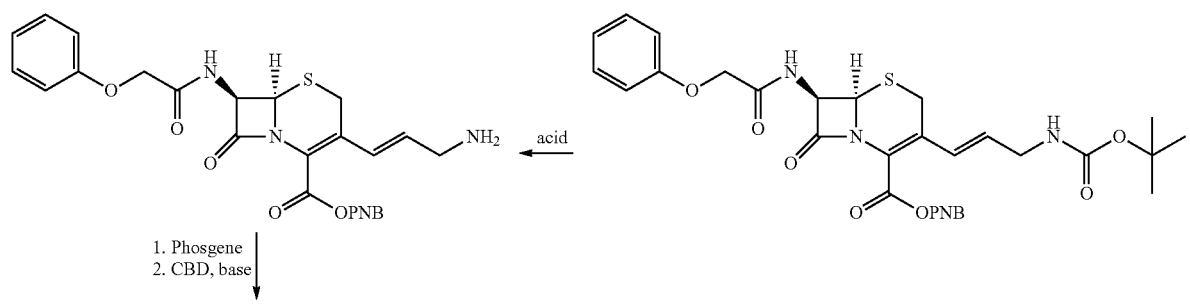

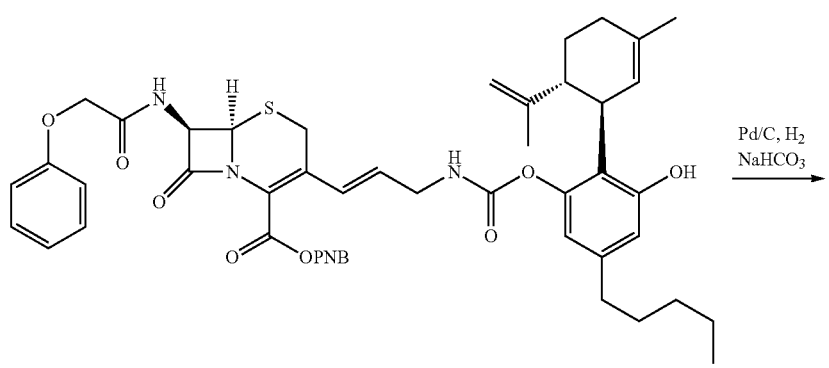

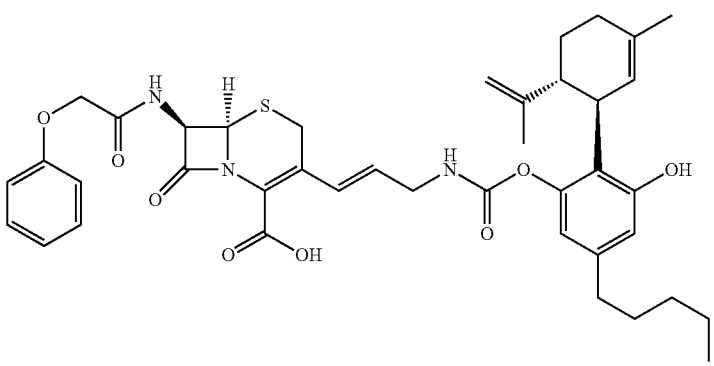

Carbacephem Conjugates

Carbacephem propenyl carbamate linked β-lactam antibiotic cannabinoid conjugate components are synthesized according to the following Scheme. The starting material [119892-46-5] (WO 2010/030810, and references cited therein) is converted under standard conditions to the enol triflate, which is reacted with the BOC-protected aminoorganostannane [139111-44-7] (use in similar cephem triflate: Bioorganic & Medicinal Chemistry Letters (2010), 20(15), 4635-4638) followed by BOC removal under standard conditions to give the propenyl amine intermediate. This amine is reacted with phosgene and the resulting intermediate reacted with the cannabinoid (CBD) under basic conditions to form the carbamate group. Removal of the PNB ester group under standard conditions produces the desired product.

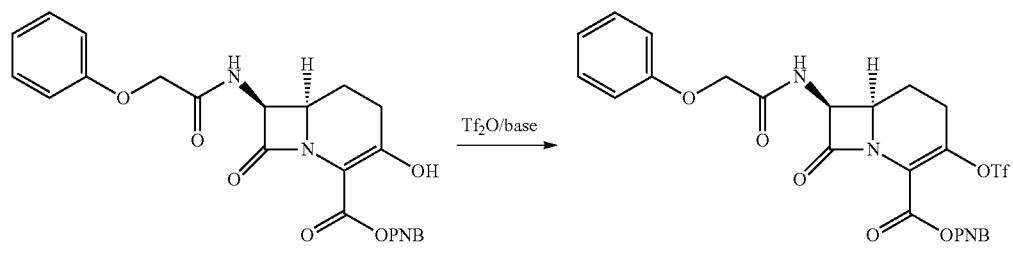

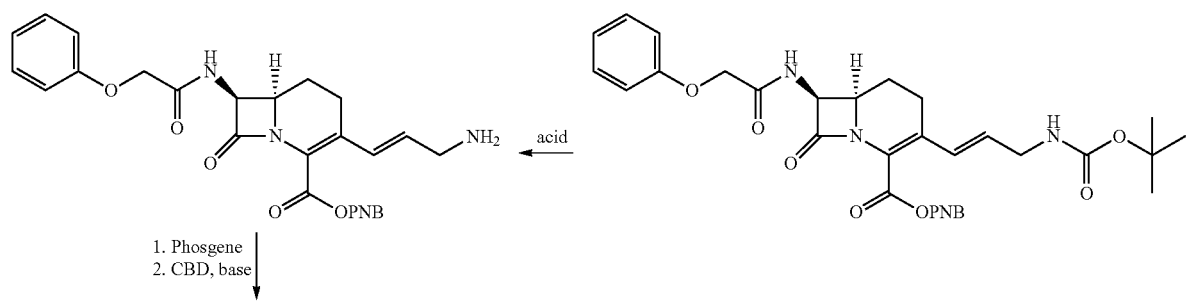

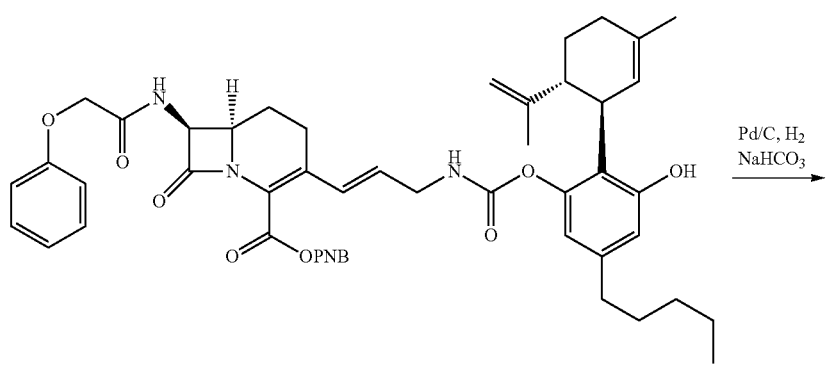

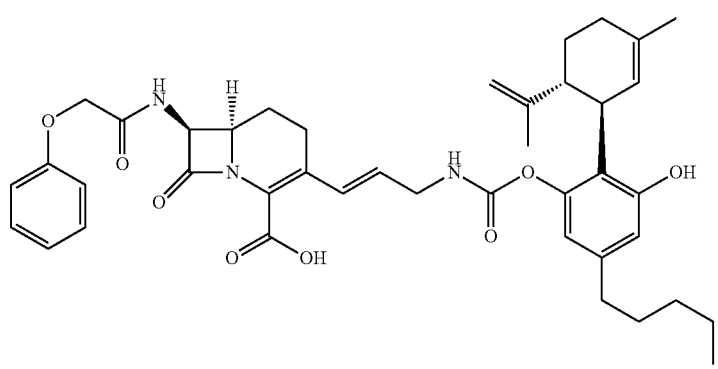

Penem Conjugates

Penem propenyl carbamate linked β-lactam antibiotic cannabinoid conjugate components are synthesized according to the following Scheme. The starting material [127941-62-2] has been previously reported (U.S. Pat. No. 4,895,940). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with phosgene and the resulting intermediate reacted with the cannabinoid (CBD) under basic conditions to form the carbamate group. Removal of the TES ether and trimethylsilylethyl ester groups under standard conditions produces the desired product.

199  200

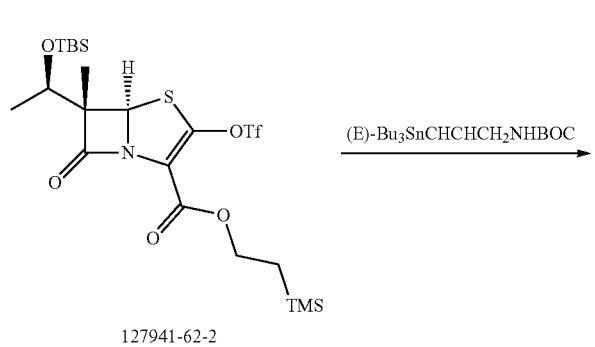
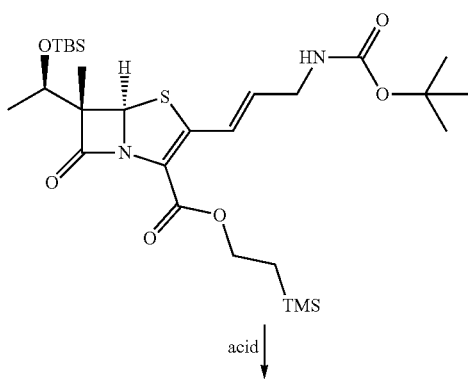
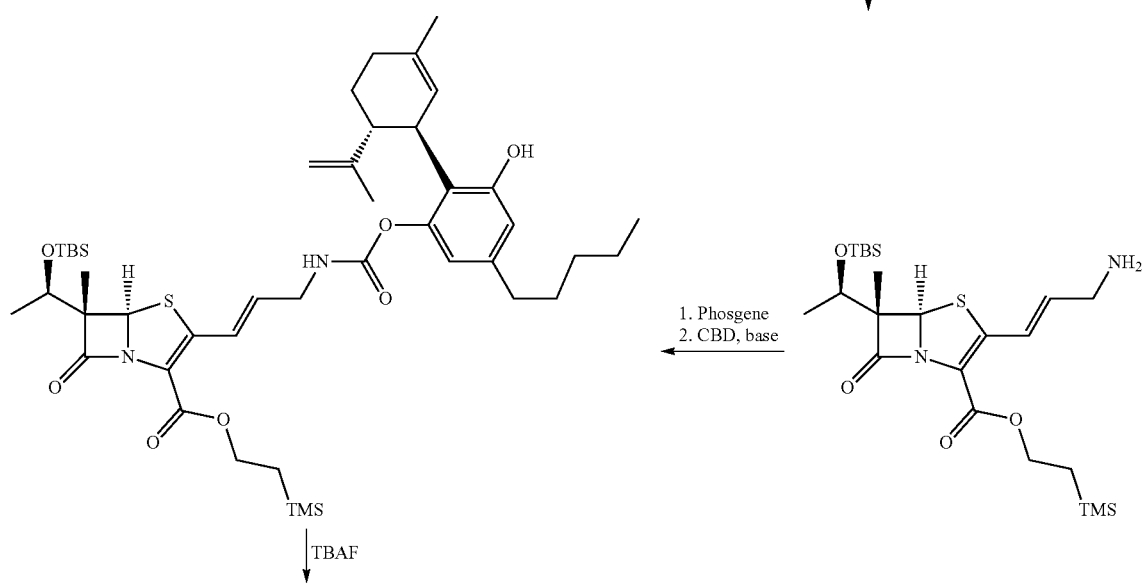
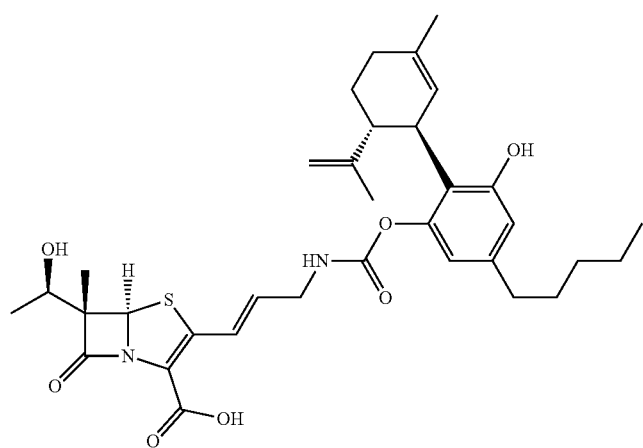

Carbapenem Conjugates

Carbapenem propenyl carbamate linked β-lactam antibiotic cannabinoid conjugate components are synthesized according to the following Scheme. The starting material [165817-82-3] has been described previously (WO 99/62906). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with phosgene and the resulting intermediate reacted with the cannabinoid (CBD) under basic conditions to form the carbamate group. Removal of the TES ether and PNB ester groups under standard conditions produces the desired product.

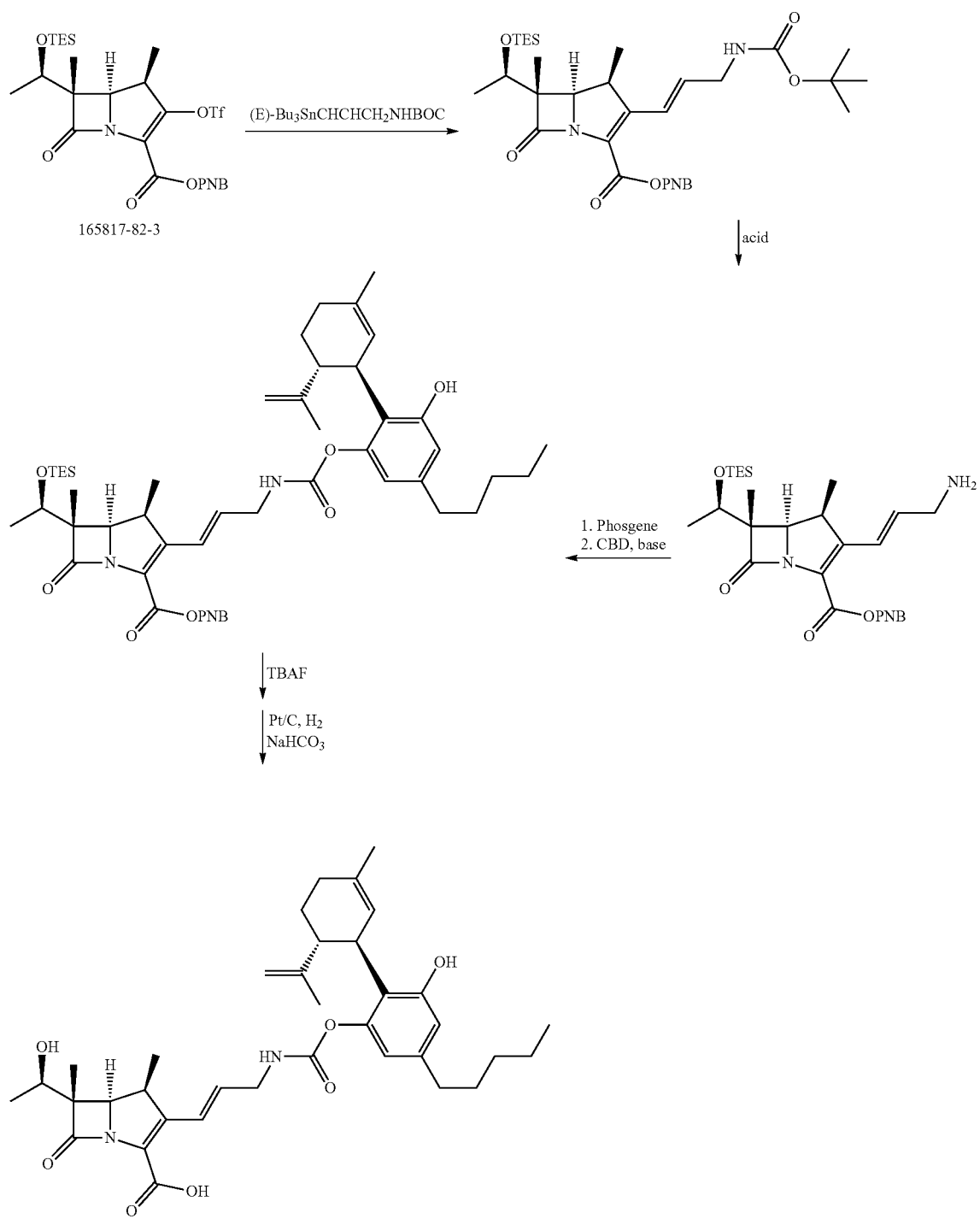

Example 11. Propenyl Thiocarbamate-Linked β-Lactam Antibiotic Cannabinoid Conjugate Components Cephem Conjugates Cephem propenyl thiocarbamate linked β-lactam antibiotic cannabinoid conjugate components are synthesized according to the following Scheme. The starting material [57562-43-3] has been reported (CN 103588788 A 20140219). It is converted under standard conditions to the enol triflate, which is reacted with the BOC-protected aminoorganostannane [139111-44-7](use in similar cephem triflate: Bioorganic & Medicinal Chemistry Letters (2010), 20(15), 4635-4638) followed by BOC removal under standard conditions to give the propenyl amine intermediate. This amine is reacted with thiophosgene and the resulting intermediate reacted with the cannabinoid (CBD) under basic conditions to form the thiocarbamate group. Removal of the PNB ester group under standard conditions produces the desired product.

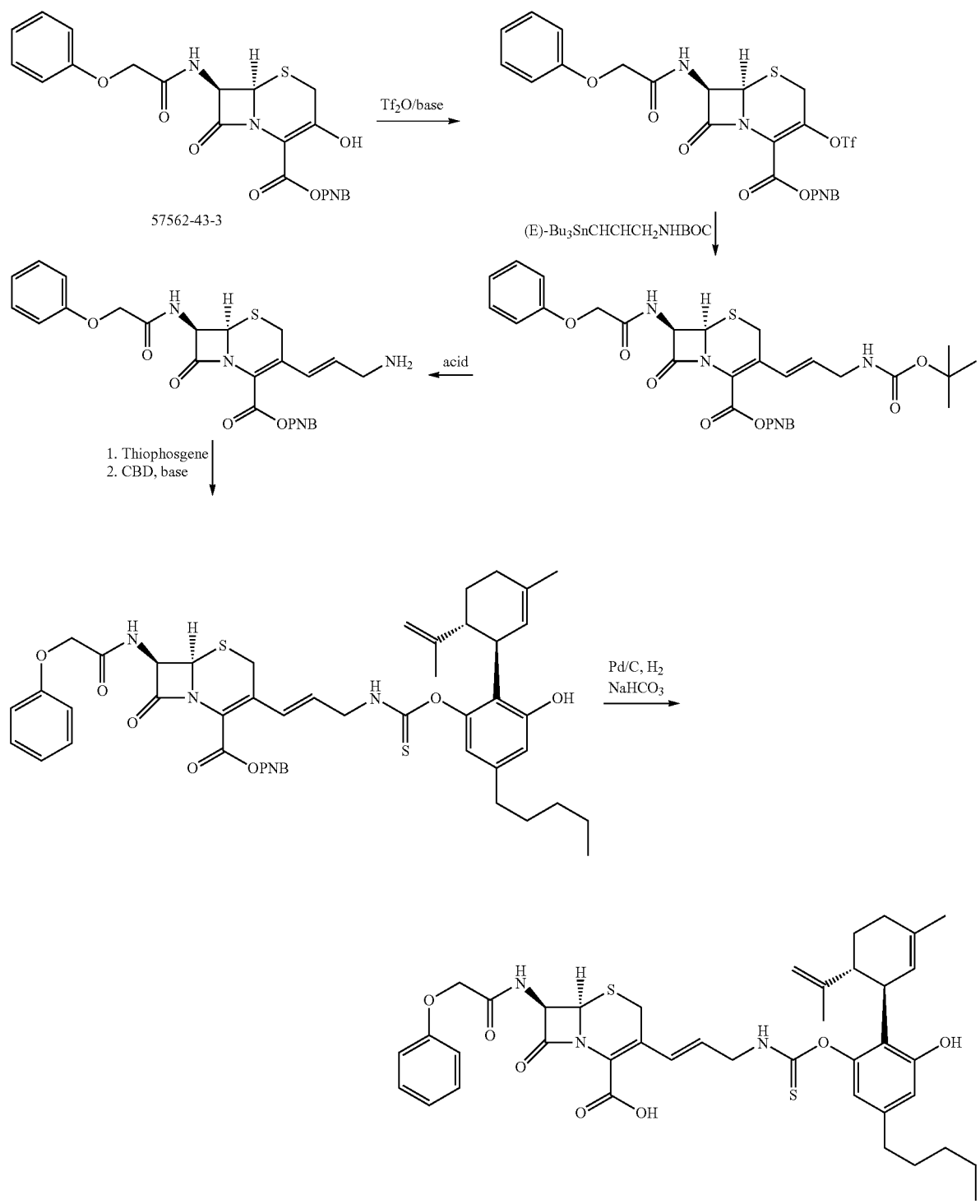

Carbacephem Conjugates

Carbacephem propenyl thiocarbamate linked β-lactam antibiotic cannabinoid conjugate components are synthesized according to the following Scheme. The starting material [119892-46-5] (WO 2010/030810, and references cited therein) is converted under standard conditions to the enol triflate, which is reacted with the BOC-protected aminoorganostannane [139111-44-7] (use in similar cephem triflate: Bioorganic & Medicinal Chemistry Letters (2010), 20(15), 4635-4638) followed by BOC removal under standard conditions to give the propenyl amine intermediate. This amine is reacted with thiophosgene and the resulting intermediate reacted with the cannabinoid (CBD) under basic conditions to form the thiocarbamate group. Removal of the PNB ester group under standard conditions produces the desired product.

205

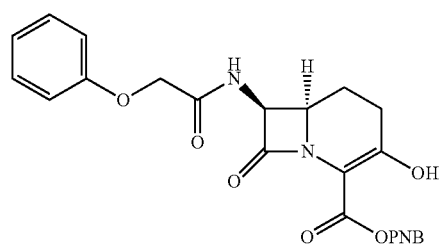

119892-46-5

Tf₂O/base →

206

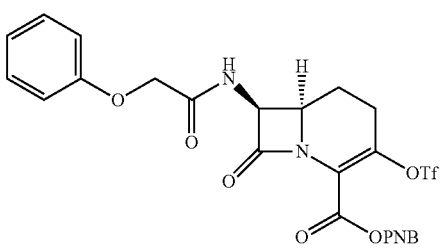

(E)-Bu₃SnCHCHCH₂NHBOC ↓

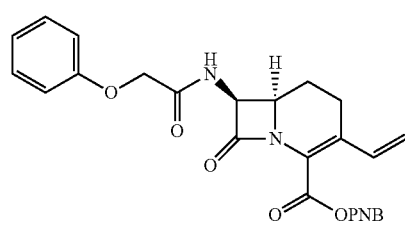

← acid

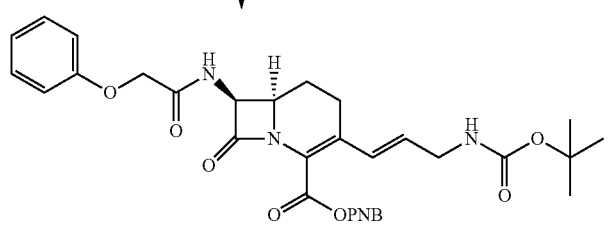

1. Triophosgene
2. CBD, base ↓

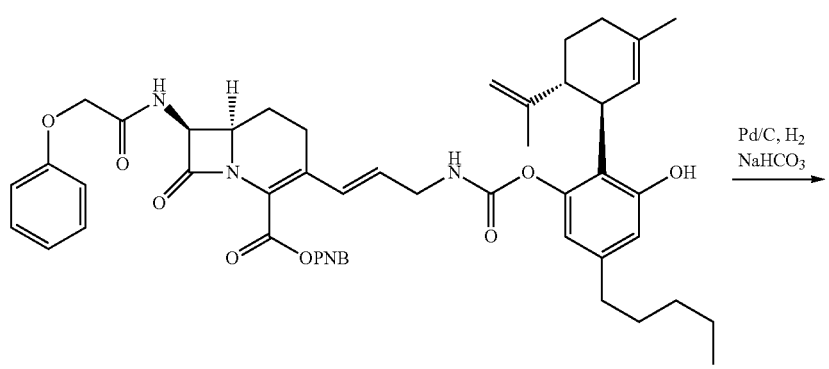

Pd/C, H₂
NaHCO₃ →

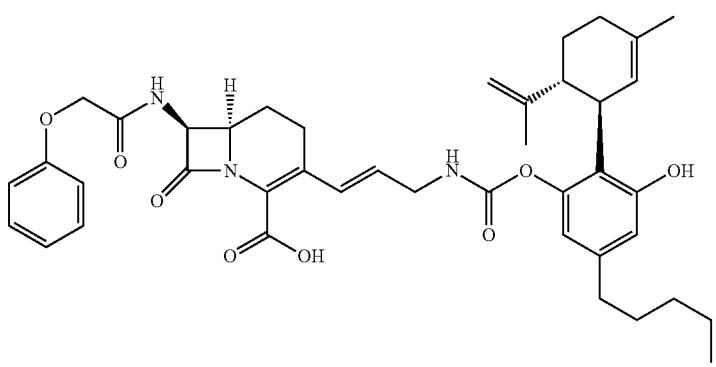

Penem Conjugates

Penem propenyl thiocarbamate linked β-lactam antibiotic cannabinoid conjugate components are synthesized according to the following Scheme. The starting material [127941-62-2] has been previously reported (U.S. Pat. No. 4,895,940). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with thiophosgene and the resulting intermediate reacted with the cannabinoid (CBD) under basic conditions to form the thiocarbamate group. Removal of the TES ether and trimethylsilylethyl ester groups under standard conditions produces the desired product.

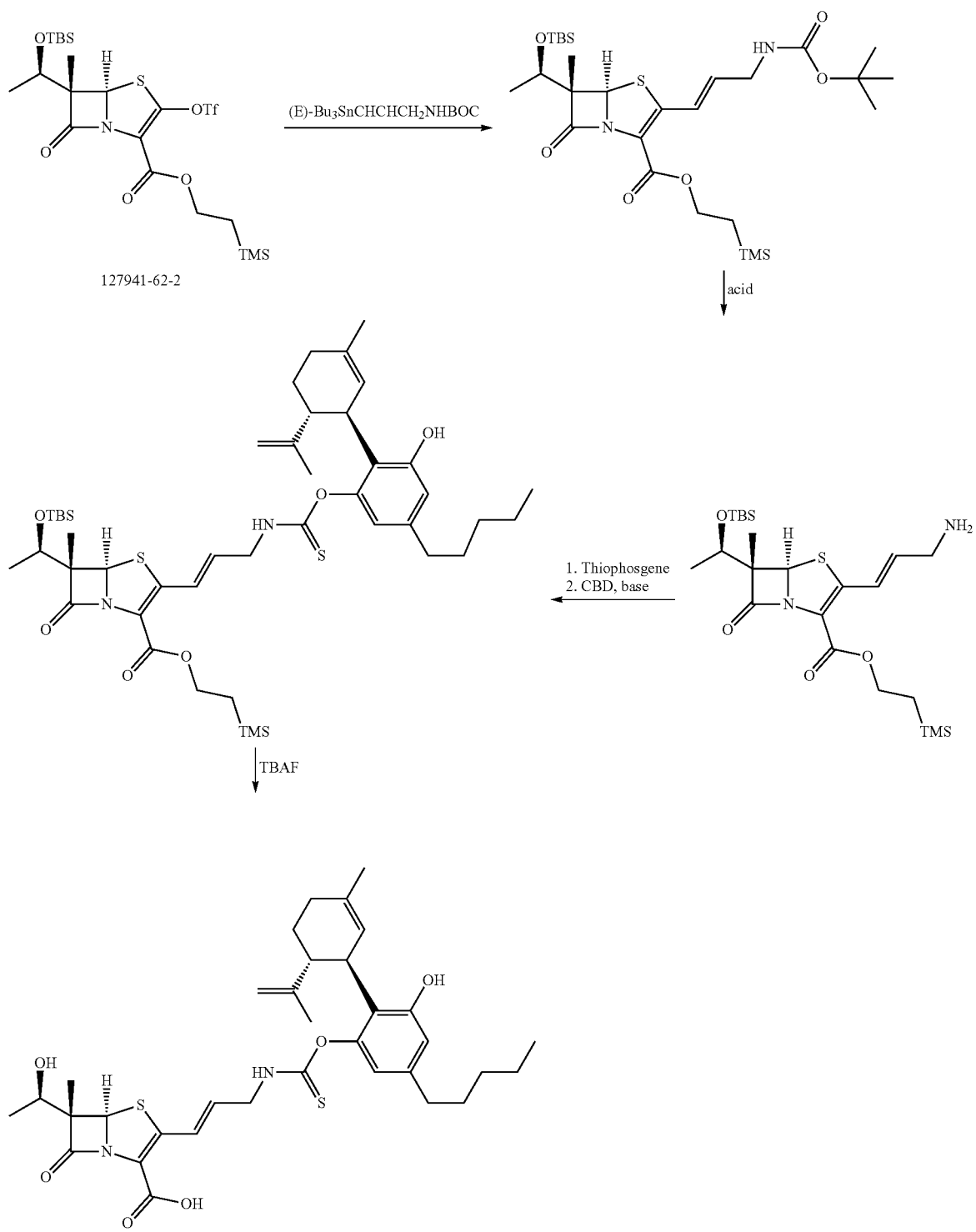

Carbapenem Conjugates

Carbapenem propenyl thiocarbamate linked β-lactam antibiotic cannabinoid conjugate components are synthesized according to the following Scheme. The starting material [165817-82-3] has been described previously (WO 99/62906). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with thiophosgene and the resulting intermediate reacted with the cannabinoid (CBD) under basic conditions to form the thiocarbamate group. Removal of the TES ether and PNB ester groups under standard conditions produces the desired product.

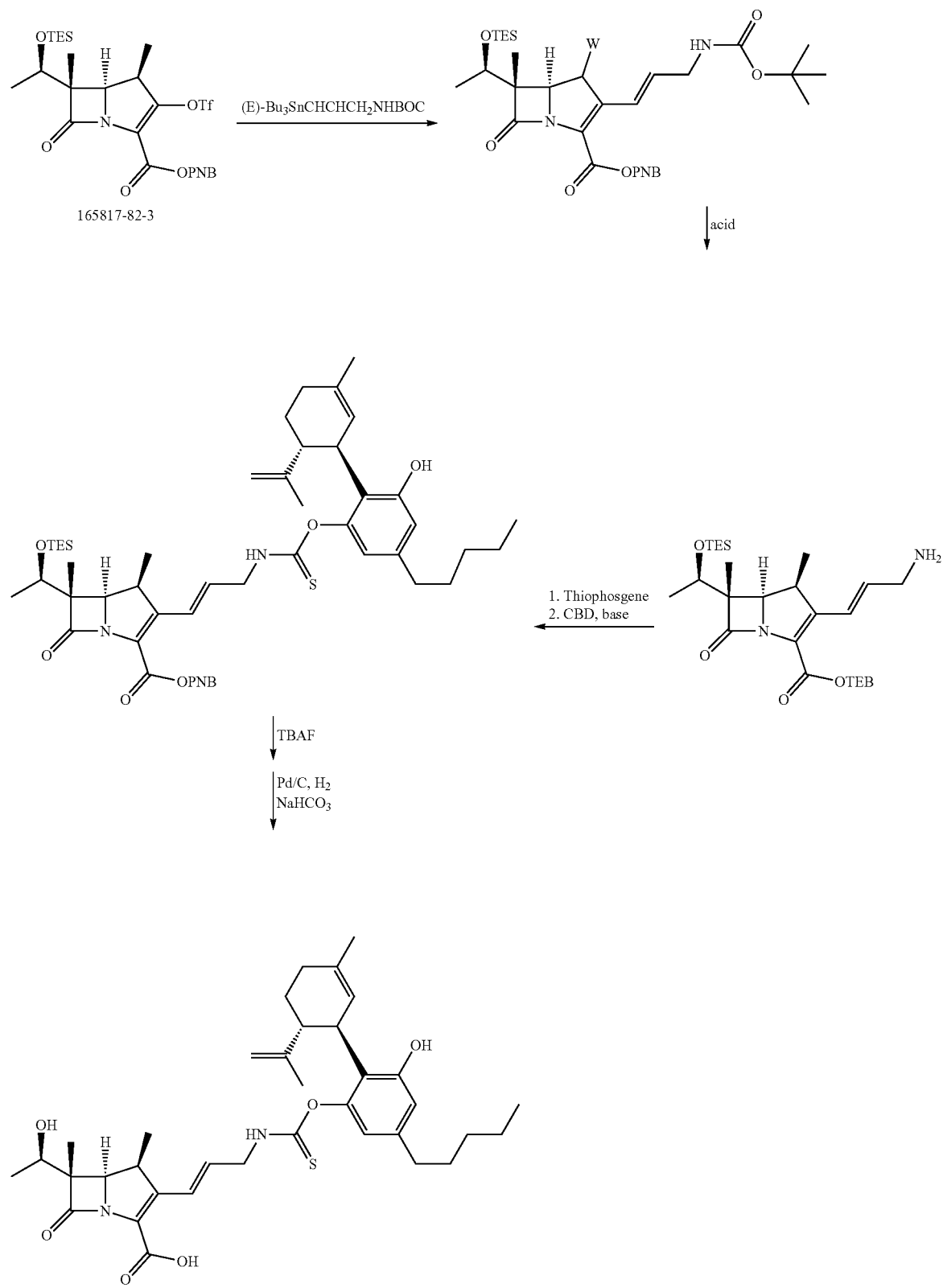

Example 12. S-Alkyl Thiocarbonate-Linked β-Lactam Antibiotic Cannabinoid Conjugate Components

Cephem Conjugates

Cephem S-alkyl thiocarbonate linked β-lactam antibiotic cannabinoid conjugate components are synthesized according to the following Scheme. The starting material [61781-78-0] has been described previously (U.S. (1976), U.S. Pat. No. 3,979,384 A 19760907). Reaction with phosgene and the cannabinoid (CBD) under standard basic conditions to form the S-alkyl thiocarbonate linked intermediate. Removal of the diphenylmethyl ester protecting group gives the desired product.

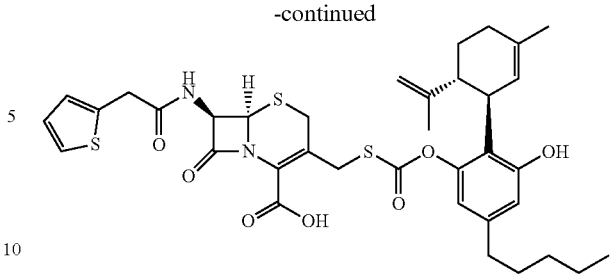

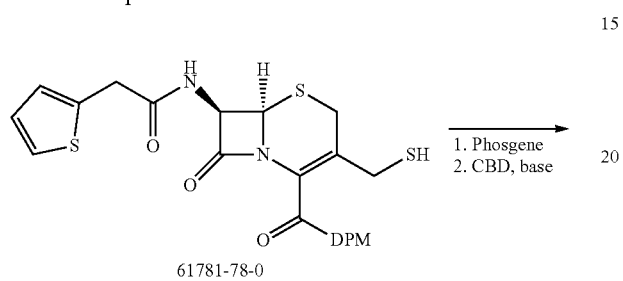

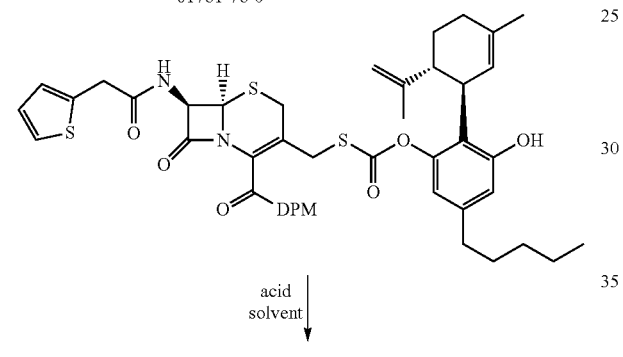

Carbacephem Conjugates

Carbacephem S-alkyl thiocarbonate linked β-lactam antibiotic cannabinoid conjugate components are synthesized according to the following Scheme. The starting material [177325-29-0] is converted to the thiol intermediate using previously described (Faming Zhuanli Shenging, 108623617, 9 Oct. 2018) conditions for a related system. The thiol intermediate is reacted with phosgene and the cannabinoid (CBD) under standard basic conditions to form the S-alkyl thiocarbonate linked intermediate. Removal of the diphenylmethyl ester protecting group gives the desired product.

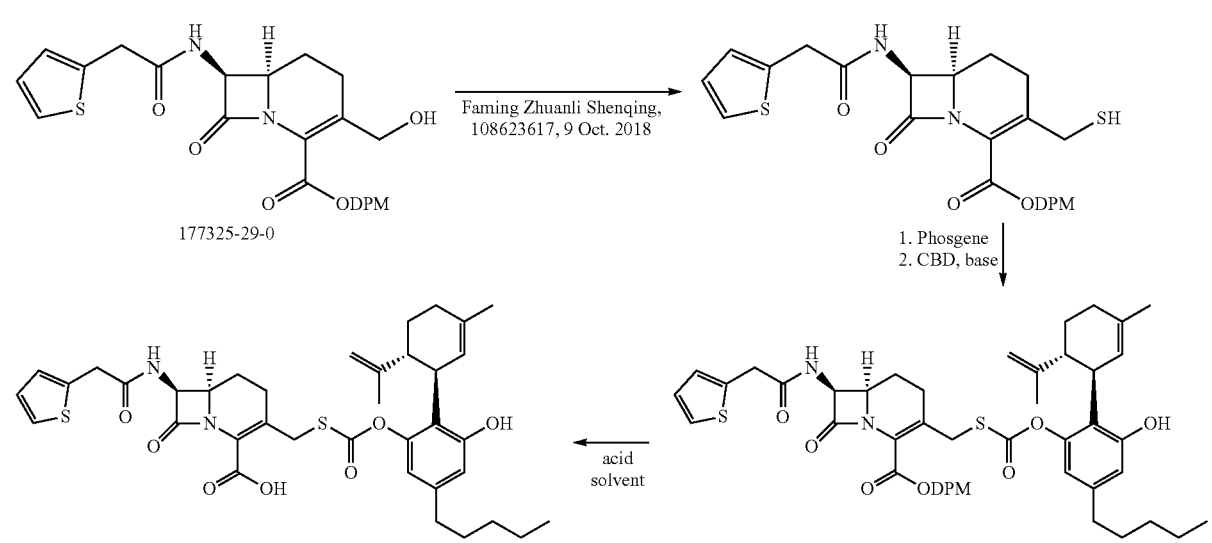

Penem Conjugates

Penem S-alkyl thiocarbonate linked β-lactam antibiotic cannabinoid conjugate components are synthesized according to the following Scheme. The starting material [88585-78-8] is converted to the thiol intermediate using previously described (Faming Zhuanli Shenging, 108623617, 9 Oct. 2018) conditions for a related system. The thiol intermediate is reacted with phosgene and the cannabinoid (CBD) under standard basic conditions to form the S-alkyl thiocarbonate linked intermediate. Removal of the silyl ether and allyl ester protecting groups gives the desired product.

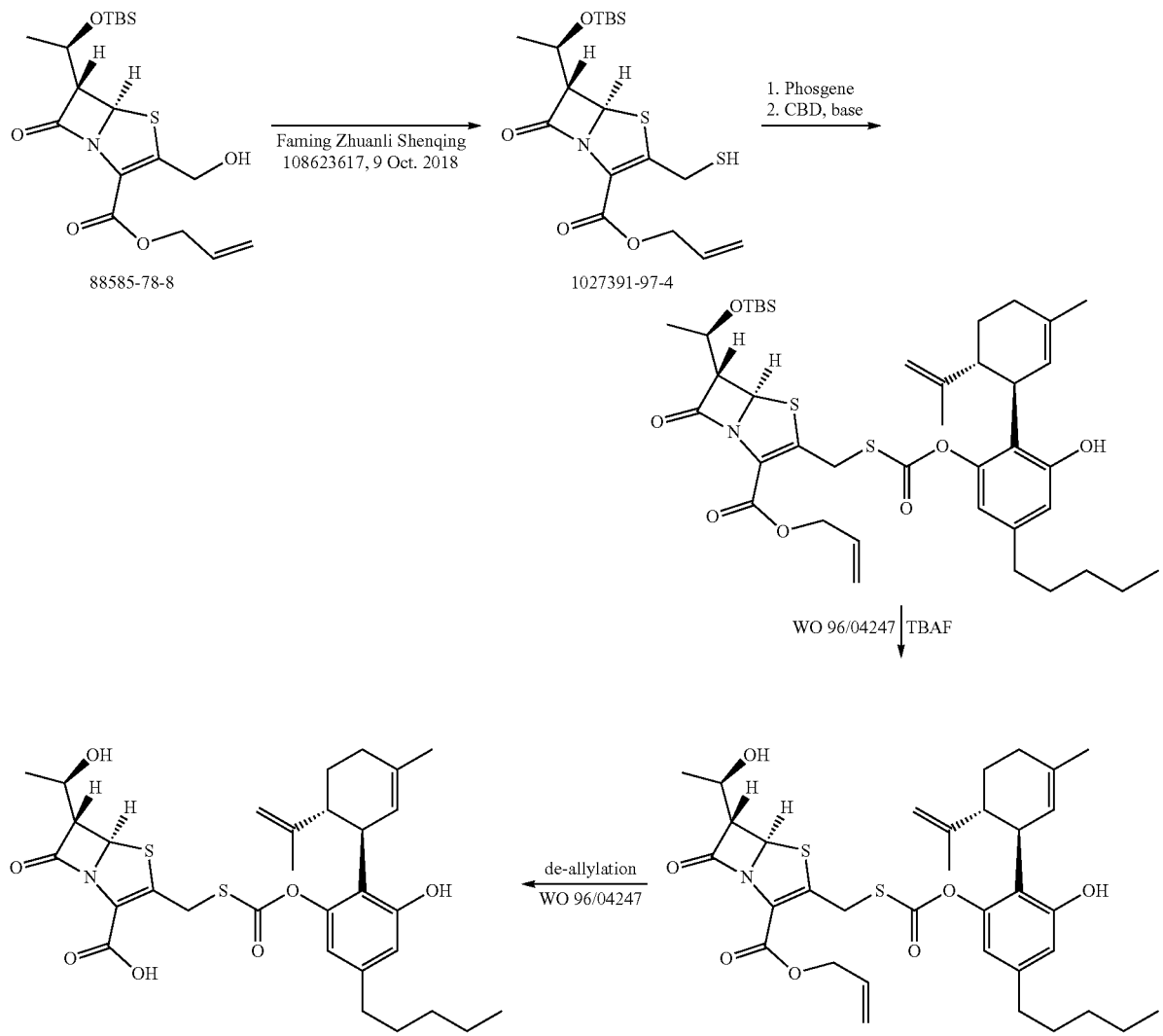

Carbapenem Conjugates

Carbapenem S-alkyl thiocarbonate linked β-lactam antibiotic cannabinoid conjugate components are synthesized according to the following Scheme. The starting material [118990-99-1] is converted to the thiol intermediate using previously described (Faming Zhuanli Shenging, 108623617, 9 Oct. 2018) conditions for a related system. The thiol intermediate is reacted with phosgene and the cannabinoid (CBD) under standard basic conditions to form the S-alkyl thiocarbonate linked intermediate. Removal of the allyl protecting groups gives the desired product.

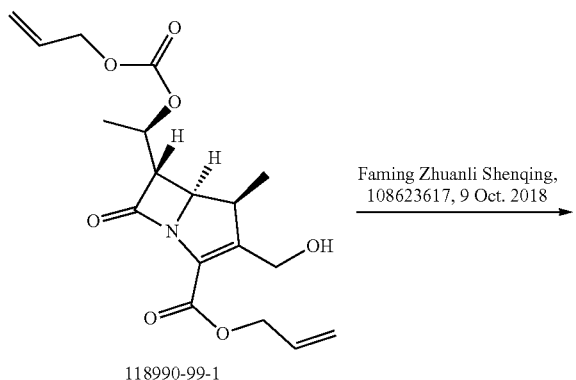

118990-99-1

Faming Zhuanli Shenqing, 108623617, 9 Oct. 2018

1. Phosgene
2. CBD, base, solvent
   WO 96/04247 deallylation
WO 96/04247

Example 13. Xanthate-Linked β-Lactam Antibiotic Cannabinoid Conjugate Components Cephem Conjugates Cephem xanthate linked β-lactam antibiotic cannabinoid conjugate components are synthesized according to the following Scheme. The starting material [61781-78-0] has been described previously (U.S. (1976), U.S. Pat. No. 3,979,384 A 19760907). Reaction with thiophosgene and the cannabinoid (CBD) under standard basic conditions to form the xanthate linked intermediate. Removal of the diphenylmethyl ester protecting group gives the desired product.

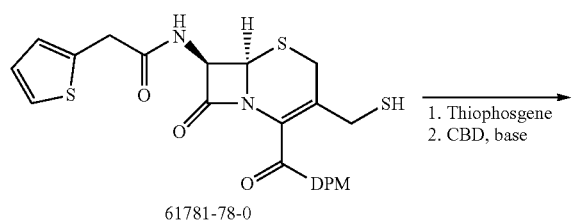

61781-78-0

1. Thiophosgene
2. CBD, base

-continued

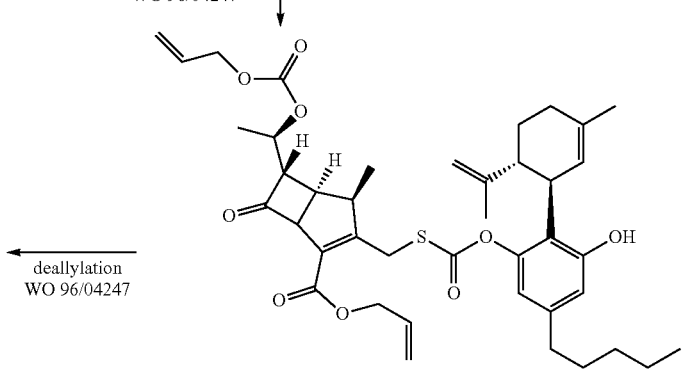

acid solvent

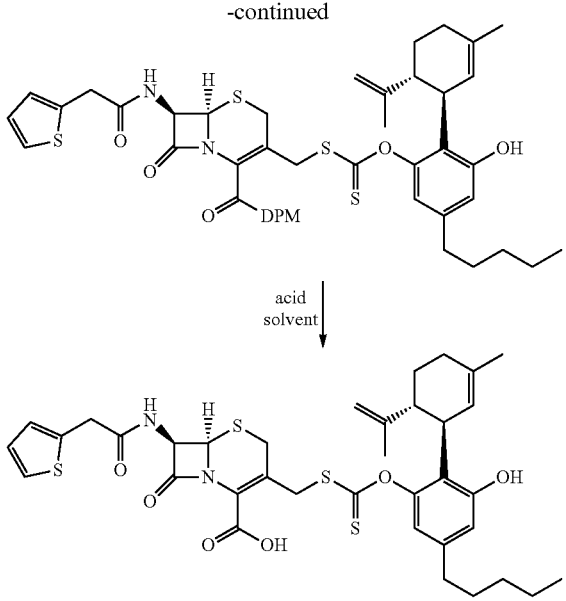

Carbacephem Conjugates

Carbacephem xanthate linked β-lactam antibiotic cannabinoid conjugate components are synthesized according to the following Scheme. The starting material [177325-29-0] is converted to the thiol intermediate using previously described (Faming Zhuanli Shenging, 108623617, 9 Oct. 2018) conditions for a related system. The thiol intermediate is reacted with thiophosgene and the cannabinoid (CBD) under standard basic conditions to form the xanthate linked intermediate. Removal of the diphenylmethyl ester protecting group gives the desired product.

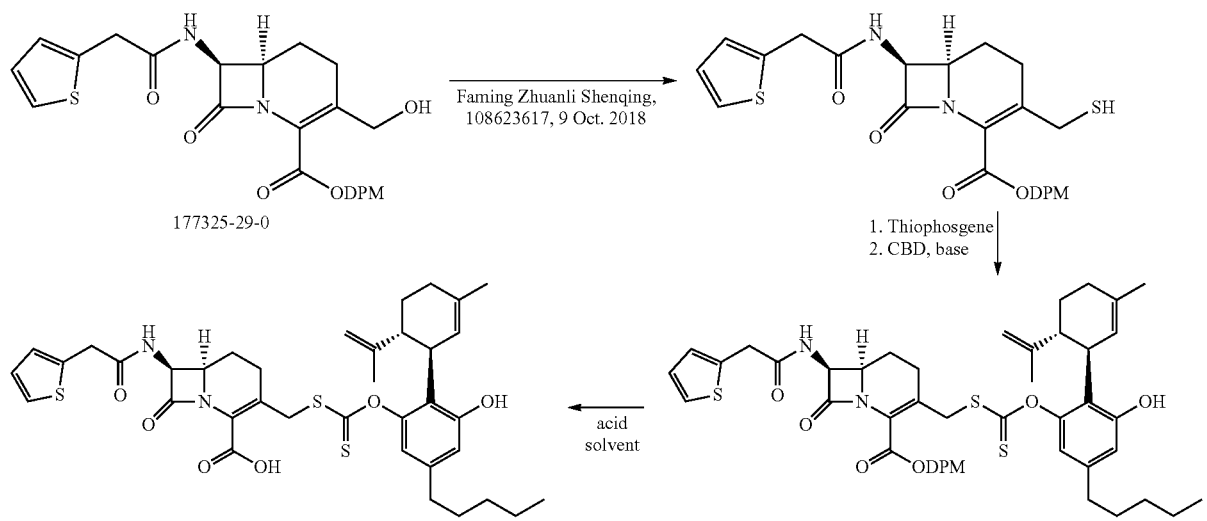

Penem Conjugates

Penem xanthate linked β-lactam antibiotic cannabinoid conjugate components are synthesized according to the following Scheme. The starting material [88585-78-8] is converted to the thiol intermediate using previously described (Faming Zhuanli Shenging, 108623617, 9 Oct. 2018) conditions for a related system. The thiol intermediate is reacted with thiophosgene and the cannabinoid (CBD) under standard basic conditions to form the xanthate linked intermediate. Removal of the silyl ether and allyl ester protecting groups gives the desired

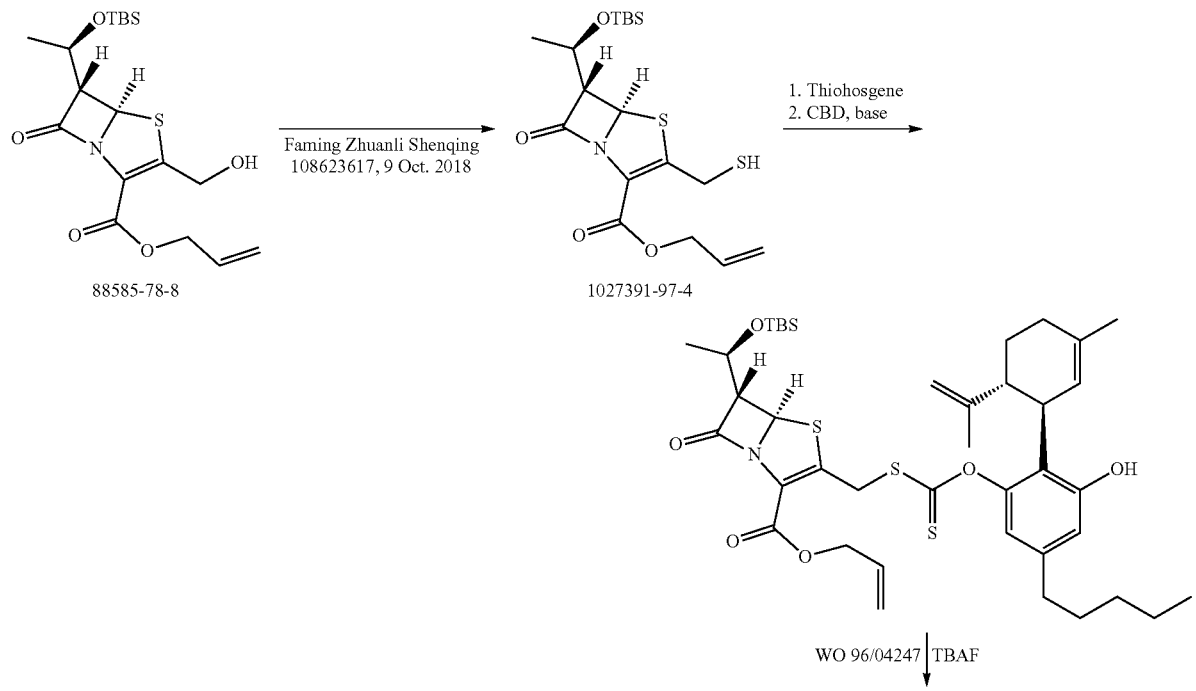

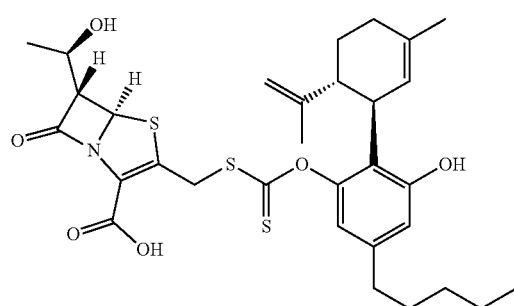
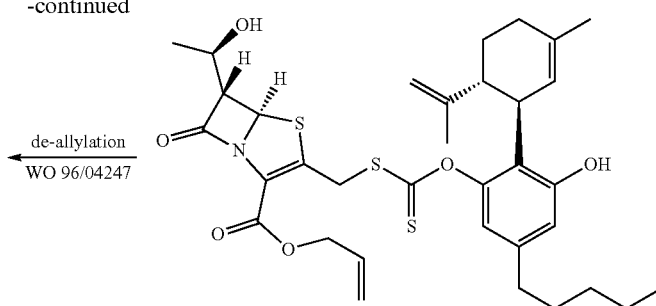

Carbapenem Conjugates

Carbapenem xanthate linked β-lactam antibiotic cannabinoid conjugate components are synthesized according to the following Scheme. The starting material [118990-99-1] is converted to the thiol intermediate using previously described (Faming Zhuanli Shenging, 108623617, 9 Oct. 2018) conditions for a related system. The thiol intermediate is reacted with thiophosgene and the cannabinoid (CBD) under standard basic conditions to form the xanthate linked intermediate. Removal of the allyl protecting groups gives the desired product.

Example 14. Acetal-Linked β-Lactam Antibiotic Cannabinoid Conjugate Components

Cephem Conjugates

Cephem acetal linked β-lactam antibiotic cannabinoid conjugate components are synthesized according to the following Scheme. The starting material [15690-38-7] is converted to a hydroxymethyl intermediate containing a side chain and protecting ester of choice as described in the literature (WO 96/04247). A cannabinoid (CBD) is converted to the O-chloromethyl intermediate via reported conditions (Bioorg. & Med. Chem., 26(2), 386-393; 2018; J.

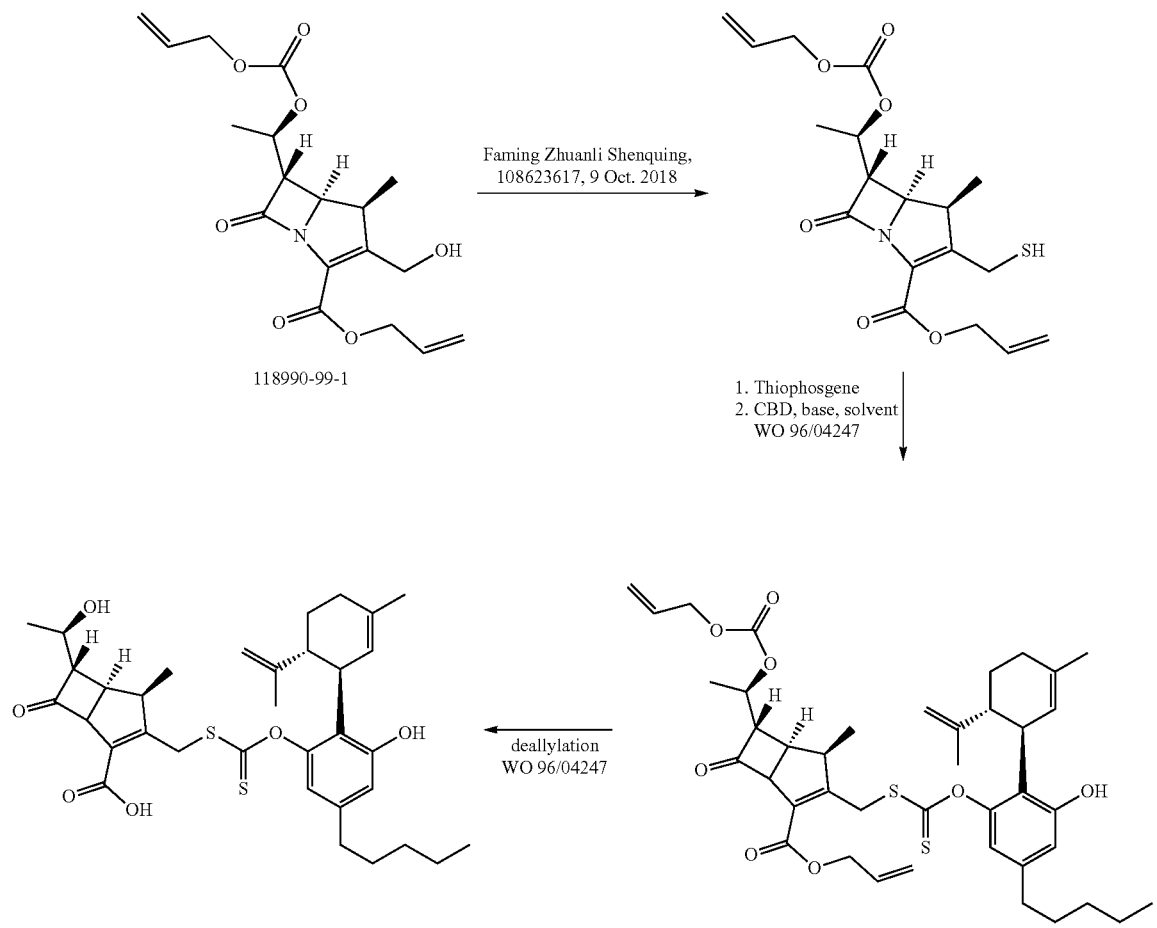

Amer. Chem. Soc., 136(26), 9260-9263; 2014; Faming Zhuanli Shenqing, 105037382, 11 Nov. 2015). The hydroxymethyl and O-chloromethyl intermediates are reacted under previously reported conditions (Tetrahedron, 60(12), 2771-2784; 2004) to generate the acetal link. Removal of the diphenylmethyl ester protecting group gives the product.

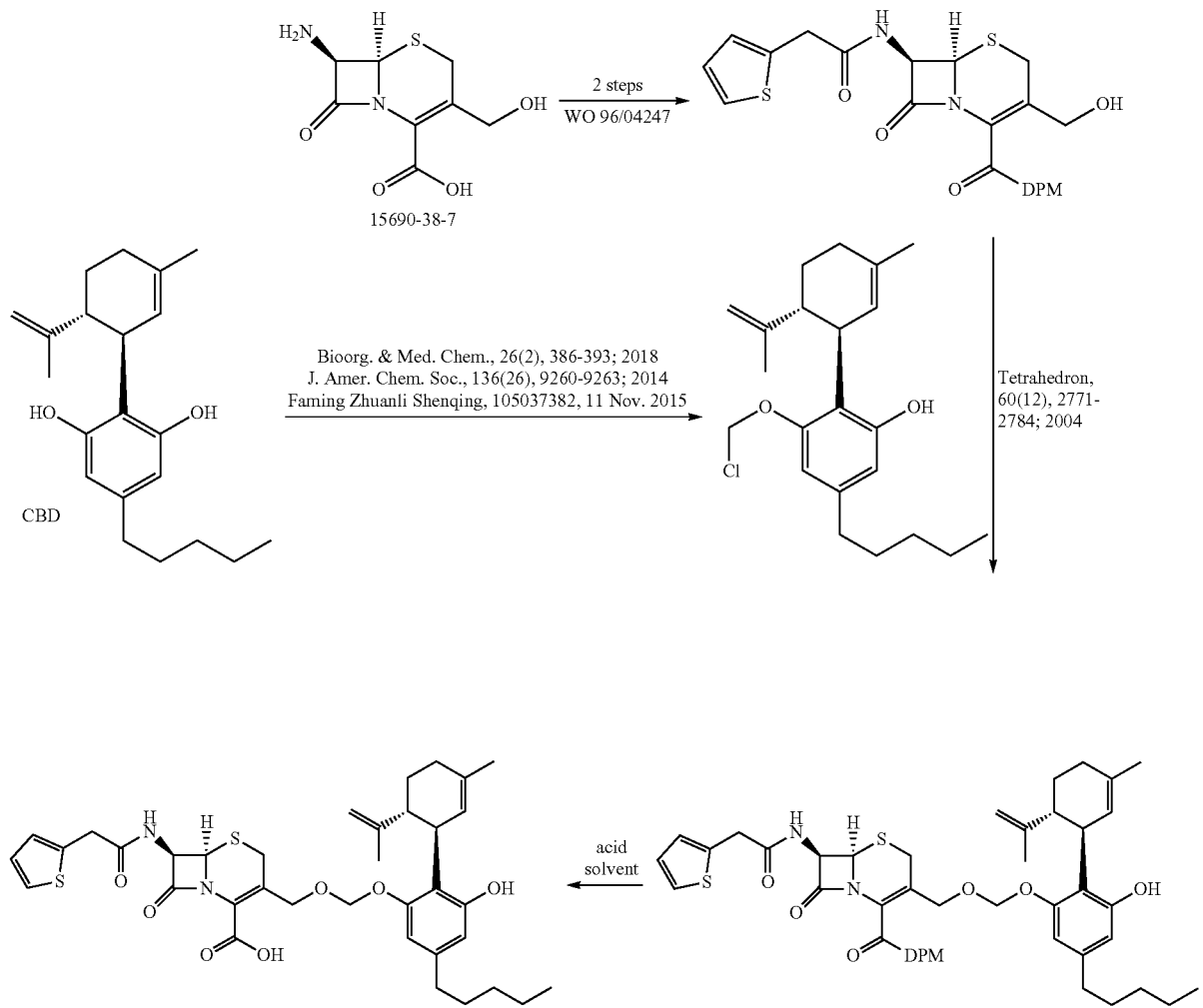

Carbacephem Conjugates

Carbacephem acetal linked β-lactam antibiotic cannabinoid conjugate components are synthesized according to the following Scheme. The starting material [177472-75-2] is converted to a hydroxymethyl intermediate containing a side chain and protecting ester of choice as described in the literature (WO 96/04247). A cannabinoid (CBD) is converted to the O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). The hydroxymethyl and O-chloromethyl intermediates are reacted under previously reported conditions (Tetrahedron, 60(12), 2771-2784; 2004) to generate the acetal link. Removal of the diphenylmethyl ester protecting group gives the product.

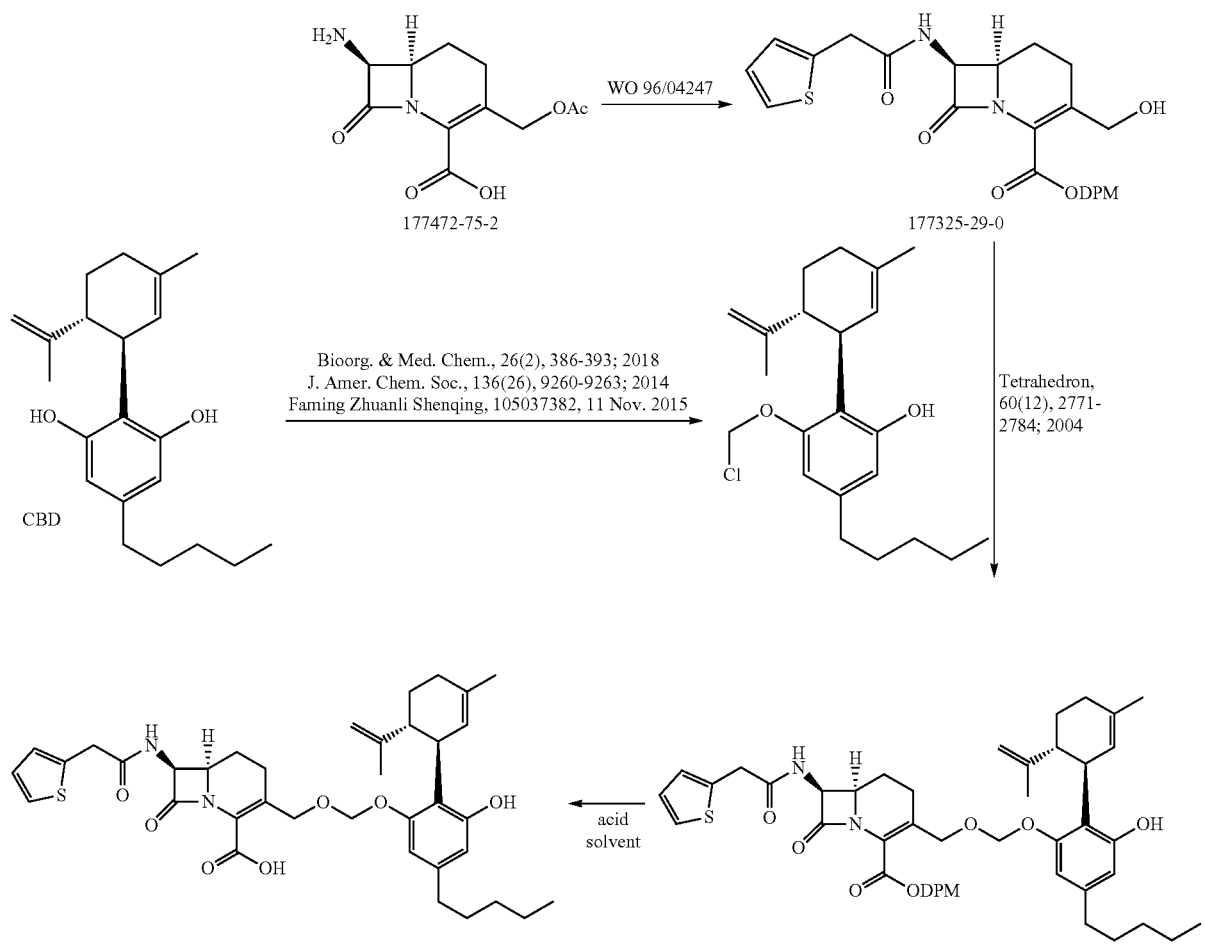

Penem Conjugates

Penem acetal linked β-lactam antibiotic cannabinoid conjugate components are synthesized according to the following Scheme. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted with a hydroxymethyl penem [88585-78-8] under reported conditions (Tetrahedron, 60(12), 2771-2784; 2004) to form the acetal link. Removal of the silyl ether and allyl ester protecting groups under standard conditions gives the product.

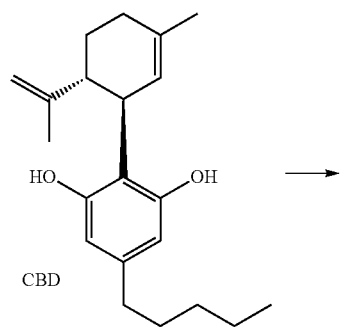

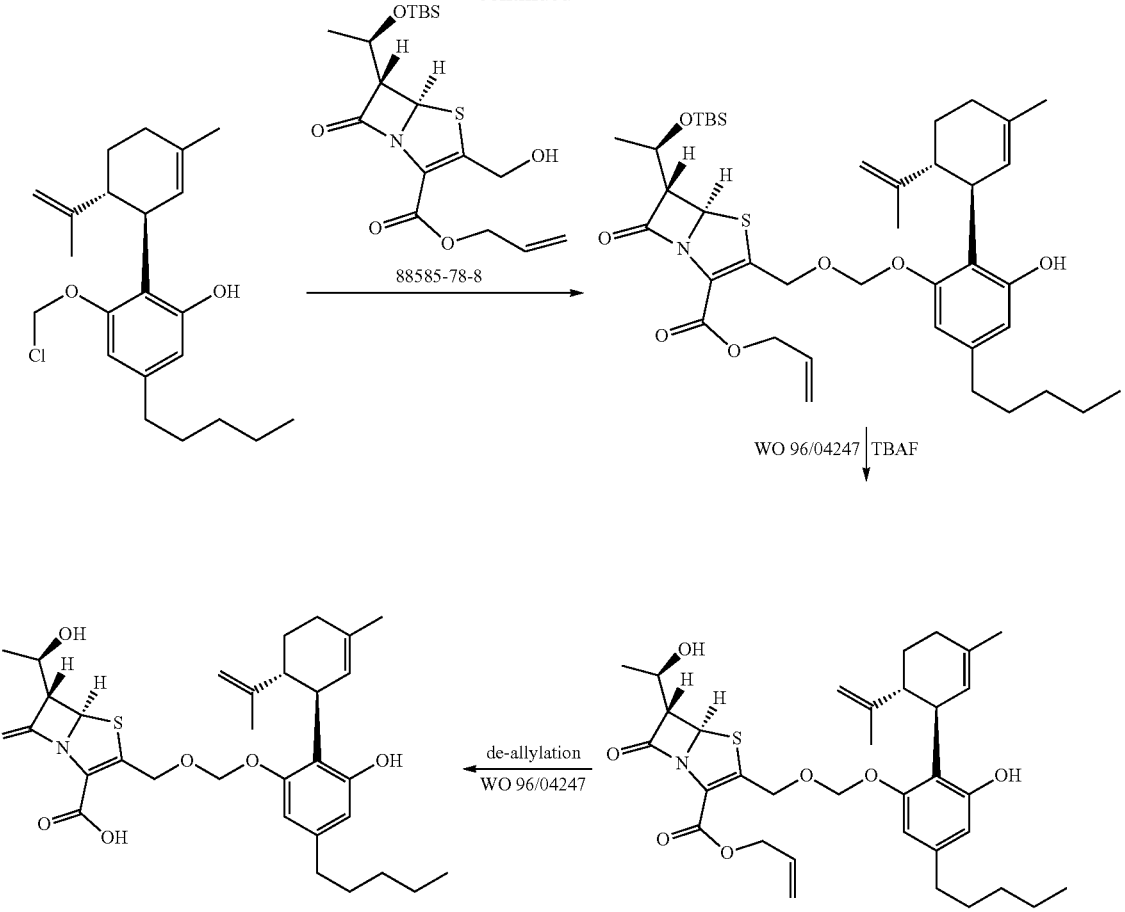

Carbapenem Conjugates

Carbapenem acetal linked β-lactam antibiotic cannabinoid conjugate components are synthesized according to the following Scheme. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted with a hydroxymethyl carbapenem [118990-99-1] under reported conditions (Tetrahedron, 60(12), 2771-2784; 2004) to form the acetal link. Removal of the allyl protecting groups under standard conditions gives the product.

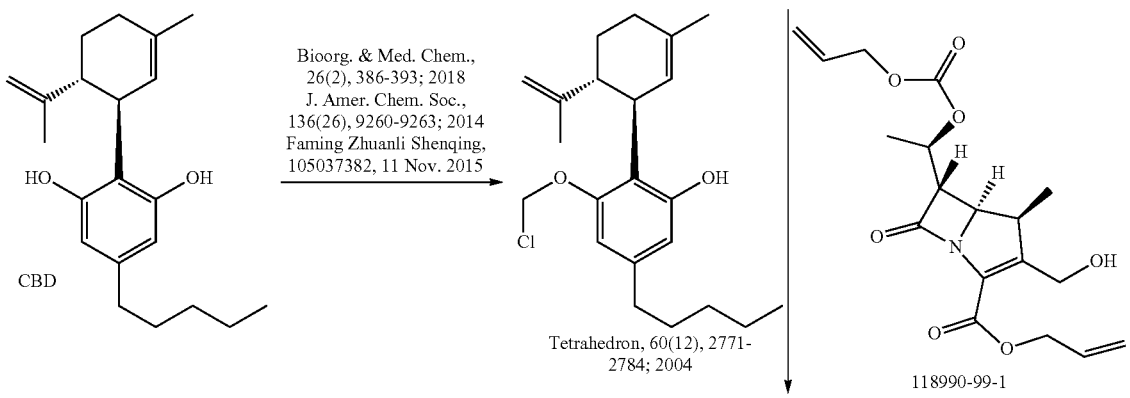

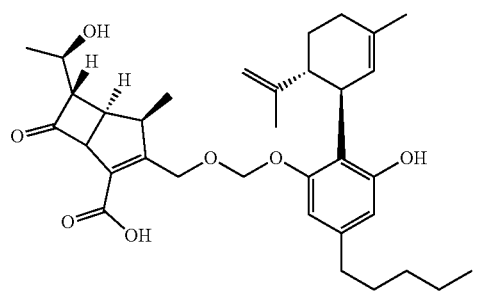
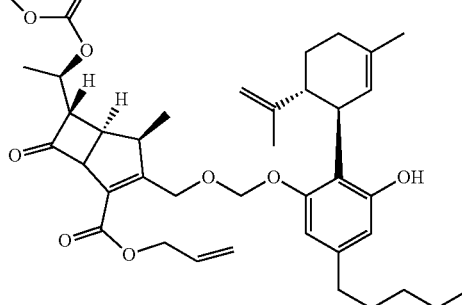

Example 15. Aminal-Linked β-Lactam Antibiotic Cannabinoid Conjugate Components Cephem Conjugates Cephem aminal linked β-lactam antibiotic cannabinoid conjugate components are synthesized according to the following Scheme. The aminomethyl cephem intermediate is synthesized according to the scheme shown above for cephem carbamate linked β-lactam antibiotic cannabinoid conjugate components. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl cephem to give the aminal linked intermediate. Removal of the t-butyl ester protecting group gives the product.

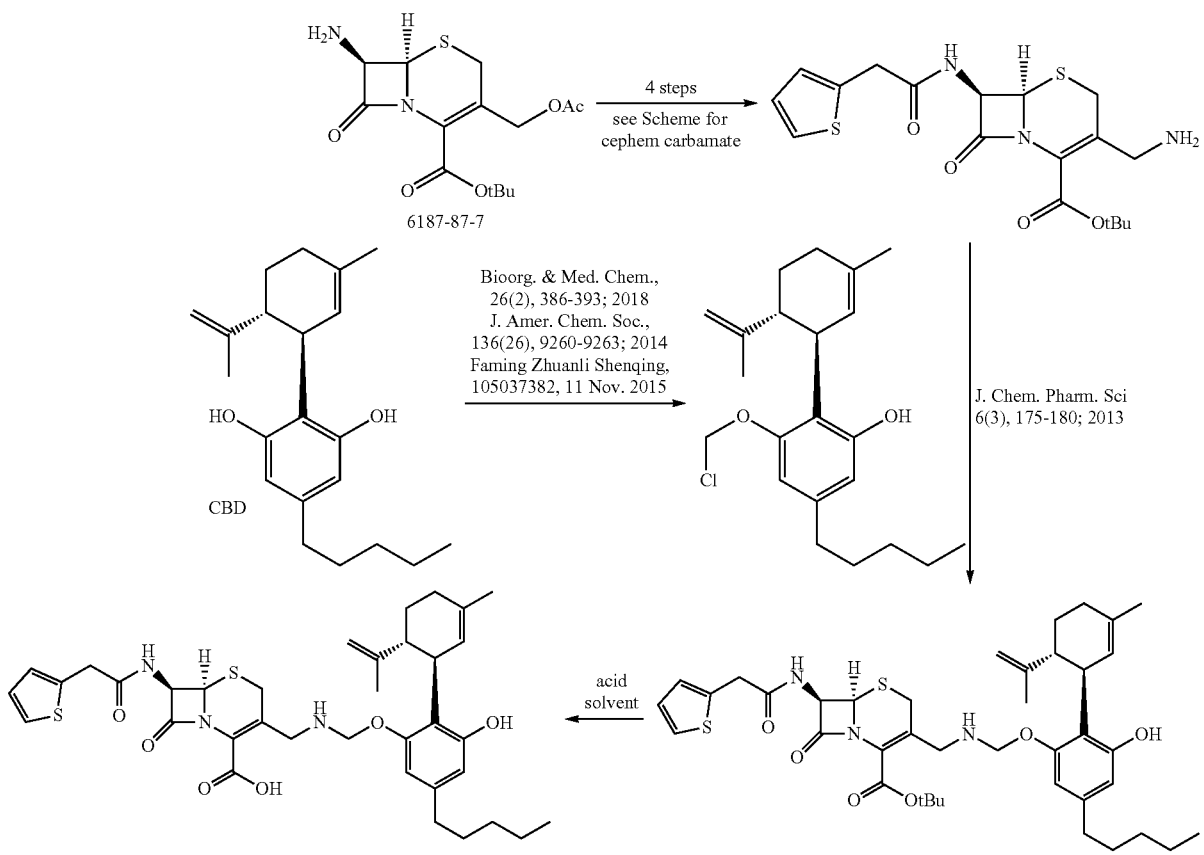

Carbacephem Conjugates

Carbacephem aminal linked β-lactam antibiotic cannabinoid conjugate components are synthesized according to the following Scheme. The aminomethyl carbacephem intermediate is synthesized according to the scheme shown above for carbacephem carbamate linked β-lactam antibiotic cannabinoid conjugate components. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl carbacephem to give the aminal linked intermediate. Removal of the t-butyl ester protecting group gives the product.

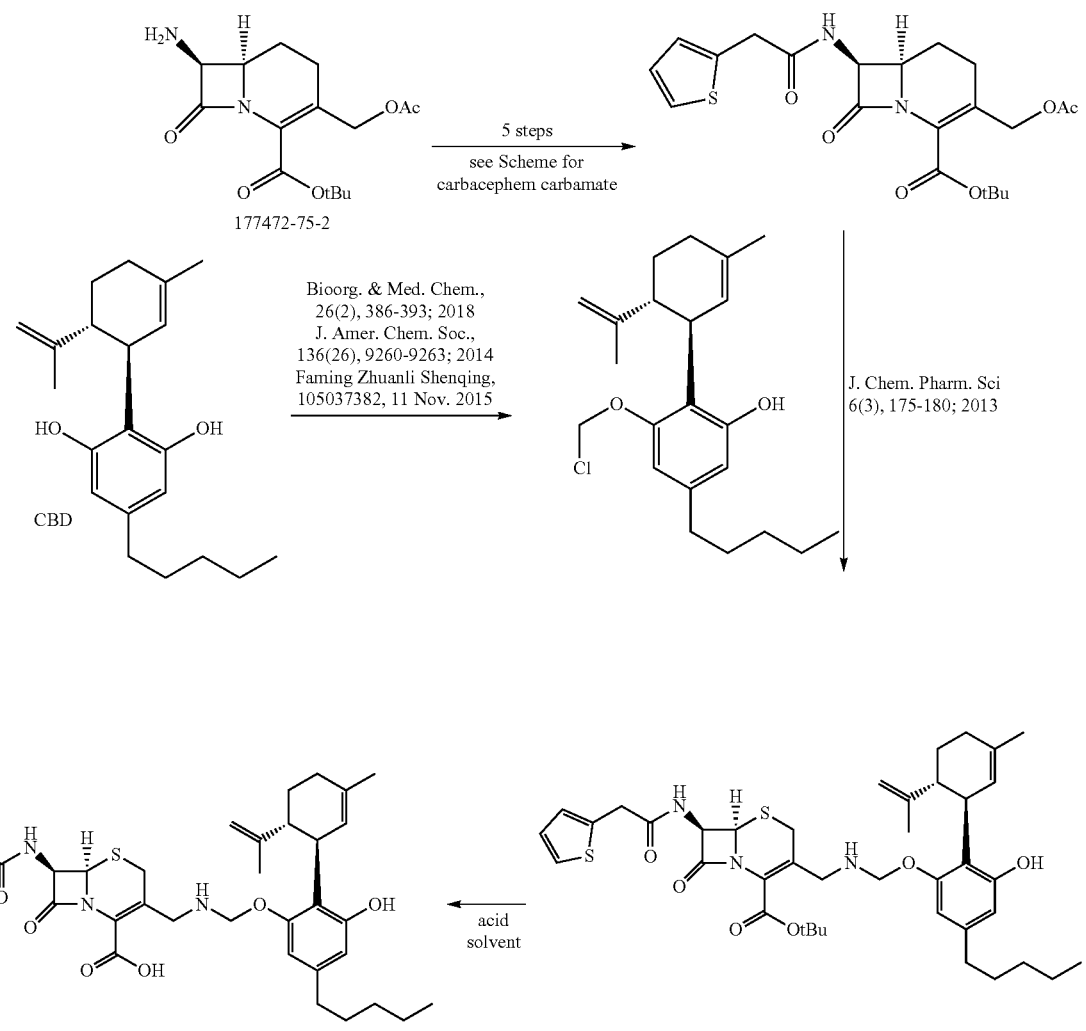

Penem Conjugates

Penem aminal linked β-lactam antibiotic cannabinoid conjugate components are synthesized according to the following Scheme. The aminomethyl penem intermediate is synthesized in 5 steps according to the scheme shown above for penem carbamate linked 3-lactam antibiotic cannabinoid conjugate components. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl penem to give the aminal linked intermediate. Removal of the t-butyl ester protecting group gives the product.

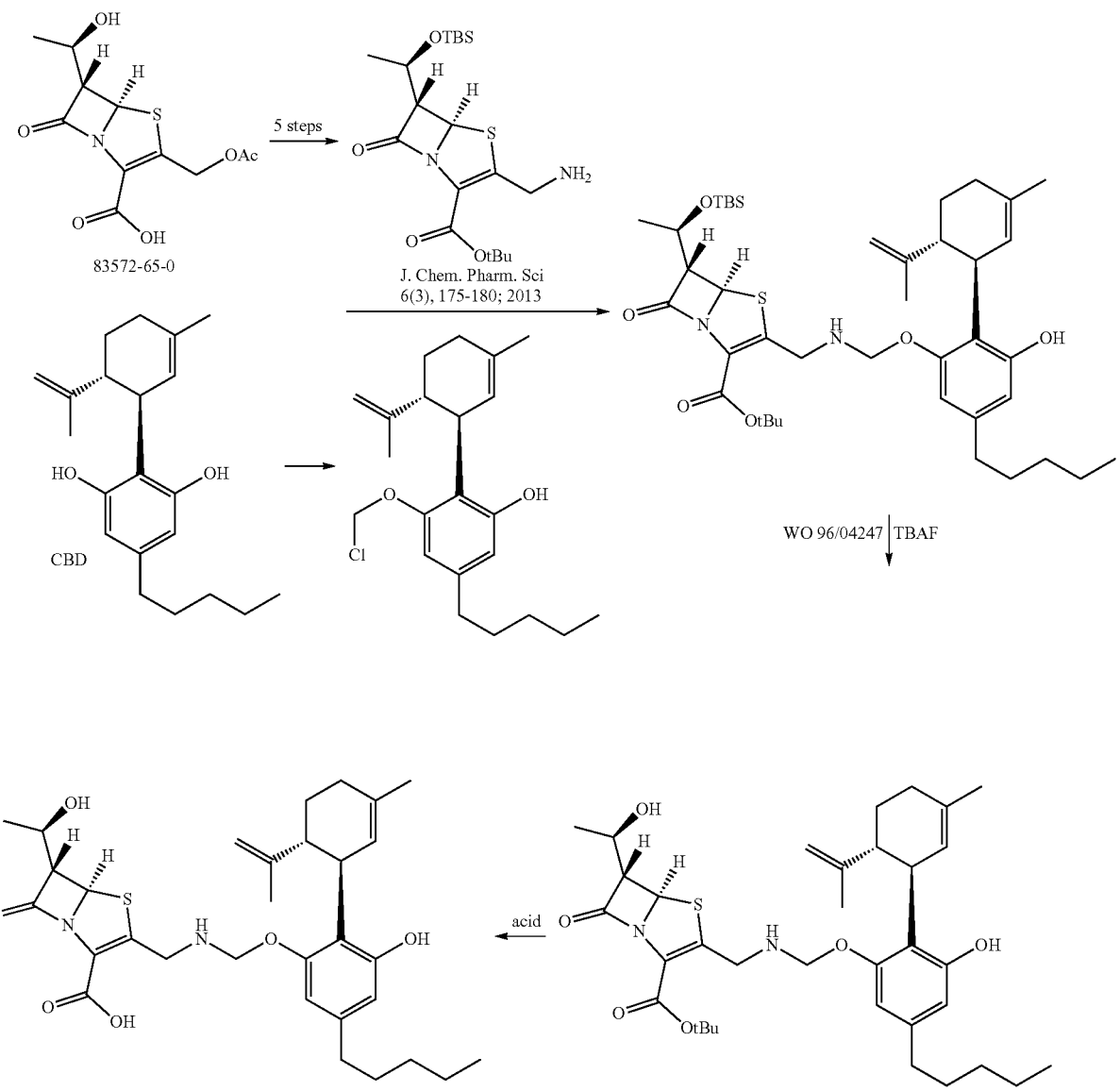

Carbapenem Conjugates

Carbapenem aminal linked β-lactam antibiotic cannabinoid conjugate components are synthesized according to the following Scheme. The aminomethyl carbapenem intermediate is synthesized in 5 steps according to the scheme shown above for carbapenem carbamate linked β-lactam antibiotic cannabinoid conjugate components. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl carbapenem to give the aminal linked intermediate. Removal of the silyl ether and t-butyl ester protecting groups gives the product.

233

234

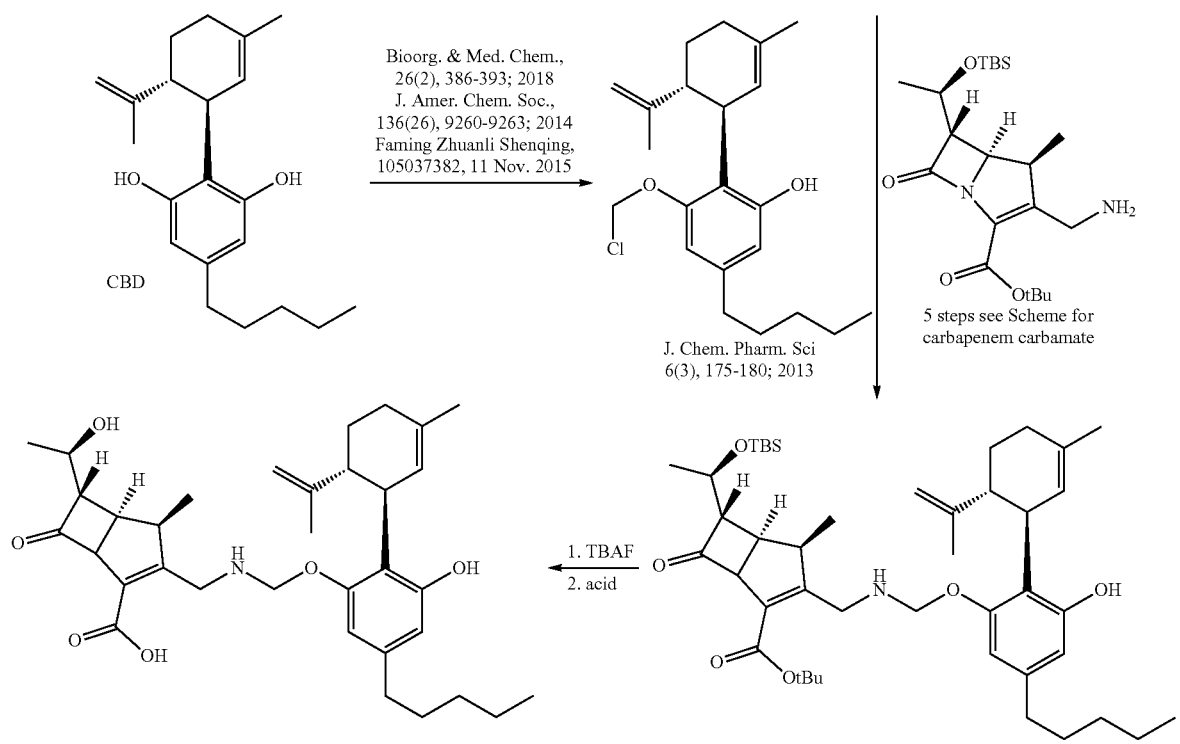 [SMILES: "CBD" ; C=C(C)[C@@H]1CCC(C)=C[C@H]1c1c(O)cc(CCCCC)cc1O ; C=C(C)[C@@H]1CCC(C)=C[C@H]1c1c(O)cc(CCCCC)cc1OCCl ; C[C@@H](O[Si](C)(C)C(C)(C)C)[C@H]1C(=O)N2C(C(=O)OC(C)(C)C)=C(CN)[C@H](C)[C@H]12 ; C=C(C)[C@@H]1CCC(C)=C[C@H]1c1c(O)cc(CCCCC)cc1OCNCC1=C(C(=O)O)C2C(=O)[C@H]([C@@H](C)O)[C@H]2[C@H]1C ; C=C(C)[C@@H]1CCC(C)=C[C@H]1c1c(O)cc(CCCCC)cc1OCNCC1=C(C(=O)OC(C)(C)C)C2C(=O)[C@H]([C@@H](C)O[Si](C)(C)C(C)(C)C)[C@H]2[C@H]1C]

Example 16. Thioacetal-Linked β-Lactam Antibiotic Cannabinoid Conjugate Components Cephem Conjugates Cephem thioacetal linked β-lactam antibiotic cannabinoid conjugate components are synthesized according to the following Scheme. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiomethyl cephem [61781-78-0] to give the thioacetal linked intermediate. Removal of the diphenylmethyl ester protecting group gives the product.

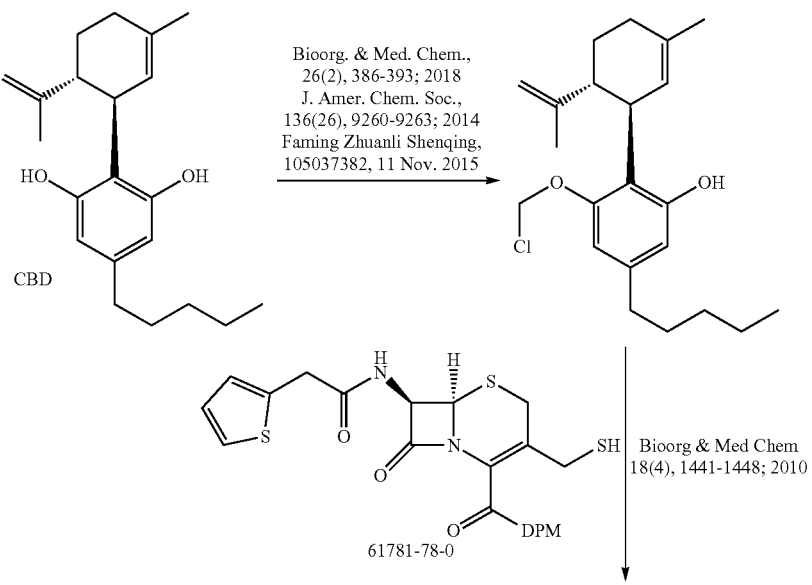

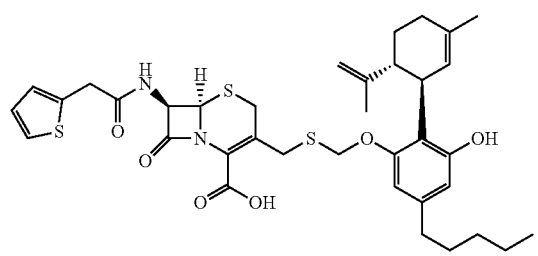
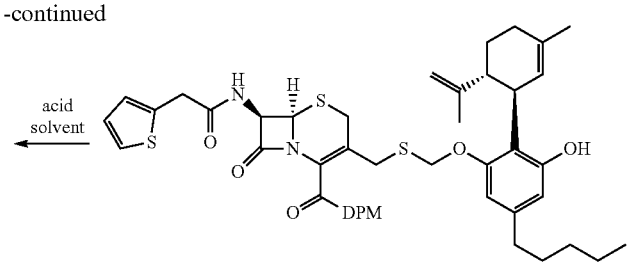

Carbacephem Conjugates

Carbacephem thioacetal linked β-lactam antibiotic cannabinoid conjugate components are synthesized according to the following Scheme. The starting material [177325-29-0] is converted to the thiol intermediate using previously described (Faming Zhuanli Shenging, 108623617, 9 Oct. 2018) conditions for a related system. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiol carbacephem intermediate to give the thioacetal linked intermediate. Removal of the diphenylmethyl ester protecting group gives the product.

Penem Conjugates

Penem thioacetal linked β-lactam antibiotic cannabinoid conjugate components are synthesized according to the following Scheme. The starting material [88585-78-8] is converted to the thiol intermediate [1027391-97-4] using previously described (Faming Zhuanli Shenging, 108623617, 9 Oct. 2018) conditions for a related system. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiol penem intermediate to give the thioacetal linked intermediate. Removal of the silyl ether and allyl ester protecting groups gives the product.

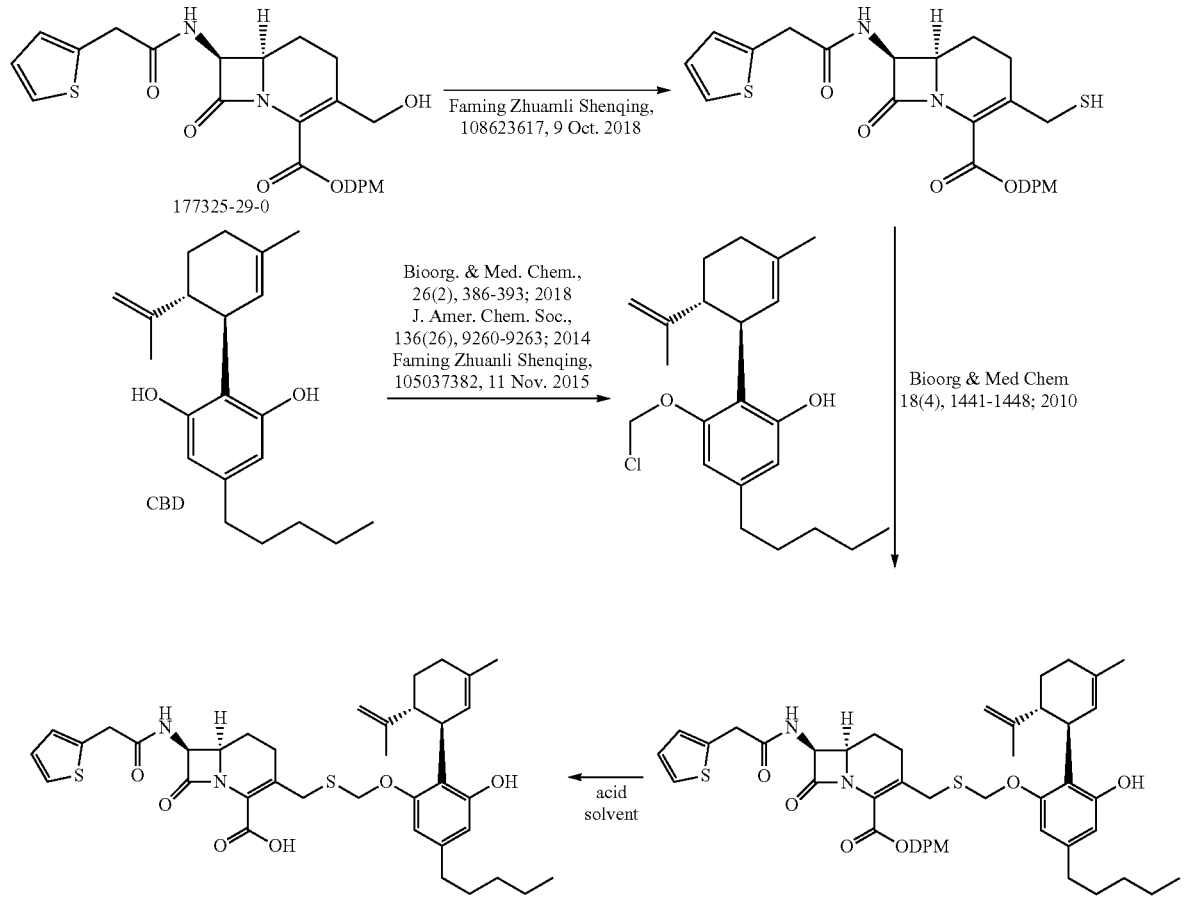

237 238

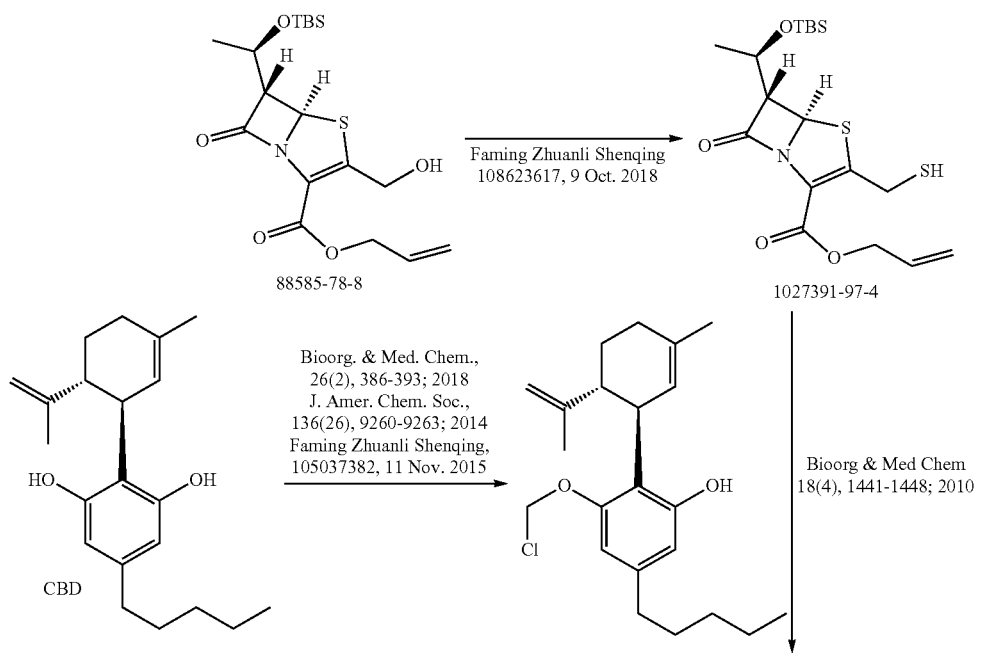

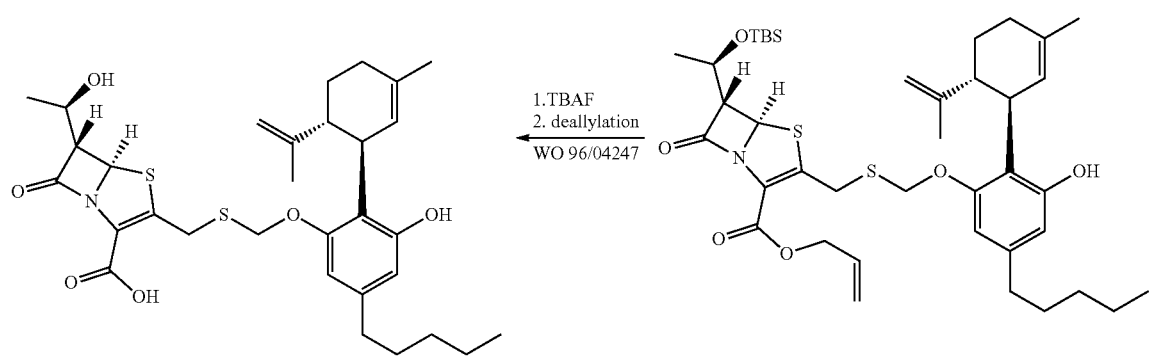

Carbapenem Conjugates

Carbapenem thioacetal linked β-lactam antibiotic cannabinoid conjugate components are synthesized according to the following Scheme. The starting material [118990-99-1] is converted to the thiol intermediate using previously described (Faming Zhuanli Shenging, 108623617, 9 Oct. 2018) conditions for a related system. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiol carbapenem intermediate to give the thioacetal linked intermediate. Removal of the allyl protecting groups gives the product.

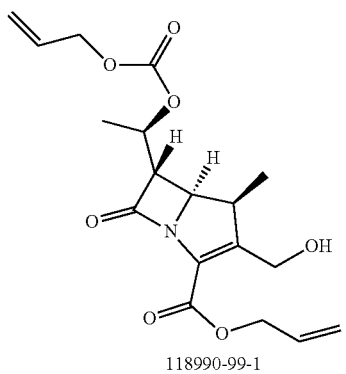
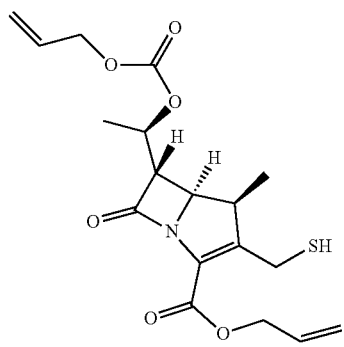
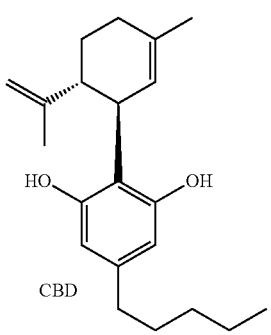
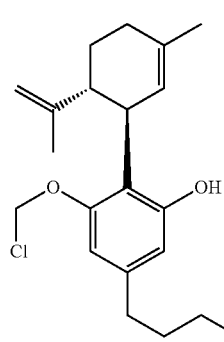
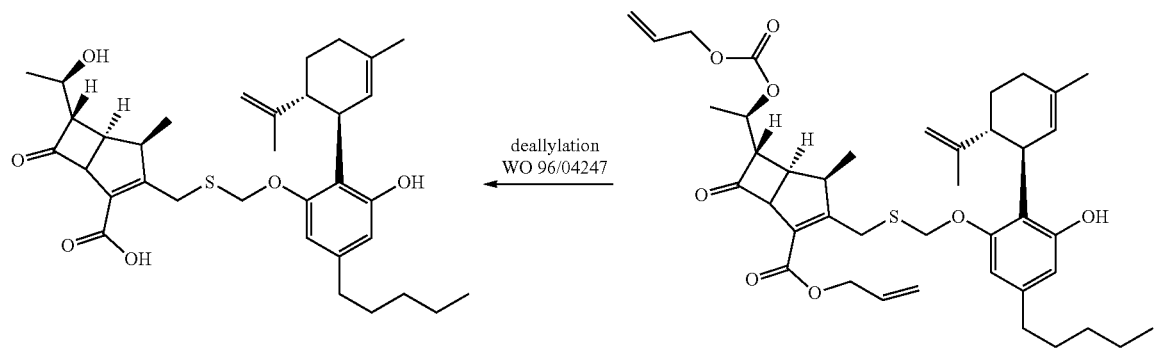

Example 17. Monobactam Ether-Linked β-Lactam Antibiotic Cannabinoid Conjugate Components Monobactam ether linked β-lactam antibiotic cannabinoid conjugate components are synthesized according to the following Scheme. The starting material [76855-69-1] is reacted under reported conditions (Journal of Organic Chemistry, 55(2), 434-7; 1990) for phenolic compounds to form the ether link. Removal of the silyl ether protecting group under standard conditions followed by sulfonation using established conditions gives the product.

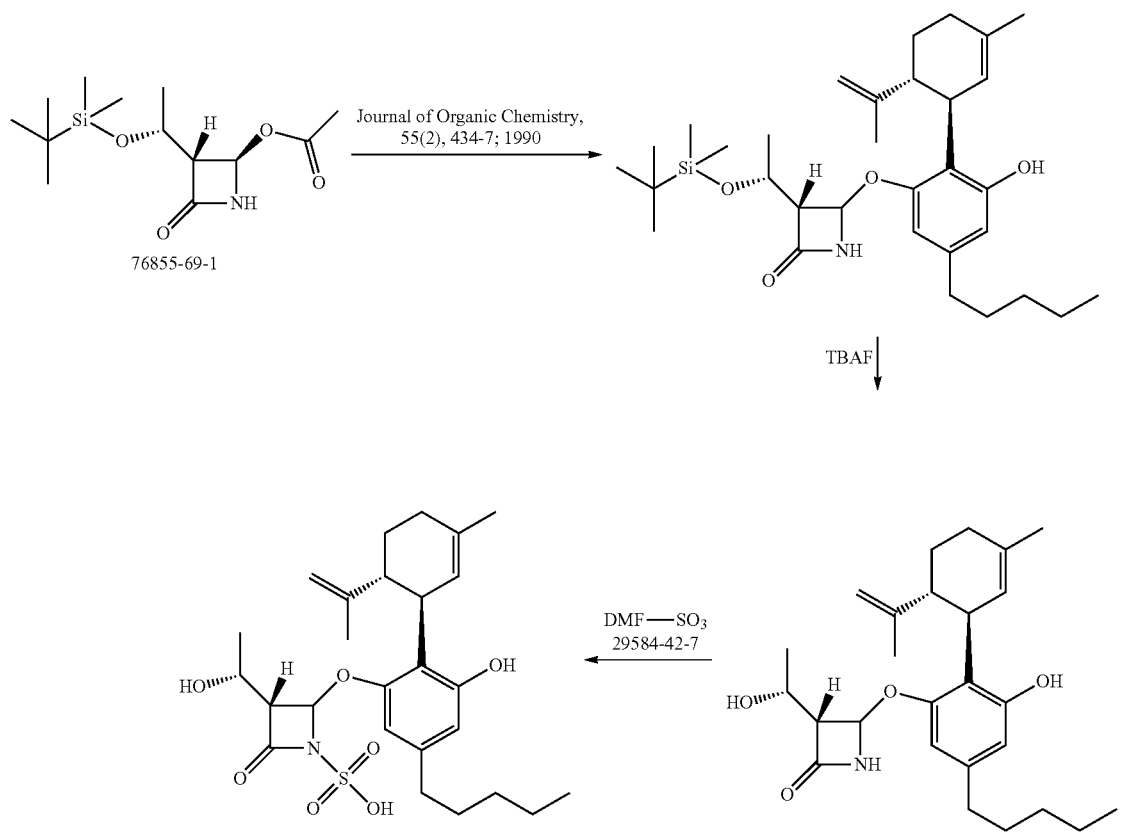

Example 18. Monobactam Acetal-Linked β-Lactam Antibiotic Cannabinoid Conjugate Components Monobactam acetal linked β-lactam antibiotic cannabinoid conjugate components are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then alkylated with the O-chloromethyl cannabinoid which is prepared as described in the cephem acetal example in this Application to form the acetal link. Removal of the silyl ether protecting group followed by sulfonation using established conditions gives the product.

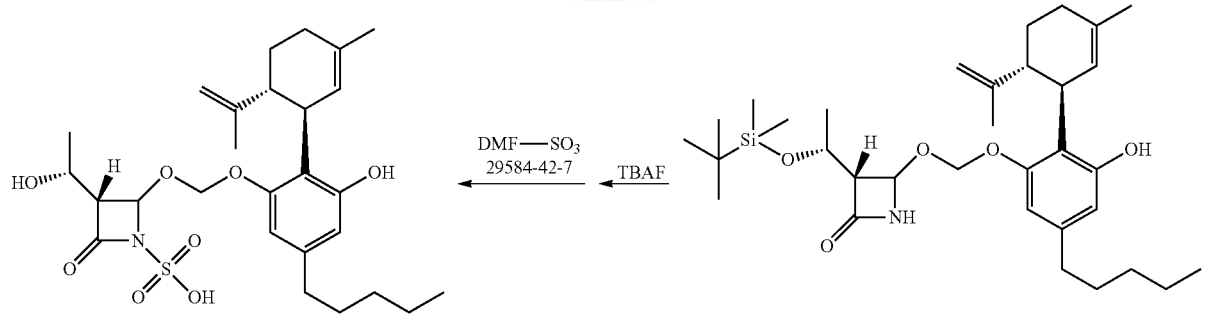

Example 19. Monobactam Carbonate-Linked β-Lactam Antibiotic Cannabinoid Conjugate Components Monobactam carbonate linked β-lactam antibiotic cannabinoid conjugate components are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then reacted with phosgene and a cannabinoid (CBD) under standard basic conditions to form the carbonate link. Removal of the silyl ether protecting group followed by sulfonation using established conditions gives the product.

Example 20. Monobactam Thiocarbonate-Linked β-Lactam Antibiotic Cannabinoid Conjugate Components Monobactam thiocarbonate linked β-lactam antibiotic cannabinoid conjugate components are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then reacted with thiophosgene and a cannabinoid (CBD) under standard basic conditions to form the carbonate link. Removal of the silyl ether protecting group followed by sulfonation using established conditions gives the

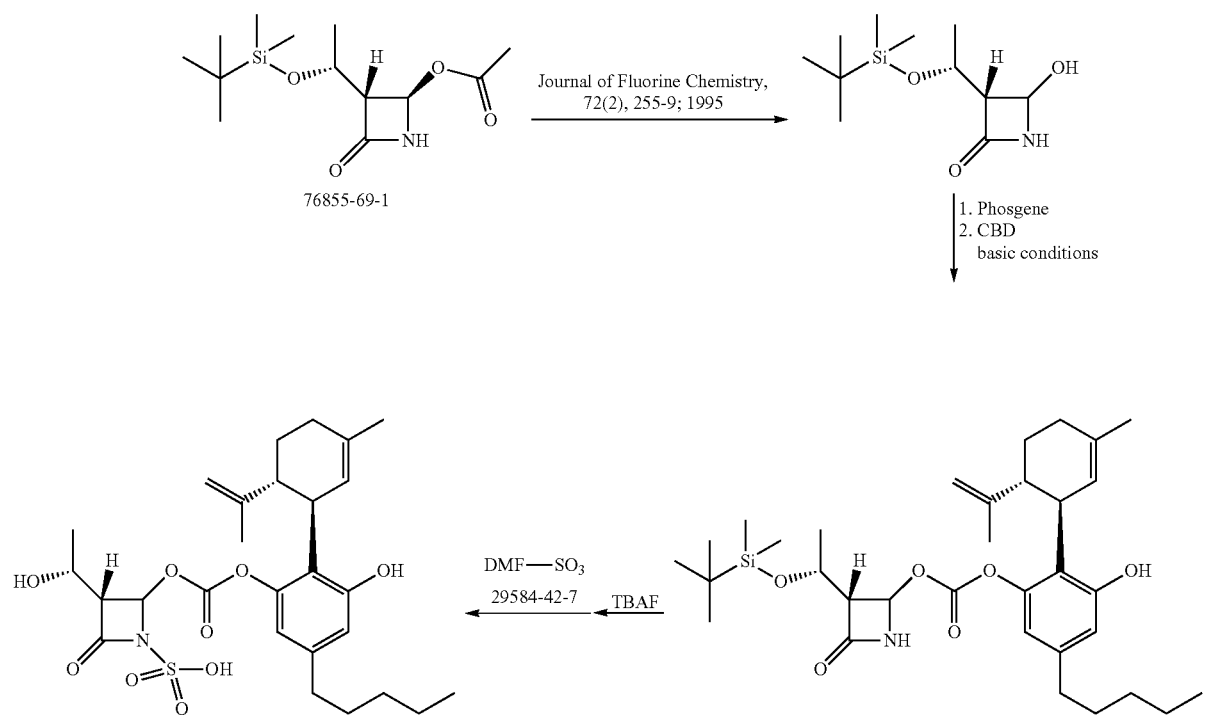

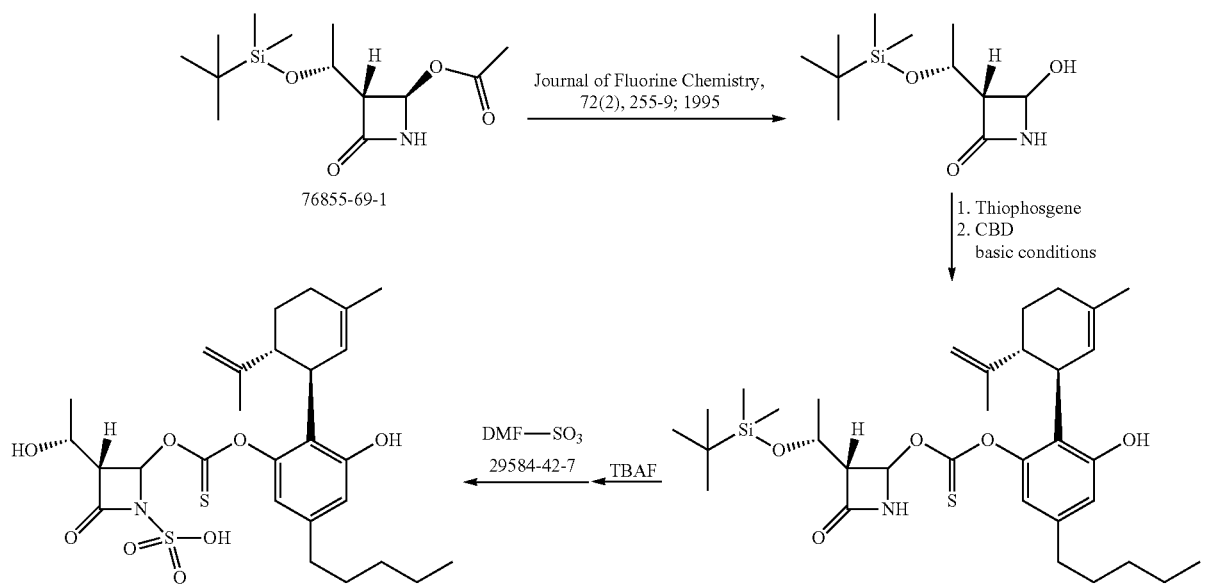

Example 21. Monobactam Imidate-Linked β-Lactam Antibiotic Cannabinoid Conjugate Components Monobactam imidate linked β-lactam antibiotic cannabinoid conjugate components are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then reacted with methyl imidocarbonyl chloride [5652-90-4] and a cannabinoid (CBD) under reported conditions (Tetrahedron Letters, 23(35), 3539-42; 1982) to form the imidate link. Removal of the silyl ether protecting group followed by sulfonation using established conditions gives the product.

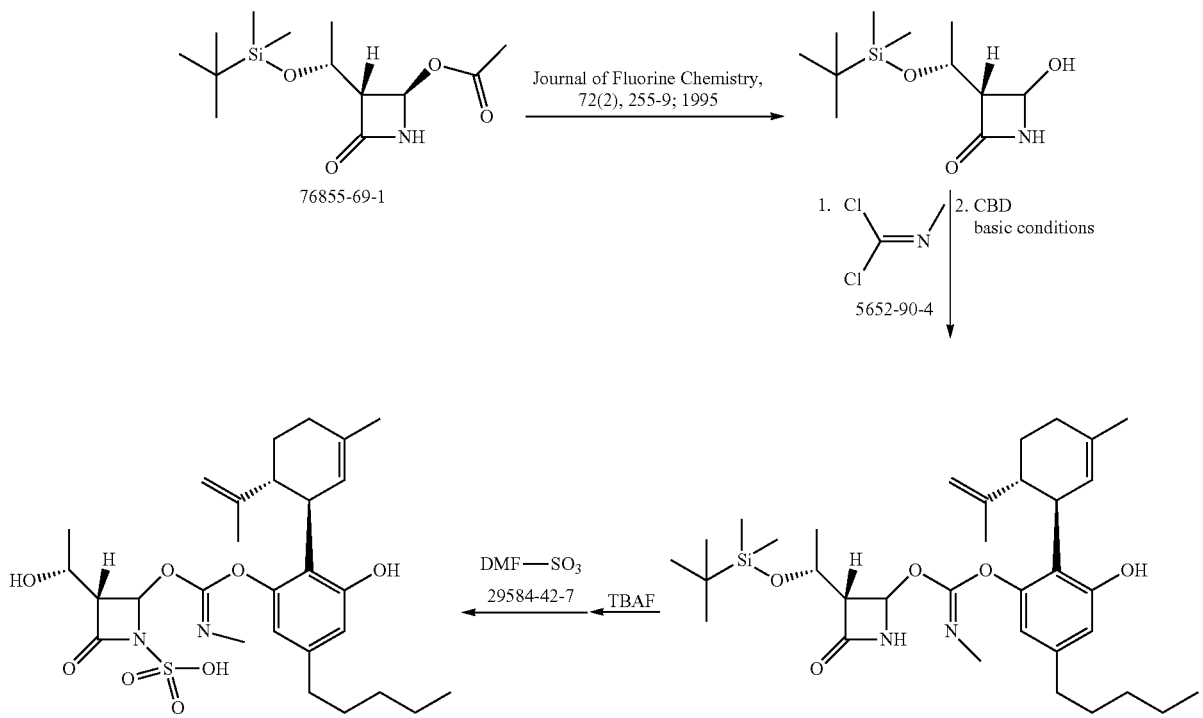

Example 22. Monobactam Aminal-Linked β-Lactam Antibiotic Cannabinoid Conjugate Components Monobactam aminal linked β-lactam antibiotic cannabinoid conjugate components are synthesized according to the following Scheme. The starting material [76855-69-1] is converted to the corresponding amine under reported conditions (Organic Chemistry: An Indian Journal, 9(6), 229-235; 2013) to give the 2-amino intermediate. This amino group is then alkylated with the O-chloromethyl cannabinoid which is prepared as described in the cephem acetal example in this Application to form the acetal link. Removal of the silyl ether protecting group followed by sulfonation using established conditions gives the product.

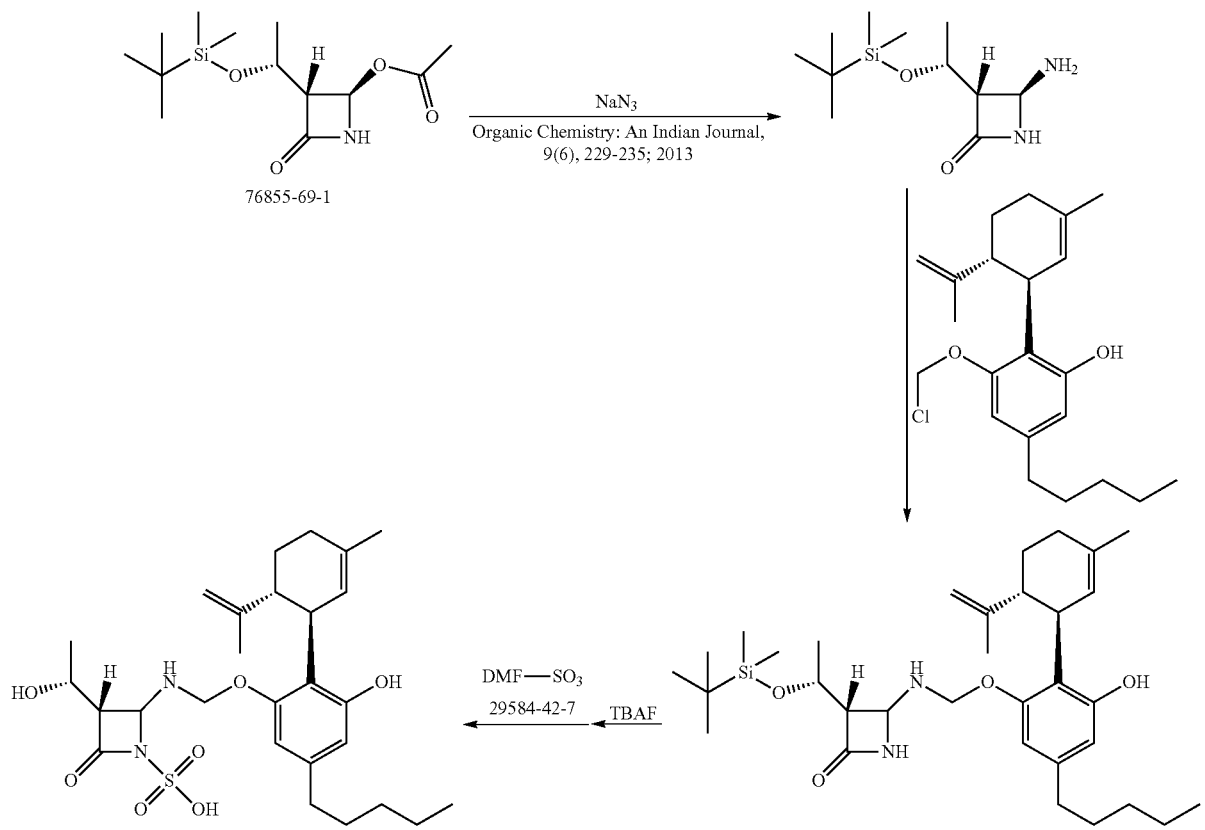

Example 23. Monobactam Carbamate-Linked β-Lactam Antibiotic Cannabinoid Conjugate Components Monobactam carbamate linked β-lactam antibiotic cannabinoid conjugate components are synthesized according to the following Scheme. The starting material [76855-69-1] is converted to the corresponding amine under reported conditions (Organic Chemistry: An Indian Journal, 9(6), 229-235; 2013) to give the 2-amino intermediate. This amino group is then reacted with phosgene and a cannabinoid (CBD) under standard basic conditions to form the carbamate link. Removal of the silyl ether protecting group followed by sulfonation using established conditions gives the product.

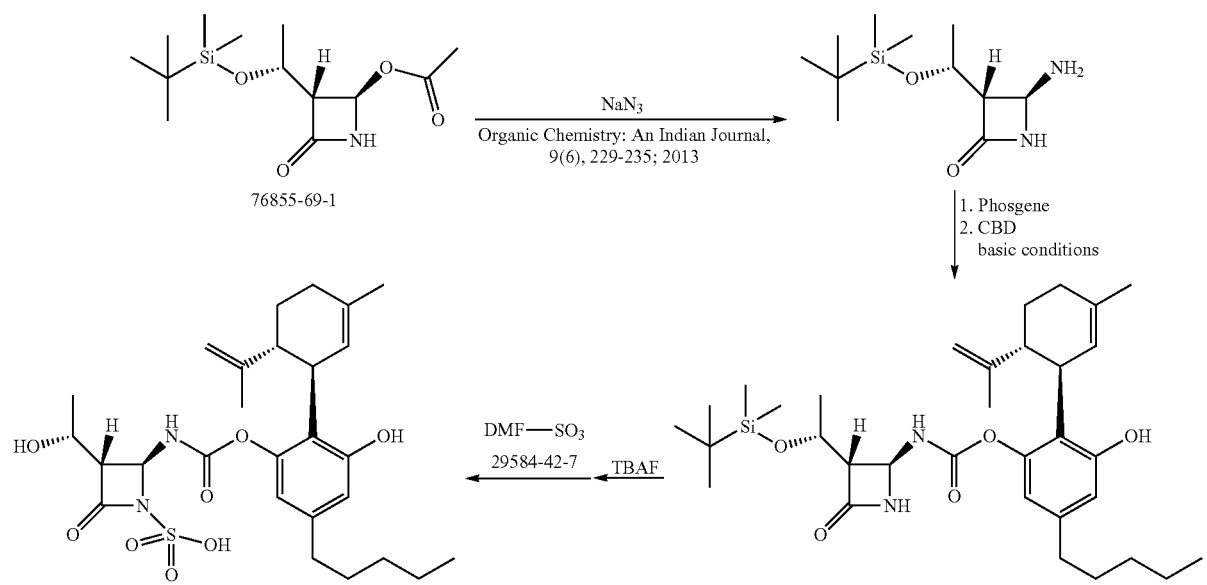

Example 24. Monobactam Thiocarbamate-Linked β-Lactam Antibiotic Cannabinoid Conjugate Components Monobactam thiocarbamate linked β-lactam antibiotic cannabinoid conjugate components are synthesized according to the following Scheme. The starting material [76855-69-1] is converted to the corresponding amine under reported conditions (Organic Chemistry: An Indian Journal, 9(6), 229-235; 2013) to give the 2-amino intermediate. This amino group is then reacted with thiophosgene and a cannabinoid (CBD) under standard basic conditions to form the thiocarbamate link. Removal of the silyl ether protecting group followed by sulfonation using established conditions gives the product.

Example 25. Monobactam Isourea-Linked β-Lactam Antibiotic Cannabinoid Conjugate Components Monobactam isourea linked β-lactam antibiotic cannabinoid conjugate components are synthesized according to the following Scheme. The starting material [76855-69-1] is converted to the corresponding amine under reported conditions (Organic Chemistry: An Indian Journal, 9(6), 229-235; 2013) to give the 4-amino intermediate. This amino group is then reacted with methyl imidocarbonyl chloride [5652-90-4] and a cannabinoid (CBD) under reported conditions (Tetrahedron Letters, 23(35), 3539-42; 1982) to form the isourea link. Removal of the silyl ether protecting group followed by sulfonation using established conditions gives the product.

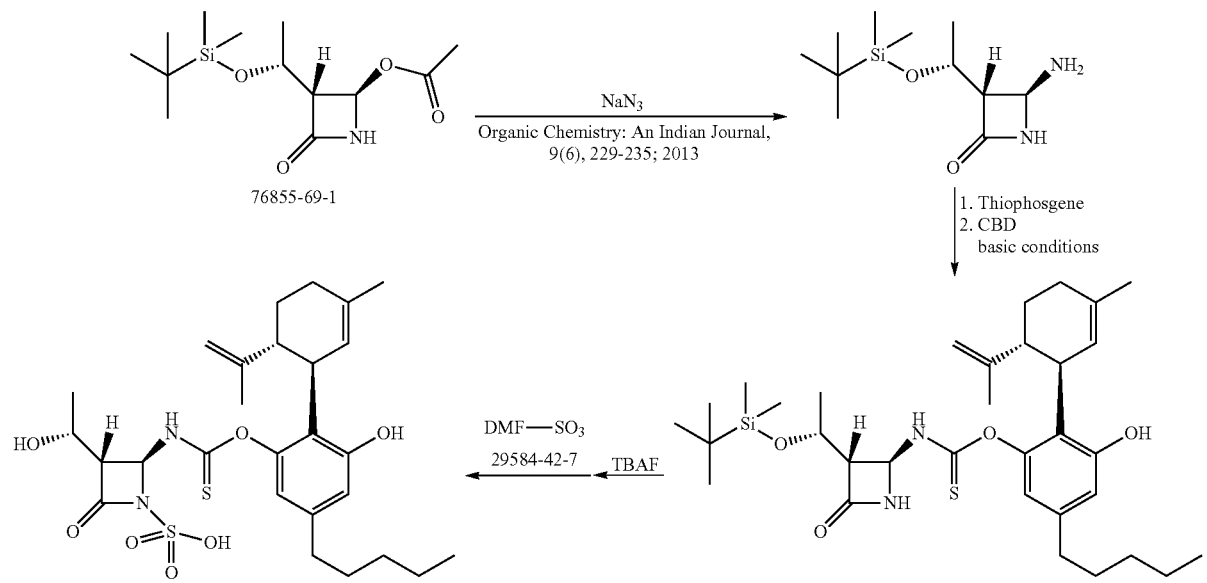

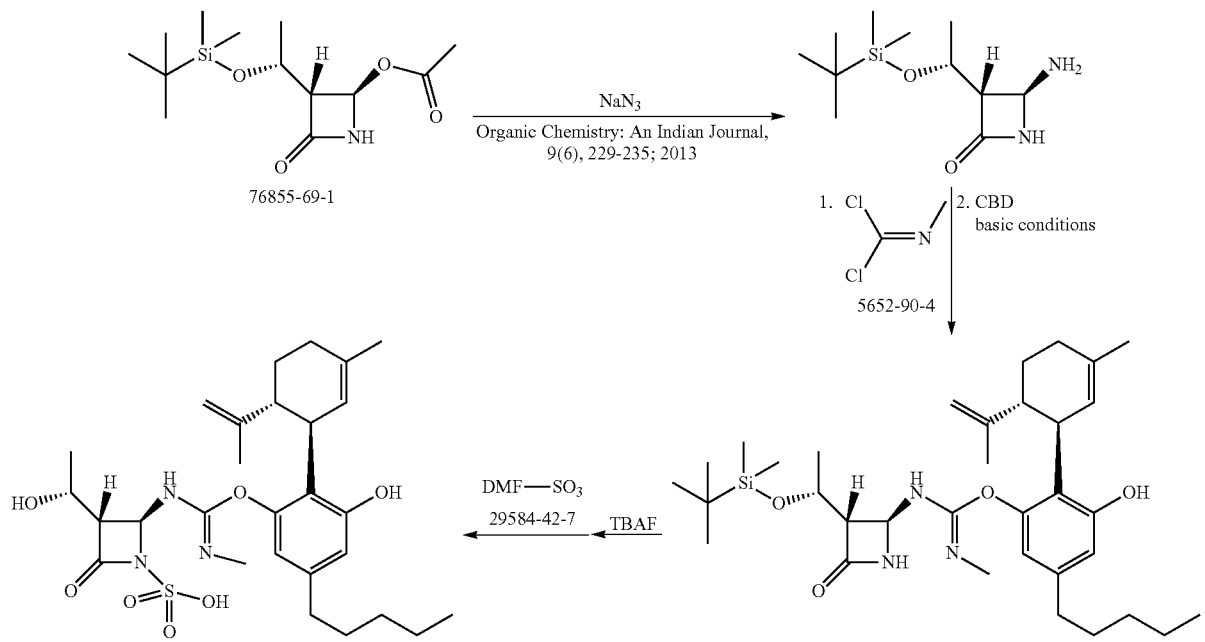

Example 26. Monobactam Thioacetal-Linked β-Lactam Antibiotic Cannabinoid Conjugate Components Monobactam thioacetal linked β-lactam antibiotic cannabinoid conjugate components are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then alkylated with the O-chloromethyl cannabinoid which is prepared as described in the cephem acetal example in this Application to form the thioacetal link. Removal of the silyl ether protecting group followed by sulfonation using established conditions gives the product.

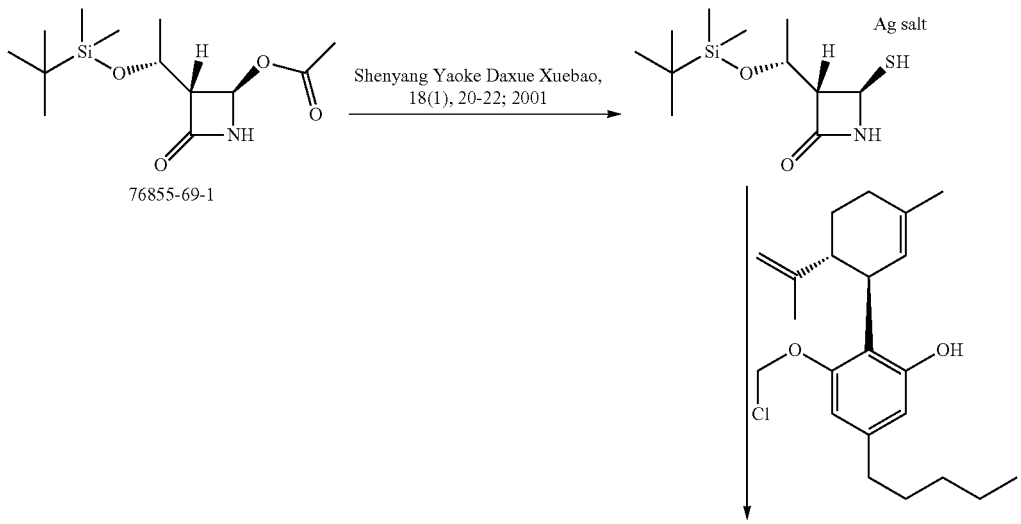

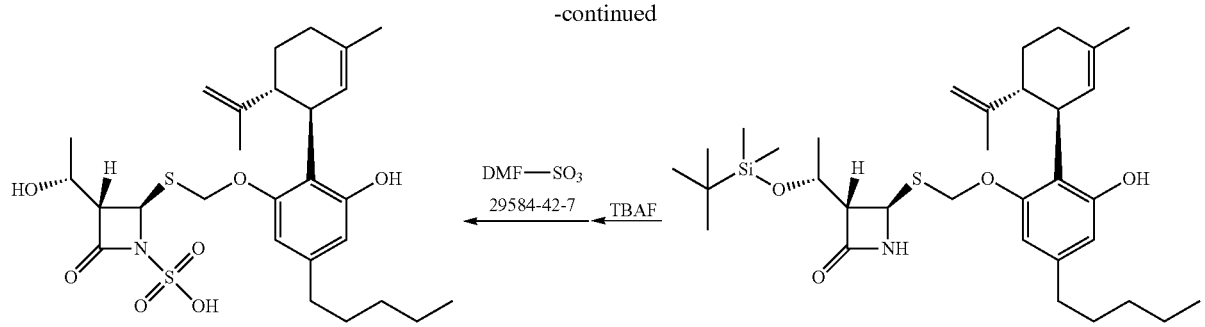

Example 27. Monobactam S-Alkyl Thiocarbonate-Linked β-Lactam Antibiotic Cannabinoid Conjugate Components Monobactam S-alkyl thiocarbonate linked β-lactam antibiotic cannabinoid conjugate components are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then reacted with phosgene and a cannabinoid (CBD) under standard basic conditions to form the S-alkyl thiocarbonate link. Removal of the silyl ether protecting group followed by sulfonation using established conditions gives the product.

Example 28. Monobactam Xanthate-Linked β-Lactam Antibiotic Cannabinoid Conjugate Components Monobactam xanthate linked β-lactam antibiotic cannabinoid conjugate components are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then reacted with thiophosgene and a cannabinoid (CBD) under standard basic conditions to form the xanthate link. Removal of the silyl ether protecting group followed by sulfonation using established conditions gives the product.

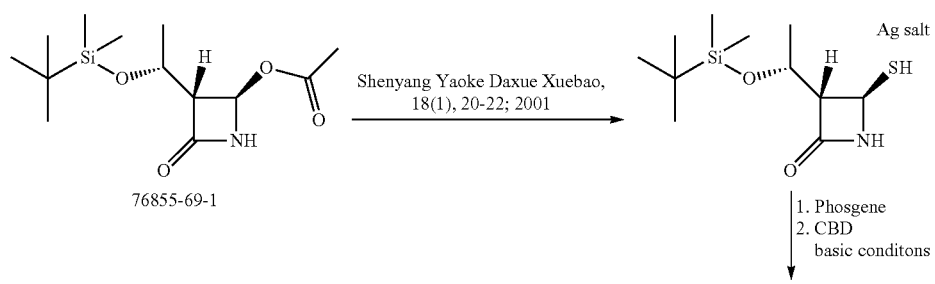

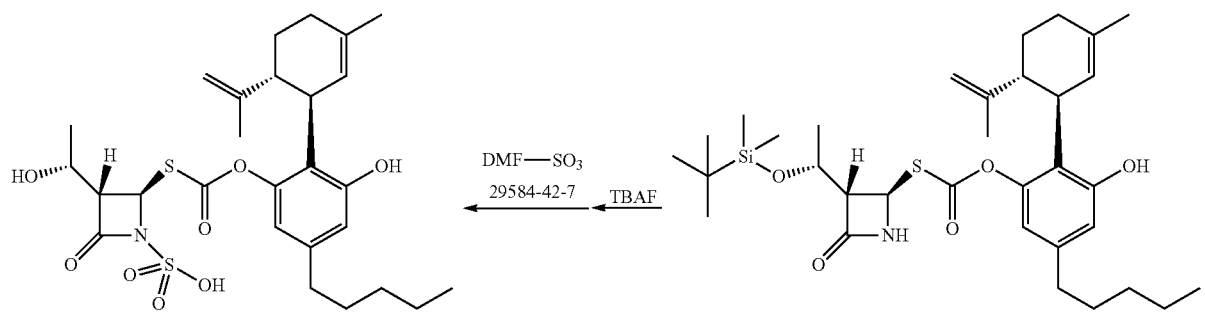

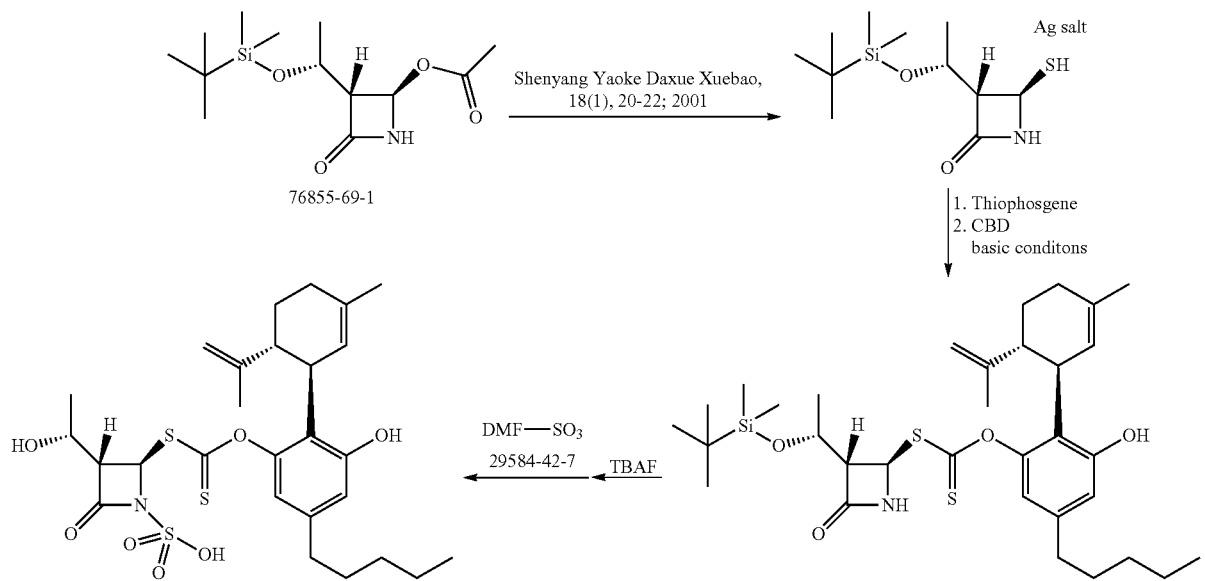

Example 29. Monobactam Thioimidate-Linked β-Lactam Antibiotic Cannabinoid Conjugate Components Monobactam thioimidate linked β-lactam antibiotic cannabinoid conjugate components are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then reacted with methyl imidocarbonyl chloride [5652-90-4] and a cannabinoid (CBD) under reported conditions (Tetrahedron Letters, 23(35), 3539-42; 1982) to form the thioimidate link. Removal of the silyl ether protecting group followed by sulfonation using established conditions gives the product.

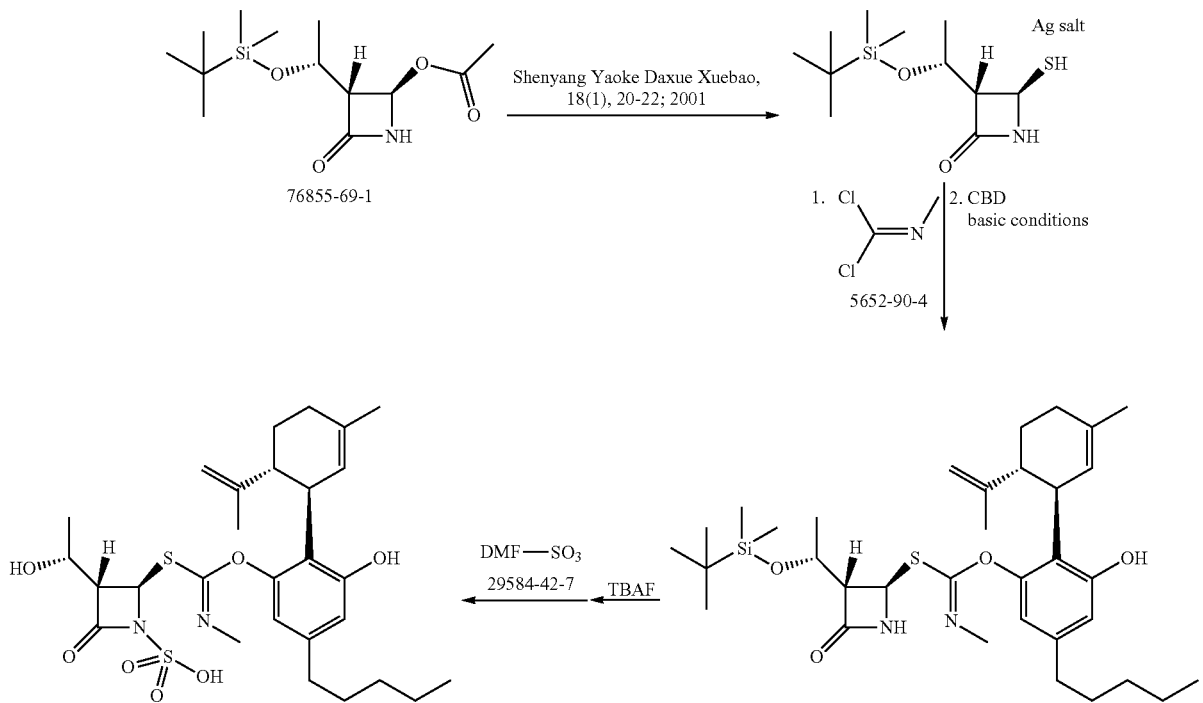

Example 30. Monobactam Alkenyl Ester-Linked β-Lactam Antibiotic Cannabinoid Conjugate Components Monobactam alkenyl ester linked β-lactam antibiotic cannabinoid conjugate components are synthesized according to the following Scheme. The starting material [592528-28-4] is esterified with a cannabinoid (CBD) under standard conditions. Removal of the silyl ether protecting group followed by sulfonation using established conditions gives the product.

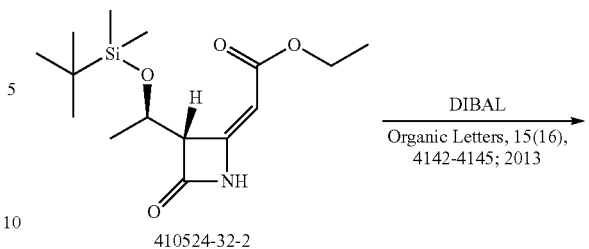

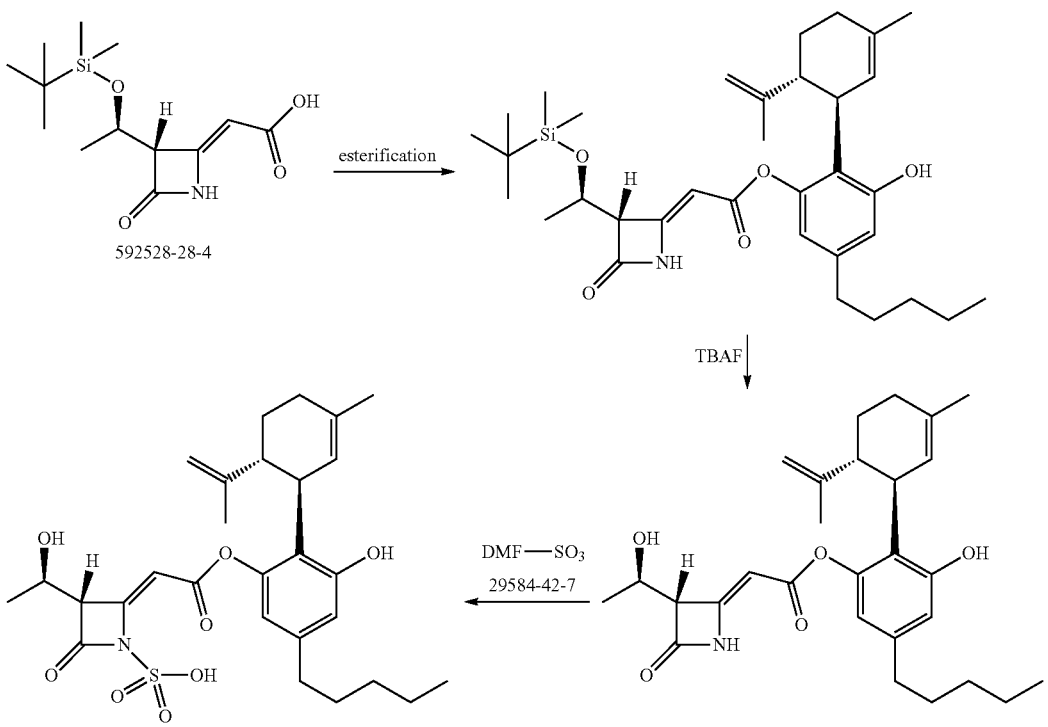

Example 31. Monobactam Alkenyl Ether-, Alkenyl Acetal-, Alkenyl Carbonate-, Alkenyl Thiocarbonate-, and Alkenyl Imidate-Linked β-Lactam Antibiotic Cannabinoid Conjugate Components Monobactam alkenyl ether, alkenyl acetal, alkenyl carbonate, alkenyl thiocarbonate, and alkenyl imidate linked β-lactam antibiotic cannabinoid conjugate components are synthesized as shown in the Scheme below. The starting material [410524-32-2] is reduced to the alcohol intermediate using previously reported conditions (Organic Letters, 15(16), 4142-4145; 2013). This alcohol is reacted and connected to a cannabinoid by any of the aforementioned links, using the previously described chemistry and conditions associated with the non-alkenyl variant.

-continued

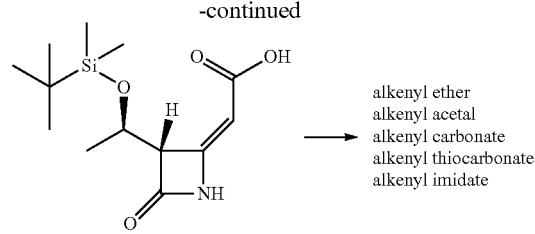

alkenyl ether
alkenyl acetal
→ alkenyl carbonate
alkenyl thiocarbonate
alkenyl imidate

Example 32. Monobactam Alkenyl Aminal-, Alkenyl Carbamate-, Alkenyl Thiocarbamate-, and Alkenyl Isourea-Linked β-Lactam Antibiotic Cannabinoid Conjugate Components Monobactam alkenyl aminal, alkenyl carbamate, alkenyl thiocarbamate, and alkenyl isourea linked β-lactam antibiotic cannabinoid conjugate components are synthesized as shown in the Scheme below. The starting material [410524-32-2] is reduced to the alcohol intermediate. This alcohol is then converted to the iodide using known (Tetrahedron, 73(29), 4150-4159; 2017) conditions. The iodide intermediate is converted to the primary amine using the two step azide addition/reduction protocol described above for synthesis of propenylamine cephem β-lactam antibiotic cannabinoid conjugate components. This amine is then reacted and connected to a cannabinoid by any of the aforementioned links, using the previously described chemistry and conditions associated with the non-alkenyl variant.

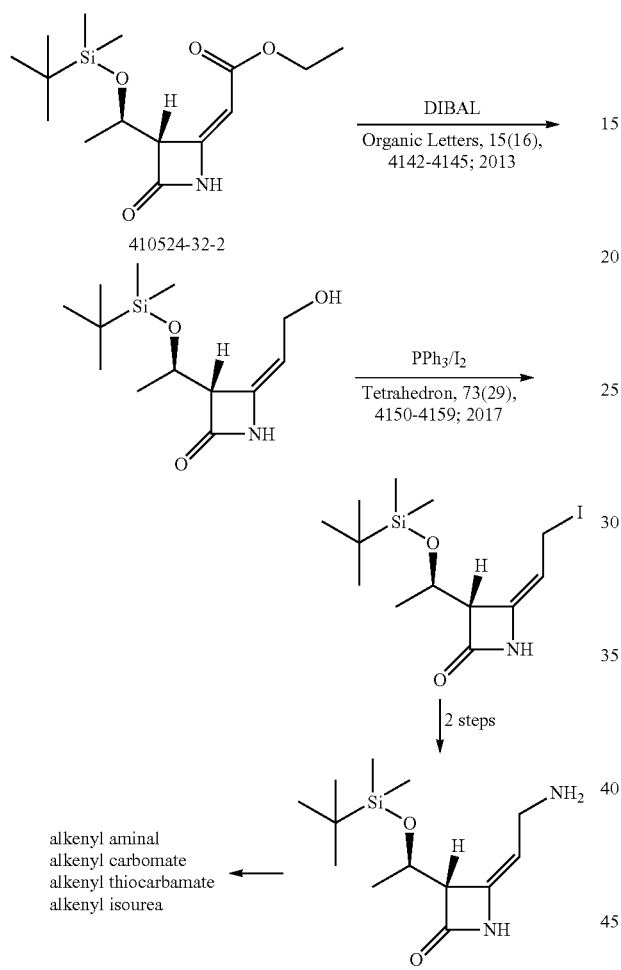

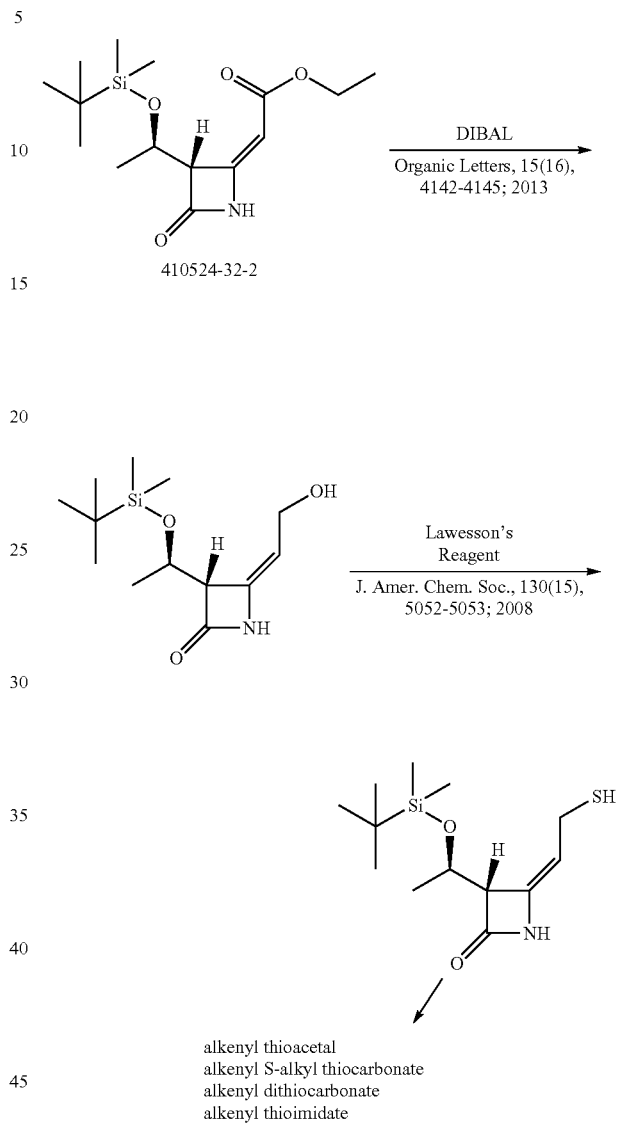

of the aforementioned links, using the previously described chemistry and conditions associated with the non-alkenyl variant.

Example 33. Monobactam Alkenyl Thioacetal-, Alkenyl S-Alkyl Thiocarbonate-, Alkenyl Dithiocarbonate-, and Alkenyl Thioimidate-Linked β-Lactam Antibiotic Cannabinoid Conjugate Components Monobactam alkenyl thioacetal, alkenyl S-alkyl thiocarbonate, alkenyl dithiocarbonate, and alkenyl thioimidate linked β-lactam antibiotic cannabinoid conjugate components are synthesized as shown in the Scheme below. The starting material [410524-32-2] is reduced to the alcohol intermediate using previously reported conditions (Organic Letters, 15(16), 4142-4145; 2013). This alcohol is reacted with Lawesson's reagent under reported conditions (Journal of the American Chemical Society, 130(15), 5052-5053; 2008) to give the corresponding thiol intermediate. This thiol is then reacted and connected to a cannabinoid by any

EXAMPLES: TYPE (IA) CANNABINOID CONJUGATE COMPONENTS

Example 34. Hydroxyurea Aminal-Linked Type (IA) Cannabinoid Conjugate Components Hydroxyurea aminal linked cannabinoid conjugate components are synthesized as follows. A cannabinoid (CBD in this example) is converted to its chloromethyl derivative using previously described conditions (see Scheme below). The chloromethyl group is converted to the corresponding aminomethyl intermediate using standard transformations, in this case by way of the azide. The aminomethyl group is converted to the isocyanate intermediate using the referenced conditions (see Scheme). Reaction of the isocyanate with hydroxylamine gives the desired product.

261

262
-continued

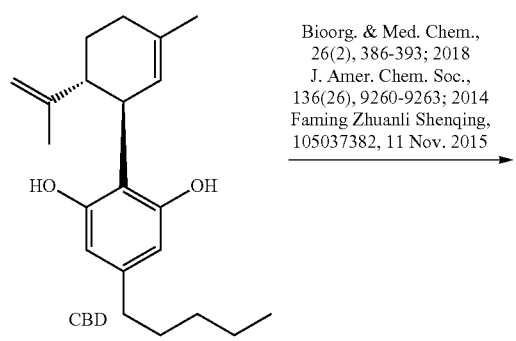
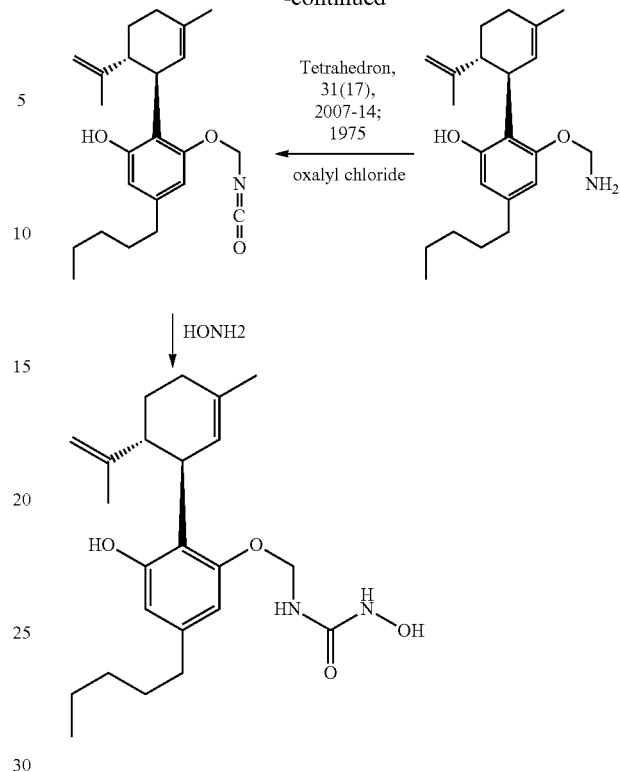

Hydroxyurea carbamate linked cannabinoid conjugate components are synthesized as follows. A cannabinoid (CBD in this example) is reacted with phosgene (or a suitable surrogate) and the adduct is converted to the carbamate intermediate using the referenced conditions (see Scheme). Conversion to the isocyanate (referenced conditions) followed by reaction with hydroxylamine gives the desired product.

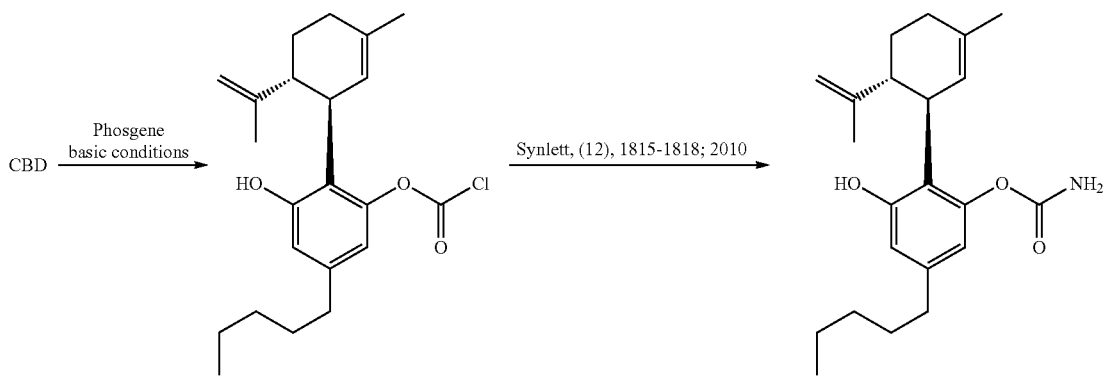

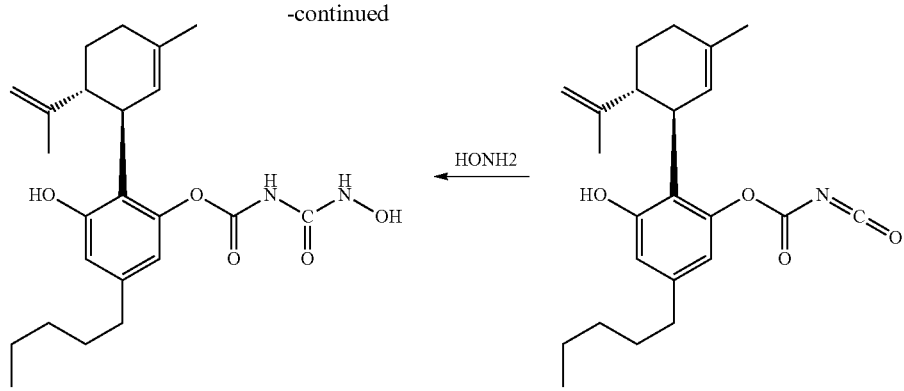

Hydroxyurea thiocarbamate linked cannabinoid conjugate components are synthesized as follows. A cannabinoid (CBD in this example) is reacted with thiophosgene (or a suitable surrogate) and the adduct is converted to the thiocarbamate intermediate using the referenced conditions (see Scheme). Conversion to the isocyanate (referenced conditions) followed by reaction with hydroxylamine gives the desired product.

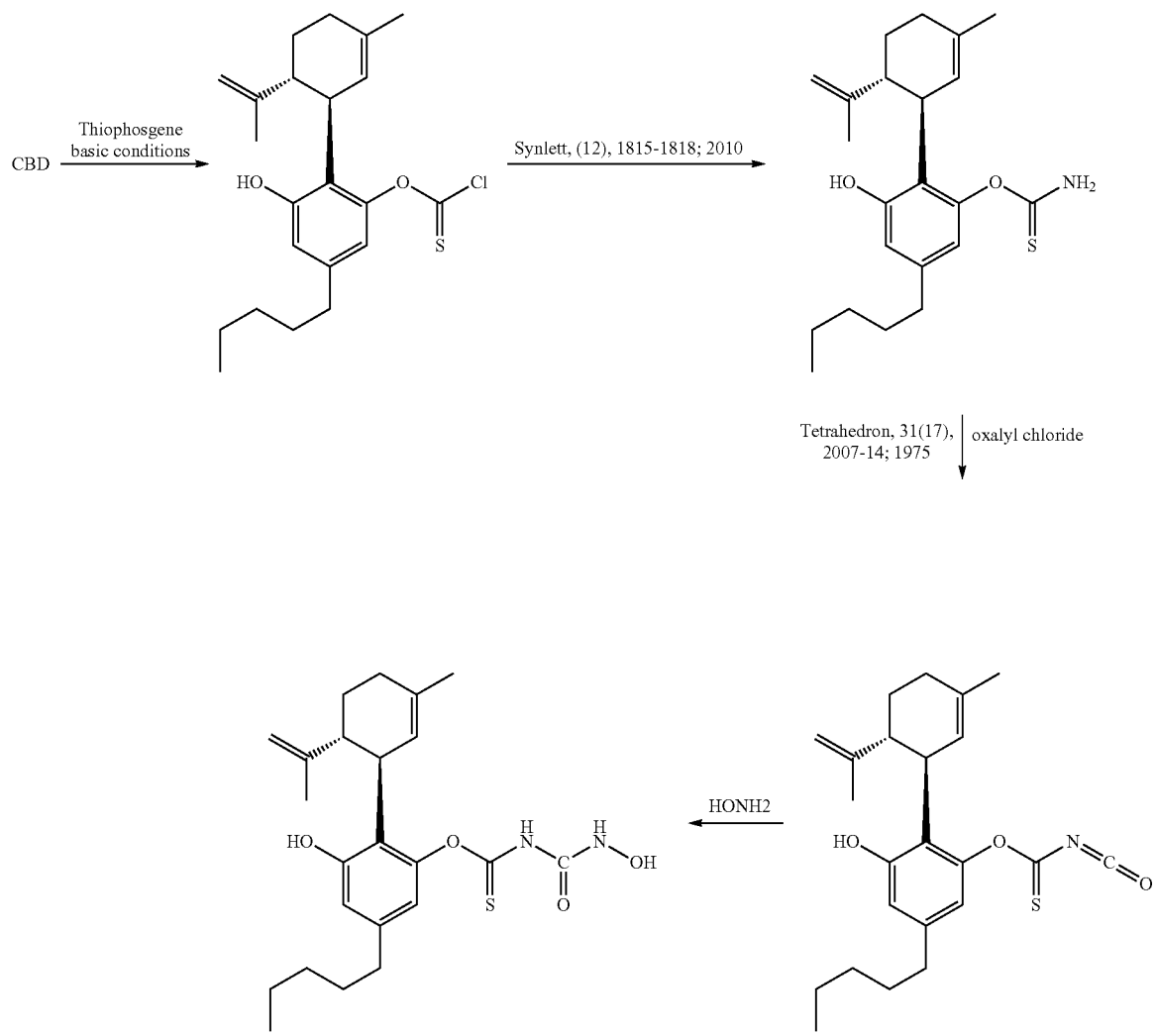

Example 35. Cannabinoid Conjugate Components Comprising a Michael Acceptor

Michael Acceptor amide cannabinoid conjugate components are synthesized as follows. A cannabinoid (CBD in this example) is reacted with an alkynyl ester, in this case [623-47-2] under reported conditions (see Scheme) to give the unsaturated acid intermediate. Reaction with an amine, in this case diethylamine, under standard amide bond forming conditions gives the desired product.

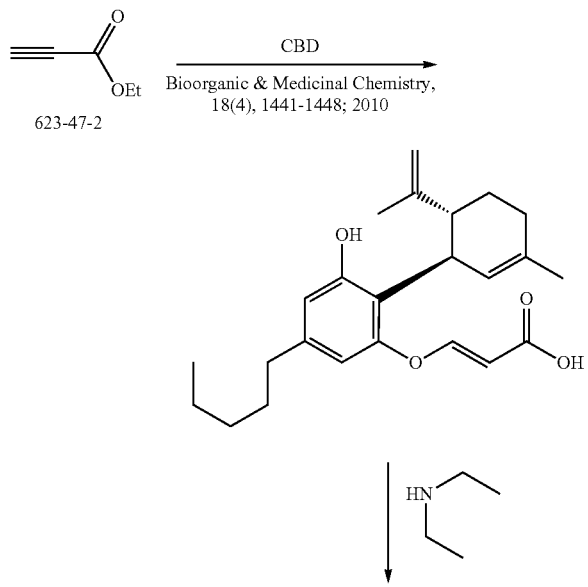

Michael Acceptor ester cannabinoid conjugate components are synthesized as follows. A cannabinoid (CBD in this example) is reacted with an alkynyl ester, in this case [623-47-2] under reported conditions (see Scheme) to give the desired product.

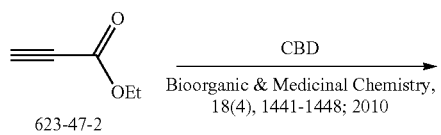

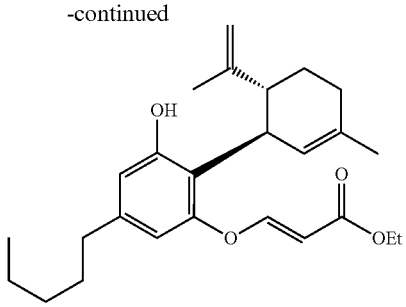

Michael Acceptor nitrile cannabinoid conjugate components are synthesized using the following referenced conditions.

To make E-isomers

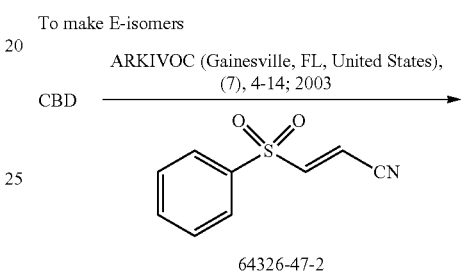

To make Z-isomers

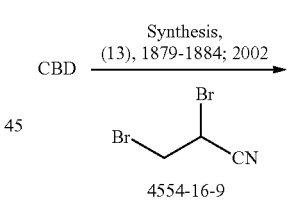

Michael Acceptor amide cannabinoid conjugate components containing a neratinib component are synthesized as follows. A cannabinoid (CBD in this example) is reacted with an alkynyl ester, in this case [623-47-2] under reported conditions (see Scheme) to give the unsaturated acid intermediate. Reaction with an amine, in this case [848139-78-6], under standard amide bond forming conditions gives the desired product.

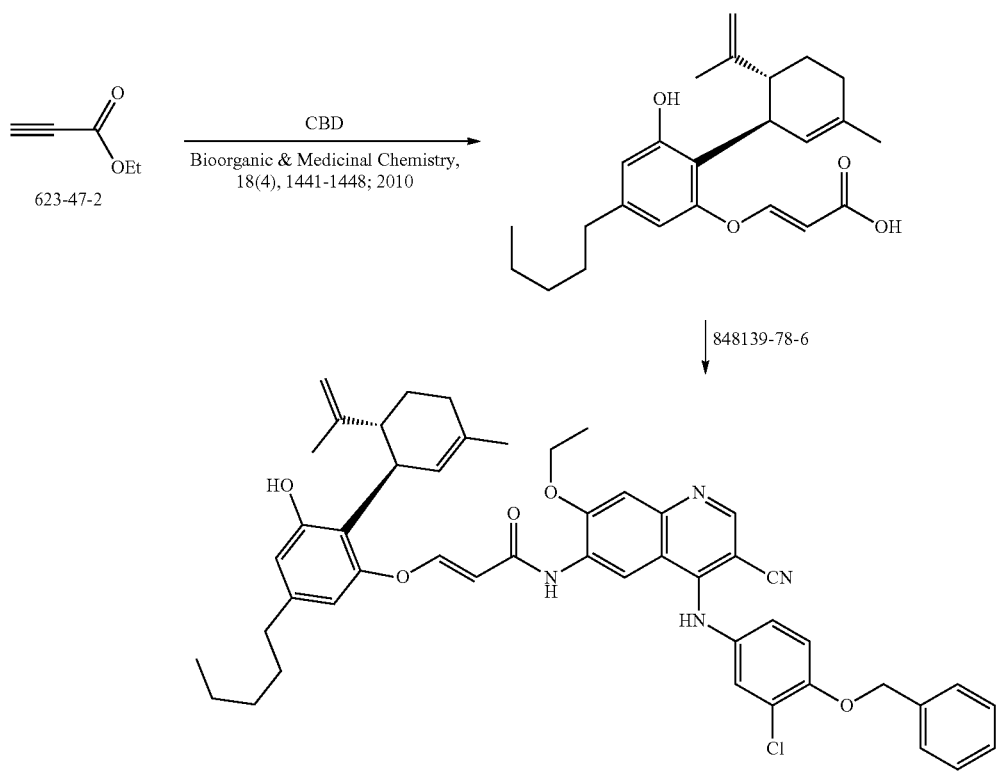

Michael Acceptor amide cannabinoid conjugate components containing a dacomitinib component are synthesized as follows. A cannabinoid (CBD in this example) is reacted with an alkynyl ester, in this case [623-47-2] under reported conditions (see Scheme) to give the unsaturated acid intermediate. Reaction with an amine, in this case [179552-75-1], under standard amide bond forming conditions gives the desired product.

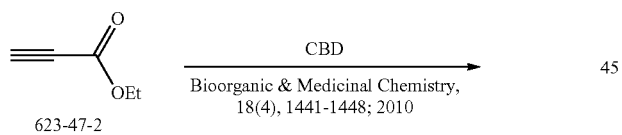

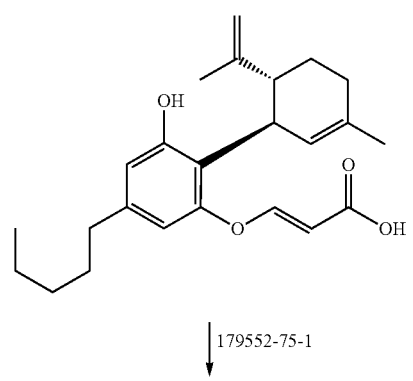

-continued

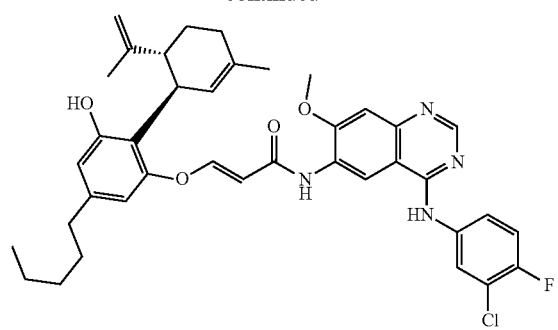

Michael Acceptor amide cannabinoid conjugate components containing an osimertinib component are synthesized as follows. A cannabinoid (CBD in this example) is reacted with an alkynyl ester, in this case [623-47-2] under reported conditions (see Scheme) to give the unsaturated acid intermediate. Reaction with an amine, in this case [1421372-66-8], under standard amide bond forming conditions gives the desired product.

269
-continued

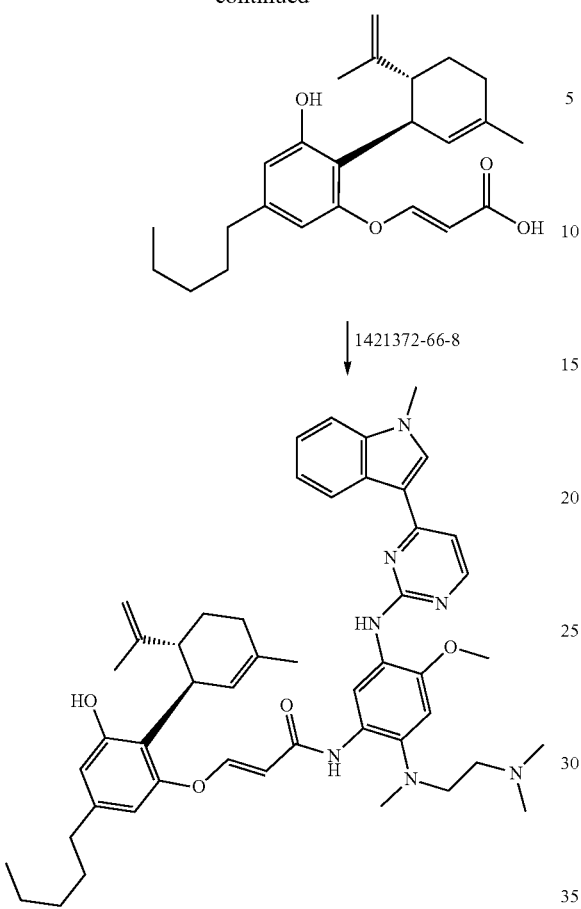

270
-continued

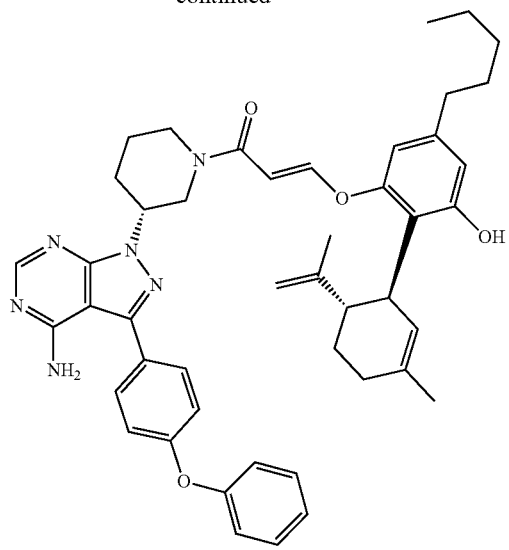

Michael Acceptor amide cannabinoid conjugate components containing an afatinib component are synthesized as follows. A cannabinoid (CBD in this example) is reacted with an alkynyl ester, in this case [623-47-2] under reported conditions (see Scheme) to give the unsaturated acid intermediate. Reaction with an amine, in this case [314771-76-1], under standard amide bond forming conditions gives the desired product.

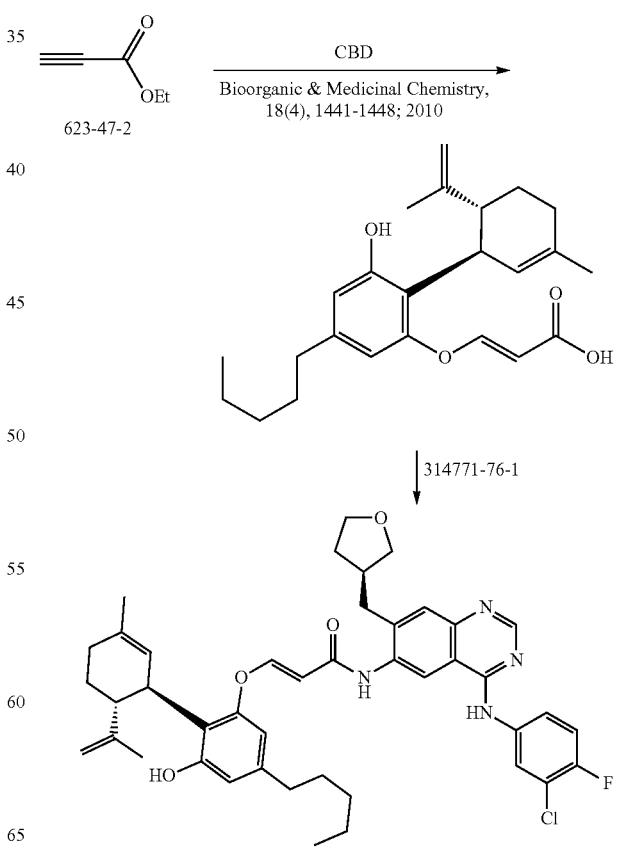

Michael Acceptor amide cannabinoid conjugate components containing an ibrutinib component are synthesized as follows. A cannabinoid (CBD in this example) is reacted with an alkynyl ester, in this case [623-47-2] under reported conditions (see Scheme) to give the unsaturated acid intermediate. Reaction with an amine, in this case [1022150-12-4], under standard amide bond forming conditions gives the desired product.

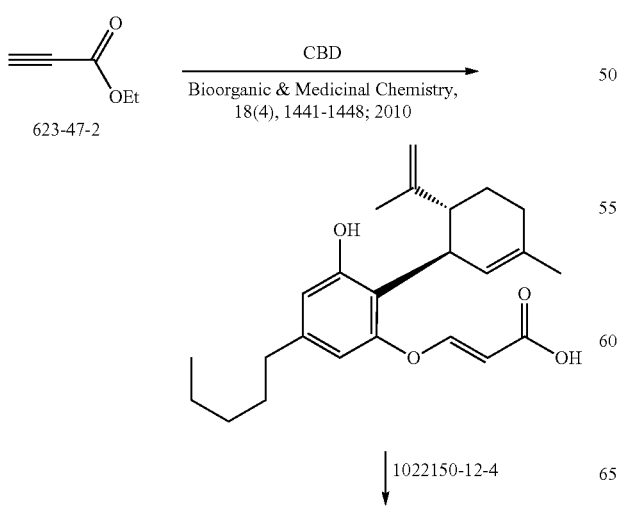

Michael Acceptor vinyl sulfone cannabinoid conjugate components are prepared from CBD and the building block [13894-21-8] using conditions similar to those referenced in the Scheme below. The double bond isomers may be separated and isolated by chromatography.

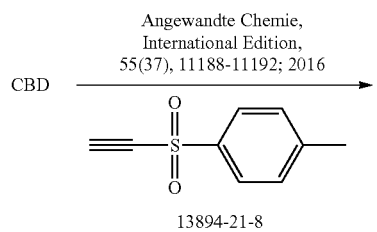

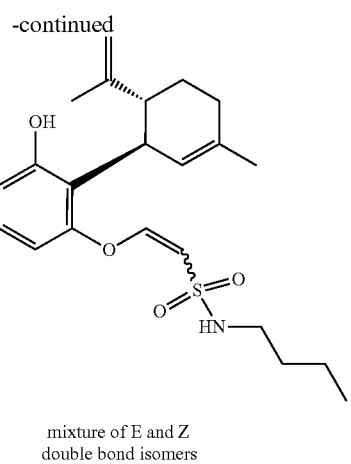

mixture of E and Z
double bond isomers

Carbamate cannabinoid type (I) conjugate components may be synthesized as shown in the scheme below, by reacting a cannabinoid (CBD) with phosgene (or a suitable surrogate) and the appropriate amine building block under standard basic conditions.

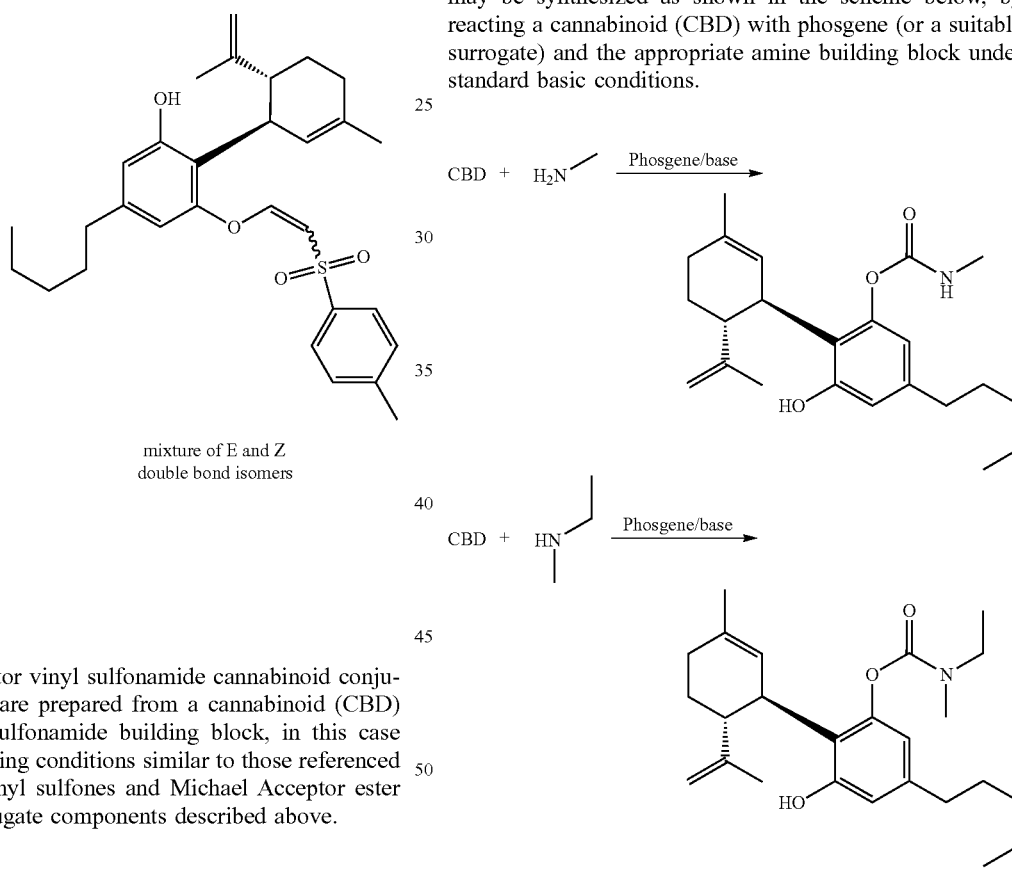

mixture of E and Z
double bond isomers

Michael Acceptor vinyl sulfonamide cannabinoid conjugate components are prepared from a cannabinoid (CBD) and an alkynyl sulfonamide building block, in this case [250583-24-5], using conditions similar to those referenced for the related vinyl sulfones and Michael Acceptor ester cannabinoid conjugate components described above.

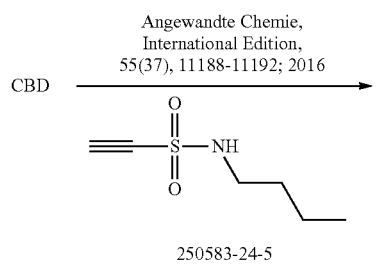

EXAMPLES: TYPE (IB) CANNABINOID CONJUGATE COMPONENTS

The following procedures for synthesizing various types and classes of type (II) cannabinoid conjugate components are general representative procedures for building in the primary functionality of the cannabinoid conjugate components. The reagent system, reaction conditions, and protecting group strategy may vary for any specific analog. Specific building blocks vary in accordance with the specific desired product. The bromide cannabinoid conjugate components may be synthesized as corresponding chloride or iodide cannabinoid conjugate components. The procedures below show cannabidiol (CBD) as a representative cannabinoid, although other cannabinoids containing hydroxyl groups may be substituted to generate alternative analogs.

Example 36. Epoxide-Containing Cannabinoid Conjugate Components

Epoxide carbamate linked cannabinoid conjugate components are synthesized as follows. A cannabinoid (CBD in this example) is reacted with phosgene (or a suitable phosgene surrogate) and an aminoepoxide ([5689-75-8] in this example) under standard basic conditions to form the desired carbamate linked product.

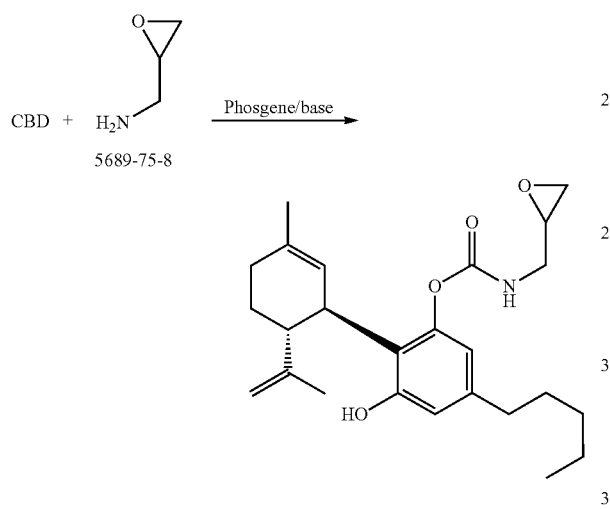

Epoxide carbonate linked cannabinoid conjugate components are synthesized as follows. A cannabinoid (CBD in this example) is reacted with phosgene (or a suitable phosgene surrogate) and a hydroxyepoxide ([556-52-5] in this example) under standard basic conditions to form the desired carbonate linked product.

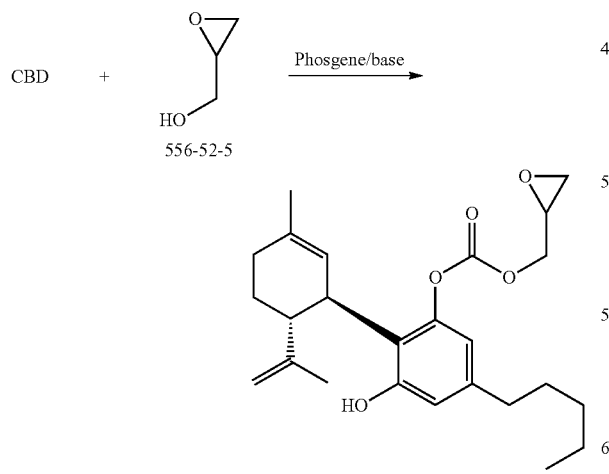

Epoxide ester linked cannabinoid conjugate components are synthesized as follows. A cannabinoid (CBD in this example) is esterified under standard conditions, in this example with the epoxy acid building block [86310-98-7] to give the desired product.

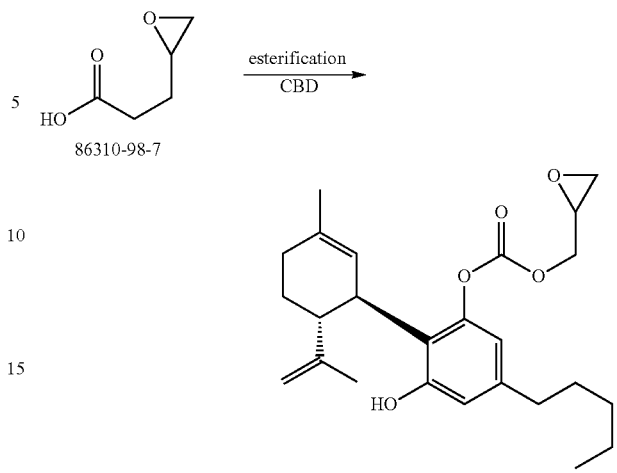

Epoxide imidate linked cannabinoid conjugate components are synthesized as follows. A cannabinoid (CBD in this example) is reacted with an imidocarbonyl chloride (in this case [5652-90-4]) and a hydroxyepoxide ([556-52-5] in this example) under standard basic conditions to form the desired imidate linked product.

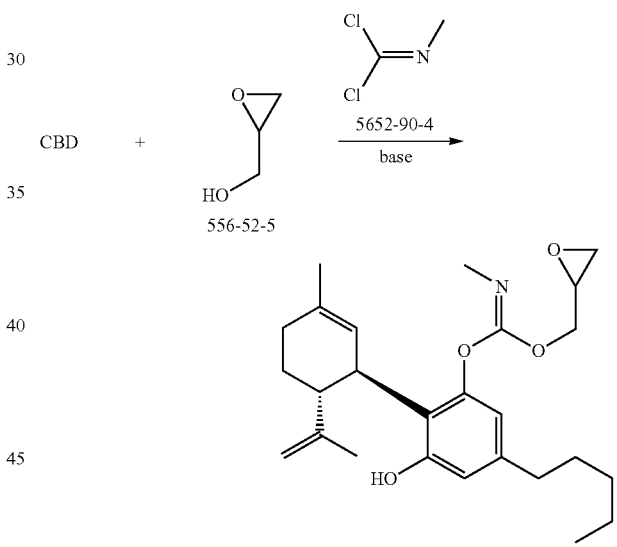

Epoxide isourea linked cannabinoid conjugate components are synthesized as follows. A cannabinoid (CBD in this example) is reacted with an imidocarbonyl chloride (in this case [5652-90-4]) and an aminoepoxide ([5689-75-8] in this example) under standard basic conditions to form the desired isourea linked product.

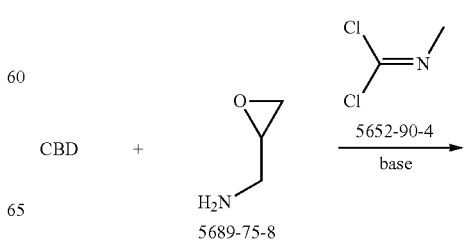

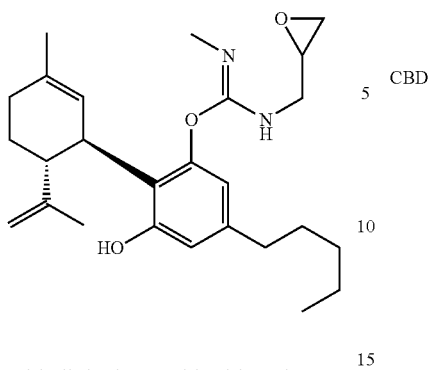

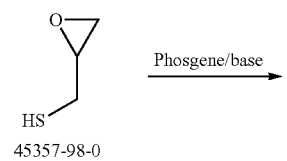

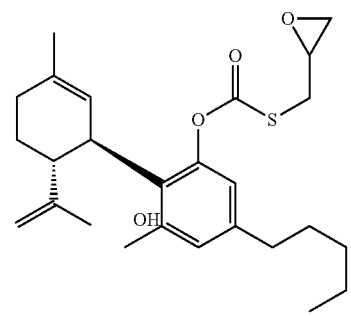

Epoxide phosphorodiamide linked cannabinoid conjugate components are synthesized as follows. Using conditions similar to those referenced in the Scheme, N,N-Dimethylphosphoramidodichloridate ([677-43-0]) is reacted with an aminoepoxide ([5689-75-8] in this example). The adduct is then reacted with a cannabinoid (CBD in this example) under standard basic conditions to form the desired product.

Epoxide thiocarbamate linked cannabinoid conjugate components are synthesized as follows. A cannabinoid (CBD in this example) is reacted with thiophosgene (or a suitable thiophosgene surrogate) and an aminoepoxide ([5689-75-8] in this example) under standard basic conditions to form the desired thiocarbamate linked product.

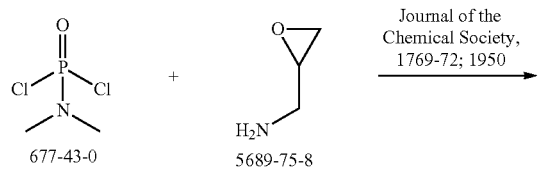

Journal of the Chemical Society, 1769-72; 1950

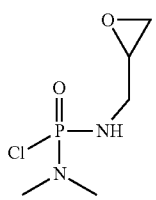

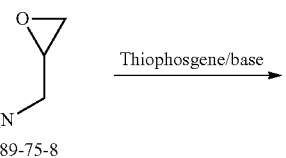

Canadian Journal of Chemistry, 64(9), 1702-8; 1986 CBD | base

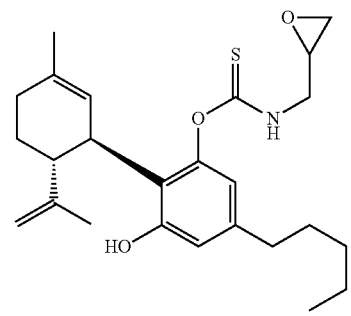

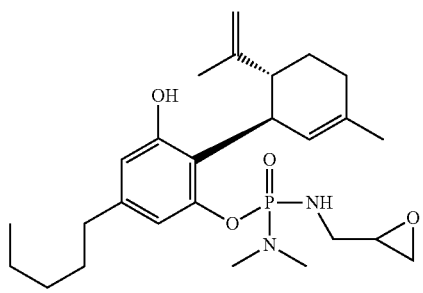

Epoxide S-alkyl thiocarbonate linked cannabinoid conjugate components are synthesized as follows. A cannabinoid (CBD in this example) is reacted with phosgene (or a suitable phosgene surrogate) and a thiol-epoxide ([45357-98-0] in this example) under standard basic conditions to form the desired S-alkyl thiocarbonate linked product.

Epoxide thiocarbonate linked cannabinoid conjugate components are synthesized as follows. A cannabinoid (CBD in this example) is reacted with thiophosgene (or a suitable thiophosgene surrogate) and a hydroxyepoxide ([556-52-5] in this example) under standard basic conditions to form the desired thiocarbonate linked product.

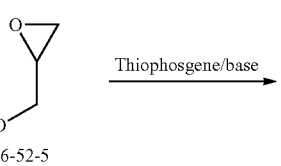

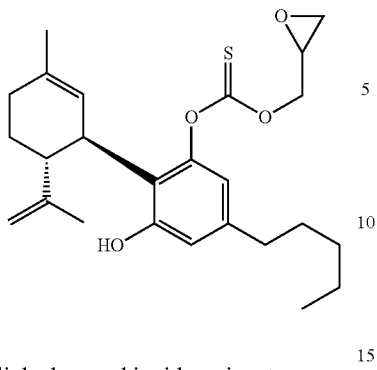

Epoxide thioimidate linked cannabinoid conjugate components are synthesized as follows. A cannabinoid (CBD in this example) is reacted with an imidocarbonyl chloride (in this case [5652-90-4]) and a thiol-epoxide ([45357-98-0] in this example) under standard basic conditions to form the desired thioimidate linked product.

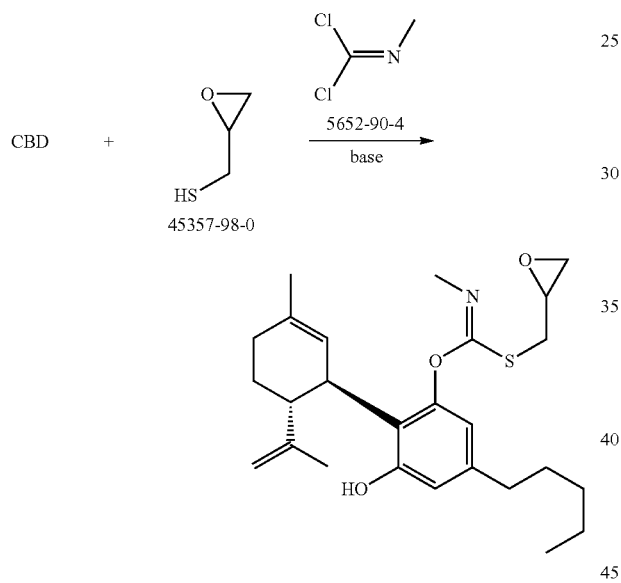

Epoxide thiophosphinodiamide linked cannabinoid conjugate components are synthesized as follows. Using conditions similar to those referenced in the Scheme, dimethylphosphoramidothioic dichloride ([1498-65-3]) is reacted with an aminoepoxide ([5689-75-8] in this example). The adduct is then reacted with a cannabinoid (CBD in this example) under standard basic conditions, to form the desired product.

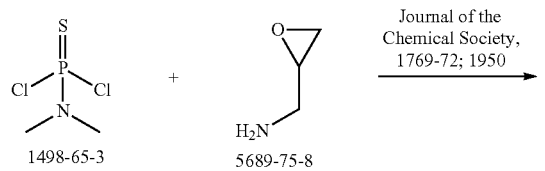

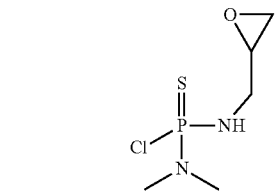

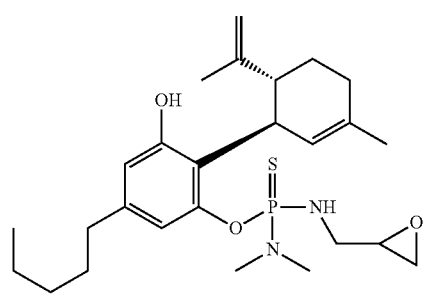

Epoxide xanthate linked cannabinoid conjugate components are synthesized as follows. A cannabinoid (CBD in this example) is reacted with thiophosgene (or a suitable thiophosgene surrogate) and a thiol-epoxide ([45357-98-0] in this example) under standard basic conditions to form the desired xanthate linked product.

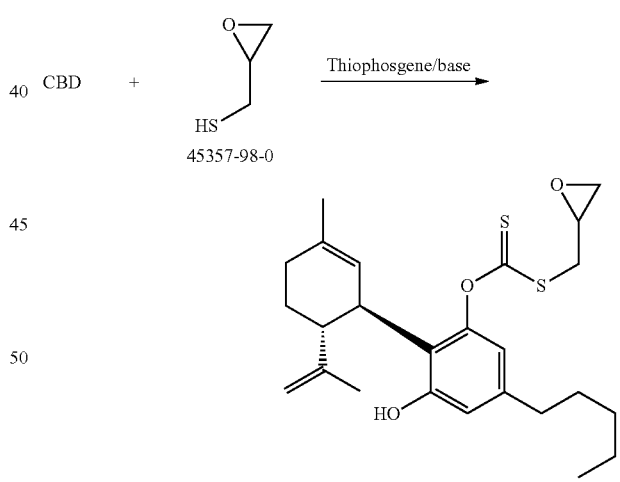

Example 37. Aziridine-Containing Cannabinoid Conjugate Components

Aziridine carbamate linked cannabinoid conjugate components are synthesized as follows. A cannabinoid (CBD in this example) is reacted with phosgene (or a suitable phosgene surrogate) and an aminoaziridine ([88714-40-3] in this example) under standard basic conditions to form the desired carbamate linked product.

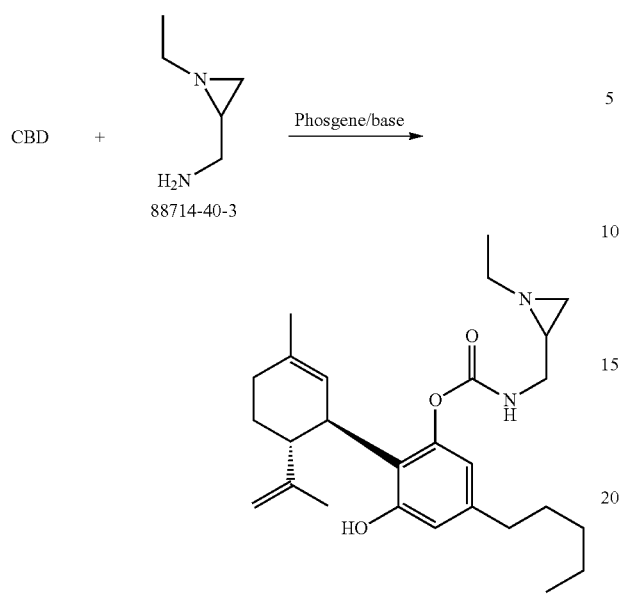

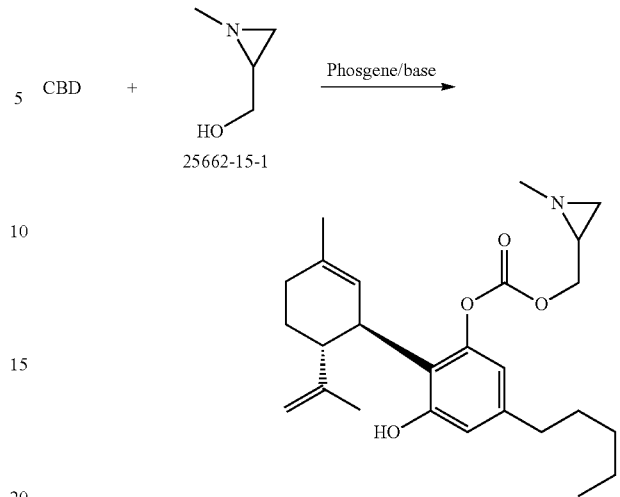

Aziridine carbonate linked cannabinoid conjugate components are synthesized as follows. A cannabinoid (CBD in this example) is reacted with phosgene (or a suitable phosgene surrogate) and a hydroxyaziridine ([25662-15-1] in this example) under standard basic conditions to form the desired carbonate linked product.

Aziridine ester linked cannabinoid conjugate components are synthesized as follows. The previously reported hydroxymethyl building block [126587-35-7] is treated with base, in this example sodium hydride, to generate the aziridinyl intermediate. Removal of the BOC protecting group followed by alkylation of the resulting amine gives the alkyl aziridine-ester intermediate. Standard hydrolysis of the ester gives the carboxylic acid precursor, which is esterified with the cannabinoid under standard esterification conditions to give the desired product.

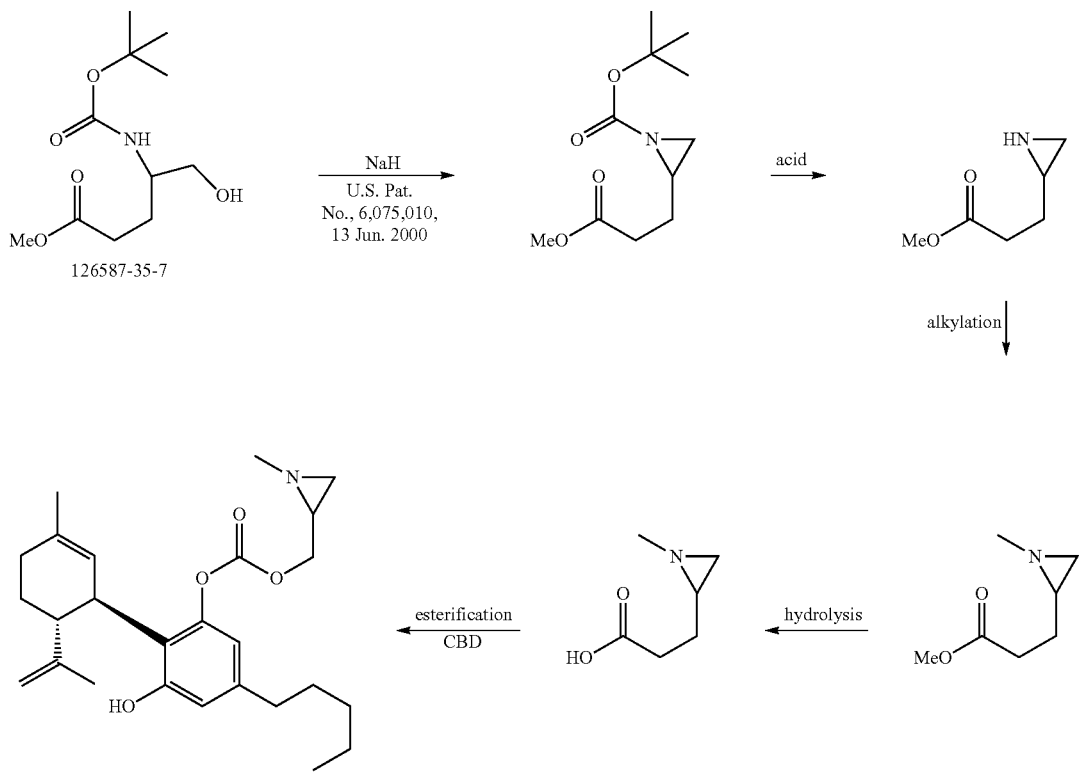

Aziridine imidate linked cannabinoid conjugate components are synthesized as follows. A cannabinoid (CBD in this example) is reacted with an imidocarbonyl chloride (in this case [5652-90-4]) and a hydroxyaziridine ([25662-15-1] in this example) under standard basic conditions to form the desired imidate linked product.

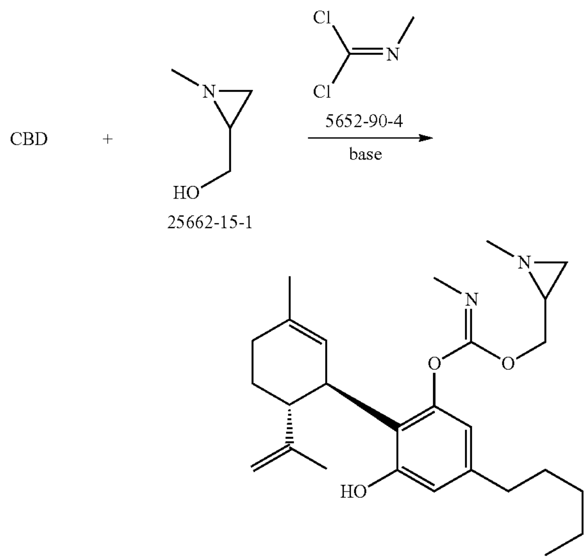

Aziridine isourea linked cannabinoid conjugate components are synthesized as follows. A cannabinoid (CBD in this example) is reacted with an imidocarbonyl chloride (in this case [5652-90-4]) and an aminoaziridine ([88714-40-3] in this example) under standard basic conditions to form the desired isourea linked product.

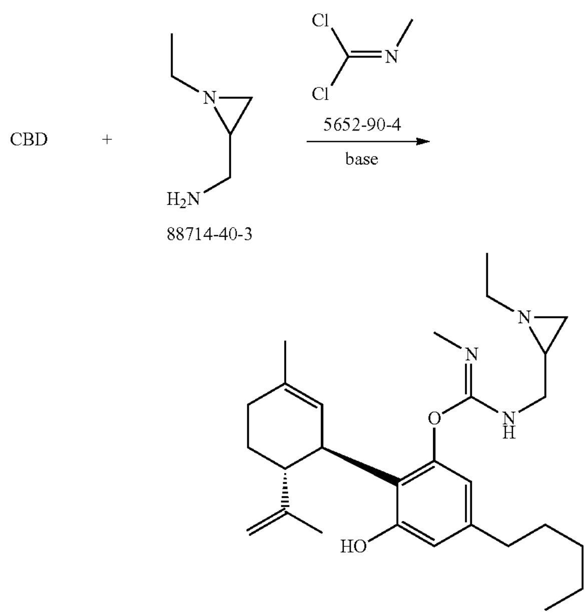

Aziridine phosphorodiamide linked cannabinoid conjugate components are synthesized as follows. Using conditions similar to those referenced in the Scheme, N,N-Dimethylphosphoramidodichloridate ([677-43-0]) is reacted with an aminoaziridine ([88714-40-3] in this example). The adduct is then reacted with a cannabinoid (CBD in this example) under standard basic conditions to form the desired product.

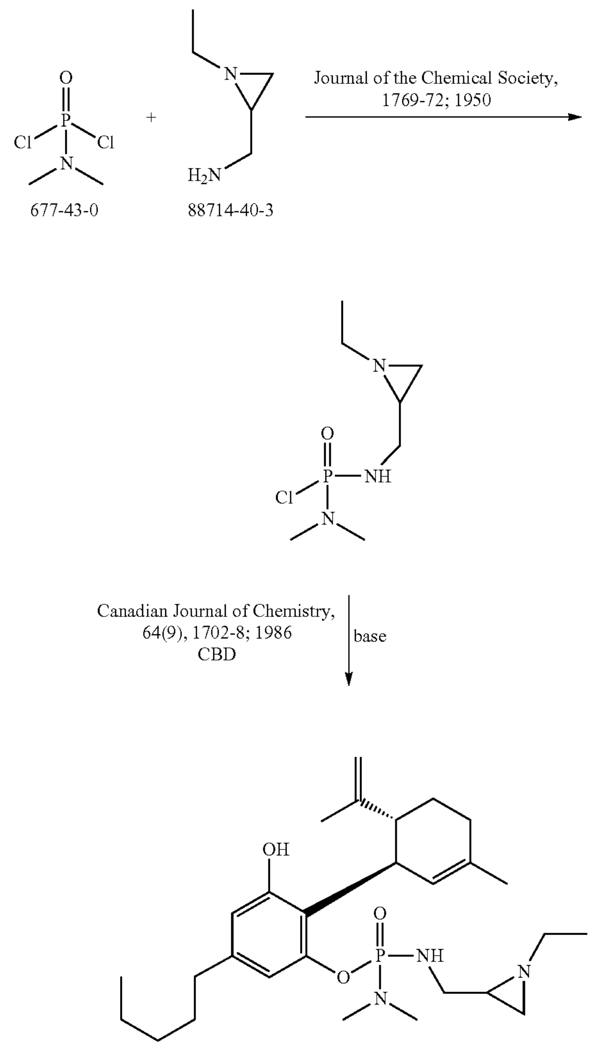

Aziridine thiocarbamate linked cannabinoid conjugate components are synthesized as follows. A cannabinoid (CBD in this example) is reacted with thiophosgene (or a suitable thiophosgene surrogate) and an aminoaziridine ([88714-40-3] in this example) under standard basic conditions to form the desired thiocarbamate linked product.

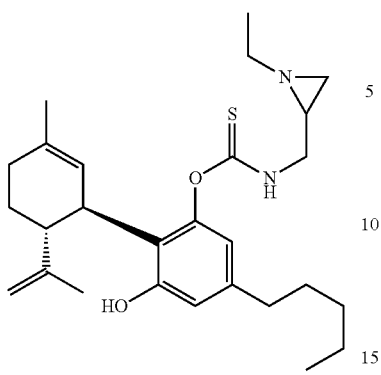

Aziridine thiocarbonate linked cannabinoid conjugate components are synthesized as follows. A cannabinoid (CBD in this example) is reacted with thiophosgene (or a suitable thiophosgene surrogate) and a hydroxyaziridine ([25662-15-1] in this example) under standard basic conditions to form the desired thiocarbonate linked product.

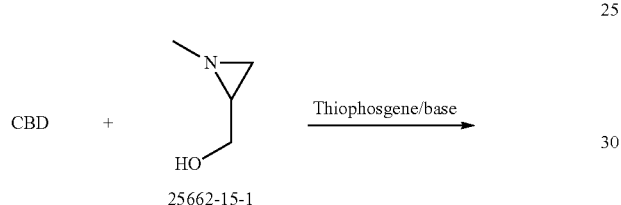

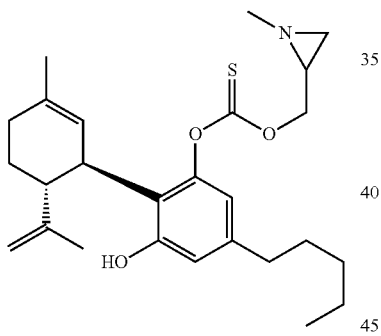

Aziridine thiophosphinodiamide linked cannabinoid conjugate components are synthesized as follows. Using conditions similar to those referenced in the Scheme, dimethylphosphoramidothioic dichloride ([1498-65-3]) is reacted with an aminoaziridine ([88714-40-3] in this example). The adduct is then reacted with a cannabinoid (CBD in this example) under standard basic conditions, to form the desired product.

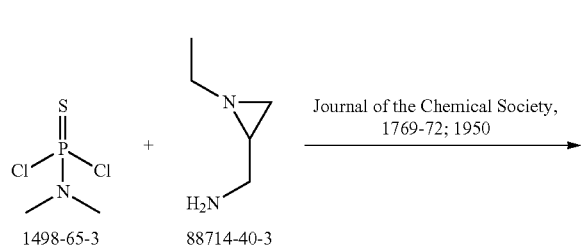

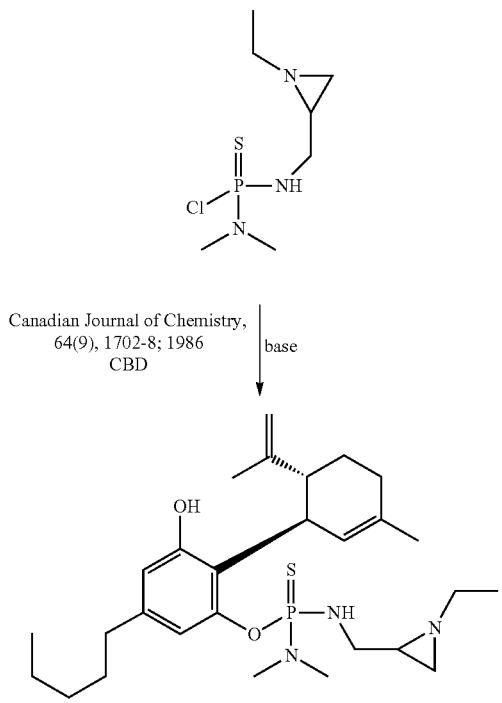

Example 38. Sulfonate-Linked Conjugate Components

Sulfonate carbamate linked cannabinoid conjugate components are synthesized as follows. A cannabinoid (CBD in this example) is reacted with phosgene (or a suitable phosgene surrogate) and an amino-alcohol ([156-87-6] in this example) under standard basic conditions to form the carbamate linked intermediate. Reaction with a sulfonyl chloride, in this case mesyl chloride, gives the desired product.

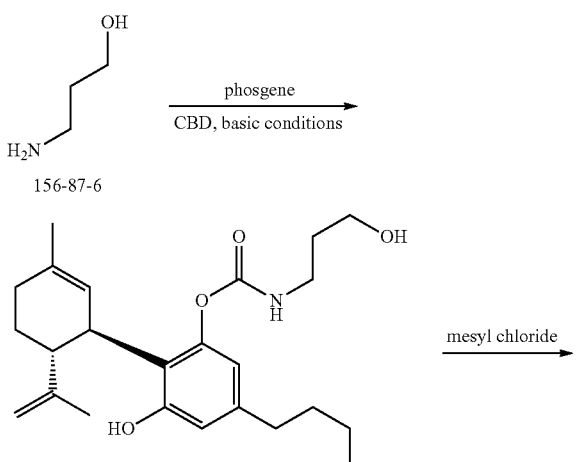

-continued

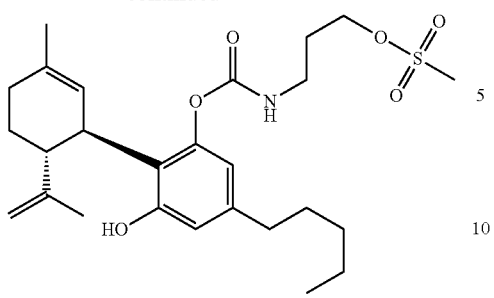

Sulfonate carbonate linked cannabinoid conjugate components are synthesized as follows. A diol compound, in this case 1,3-propanediol [13392-69-3] is reacted with a sulfonyl chloride, in this case tosyl chloride, to give the mono-sulfonate intermediate. Reaction of the remaining hydroxyl group in this intermediate with phosgene (or a suitable surrogate) and a cannabinoid (CBD in this example) under standard basic conditions forms the desired carbonate linked product.

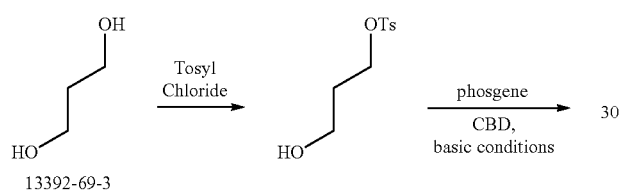

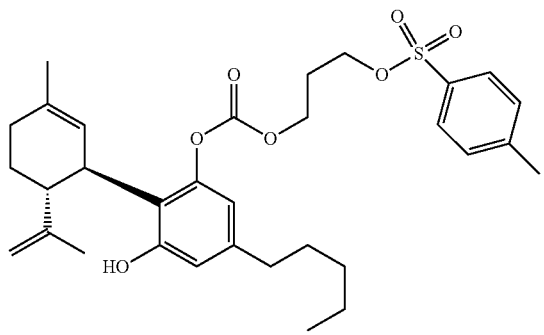

Sulfonate ester linked cannabinoid conjugate components are synthesized as follows. A hydroxyacid starting material, in this case [13392-69-3], is esterified under referenced conditions for selective esterification of an aromatic OH in the presence of an aliphatic OH. The ester linked intermediate then undergoes sulfonylation, in this case with mesyl chloride, under referenced conditions to give the desired product.

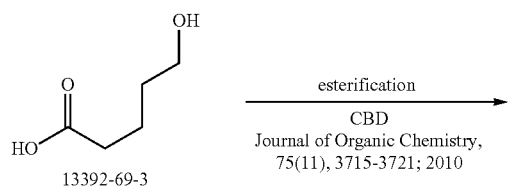

-continued

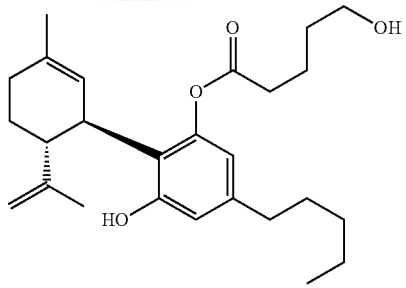

Bioorganic & Medicinal Chemistry Letters, 18(1), 355-359; 2008
Synthesis, (4), 509-512; 2003
Mesyl Chloride
base

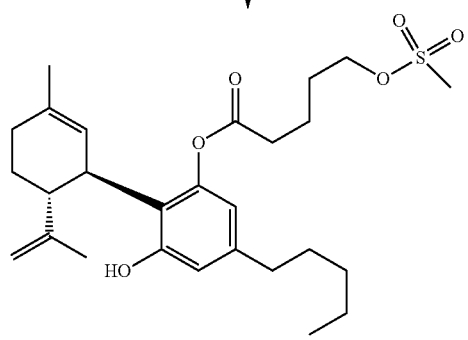

Sulfonate imidate linked cannabinoid conjugate components are synthesized as follows. A diol compound, in this case 1,3-propanediol [13392-69-3] is reacted with a sulfonyl chloride, in this case tosyl chloride, to give the mono-sulfonate intermediate. Reaction of the remaining hydroxyl group in this intermediate with an imidocarbonyl chloride (in this case [5652-90-4]) under standard basic conditions forms the desired imidate linked product.

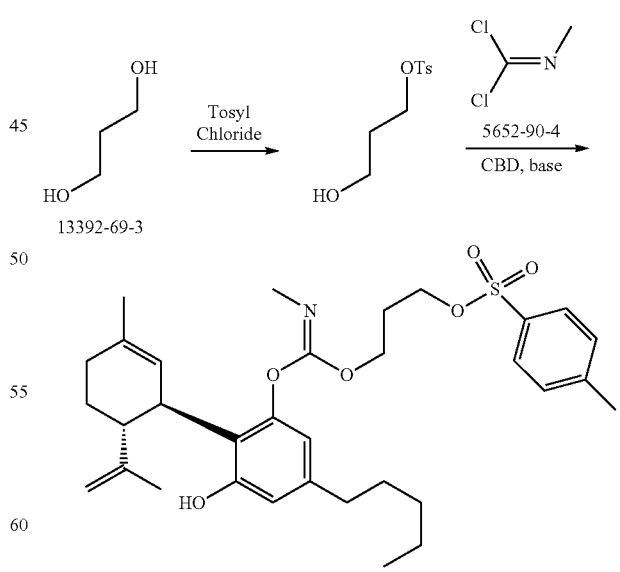

Sulfonate isourea linked cannabinoid conjugate components are synthesized as follows. A cannabinoid (CBD in this example) is reacted with an imidocarbonyl chloride (in this case [5652-90-4]) and an amino-alcohol ([156-87-6] in this example) under standard basic conditions to form the isourea linked intermediate. Sulfonylation, in this case with mesyl chloride, under referenced conditions (see sulfonate ester above) gives the desired product.

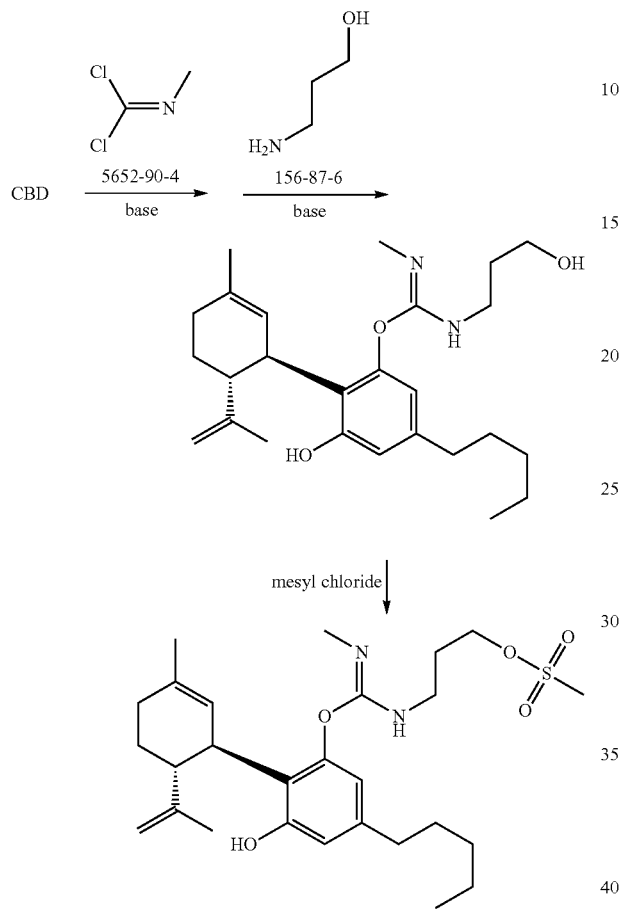

Sulfonate phosphorodiamide linked cannabinoid conjugate components are synthesized as follows. Using conditions similar to those referenced in the epoxide phosphorodiamide Scheme, N,N-Dimethylphosphoramidodichloridate ([677-43-0]) is reacted with a cannabinoid (CBD in this example) and an amino-alcohol ([156-87-6] in this example). The adduct then undergoes sulfonylation, in this case with mesyl chloride, under referenced conditions (see sulfonate ester above) gives the desired product.

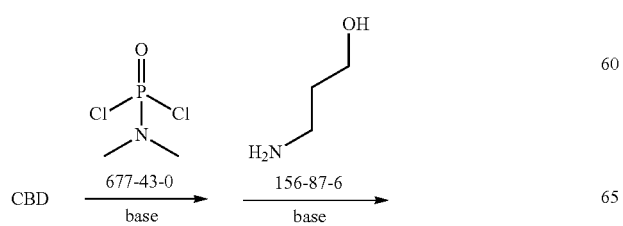

-continued

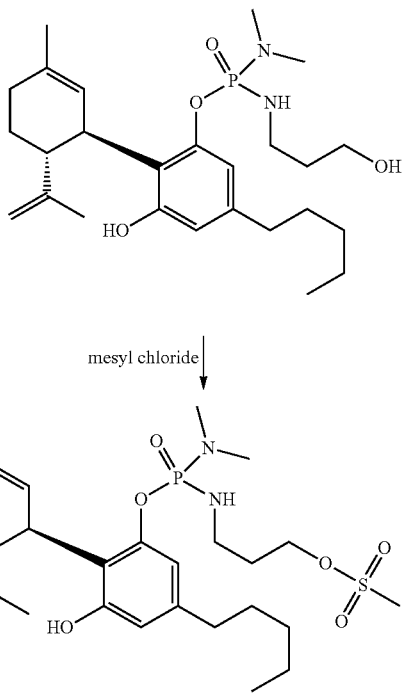

Sulfonate S-alkyl thiocarbonate linked cannabinoid conjugate components are synthesized as follows. A cannabinoid (CBD in this example) is reacted with phosgene (or a suitable phosgene surrogate) and a thiol-alcohol ([19721-22-3] in this example) under standard basic conditions, to form the S-alkyl thiocarbonate linked intermediate. Sulfonylation, in this case with tosyl chloride, gives the desired product.

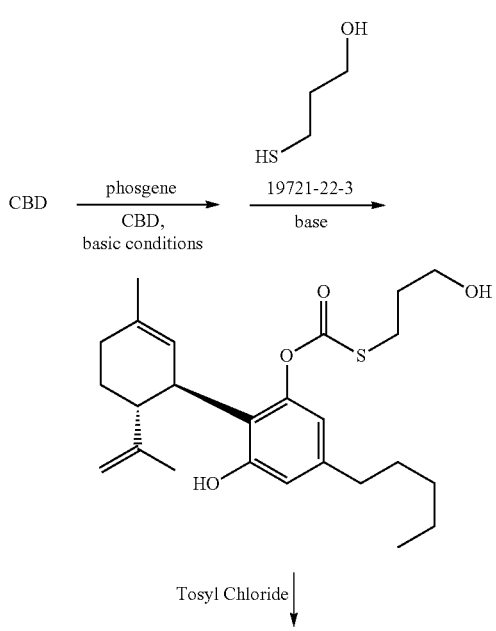

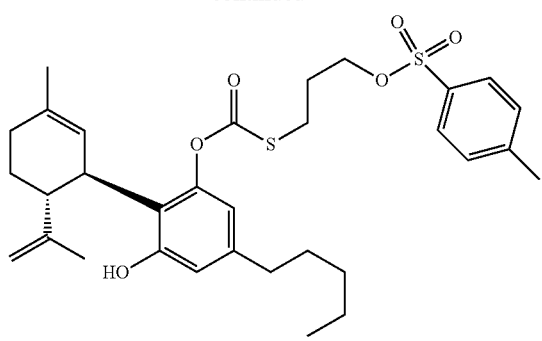

Sulfonate thiocarbamate linked cannabinoid conjugate components are synthesized as follows. A cannabinoid (CBD in this example) is reacted with thiophosgene (or a suitable thiophosgene surrogate) and an amino-alcohol ([156-87-6] in this example) under standard basic conditions to form the thiocarbamate linked intermediate. Sulfonylation, in this case with mesyl chloride, under referenced conditions (see sulfonate ester above) gives the desired product.

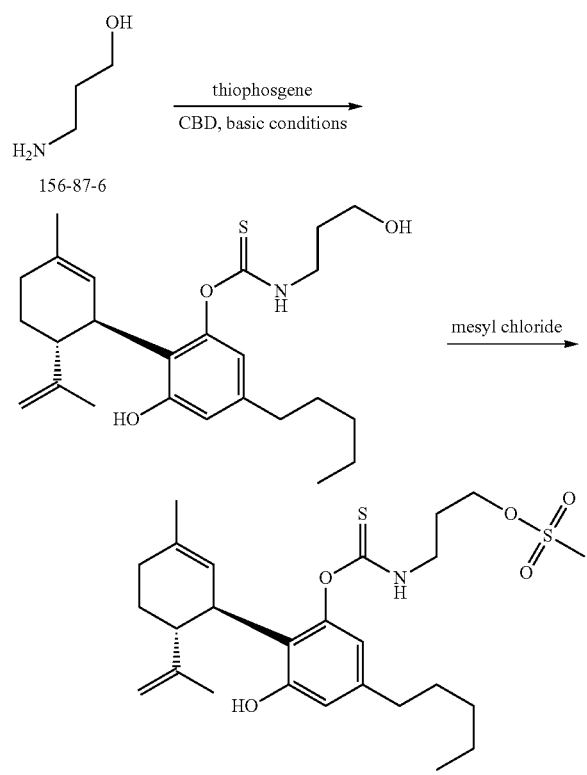

Sulfonate thiocarbonate linked cannabinoid conjugate components are synthesized as follows. A diol compound, in this case 1,3-propanediol [13392-69-3] is reacted with a sulfonyl chloride, in this case tosyl chloride, to give the monosulfonate intermediate. Reaction of the remaining hydroxyl group in this intermediate with thiophosgene (or a suitable thiophosgene surrogate) and a cannabinoid (CBD in this example) under standard basic conditions forms the desired thiocarbonate linked product.

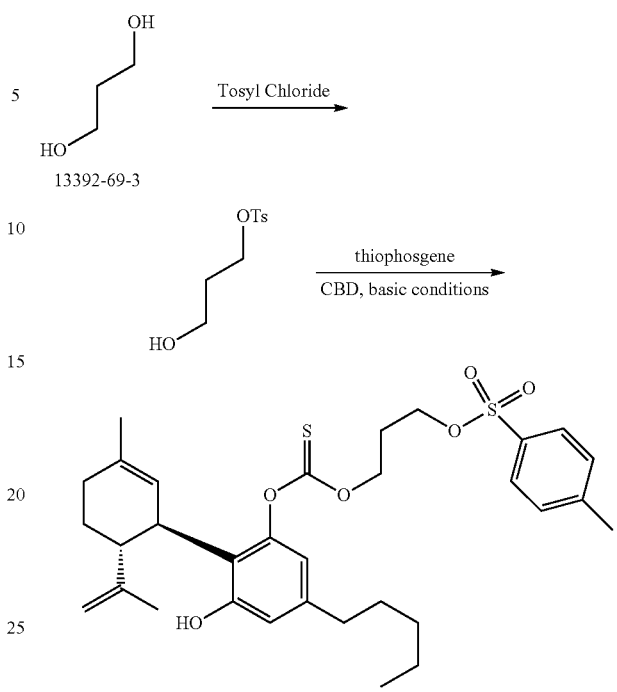

Sulfonate thioimidate linked cannabinoid conjugate components are synthesized as follows. A cannabinoid (CBD in this example) is reacted with an imidocarbonyl chloride (in this case [5652-90-4]) and a thiol-alcohol ([19721-22-3] in this example) under standard basic conditions to form the thioimidate linked intermediate. Sulfonylation, in this case with tosyl chloride, under referenced conditions (see sulfonate ester above) gives the desired product.

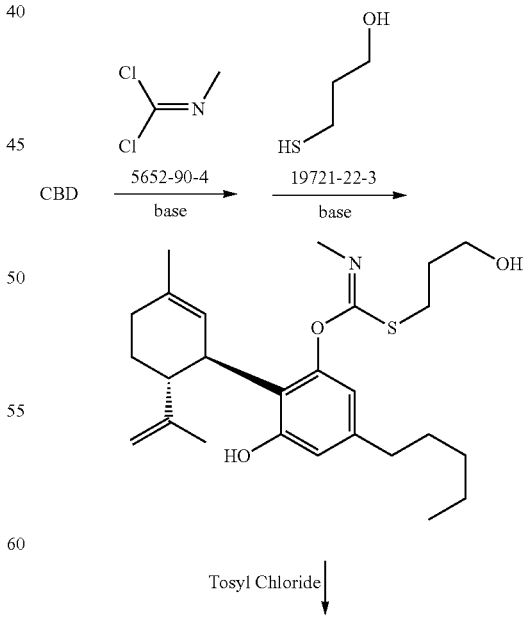

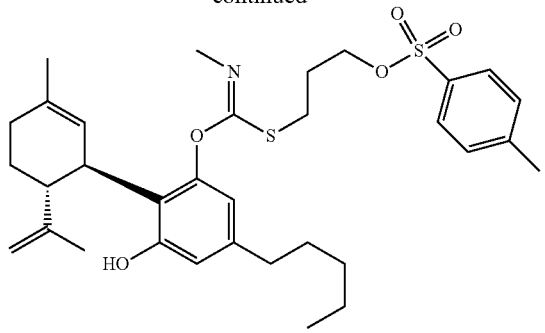

Sulfonate thiophosphinodiamide linked cannabinoid conjugate components are synthesized as follows. Using conditions similar to those referenced in the epoxide thiophosphinodiamide Scheme, dimethylphosphoramidothioic dichloride ([1498-65-3]) is reacted with a cannabinoid (CBD in this example) and an amino-alcohol ([156-87-6] in this example). Sulfonylation of the adduct, in this case with mesyl chloride, under referenced conditions (see sulfonate ester above) gives the desired product.

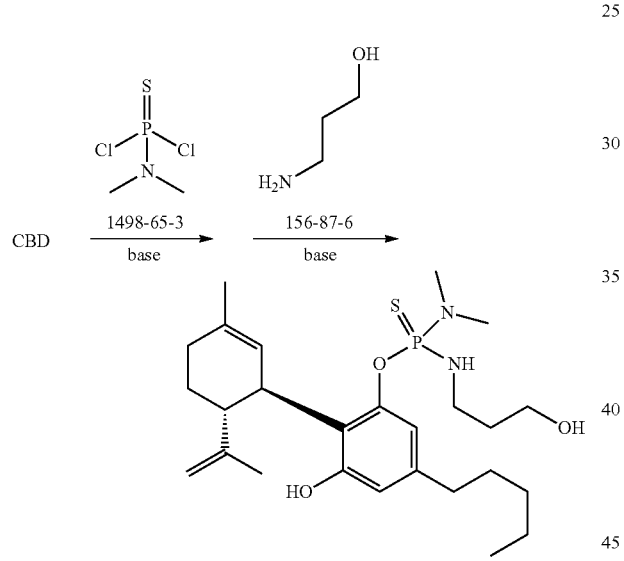

Sulfonate xanthate linked cannabinoid conjugate components are synthesized as follows. A cannabinoid (CBD in this example) is reacted with thiophosgene (or a suitable thiophosgene surrogate) and a thiol-alcohol ([19721-22-3] in this example) under standard basic conditions to form the xanthate linked intermediate. Sulfonylation, in this case with mesyl chloride, under referenced conditions (see sulfonate ester above) gives the desired product.

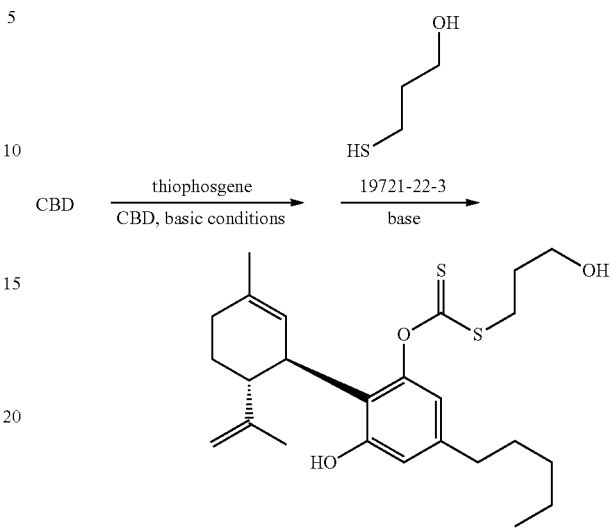

Example 39. Cannabinoid Conjugate Components Comprising Halides

Halide carbamate linked cannabinoid conjugate components are synthesized as follows. A cannabinoid (CBD in this example) is reacted with phosgene (or a suitable phosgene surrogate) and an aminohalide ([18370-81-5] in this example) under standard basic conditions to form the desired carbamate linked product.

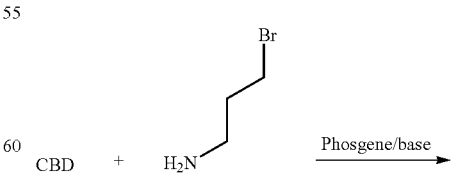

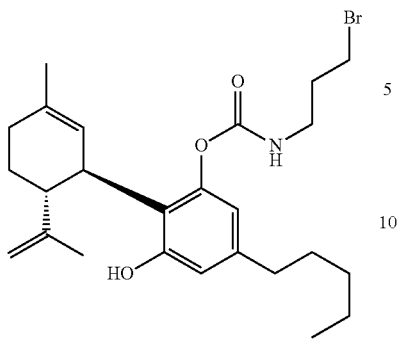

Halide carbonate linked cannabinoid conjugate components are synthesized as follows. A cannabinoid (CBD in this example) is reacted with phosgene (or a suitable phosgene surrogate) and a hydroxyalkyl halide ([627-18-9] in this example) under standard basic conditions to form the desired carbonate linked product.

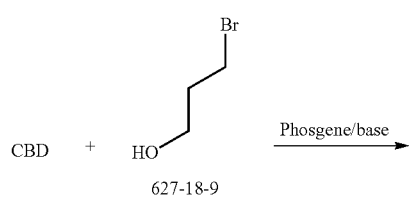

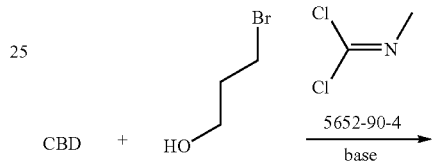

Halide imidate linked cannabinoid conjugate components are synthesized as follows. A cannabinoid (CBD in this example) is reacted with an imidocarbonyl chloride (in this case [5652-90-4]) and a hydroxyalkyl halide ([627-18-9] in this example) under standard basic conditions to form the desired imidate linked product.

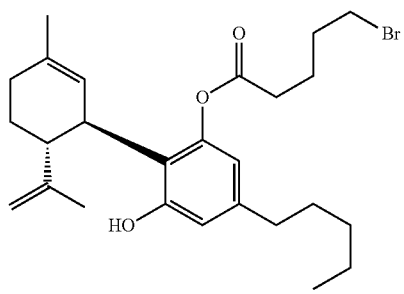

Halide ester linked cannabinoid conjugate components are synthesized as follows. A cannabinoid (CBD in this example) is esterified under standard conditions, in this example with the haloalkyl acid building block [2067-33-6] to give the desired product.

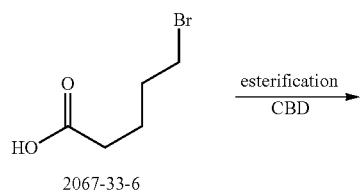

Halide isourea linked cannabinoid conjugate components are synthesized as follows. A cannabinoid (CBD in this example) is reacted with an imidocarbonyl chloride (in this case [5652-90-4]) and an aminoalkyl halide ([18370-81-5] in this example) under standard basic conditions to form the desired isourea linked product.

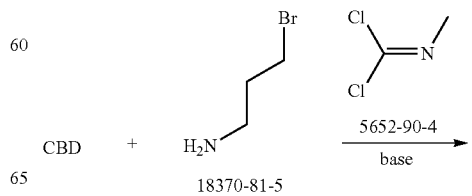

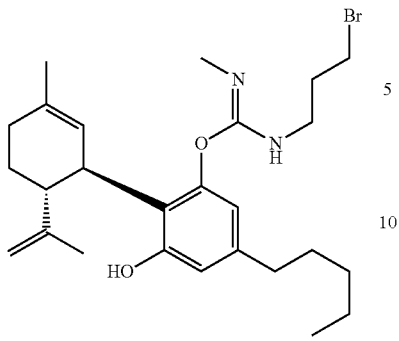

Halide phosphorodiamide linked cannabinoid conjugate components are synthesized as follows. Using conditions similar to those referenced in the epoxide phosphorodiamide Scheme, N,N-Dimethylphosphoramidodichloridate ([677-43-0]) is reacted with a cannabinoid (CBD in this example) and an aminoalkyl halide ([18370-81-5] in this example) to form the desired product.

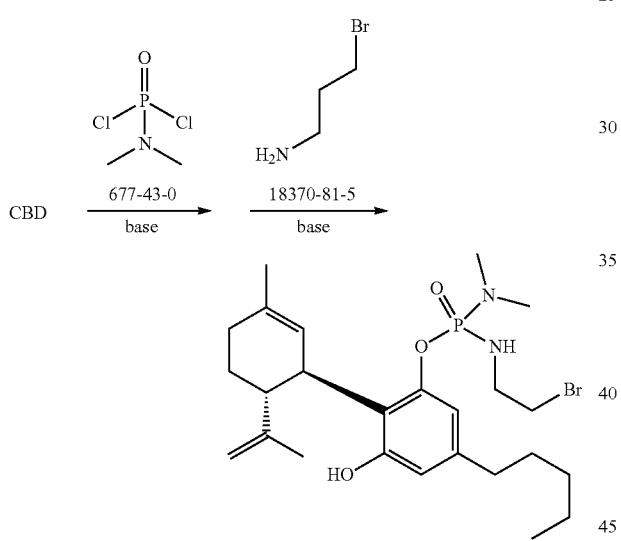

Halide S-alkyl thiocarbonate linked cannabinoid conjugate components are synthesized as follows. A cannabinoid (CBD in this example) is reacted with phosgene (or a suitable phosgene surrogate) and a haloalkyl thiol ([75694-39-2] in this example) under standard basic conditions, to form the desired S-alkyl thiocarbonate linked product.

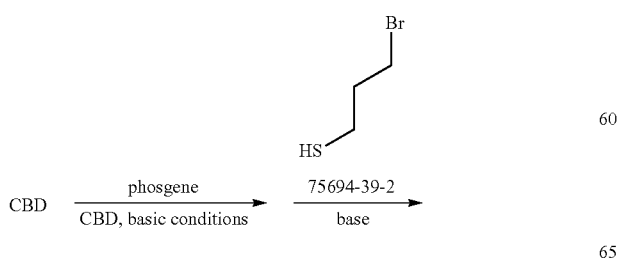

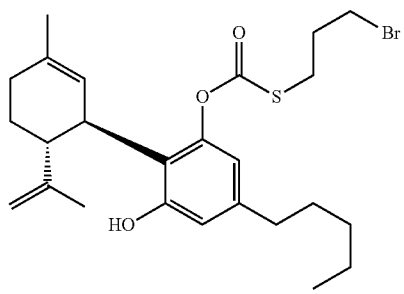

Halide thiocarbamate linked cannabinoid conjugate components are synthesized as follows. A cannabinoid (CBD in this example) is reacted with thiophosgene (or a suitable thiophosgene surrogate) and an aminoalkyl halide ([18370-81-5] in this example) under standard basic conditions to form the desired thiocarbamate linked product.

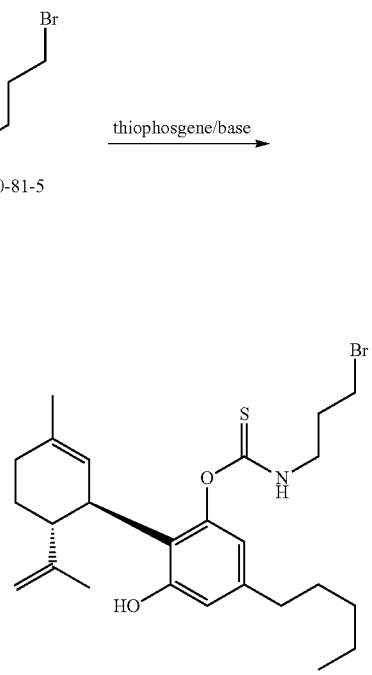

Halide thiocarbonate linked cannabinoid conjugate components are synthesized as follows. A cannabinoid (CBD in this example) is reacted with thiophosgene (or a suitable thiophosgene surrogate) and a hydroxyalkyl halide ([627-18-9] in this example) under standard basic conditions to form the desired thiocarbonate linked product.

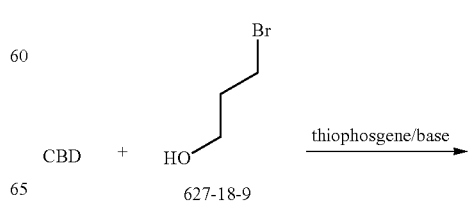

297

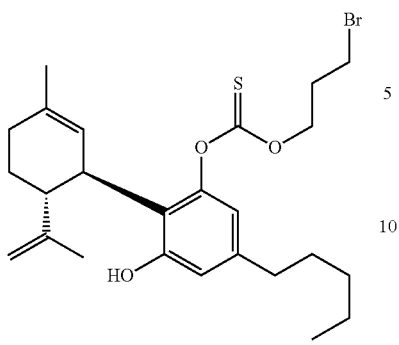

Halide thioimidate linked cannabinoid conjugate components are synthesized as follows. A cannabinoid (CBD in this example) is reacted with an imidocarbonyl chloride (in this case [5652-90-4]) and a haloalkyl thiol ([75694-39-2] in this example) under standard basic conditions to form the desired thioimidate linked product.

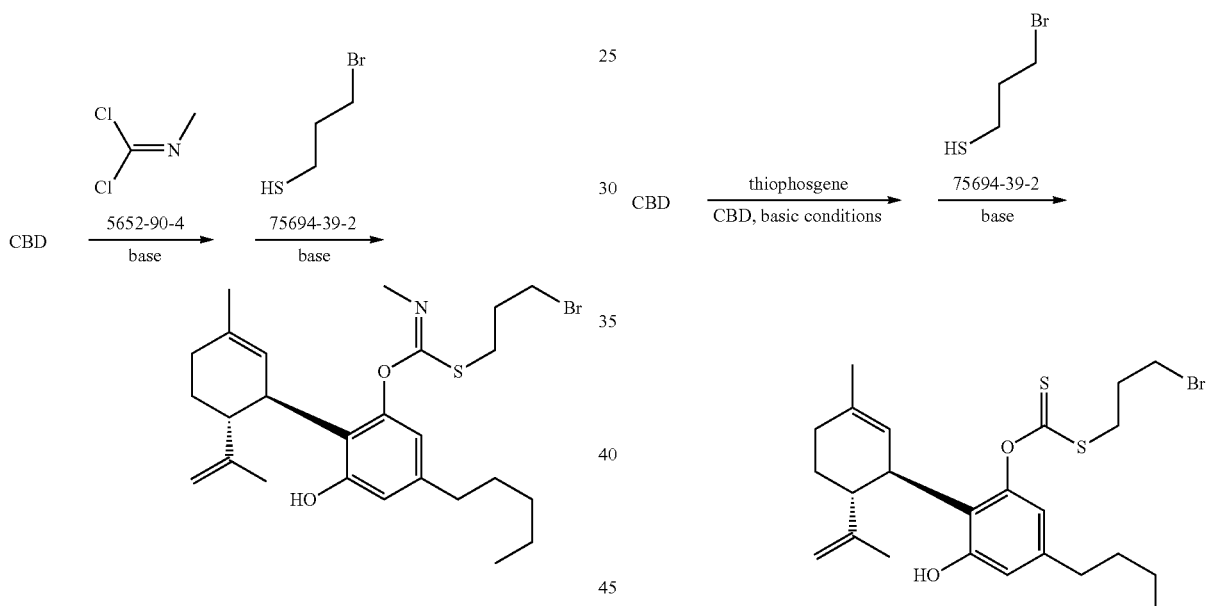

Halide thiophosphinodiamide linked cannabinoid conjugate components are synthesized as follows. Using conditions similar to those referenced in the epoxide thiophosphinodiamide Scheme, dimethylphosphoramidothioic dichloride ([1498-65-3]) is reacted with a cannabinoid (CBD in this example) and an aminoalkyl halide ([18370-81-5] in this example) to form the desired product.

298

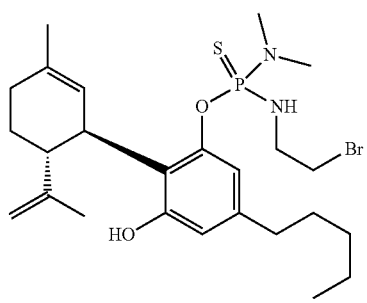

Halide xanthate linked cannabinoid conjugate components are synthesized as follows. A cannabinoid (CBD in this example) is reacted with thiophosgene (or a suitable thiophosgene surrogate) and a haloalkyl thiol ([75694-39-2] in this example) under standard basic conditions to form the desired xanthate linked product.

The building block [18709-11-0] for the cannabinoid conjugate component shown below is commercially available from Synnovator (SYNN76481); alternatively, it can be synthesized by reacting 2-chloroethylmethylamine [32315-92-7] with ethyl bromoacetate [105-36-2], followed by hydrolysis under standard conditions. Esterification is then carried out under standard conditions such as carbodiimide. A di-ester product may also be obtained.

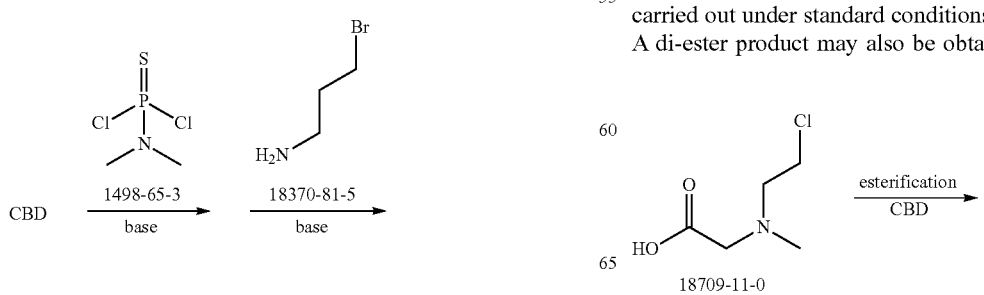

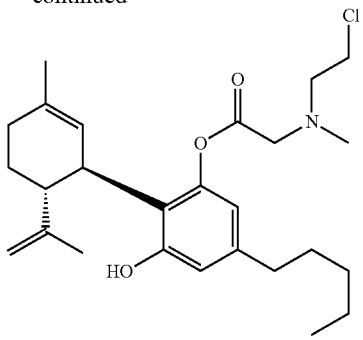

The cannabinoid conjugate component shown below can be synthesized by reacting reagent [677-43-0] (Alfa Aesar, L07231) with one equivalent of 2-chloroethylmethylamine [32315-92-7] to give a monochloro adduct. See Asian J. Chem. 21, 195-205, 2009. Addition of CBD to this intermediate gives the desired product after purification. See Organic Lett. 20, 8057-60, 2018.

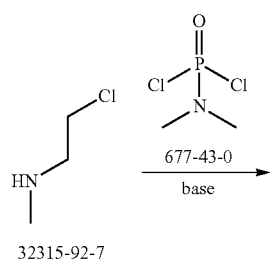

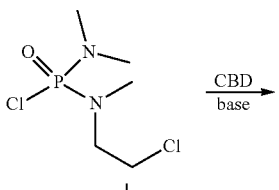

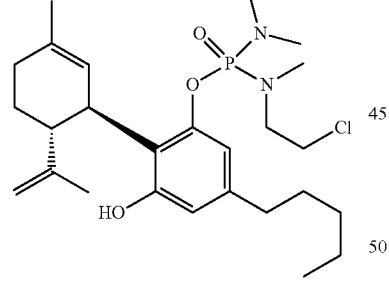

Cannabinoid conjugate component D1 is synthesized using chemistry employed for the synthesis of [98650-18-1] (J. Med. Chem. 32, 1491-96, 1989). The initial reaction of a phenolic group with $POCl_3$ is disclosed, for example, in Bioorganic & Medicinal Chemistry 13, 3219-27, 2005.

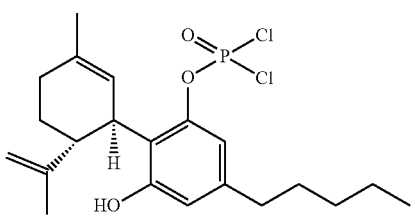

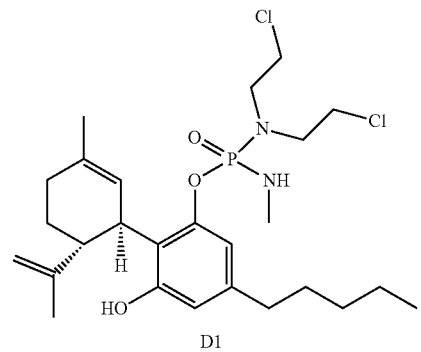

Cannabinoid conjugate component F1 can be synthesized by esterification of chlorambucil [305-03-3] with CBD under standard esterification conditions. Cannabinoid conjugate component F2 may also be synthesized.

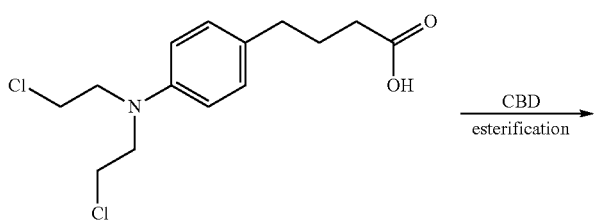

[305-03-3]

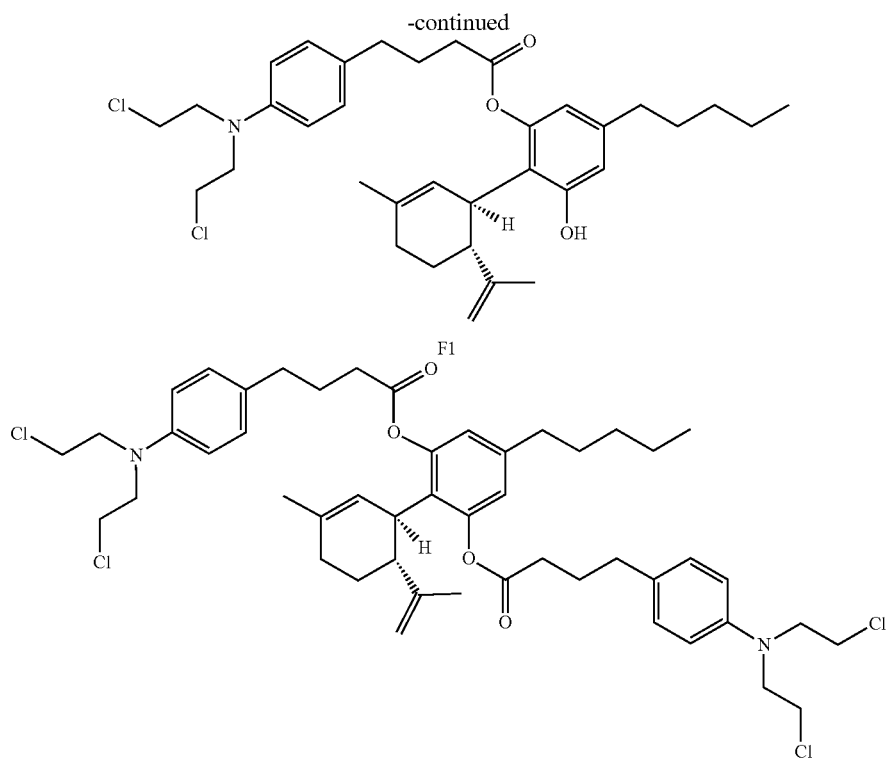

F1

F2

Example 40. Cannabinoid Conjugate Components Comprising a Temozolomide Component Compounds linked to the temozolomide component are synthesized as follows. The iodo acid [7425-27-6] is reacted with a cannabinoid (CBD) under standard esterification conditions to give the iodo ester intermediate. Following conditions (see Scheme) similar to those published for the synthesis of temozolomide from iodomethane, the desired cannabinoid conjugate component is produced by N-alkylation of [108030-65-5]. A cannabinoid conjugate component comprising two temozolomide components may also be obtained.

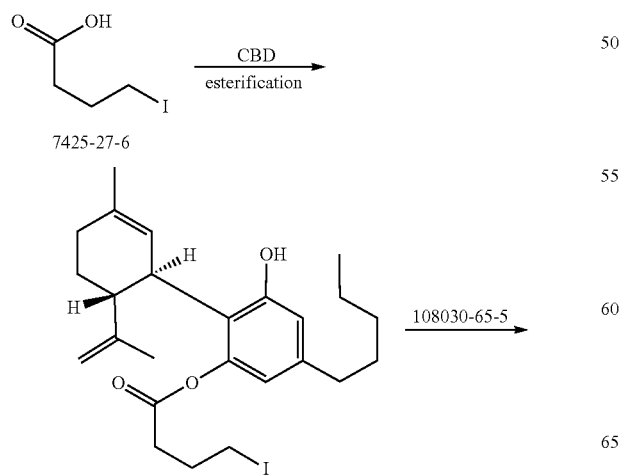

-continued

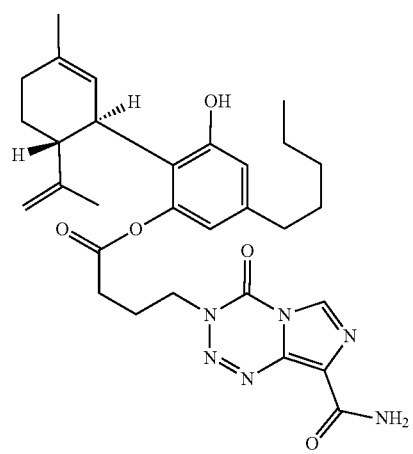

Organic Letters, 14(23, 5872-5875; 2012

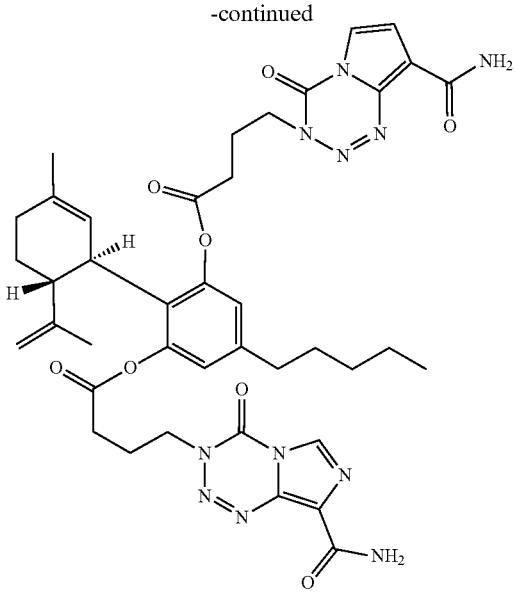

Alternatively, the heterocycle first can be alkylated with an iodo ester. The ester is then removed, and the heterocycle is esterified with CBD to form the cannabinoid-temozolomide conjugate component.

Building block [108030-65-5] can be obtained commercially or synthesized, for example using the published two-step route shown below (Bioorganic & Medicinal Chemistry Letters 6, 185-88, 1996):

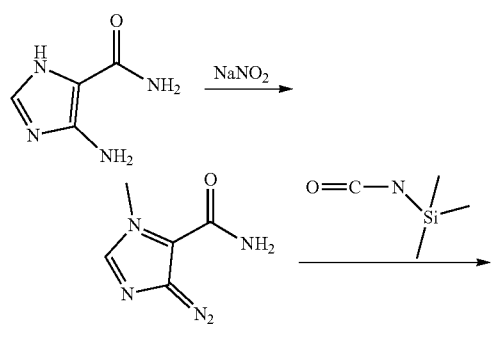

7008-85-7

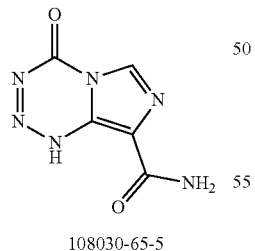

108030-65-5

Example 41. Cannabinoid Conjugate Components Comprising a 5-FU Component a. Linkage at the 1-Position of 5-FU Cannabinoid conjugate components comprising an ester linkage to a 5-fluorouracil component at the 1-position are synthesized as follows. The known building block [6214-60-4] is reacted with a cannabinoid (CBD) under standard esterification conditions to give the product.

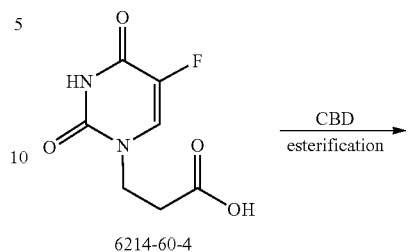

6214-60-4

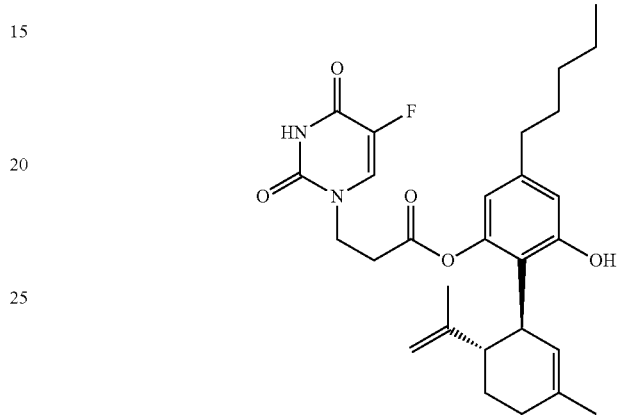

Cannabinoid conjugate components comprising a carbonate linkage to a 5-fluorouracil component at the 1-position are synthesized as follows. The building block [106206-99-9] is reacted with phosgene (or a suitable surrogate) and CBD under standard basic conditions to give the product.

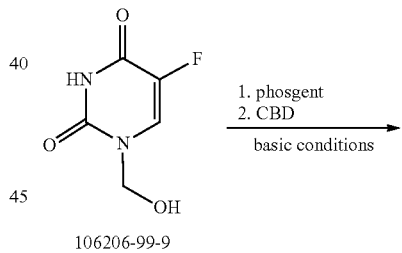

106206-99-9

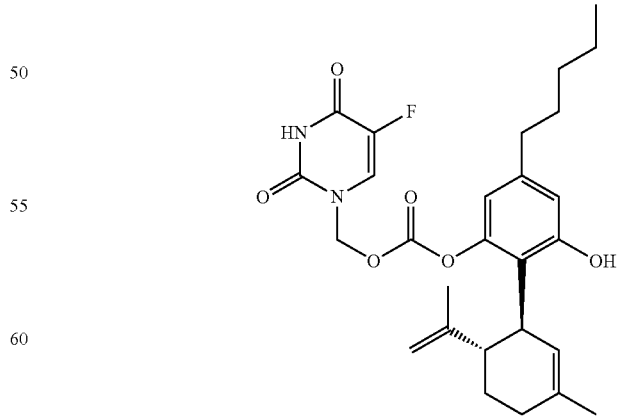

Cannabinoid conjugate components comprising carbamate linkage to a 5-fluorouracil component at the 1-position are synthesized as follows. The building block [1339797-

10-2] is reacted with phosgene (or a suitable surrogate) and CBD under standard basic conditions to give the product.

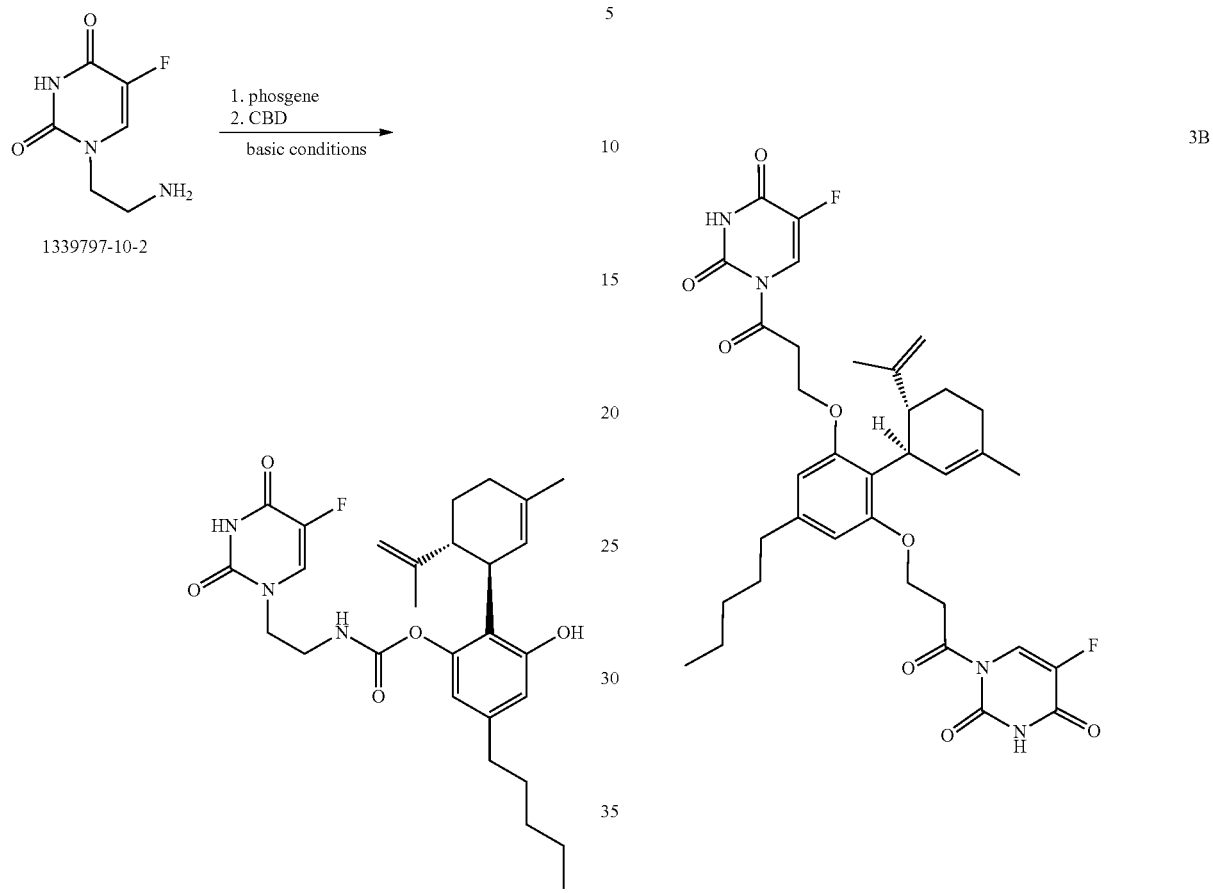

Cannabinoid conjugate components 3A and 3B can be synthesized by alkylation of CBD followed by acylation:

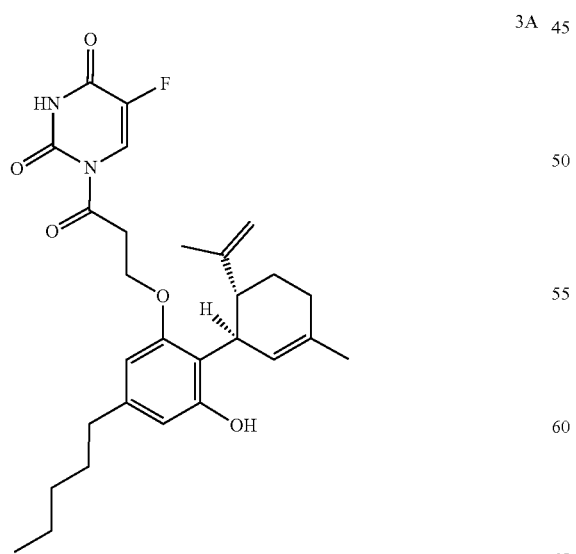

One approach to preparing cannabinoid conjugate component 8A involves reaction of a tosylate with a thiocyanate (RSC Advances, 4(54), 28794-28797; 2014). Thus, acylation of 5-FU with 4-hydroxybutyric acid followed by tosylation provides the tosylate intermediate. Reaction of [71999-74-1] with ammonium thiocyanate provides the thiocyanate intermediate. The intermediates are reacted (citation above) to give the disulfide intermediate. After removal of the BOC group, the amine is reacted with CBD and phosgene or an equivalent reagent to give cannabinoid conjugate component 8A. Cannabinoid conjugate component 5B may also be produced.

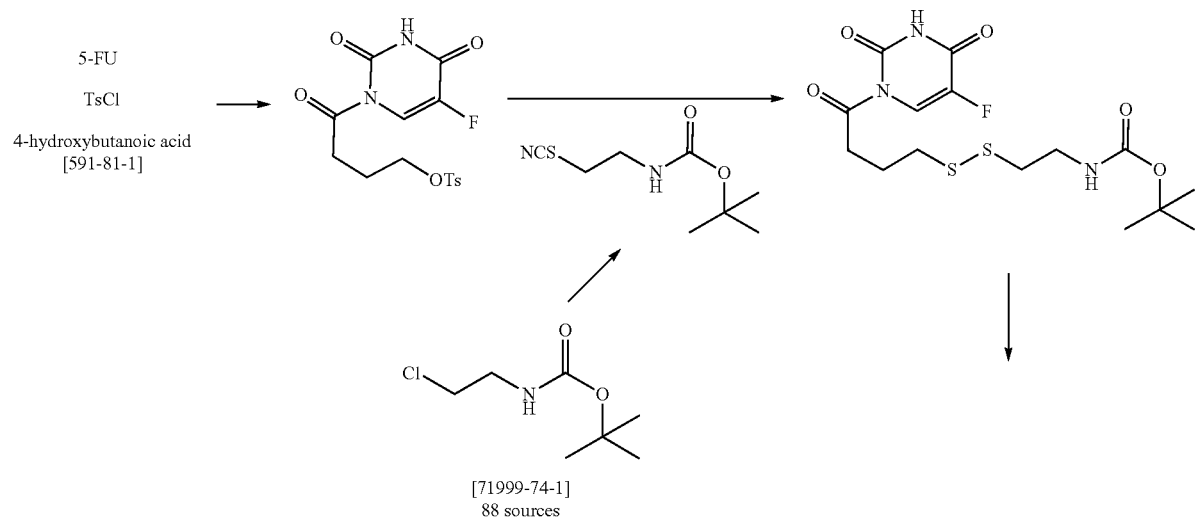
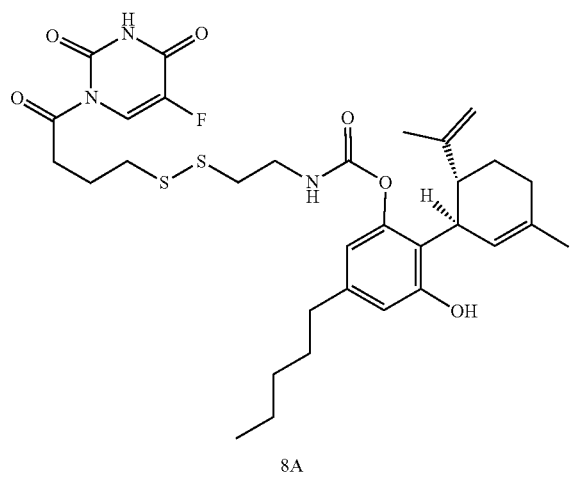
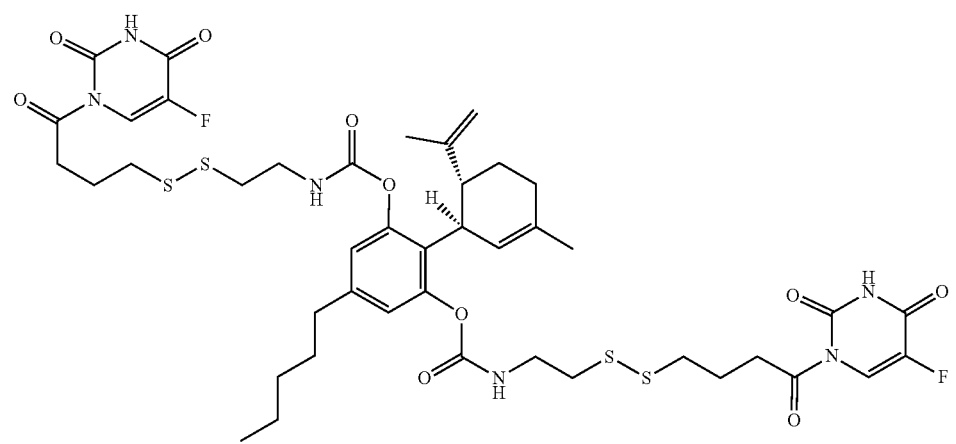

The synthesis of cannabinoid conjugate component 9A can be achieved by acylating 5-FU at the 1-position with [57294-38-9]. Removal of the BOC group followed by reaction with CBD and phosgene or an equivalent reagent forms cannabinoid conjugate component 9A. Cannabinoid conjugate component 9B may also be produced.

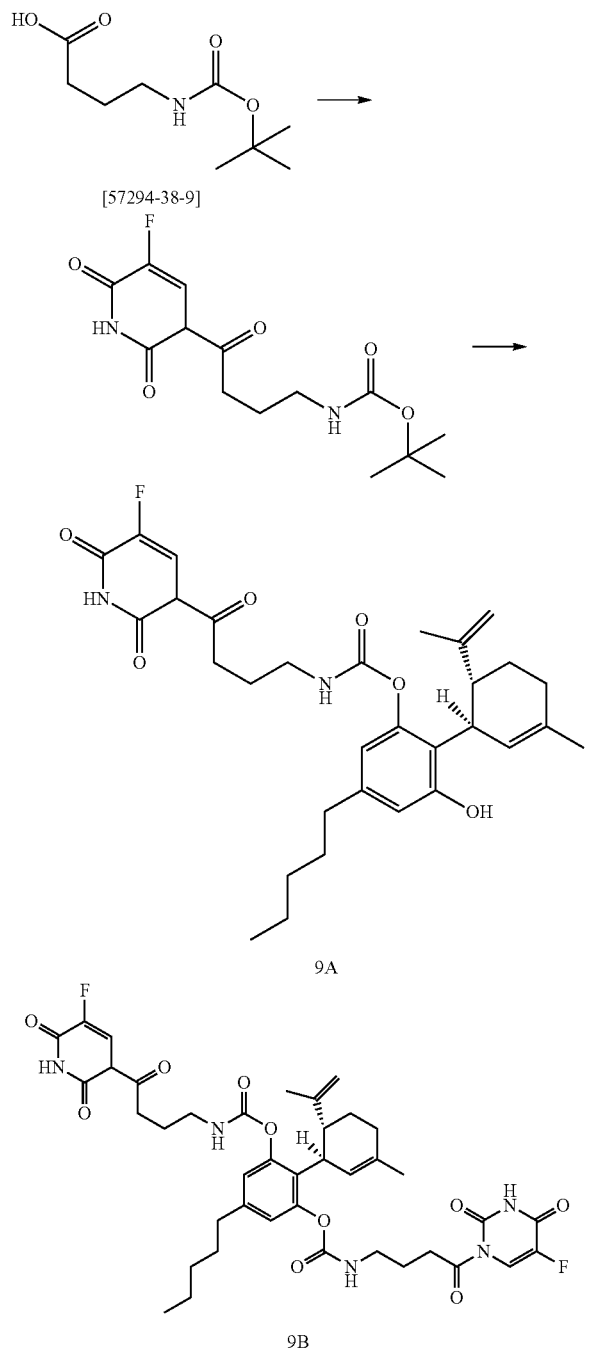

9A

9B b. Linkage at the 3-Position of 5-FU

Cannabinoid conjugate components comprising an ester linkage to a 5-fluorouracil component at the 3-position are synthesized as follows. The known building block [905265-53-4] is reacted with a cannabinoid (CBD) under standard esterification conditions to give the product.

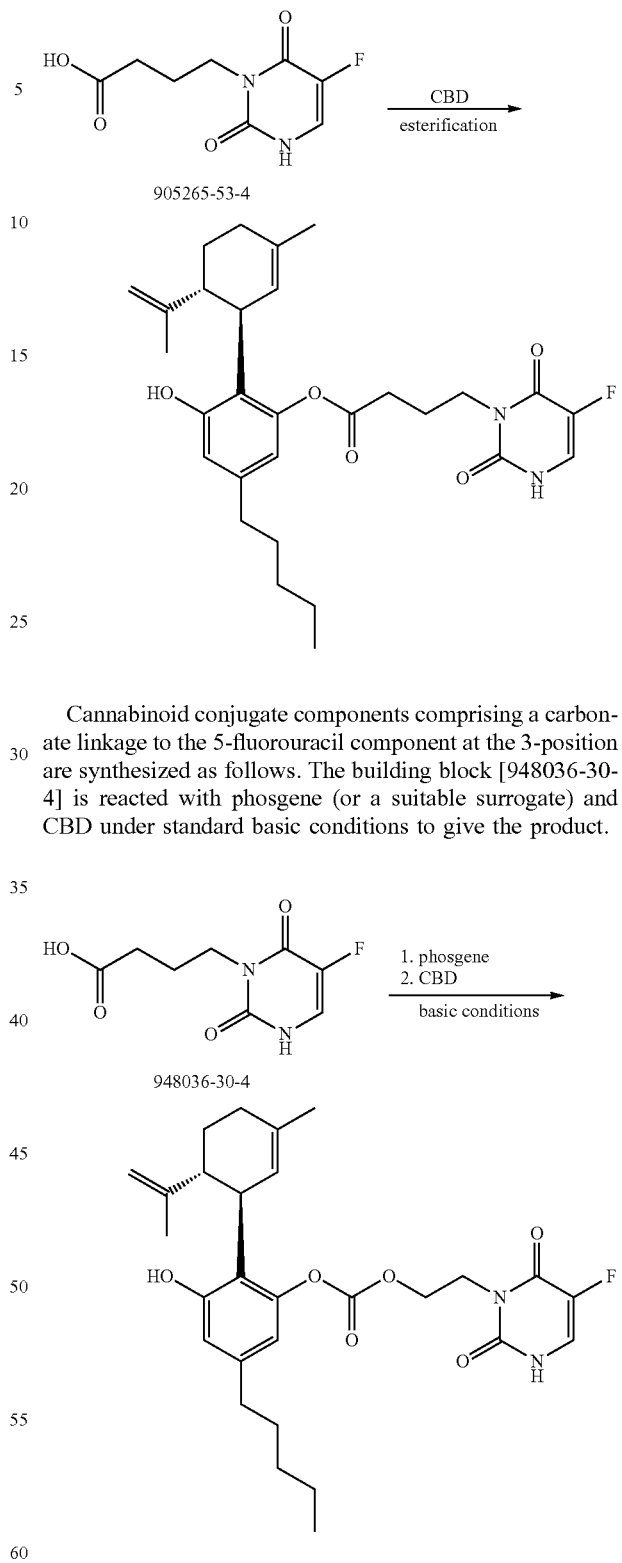

Cannabinoid conjugate components comprising a carbonate linkage to the 5-fluorouracil component at the 3-position are synthesized as follows. The building block [948036-30-4] is reacted with phosgene (or a suitable surrogate) and CBD under standard basic conditions to give the product.

Synthesis of cannabinoid conjugate components 1A and 1B can be carried out with protection of the NH group, such as BOC as reported in the synthesis of the corresponding ethyl compound [192625-76-6] or [[(benzyloxy)carbonyl]oxy]methyl in the synthesis of the corresponding propyl compound [118004-34-5].

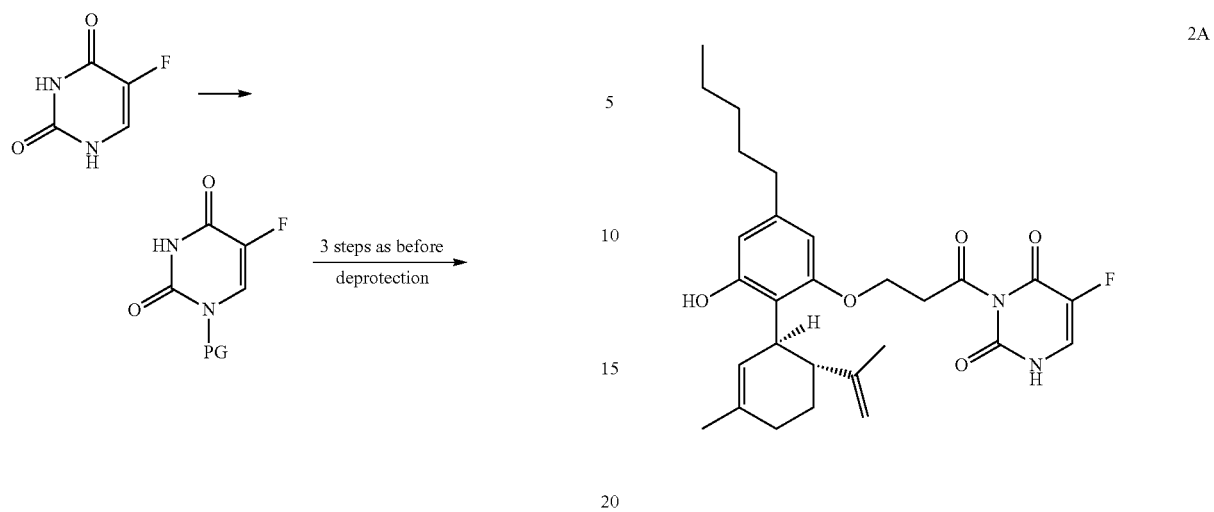

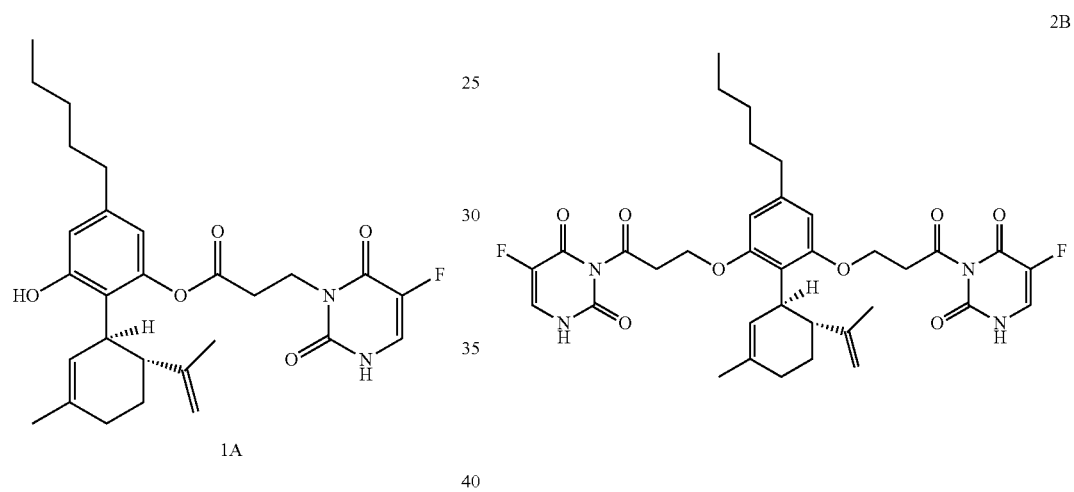

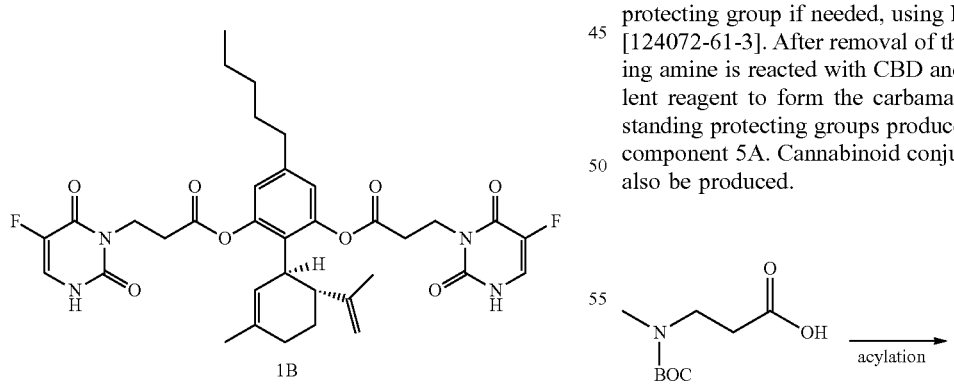

Synthesis of cannabinoid conjugate components 2A and 2B can proceed by alkylation of CBD followed by acylation at the 3-position of 5-FU, employing protection at the 1-position if needed. Alternatively, the acylation can be done first, and the CBD added as the last step.

Synthesis of cannabinoid conjugate component 5A can proceed by 3-acylation of 5-FU as described above, with a protecting group if needed, using N-methyl BOC-β-alanine [124072-61-3]. After removal of the BOC group, the resulting amine is reacted with CBD and phosgene or an equivalent reagent to form the carbamate. Removal of any outstanding protecting groups produces cannabinoid conjugate component 5A. Cannabinoid conjugate component 5B may also be produced.

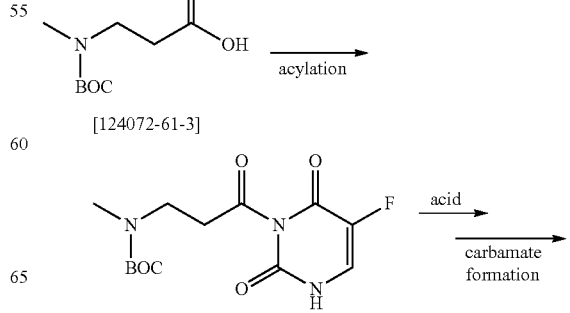

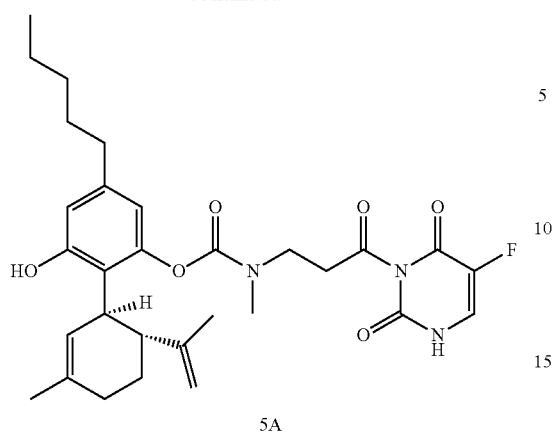

5A

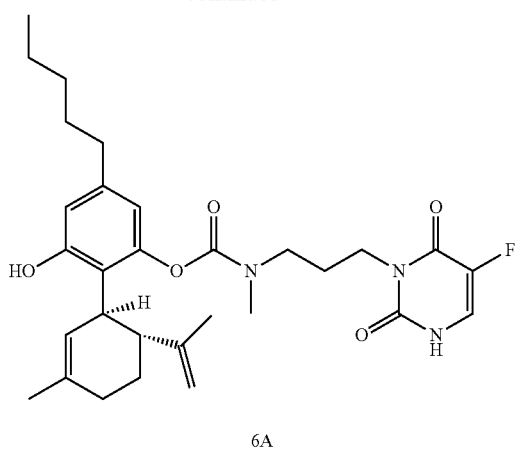

6A

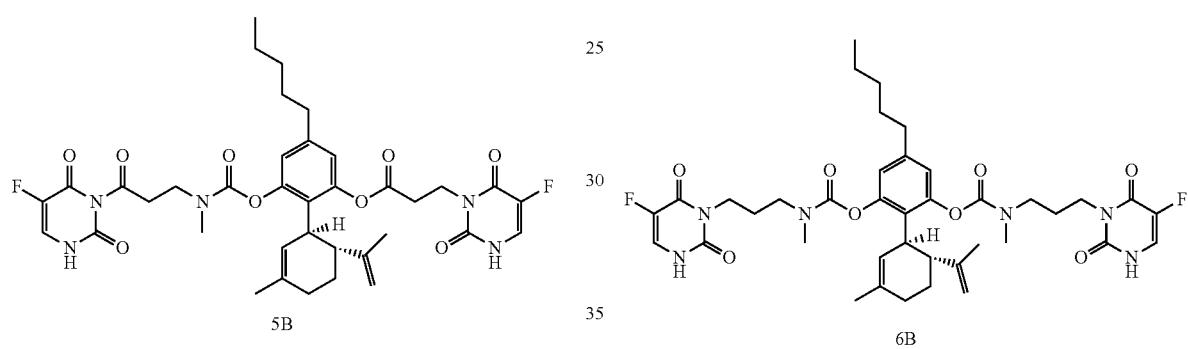

5B    6B

Synthesis of cannabinoid conjugate component 6A can proceed by 3-alkylation of 5-FU as described above, with a protecting group if needed, using BOC-protected N-methyl-3-chloropropylamine [114326-14-6] along with NaI if necessary. After removal of the BOC group, the resulting amine is reacted with phosgene or an equivalent reagent and CBD to form the carbamate. Removal of any outstanding protecting groups produces cannabinoid conjugate component 6A. Cannabinoid conjugate component 6B may also be produced.

c. Linkage at the 6-Position of 5-FU

Cannabinoid conjugate component 4A can be produced using Cannabinoid conjugate component 4A can be prepared by adding CBD to [13593-36-7], using a method similar to that for the synthesis of 6-phenoxyuracil [15422-04-5], reportedly carried out by adding phenol to 6-chlorouracil [4270-27-3] (Journal of Heterocyclic Chemistry, 19(2), 301-4; 1982). Cannabinoid conjugate component 4B may also be produced.

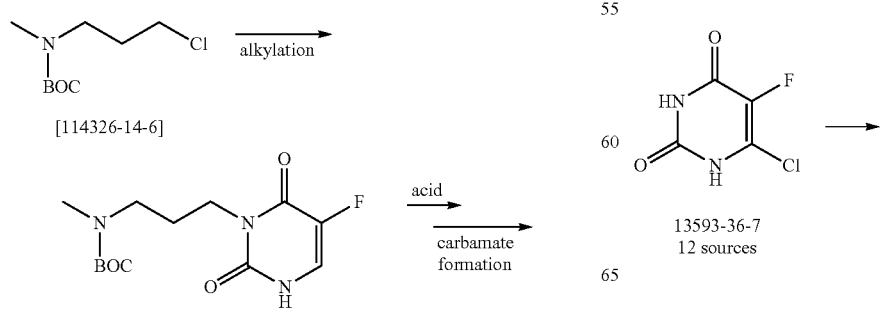

[114326-14-6]

13593-36-7
12 sources

315
-continued

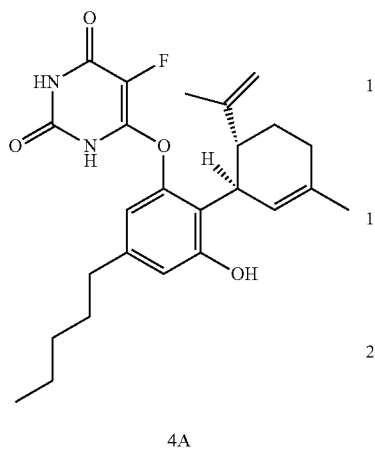

4A

316
-continued

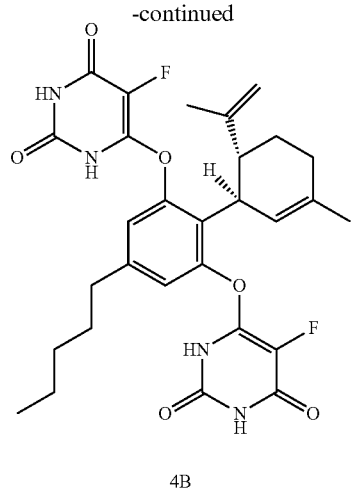

4B

Synthesis of cannabinoid conjugate component 7A begins with the addition of the diamine [111-33-1] to [13593-36-7]. For a report of adding a secondary amine to 6-chlorouracil [4270-27-3], see PCT Int. Appl., 2013013503, 31 Jan. 2013. The remaining unreacted secondary amine is then reacted with CBD and phosgene or an equivalent reagent to form the cannabinoid conjugate component 7A. Cannabinoid conjugate component 7B may also be produced.

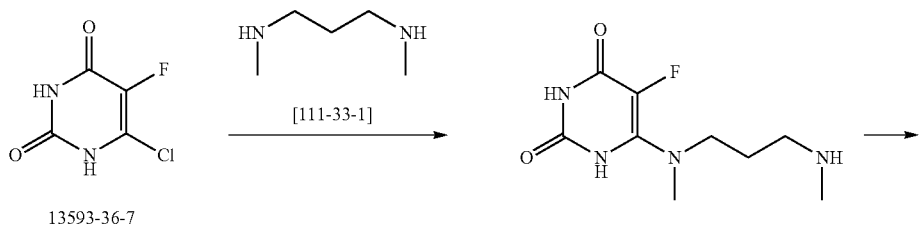

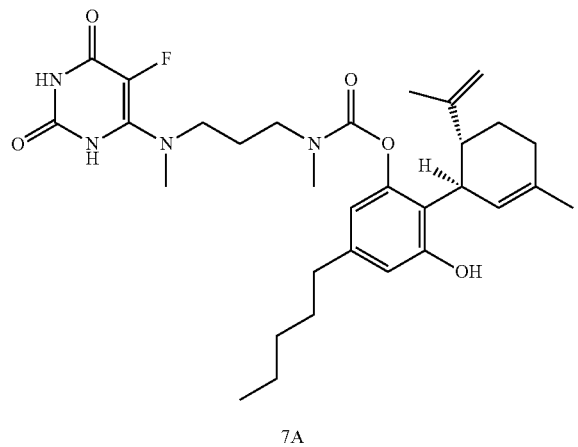

7A

-continued

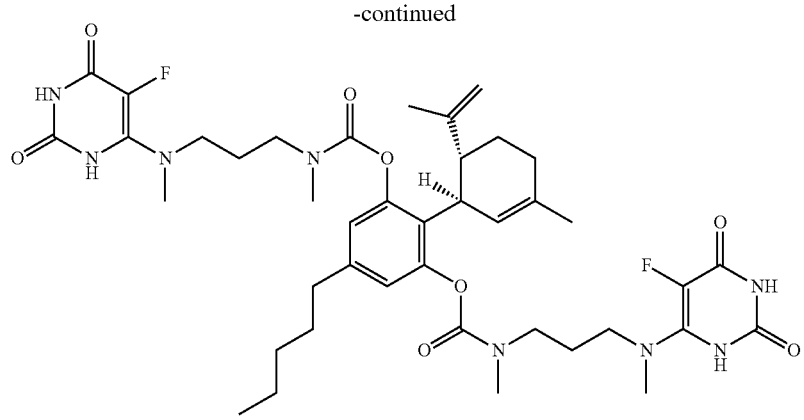

7B

EXAMPLES: SYNTHESIS OF PCAN COMPONENTS

Example 42. Synthesis of PCAN Component 1

PCAN component 1 can be synthesized as follows.

Ortho-dihydroxybenzenes are connected to platinum in the presence of AgNO$_3$ (Faming Zhuanli Shenqing, 101177435, 14 May 2008, Faming Zhuanli Shenqing, 101177434, 14 May 2008). Connection of one or two (as shown) phenolic groups, in this case from a cannabinoid (CBD in this example) are connected in a similar fashion.

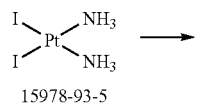

15978-93-5

PCAN component 1a may also be formed:

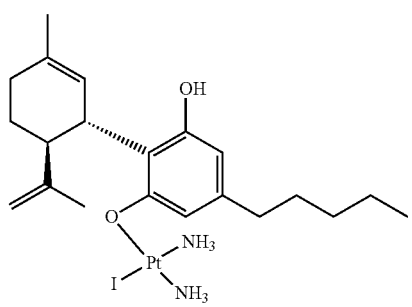

1a

Example 43. Synthesis of PCAN Components 2a, 2b, and 2c

PCAN component 2a can be synthesized as follows.

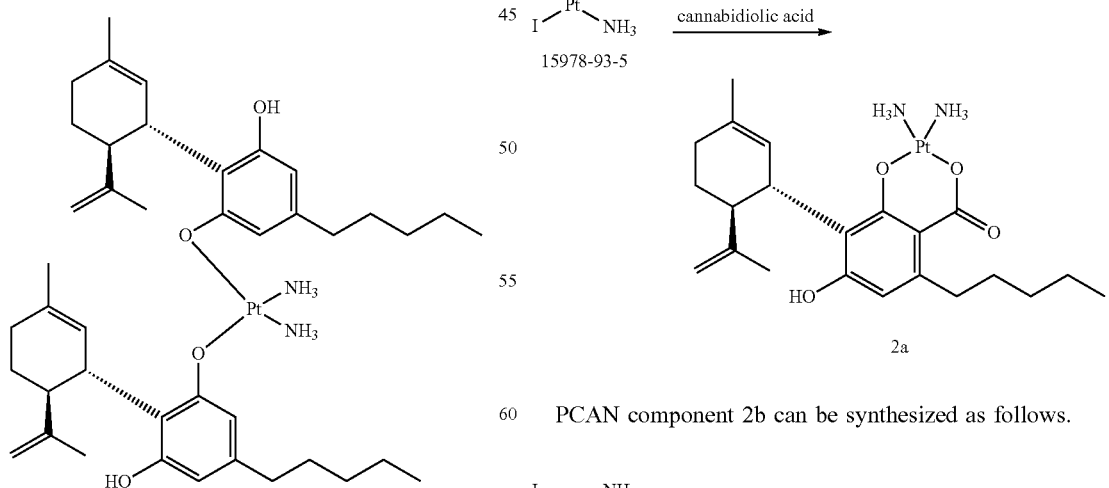

2a

PCAN component 2b can be synthesized as follows.

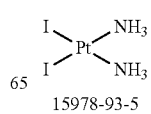

15978-93-5

319
-continued
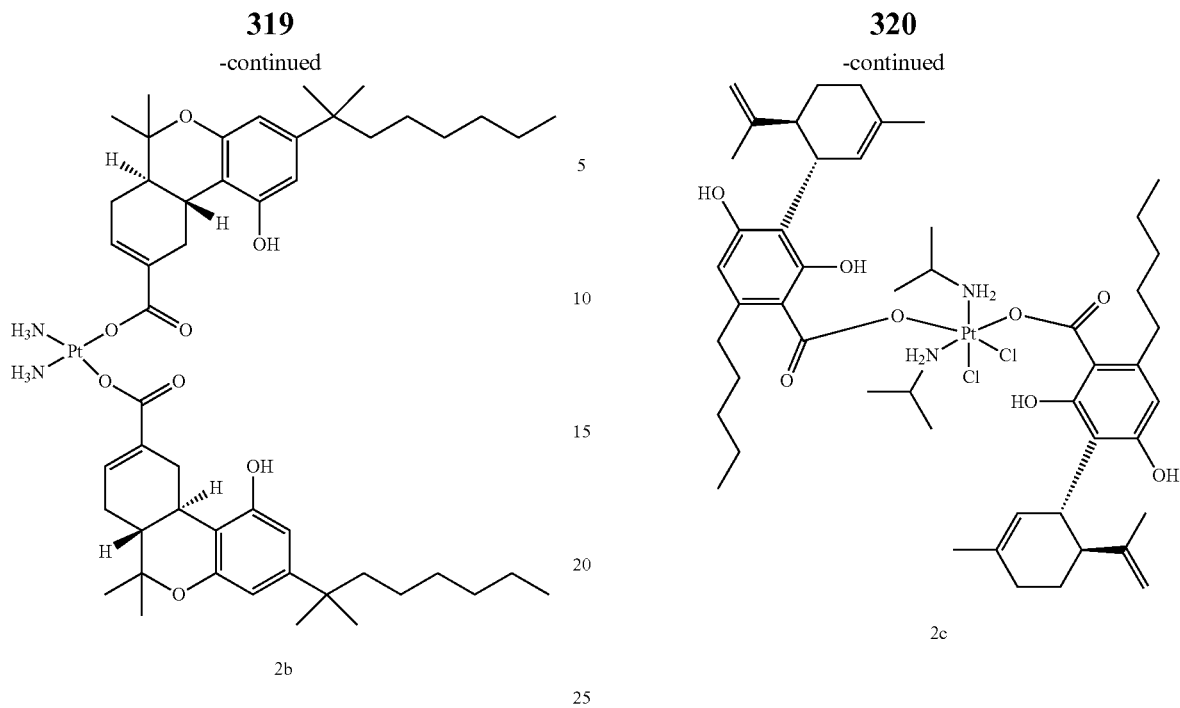
2b
320
-continued
2c
PCAN component 2c can be synthesized as follows.
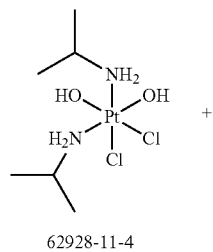
62928-11-4
+
Example 44. Synthesis of PCAN Components 3a and 3b
PCAN component 3a can be synthesized as follows.
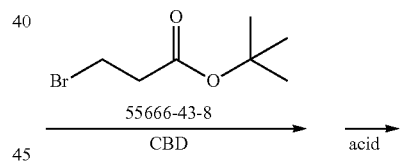
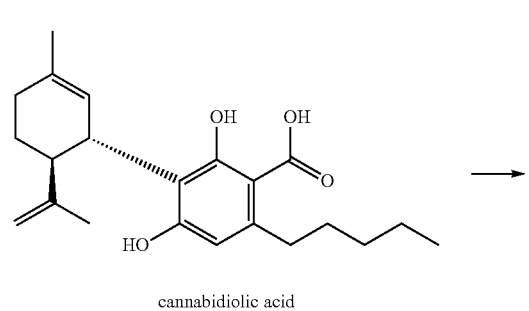
cannabidiolic acid
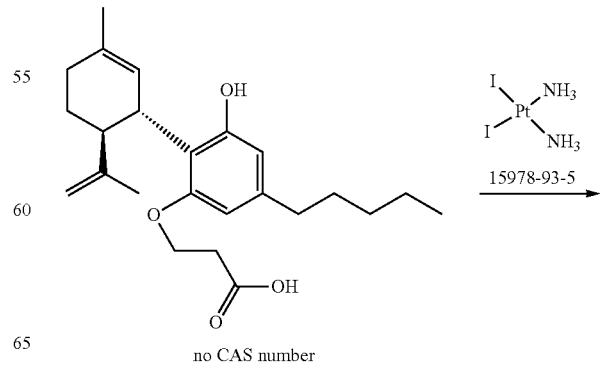
no CAS number -continued

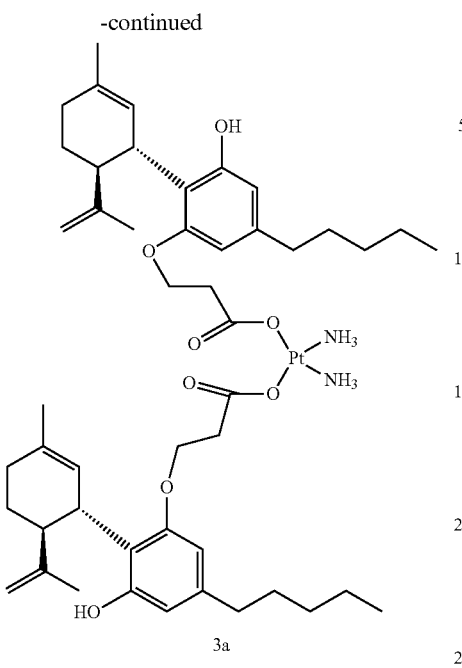

3a

-continued

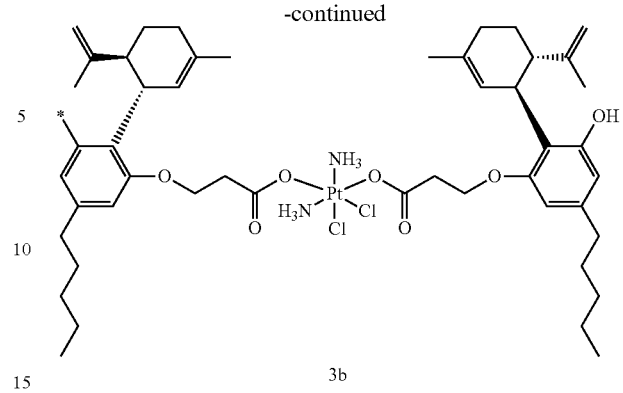

3b

Example 45. Synthesis of PCAN Component 4

PCAN component 4 can be synthesized as follows. Related Pt dicarbonates (129551-82-2, 129551-94-6, 160953-30-0, Inorganic Chemistry (1995), 34(5), 1015-2, EP 328274 A1 19890816) have been made from [62928-11-4] and pyrocarbonates. Acylation of OH groups on $Pt^{4+}$ is well known. Accordingly, reaction of CBD and [62928-11-4] with phosgene or an appropriate surrogate reagent system forms the carbonate link between the cannabinoid and platinum. Alternatively, $Pt^{4+}$ OH groups can react with alkyl carbonates to form new alkyl carbonates; thus, it may also be possible to generate the reagent where both X groups are CBD and react it with the Pt reagent.

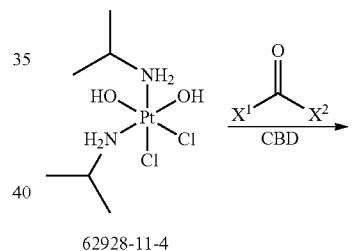

62928-11-4

PCAN component 3b can be synthesized as follows.

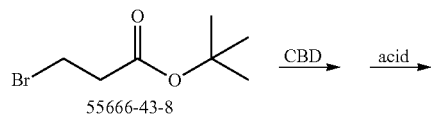

55666-43-8

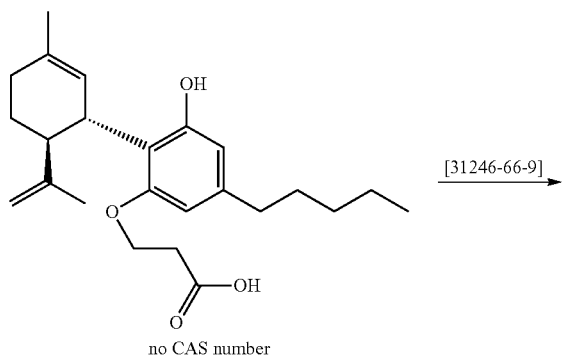

no CAS number

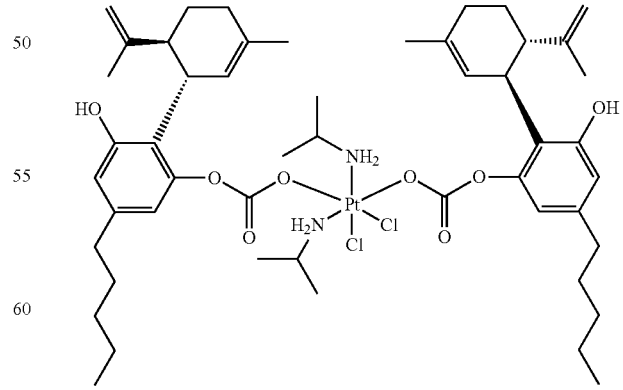

4

Example 46. Synthesis of PCAN Components 5a and 5b

PCAN component 5a can be synthesized as follows.

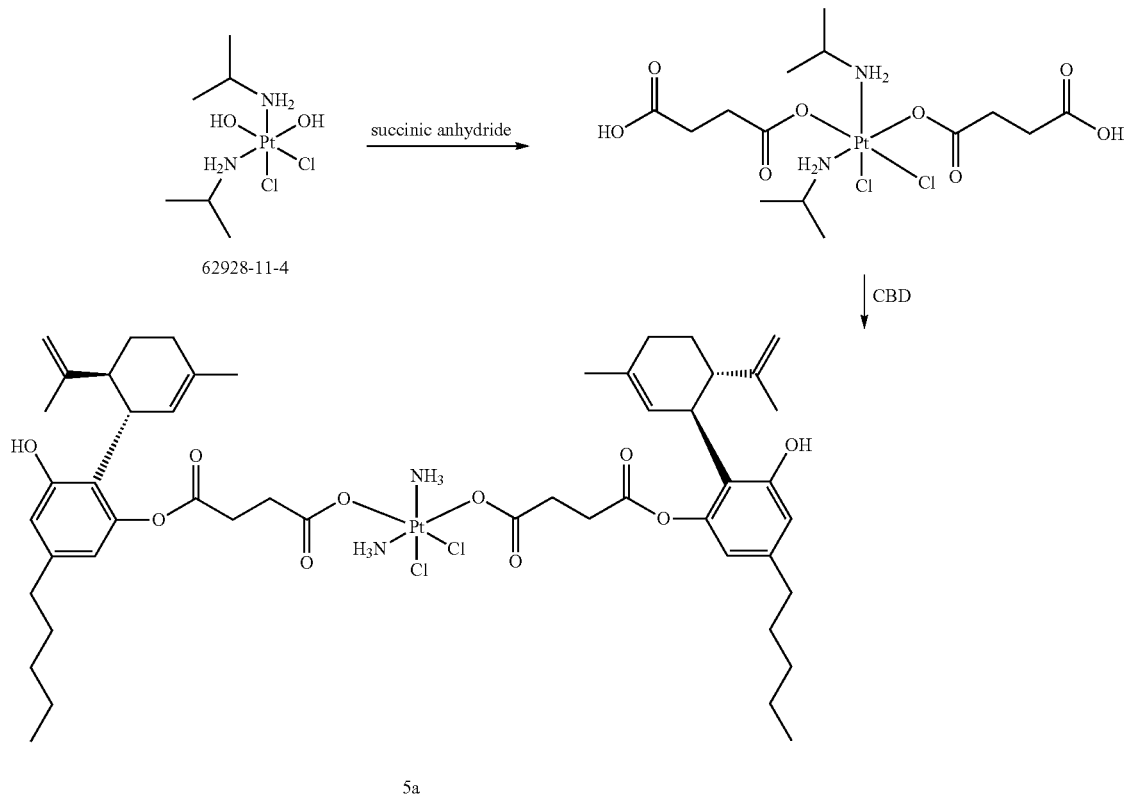

5a

Alternatively, cannabidiol can be acylated with succinic anhydride to form the cannabidiol propionic acid derivative shown in the synthesis of Compound 5b, below. Reaction of this intermediate with [62928-11-4] under esterification conditions yields cannabinoid conjugate component 5a.

PCAN component 5b can be synthesized as follows.

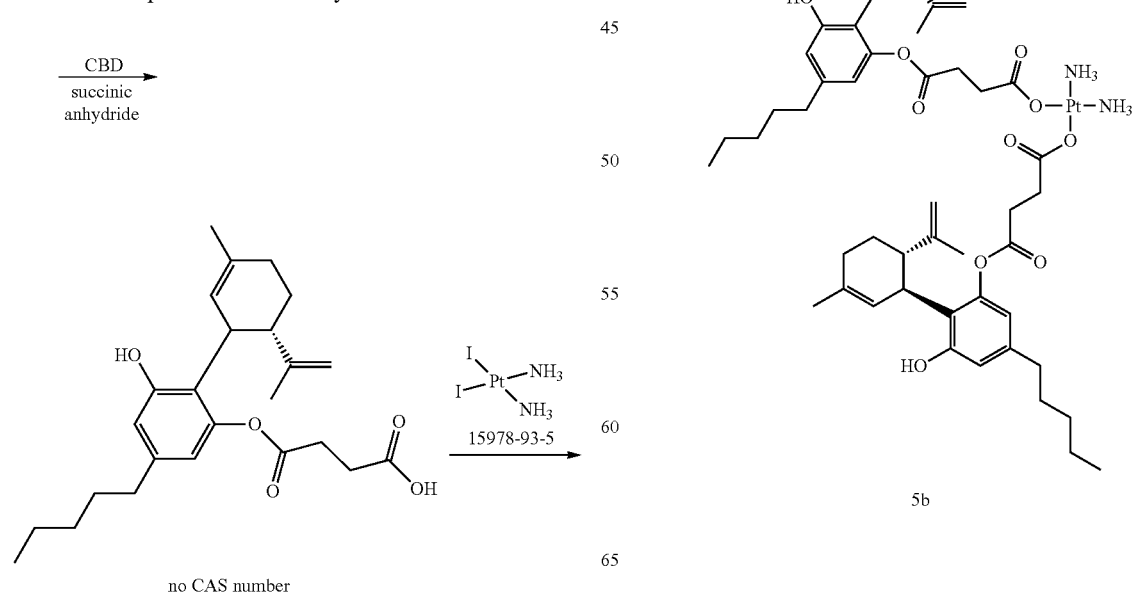

5b

-continued

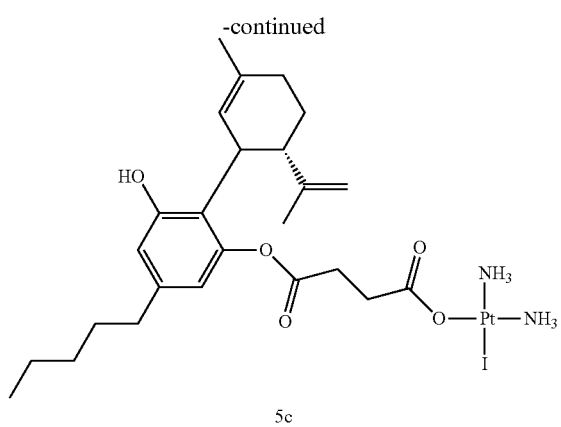

5c

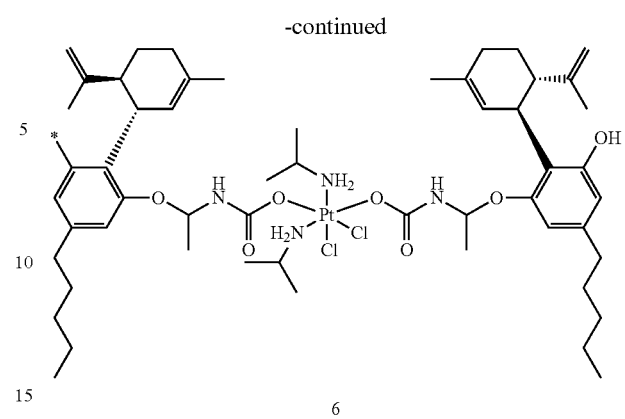

6

Example 47. Synthesis of PCAN Component 6

PCAN component 6 can be synthesized as follows.

Phenols can be converted to the corresponding vinyl ether as shown in the reference in the Scheme below. Reaction of the vinyl ether with isocyanic acid [75-13-8] (JOC, 28(8), 2082-5; 1963) generates the isocyanate. The isocyanate then reacts with [62928-11-4](Inorganic Chemistry (1995), 34(5), 1015-2; EP 328274 A1 19890816) to form Example 6.

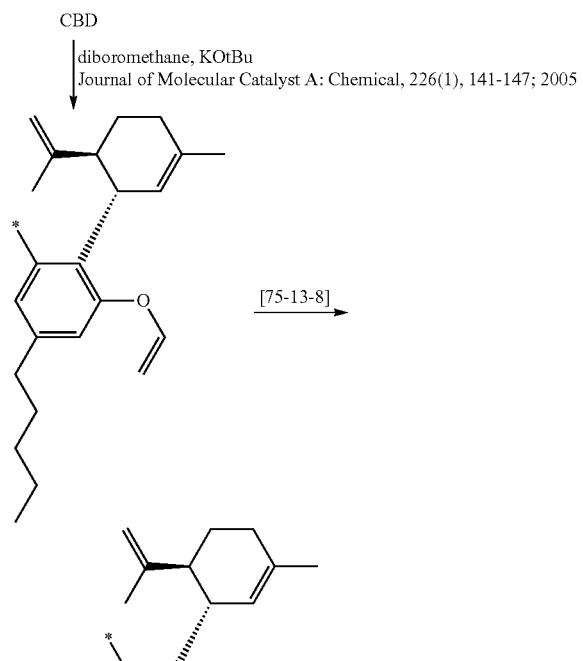

Example 48. Synthesis of PCAN Components 7 and 7a

PCAN component 7 can be synthesized as follows.

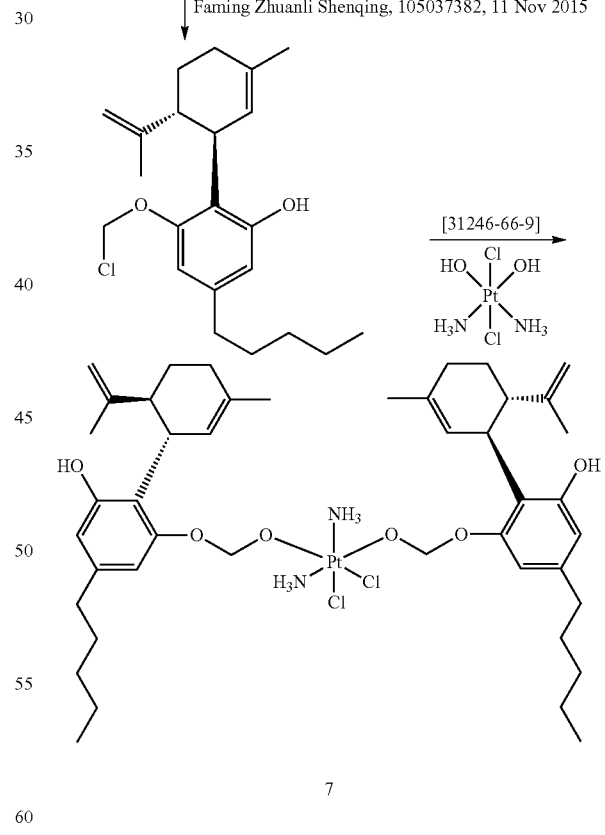

PCAN component 7a can be synthesized in a similar manner.

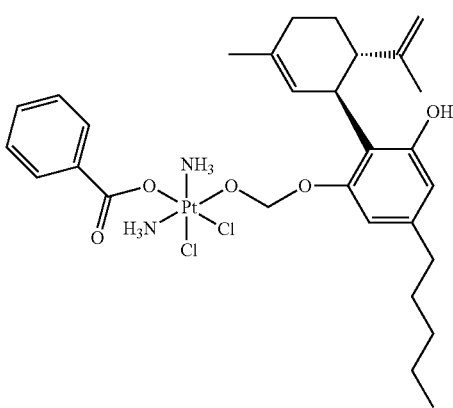

7a

The invention claimed is:

1. A conjugate molecule or a pharmaceutically acceptable salt thereof, wherein the conjugate molecule has the formula $$(CBN-L_c)_m-B \qquad (III-A)$$

wherein:
CBN is a cannabinoid component;
$L_c$ is a cannabinoid component linker, which may be absent;
B is a target binding component, wherein the target binding component is an antibody selected from the group consisting of ipilimumab, nivolumab, and pembrolizumab; and
m is 1-30.

2. The conjugate molecule of claim 1, wherein B is ipilimumab.

3. The conjugate molecule of claim 1, wherein B is nivolumab.

4. The conjugate molecule of claim 1, wherein B is pembrolizumab.

5. The conjugate molecule of claim 1, wherein m is 1.

6. The conjugate molecule of claim 1, wherein the cannabinoid component is provided by cannabidiol.

7. The conjugate molecule of claim 1, wherein the cannabinoid component is provided by cannabidiol, Le is absent, and m is 1.

8. A method of treating a cancer, comprising administering to a patient in need thereof the conjugate molecule of claim 1.

9. The method of claim 8, wherein B is a humanized antibody.

10. The method of claim 8, wherein B is an antibody that binds to a checkpoint inhibitor.

11. The method of claim 8, wherein B is ipilimumab.

12. The method of claim 8, wherein B is nivolumab.

13. The method of claim 8, wherein m is 1.

14. The method of claim 8, wherein the cannabinoid component is provided by cannabidiol, Le is absent, and m is 1.

15. The method of claim 8, wherein B is ipilimumab, the cannabinoid component is provided by cannabidiol, Le is absent, and m is 1.

16. The method of claim 8, wherein B is nivolumab, the cannabinoid component is provided by cannabidiol, Le is absent, and m is 1.

* * * * *